(12) United States Patent
Patil et al.

(10) Patent No.: US 10,526,345 B2
(45) Date of Patent: Jan. 7, 2020

(54) COMPOUNDS AS GPR119 AGONISTS

(71) Applicant: Mankind Pharma Ltd., New Delhi (IN)

(72) Inventors: Rakesh Ishwar Patil, IMT Manesar (IN); Jeevan Verma, IMT Manesar (IN); Dharmesh Shah, IMT Manesar (IN); Sazid Ali, IMT Manesar (IN); Srinivasa Reddy Bapuram, IMT Manesar (IN); Santosh Kumar Rai, IMT Manesar (IN); Anil Kumar, IMT Manesar (IN)

(73) Assignee: MANKIND PHARMA LTD., New Delhi (IN)

( * ) Notice: Subject to any disclaimer, the term of this patent is extended or adjusted under 35 U.S.C. 154(b) by 0 days.

(21) Appl. No.: 15/478,883

(22) Filed: Apr. 4, 2017

(65) Prior Publication Data

US 2017/0291910 A1   Oct. 12, 2017

(30) Foreign Application Priority Data

Apr. 8, 2016   (IN) .............. 201611012425

(51) Int. Cl.
  *C07D 513/04*   (2006.01)
  *A61P 3/10*   (2006.01)
  *A61P 3/04*   (2006.01)
(52) U.S. Cl.
  CPC .............. *C07D 513/04* (2013.01); *A61P 3/04* (2018.01); *A61P 3/10* (2018.01)
(58) Field of Classification Search
  None
  See application file for complete search history.

(56) References Cited

U.S. PATENT DOCUMENTS

| 2009/0270404 A1 | 10/2009 | Wilson et al. |
| 2011/0160222 A1 | 6/2011 | Chen et al. |
| 2012/0322784 A1 | 12/2012 | Himmelsbach et al. |
| 2013/0018030 A1 | 1/2013 | Himmelsbach et al. |
| 2013/0045986 A1* | 2/2013 | Nagarathnam ...... C07D 401/04 514/275 |
| 2013/0053345 A1 | 2/2013 | Ye et al. |
| 2015/0166480 A1 | 6/2015 | Lee et al. |

FOREIGN PATENT DOCUMENTS

| CN | 102898400 A | 1/2013 |
| WO | 2009/123992 A1 | 10/2009 |

OTHER PUBLICATIONS

STN Registry database entry for CAS RN 1340697-49-5, STN Entry Date Nov. 4, 2011, Accessed Mar. 1, 2019.*
International Search Report dated Jun. 30, 2017, for corresponding International Patent Application No. PCT/IB2017/000471.
Written Opinion dated Jun. 30, 2017, for corresponding International Patent Application No. PCT/IB2017/000471.
International Search Report dated Jun. 30, 2017, for corresponding International Patent Application No. PCT/IB2017/000466.
Written Opinion dated Jun. 30, 2017, for corresponding International Patent Application No. PCT/IB2017/000466.
Non-Final Office Action dated Aug. 21, 2017, for corresponding U.S. Appl. No. 15/478,930.
Office Action mailed by the Taiwanese Intellectual Property Office dated Nov. 8, 2017, for corresponding Taiwanese Patent Application No. 106111800. (With English Translation).

* cited by examiner

*Primary Examiner* — Alicia L Otton
(74) *Attorney, Agent, or Firm* — Pergament & Cepeda LLP; Milagros A. Cepeda; Edward D. Pergament

(57) ABSTRACT

The present invention relates to novel compounds of formula (I) as GPR119 agonist, composition compositions containing such compounds and method of preparation thereof.

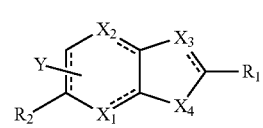

Formula (I)

27 Claims, No Drawings

COMPOUNDS AS GPR119 AGONISTS

This application claims priority to Indian Provisional Application Number 201611012425, filed on Apr. 8, 2016, which is hereby incorporated by reference in its entireties.

FIELD OF INVENTION

The present invention relates to novel GPR119 agonists that are useful in the treatment and prevention of metabolic disorders, including diabetes mellitus (type I and type II), and related disorders, pharmaceutical compositions containing such compounds and methods of preparation thereof.

BACKGROUND OF THE INVENTION

Diabetes is a life-style related disease derived from multiple causative factors. It is characterized by elevated levels of plasma glucose (hyperglycemia) in the fasting state or after administration of glucose during an oral glucose tolerance test. There are two generally recognized forms of diabetes: type 1 and type 2 diabetes mellitus. In type 1 diabetes, or insulin-dependent diabetes mellitus (IDDM), patients produce little or no insulin, the hormone which regulates glucose utilization. In type 2 diabetes, or noninsulin-dependent diabetes mellitus (T2DM), insulin is still produced in the body, and patients demonstrate resistance to the effects of insulin in stimulating glucose and lipid metabolism in the main insulin-sensitive tissues, namely, muscle, liver and adipose tissue. These patients often have normal levels of insulin, and may have hyperinsulinemia (elevated plasma insulin levels), as they compensate for the reduced effectiveness of insulin by secreting increased amounts of insulin.

The treatment of T2DM generally begins with weight loss, healthy diet and exercise program. Although these factors are important especially to resolve the increased risk of cardiovascular disorders related to diabetes mellitus, they are not generally effective for control of diabetes mellitus itself. There are many drugs useful for the treatment of diabetes mellitus, including insulin, metformin, sulfonylureas, acarbose, thiazolidinediones, GLP-1 analogue and DPP IV inhibitors. There are, however deficiencies associated with currently available treatment, including hypoglycemic episodes, weight gain, loss in responsiveness to therapy over time, gastrointestinal problems, and edema.

Although number of receptor classes exist in humans, the most abundant and therapeutically relevant is G protein-coupled receptor (GPCR) class, it is estimated that approximately 4% of the protein-coding genome encodes GPCRs. GPCRs are also known as seven-transmembrane domain receptors as they share a common structural motif, having seven sequences of between 22 to 24 hydrophobic amino acids that form seven alpha helices, each of which spans the membrane. Further, there has been renewed focus on pancreatic islet-based insulin secretion that is controlled by glucose-dependent insulin secretion (GDIS). GPR119 is a cell-surface GPCR that is highly expressed in human (and rodent) islets as well as in insulin-secreting cell lines. Activation of GPR119 stimulate intracellular cAMP leading to glucose dependent GLP-1 and insulin secretion (T. Soga et al Biochem. Biophys. Res. Commun. 2005, 326). Synthetic GPR119 agonists augment the release of insulin from isolated static mouse islets only under conditions of elevated glucose, and improve glucose tolerance in diabetic mice and diet-induced obese (DIO) C57/B6 mice without causing hypoglycemia.

There still remains a need for alternative novel synthetic compounds which acts as GPR119 agonists and are useful in the treatment and prevention of metabolic disorders, including diabetes mellitus (type I and type II), obesity and related disorders.

SUMMARY OF THE INVENTION

In one aspect, the present invention provides novel compounds of formula (I):

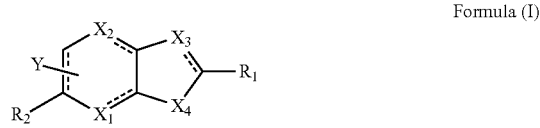

Formula (I)

wherein, $X_1$, $X_2$, $X_3$ and $X_4$ is N, O, S or CH;

Y is selected from H, OH, halogen, $C_{1-6}$ alkyl, $C_{1-6}$ alkoxy, —(CH)n, amino, —CO, —CONH, —NH(Alkyl), —N(Alkyl)$_2$, —NH-aralkyl, —OCH(CH$_3$);

n is 0, 1, 2 or 3;

" ----- " is independently either a single bond or a double bond, provided that adjacent double bonds (=C=) are not allowed;

$R_1$ is selected from

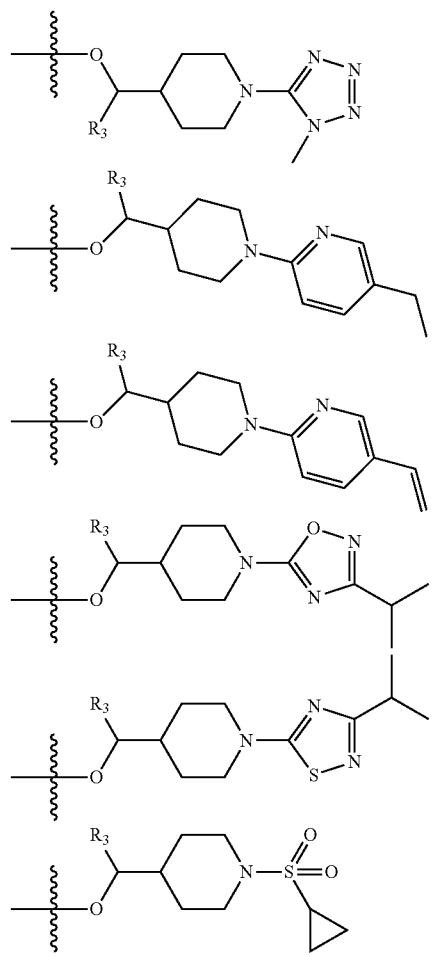

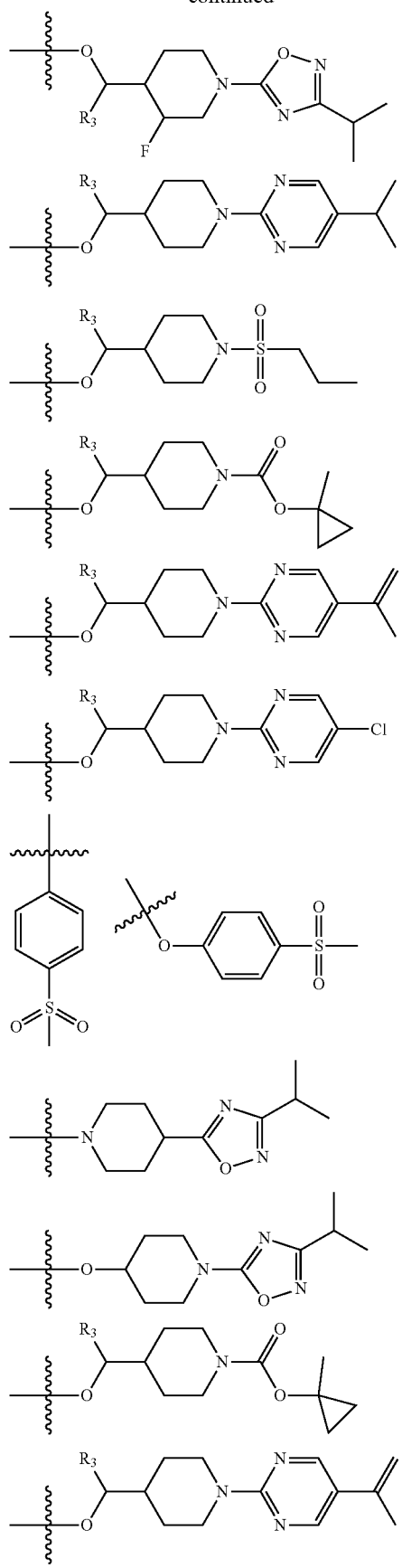
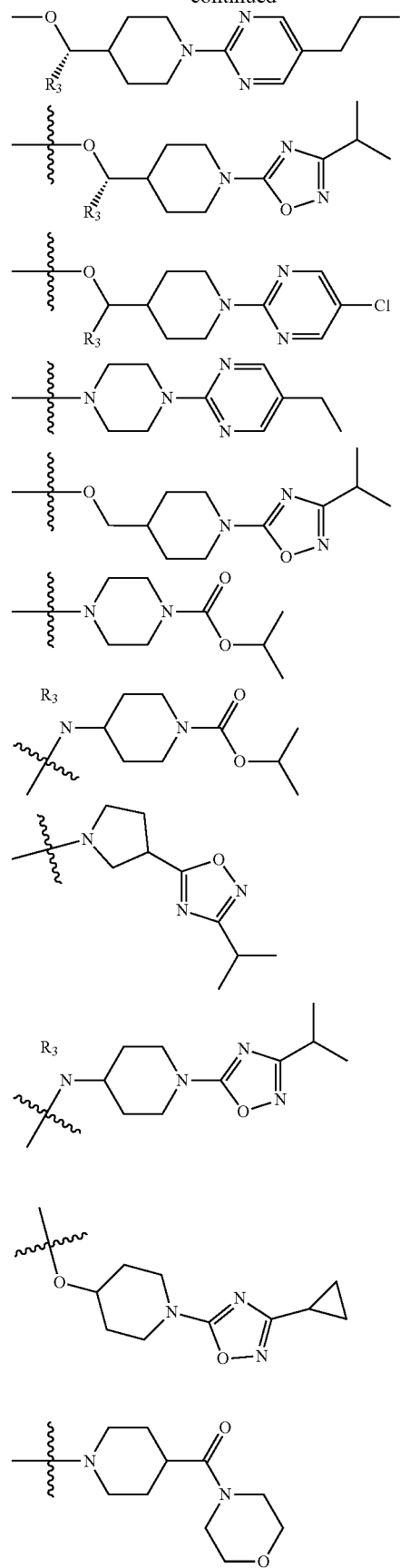

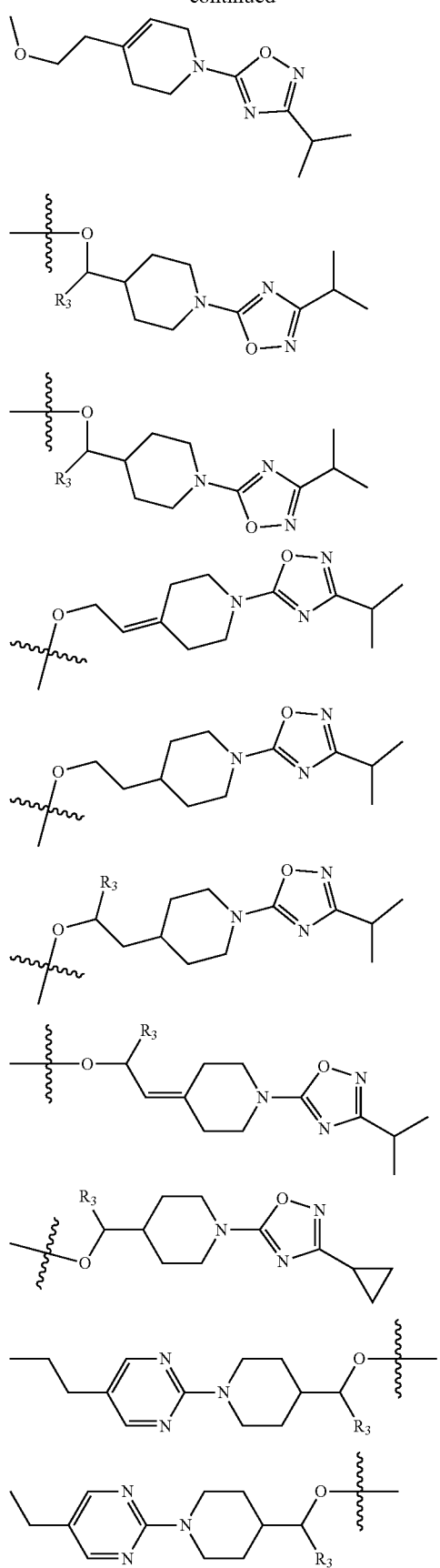
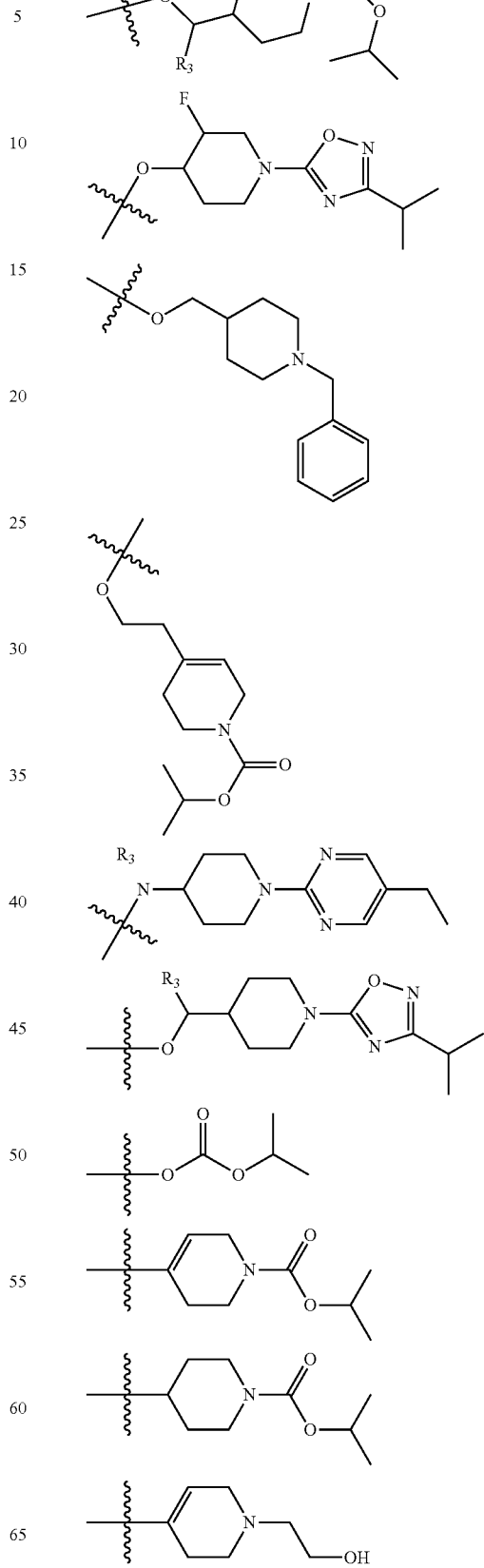

-continued
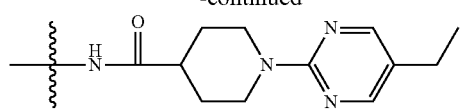
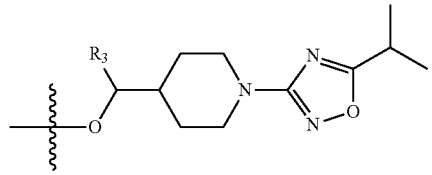
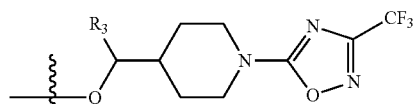
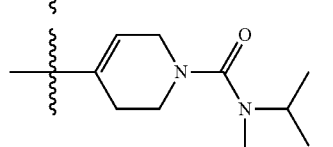
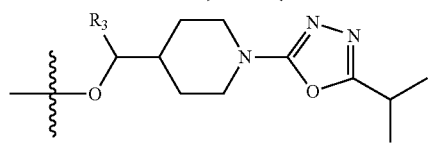
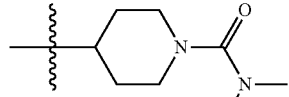
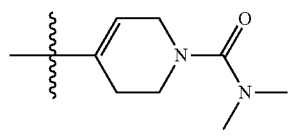
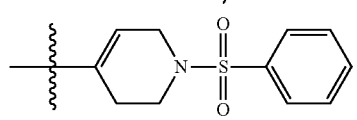
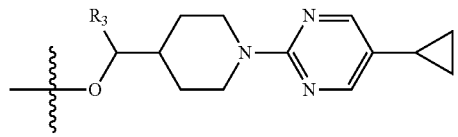
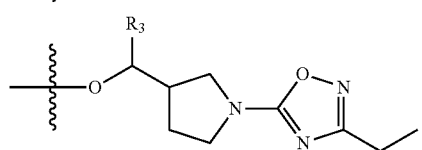
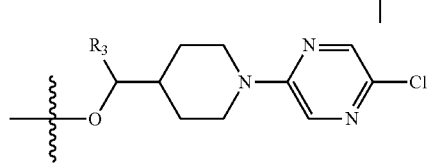
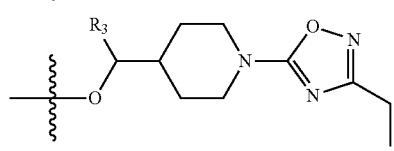
-continued
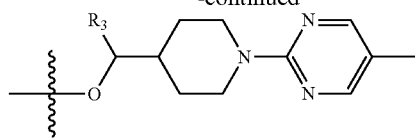
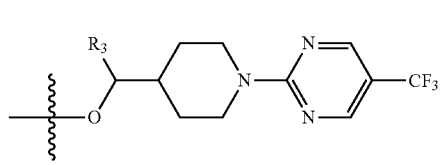
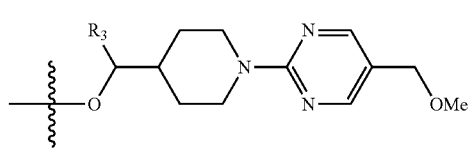
$R_2$ is selected from
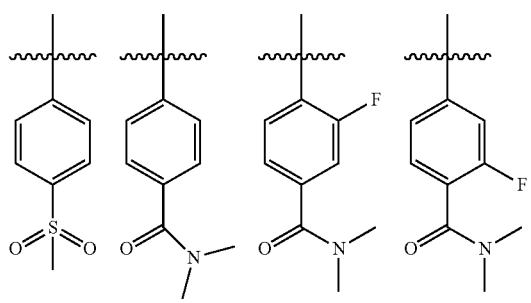
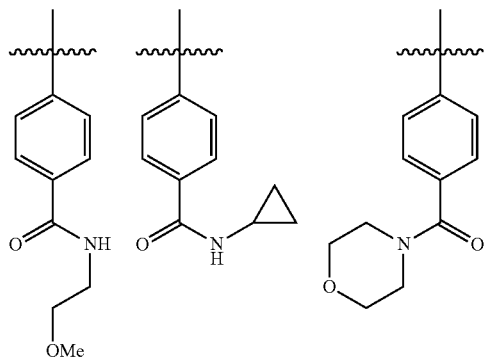
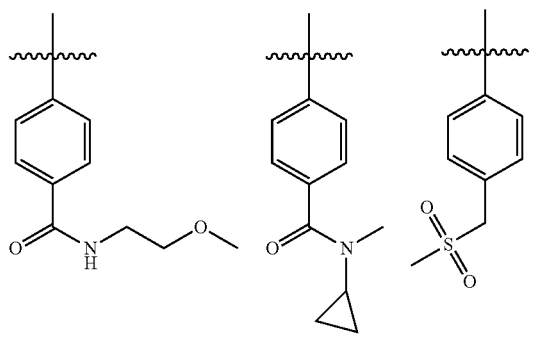

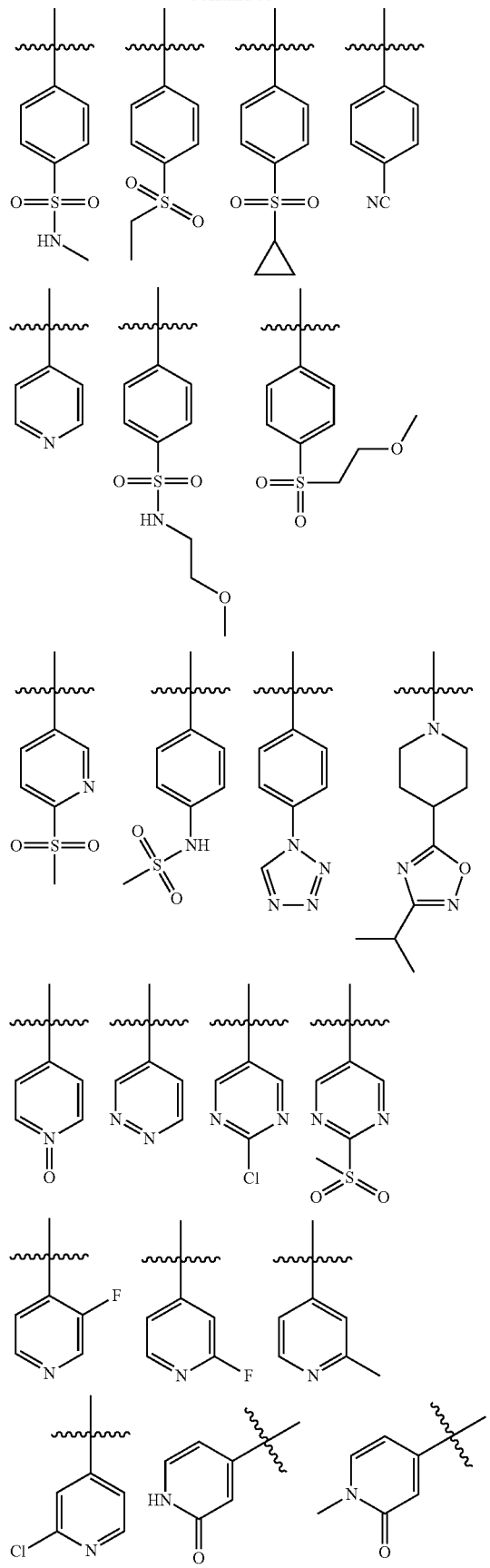
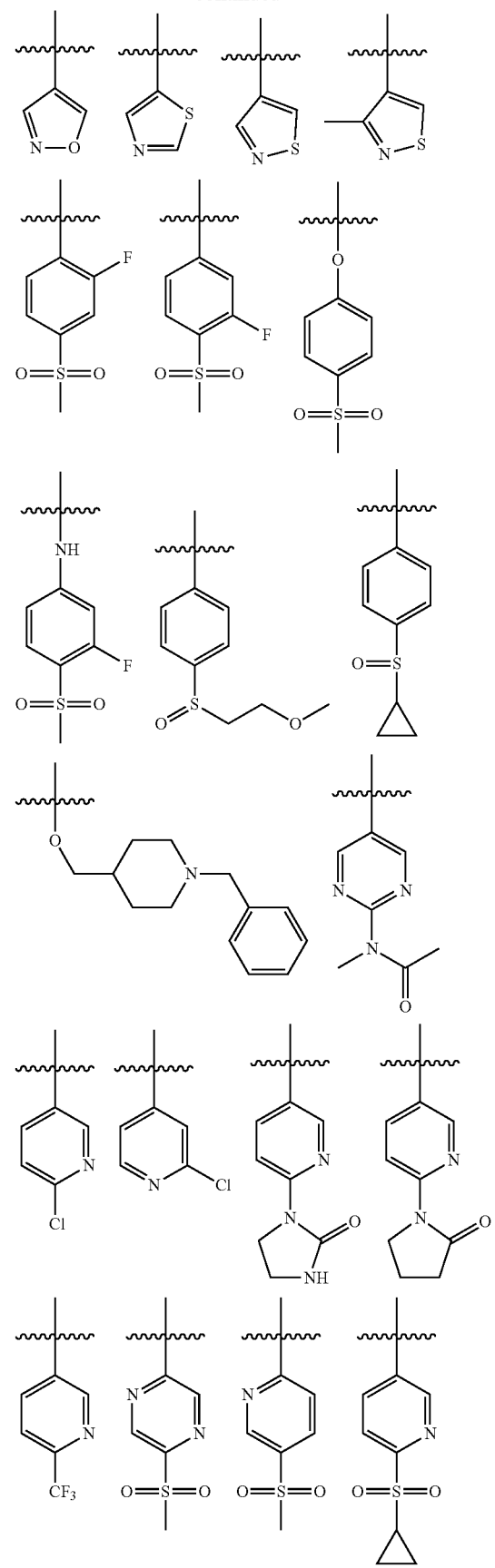

-continued

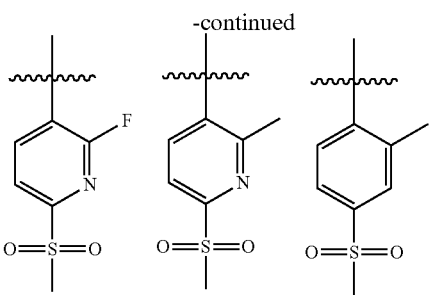

R₃ is selected from H, OH, halogen, $C_{1-6}$ alkyl, $C_{1-6}$alkoxy, —(CH)n, amino, —CO, —CONH, —NH(Alkyl), —N(Alkyl)₂, —NH-aralkyl, —CF3, —OCH(CH₃),

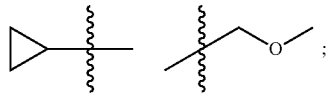;

and salts, hydrates and stereoisomers thereof.

In an embodiment, the invention provides compounds having the formula (II):

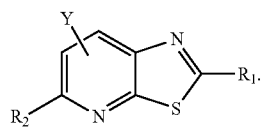

(II)

Preferably, the compounds of this embodiment of the invention have active GLP-1 secretion greater than ~1 fold with respect to vehicle.

Preferably, the compounds of this embodiment of the invention have significant glucose reduction at both 3 mpk and 10 mpk in glucose tolerance test.

Preferably, the compounds of this embodiment of the invention show increase in insulin secretion at an EC50 of less than 1 µM in an in-vitro model of pancreatic beta cells.

In one variant, there are provided the compounds wherein R1 is

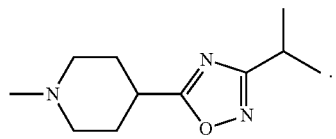

In another variant, there are provided the compound of claim 2, wherein R1 is

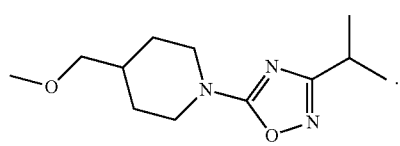 [SMILES: COCC1CCN(c2nc(C(C)C)no2)CC1]

In another variant, there are provided the compounds wherein R1 is

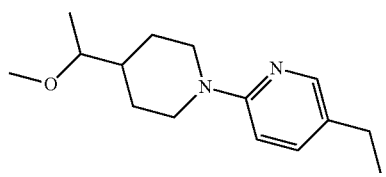

In another variant, there are provided the compounds wherein R1 is

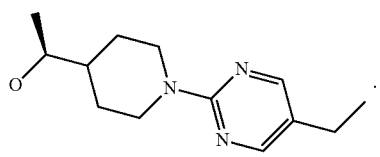 [SMILES: CCc1cnc(N2CCC([C@H](C)O)CC2)nc1]

All individual combination of substituents are separately contemplated.

In another variant, preferably Y is hydrogen.

Individual compounds disclosed and claimed herein are individually contemplated, including pharmaceutically acceptable salts, hydrates and stereoisomers.

In another aspect of the invention, there is provided a method of treating diabetes comprising administering compounds of the invention to a patient in need thereof.

DETAILED DESCRIPTION OF THE INVENTION

A. Compounds of the Present Invention

Accordingly, the present invention provides novel compound of Formula I:

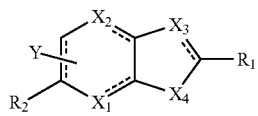

Formula (I)

wherein, $X_1$, $X_2$, $X_3$ and $X_4$ is N, O, S or CH;

Y is selected from H, OH, halogen, $C_{1-6}$ alkyl, $C_{1-6}$alkoxy, —(CH)n, amino, —CO, —CONH, —NH(Alkyl), —N(Alkyl)₂, —NH-aralkyl, —OCH(CH₃);

n is 0, 1, 2 or 3;

" ------ " is independently either a single bond or a double bond, provided that adjacent double bonds (=C=) are not allowed;

R₁ is selected from

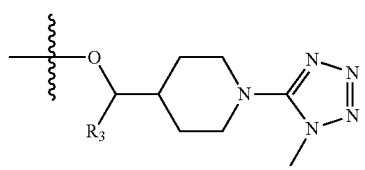

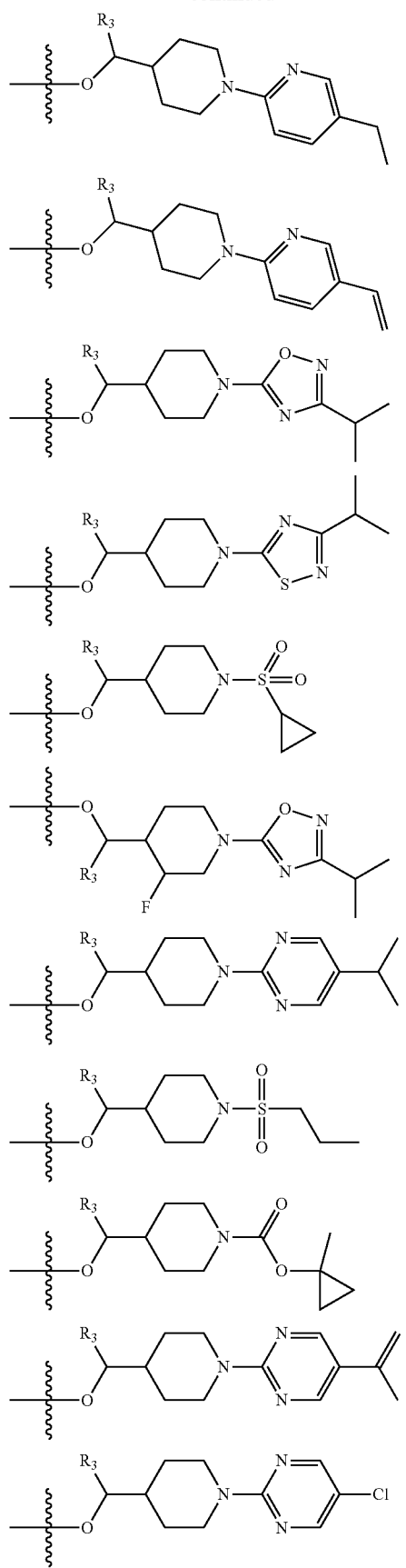
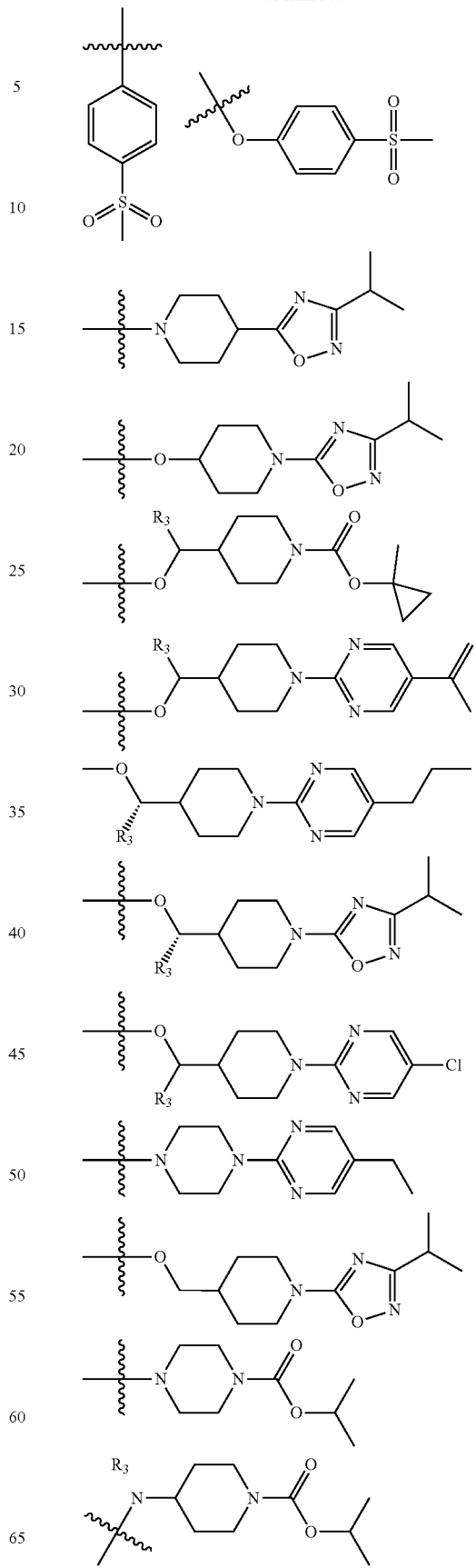

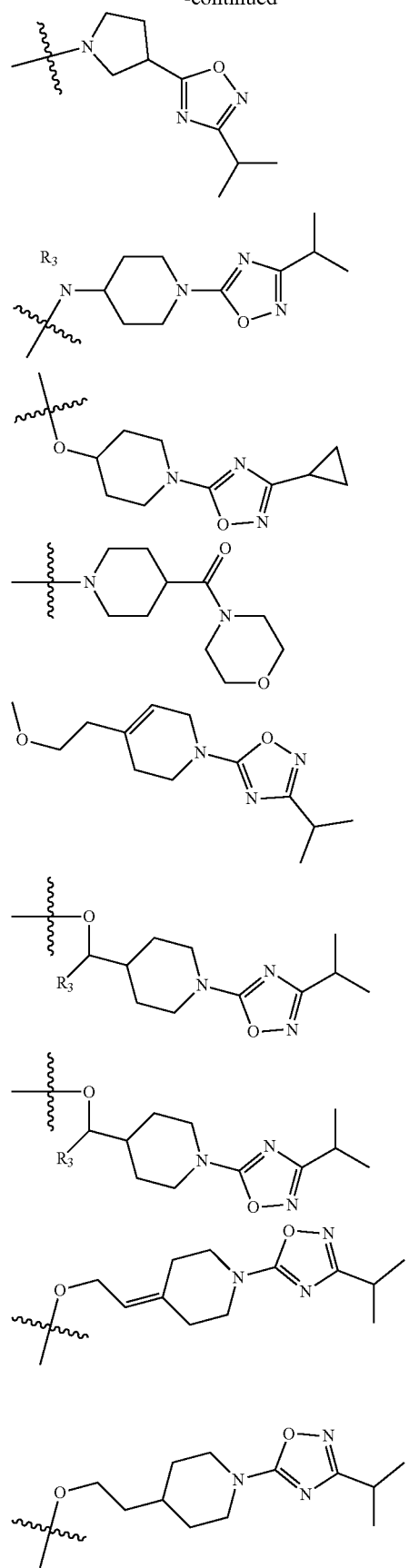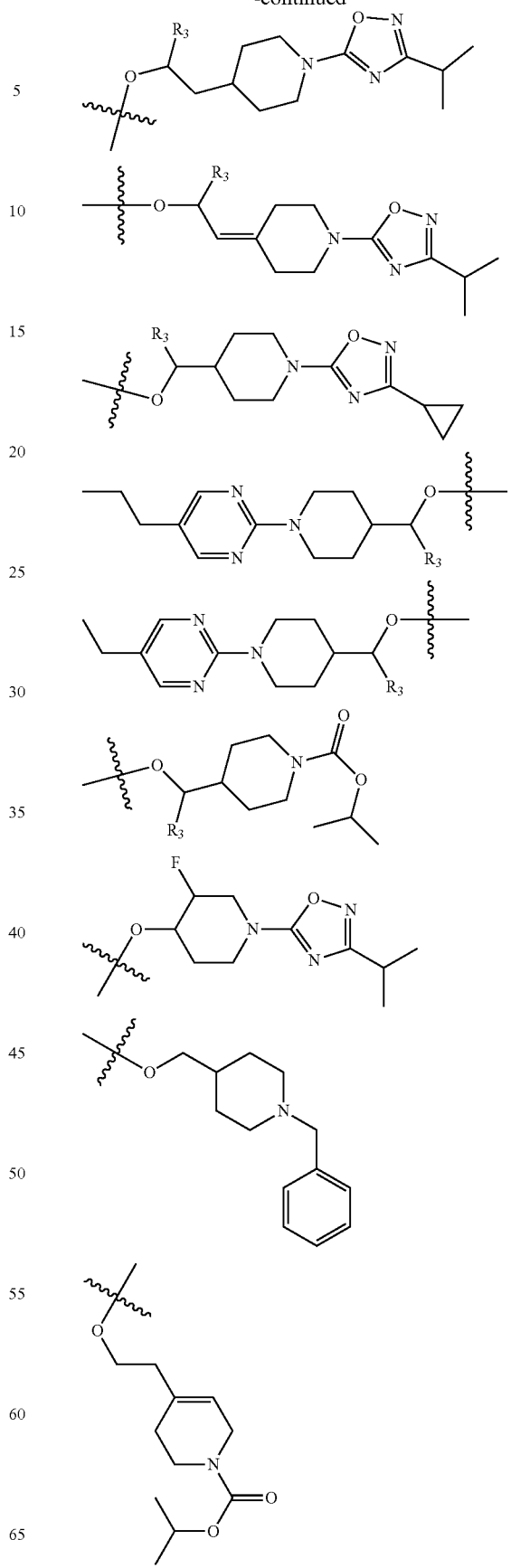

-continued
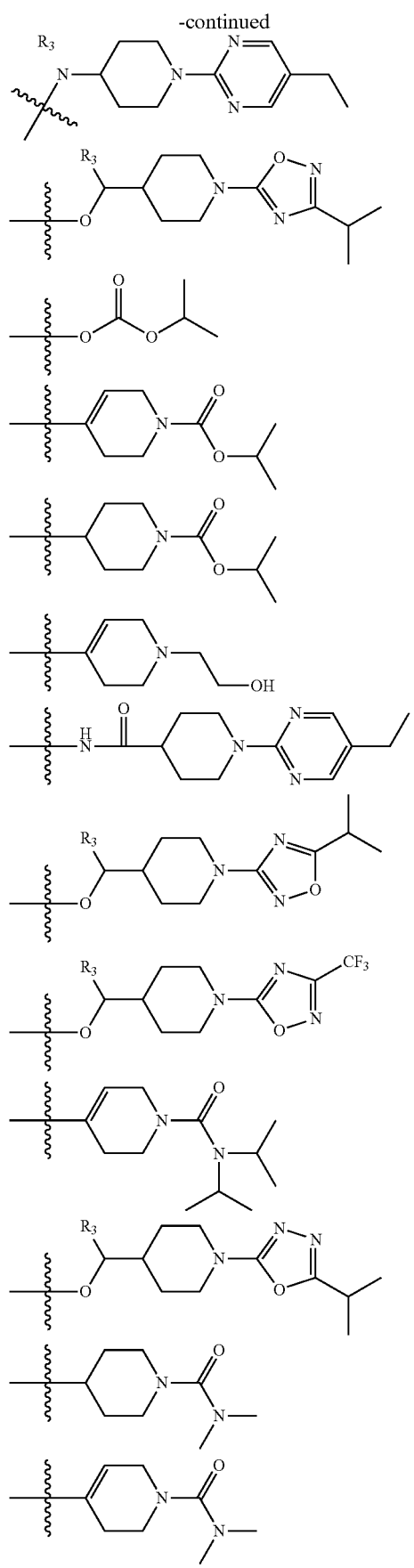
-continued
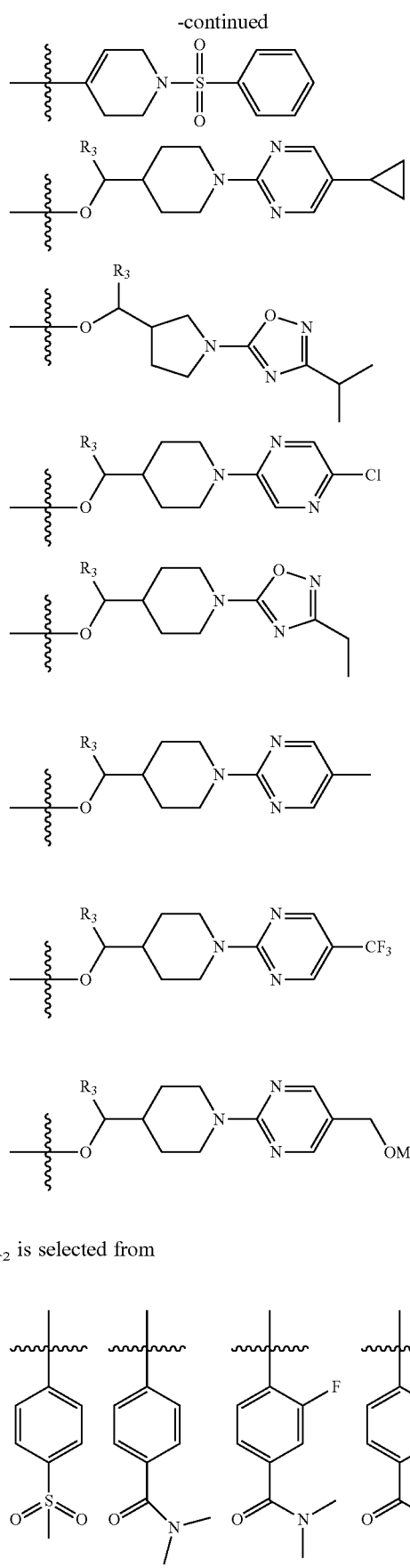
$R_2$ is selected from
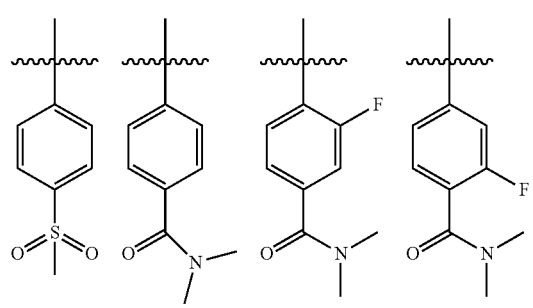

-continued
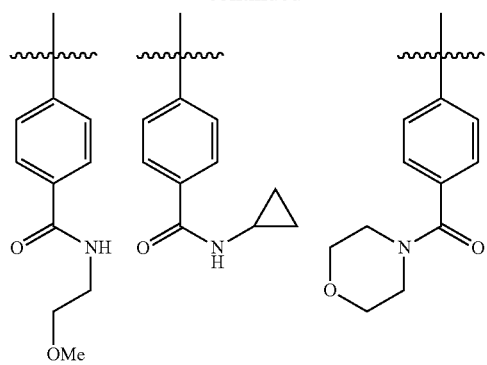
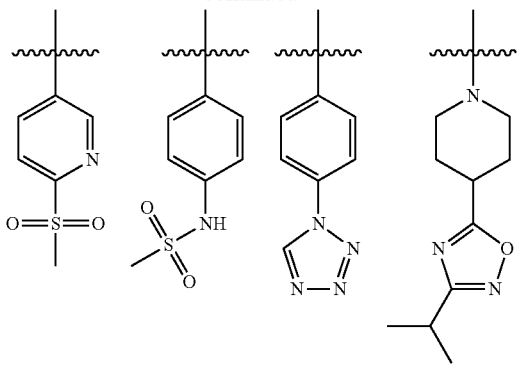
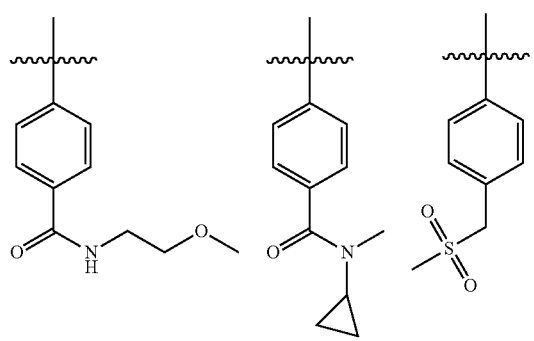
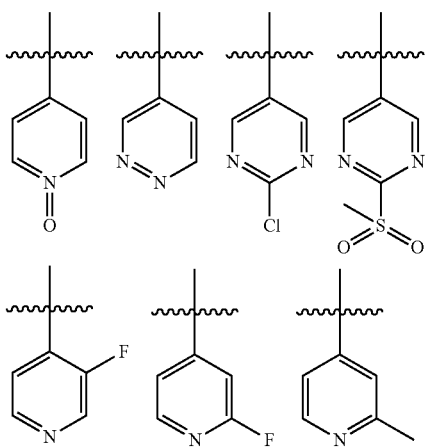
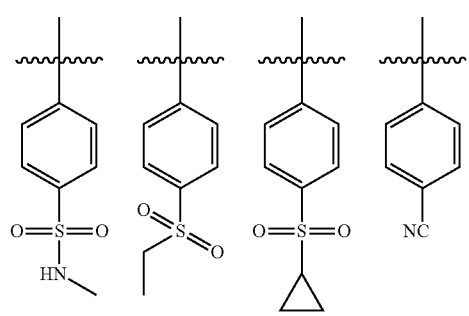
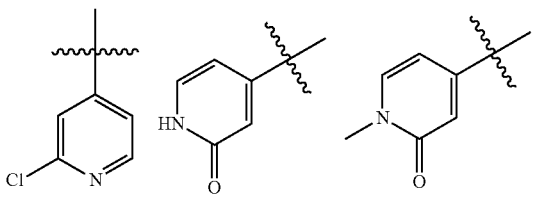
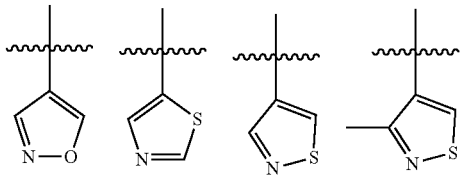
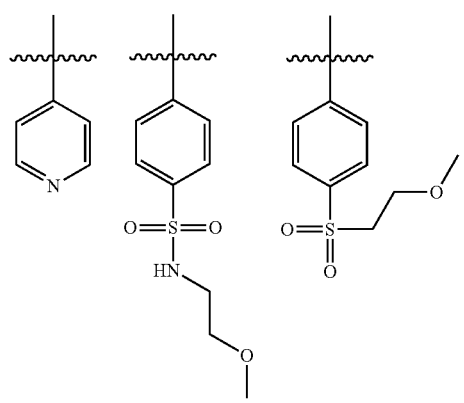
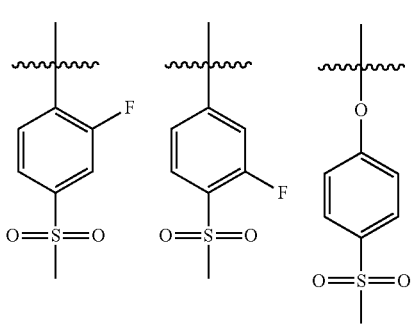

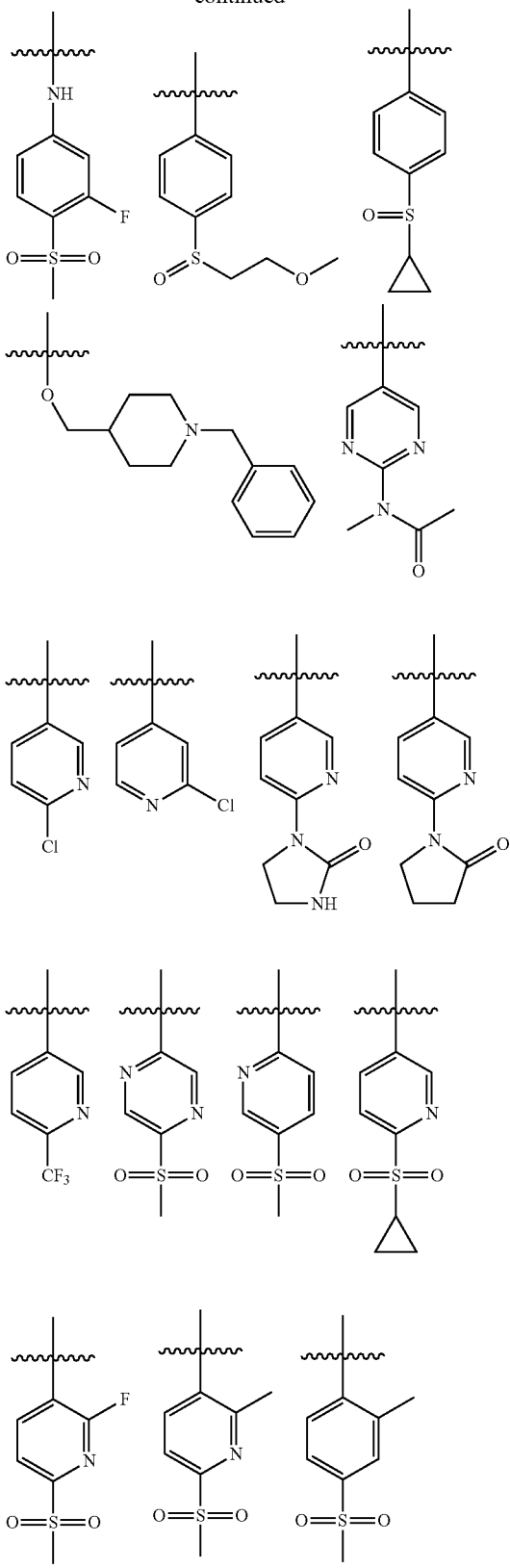

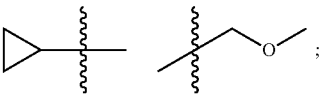

and salts, hydrates and stereoisomers thereof.

The term "alkyl" refers to a linear or branched saturated monovalent hydrocarbon, wherein the alkylene may optionally be substituted as described herein. The term "alkyl" also encompasses both linear and branched alkyl, unless otherwise specified. In certain embodiments, the alkyl is a linear saturated monovalent hydrocarbon that has the specified number of carbon atoms, or branched saturated monovalent hydrocarbon of specified number of carbon atoms. As used herein, linear C1-C6 and branched C3-C6 alkyl groups are also referred as "lower alkyl." Examples of alkyl groups include, but are not limited to, methyl, ethyl, propyl (including allisomeric forms), n-propyl, isopropyl, butyl (including all isomeric forms), n-butyl, isobutyl, sec-butyl,t-butyl, pentyl (including all isomeric forms), and hexyl (including all isomeric forms). For example, C1-C6 alkyl refers to a linear saturated monovalent hydrocarbon of 1 to 6 carbon atoms or a branched saturated monovalent hydrocarbon of 3 to 6 carbon atoms.

The term "alkoxy" refers to the group R'O— wherein R' is alkyl. The term "lower alkoxy" refers to alkoxy groups having from 1 to 3 carbon atoms; examples include methoxy, ethoxy, isopropoxy, and the like.

The term "aralkyl" or "aryl-alkyl" refers to a monovalent alkyl group substituted with aryl. In certain embodiments, the alkyl and aryl moieties are optionally substituted as described herein.

The term "halogen", "halide" or "halo" refers to fluorine, chlorine, bromine, and iodine.

The use of terms "a" and "an" and "the" and similar references in the context of describing the invention (especially in the context of the following claims) are to be construed to cover both the singular and the plural, unless otherwise indicated herein or clearly contraindicated by context.

The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise a basic moiety such as an amino group). Also included herein are quaternary ammonium salts such as alkyl ammonium salts. Pharmaceutically acceptable (i.e., non-toxic, physiologically acceptable) salts are preferred.

The term "hydrate" as used herein designates a crystalline molecular compound in which water molecules are incorporated into the crystal lattice. Generally speaking, a hydrate thus designates a crystalline form of a molecular compound, whereby the only further molecules incorporated into the crystal lattice are water molecules.

The term "stereoisomer's" refers to at least two compounds having the same molecular formula and connectivity of atoms, but having a different arrangement of atoms in a three-dimensional space. In view of the present disclosure, a stereoisomer can be, for example, an enantiomer, a diastereomer, or a meso compound.

The term "GPR119" as used herein refers to the G protein-coupled receptor that in humans is encoded by the GPR119 gene.

The present invention provides compound represented by formula (I) that act as GPR119 agonist and is used in the treatment of metabolic disorders, preferably type I and type II diabetes mellitus, obesity and related disorders.

$R_3$ is selected from H, OH, halogen, $C_{1-6}$ alkyl, $C_{1-6}$alkoxy, —(CH)n, amino, —CO, —CONH, —NH(Alkyl), —N(Alkyl)$_2$, —NH-aralkyl, —CF3, —OCH(CH$_3$), The compounds of the present invention may be illustrated but not limited to the examples as provided at Table 1.

TABLE 1

Illustrative compounds of present invention

| Compound No. | IUPAC name |
|---|---|
| 1001 | 3-isopropyl-5-(1-(5-(4-(methylsulfonyl)phenoxy)thiazolo[5,4-b]pyridin-2-yl)piperidin-4-yl)-1,2,4-oxadiazole |
| 1002 | 3-isopropyl-5-(4-(((5-(4-(methylsulfonyl)phenoxy)thiazolo[5,4-b]pyridin-2-yl)oxy)methyl)piperidin-1-yl)-1,2,4-oxadiazole |
| 1003 | 3-isopropyl-5-(1-(2-(4-(methylsulfonyl)phenyl)thiazolo[5,4-b]pyridin-5-yl)piperidin-4-yl)-1,2,4-oxadiazole |
| 1004 | 3-isopropyl-5-(1-(5-(4-(methylsulfonyl)phenyl)thiazolo[5,4-b]pyridin-2-yl)piperidin-4-yl)-1,2,4-oxadiazole |
| 1005 | 3-isopropyl-5-(4-((5-(4-(methylsulfonyl)phenoxy)thiazolo[5,4-b]pyridin-2-yl)oxy)piperidin-1-yl)-1,2,4-oxadiazole |
| 1006 | 3-isopropyl-5-(4-(((5-(4-(methylsulfonyl)phenyl)thiazolo[5,4-b]pyridin-2-yl)oxy)methyl)piperidin-1-yl)-1,2,4-oxadiazole |

TABLE 1-continued

Illustrative compounds of present invention

| Compound No. | IUPAC name |
|---|---|
| 1007 | 3-isopropyl-5-(4-((5-(4-(methylsulfonyl)phenyl)thiazolo[5,4-b]pyridin-2-yl)oxy)piperidin-1-yl)-1,2,4-oxadiazole |
| 1008 | 2-(4-(5-ethylpyrimidin-2-yl)piperazin-1-yl)-5-(4-(methylsulfonyl)phenyl)thiazolo[5,4-b]pyridine |
| 1009 | 5-((1-benzylpiperidin-4-yl)methoxy)-2-(4-(methyslulfonyl)phenyl)thiazolo[5,4-b]pyridine |
| 1010 | 2-(4-(5-ethylpyrimidin-2-yl)piperazin-1-yl)-5-(4-(methylsulfonyl)phenoxy)thiazolo[5,4-b]pyridine |
| 1011 | isopropyl 4-(5-(4-(methylsulfonyl)phenyl)thiazolo[5,4-b]pyridin-2-yl)-5,6-dihydropyridine-1(2H)-carboxylate |
| 1012 | isopropyl 4-(5-(4-(methylsulfonyl)phenyl)thiazolo[5,4-b]pyridin-2-yl)piperazine-1-carboxylate |
| 1013 | isopropyl 4-(5-(4-(methylsulfonyl)phenyl)thiazolo[5,4-b]pyridin-2-yl)piperidine-1-carboxylate |

TABLE 1-continued

Illustrative compounds of present invention

| Compound No. | IUPAC name | Structure |
|---|---|---|
| 1014 | 1-(5-ethylpyrimidin-2-yl)-N-(5-(4-(methylsulfonyl)phenyl)thiazolo[5,4-b]pyridin-2-yl)piperidine-4-carboxamide | 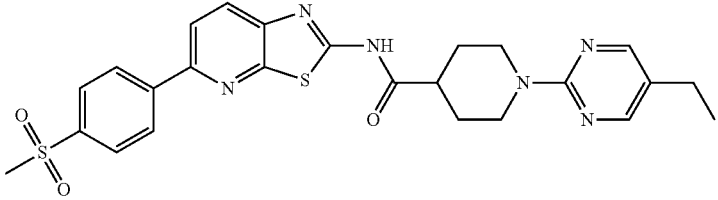 [SMILES: CCc1cnc(N2CCC(C(=O)Nc3nc4ccc(-c5ccc(S(C)(=O)=O)cc5)nc4s3)CC2)nc1] |
| 1015 | 2-(4-(5-(4-(methylsulfonyl)phenyl)thiazolo[5,4-b]pyridin-2-yl)-5,6-dihydropyridin-1(2H)-yl)ethanol | 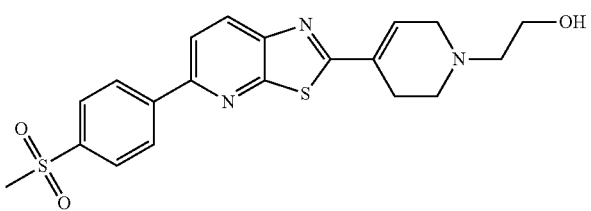 [SMILES: CS(=O)(=O)c1ccc(-c2ccc3nc(C4=CCN(CCO)CC4)sc3n2)cc1] |
| 1016 | isopropyl 4-(methyl(5-(4-(methylsulfonyl)phenyl)thiazolo[5,4-b]pyridin-2-yl)amino)piperidine-1-carboxylate | 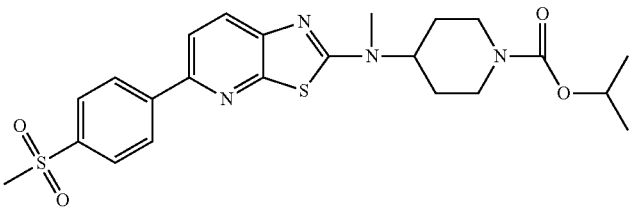 [SMILES: CC(C)OC(=O)N1CCC(N(C)c2nc3ccc(-c4ccc(S(C)(=O)=O)cc4)nc3s2)CC1] |
| 1017 | N-(1-(5-ethylpyrimidin-2-yl)piperidin-4-yl)-N-methyl-5-(4-(methylsulfonyl)phenyl)thiazolo[5,4-b]pyridin-2-amine | 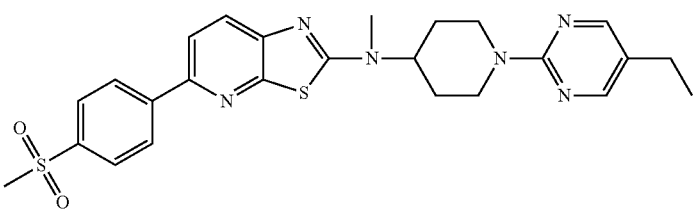 [SMILES: CCc1cnc(N2CCC(N(C)c3nc4ccc(-c5ccc(S(C)(=O)=O)cc5)nc4s3)CC2)nc1] |
| 1018 | isopropyl 4-((5-(4-(dimethylcarbamoyl)phenyl)thiazolo[5,4-b]pyridin-2-yl)(methyl)amino)piperidine-1-carboxylate | 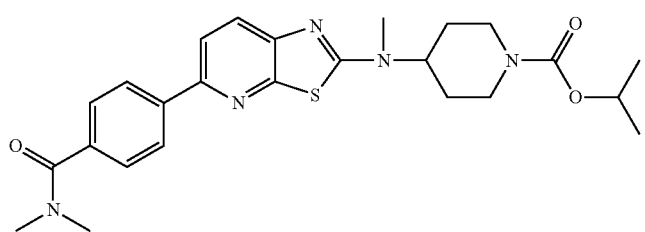 [SMILES: CC(C)OC(=O)N1CCC(N(C)c2nc3ccc(-c4ccc(C(=O)N(C)C)cc4)nc3s2)CC1] |
| 1019 | isopropyl (5-(4-(methylsulfonyl)phenyl)thiazolo[5,4-b]pyridin-2-yl)carbonate | 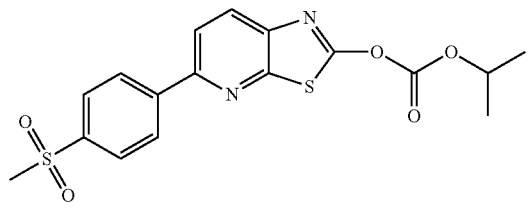 [SMILES: CC(C)OC(=O)Oc1nc2ccc(-c3ccc(S(C)(=O)=O)cc3)nc2s1] |

TABLE 1-continued

Illustrative compounds of present invention

| Compound No. | IUPAC name | Structure |
|---|---|---|
| 1020 | 3-isopropyl-5-(4-(1-((5-(4-(methylsulfonyl)phenyl)thiazolo[5,4-b]pyridin-2-yl)oxy)ethyl)piperidin-1-yl)-1,2,4-oxadiazole | 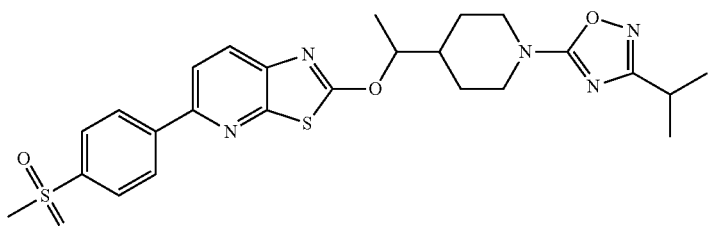 |
| 1021 | 3-isopropyl-5-(1-(5-(4-(methylsulfonyl)phenyl)thiazolo[5,4-b]pyridin-2-yl)pyrrolidin-3-yl)-1,2,4-oxadiazole | 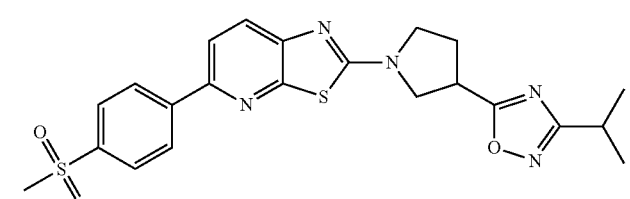 |
| 1022 | 4-(2-(4-(3-isopropyl-1,2,4-oxadiazol-5-yl)piperidin-1-yl)thiazolo[5,4-b]pyridin-5-yl)-N,N-dimethylbenzamide | 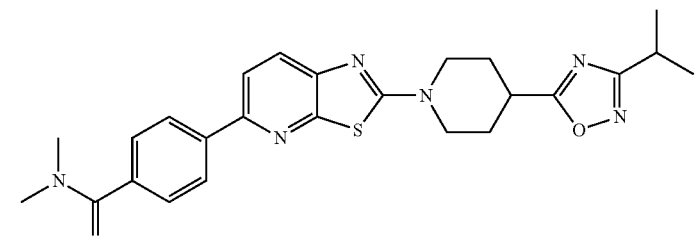 |
| 1023 | N-(1-(3-isopropyl-1,2,4-oxadiazol-5-yl)piperidin-4-yl)-N-methyl-5-(4-(methylsulfonyl)phenyl)thiazolo[5,4-b]pyridin-2-amine | 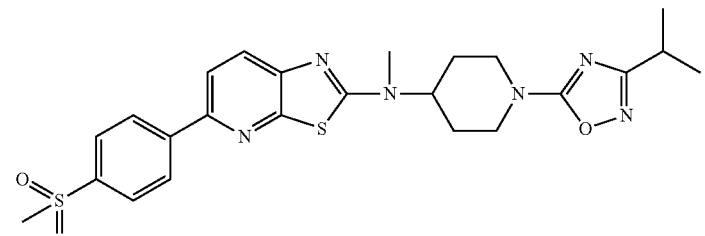 |
| 1024 | 4-(2-(4-(3-isopropyl-1,2,4-oxadiazol-5-yl)piperidin-1-yl)thiazolo[5,4-b]pyridin-5-yl)-N-(2-methoxyethyl)benzamide | 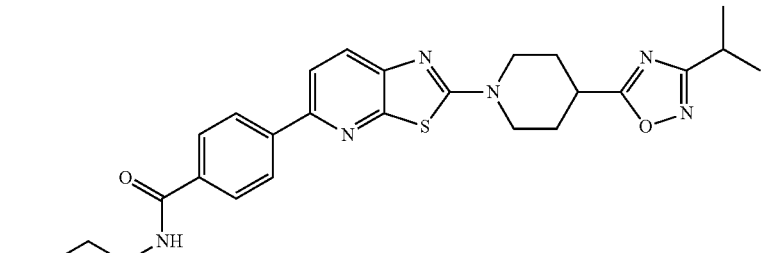 |
| 1025 | N-(3-fluoro-4-(methylsulfonyl)phenyl)-2-(4-(3-isopropyl-1,2,4-oxadiazol-5-yl)piperidin-1-yl)thiazolo[5,4-b]pyridin-5-amine | 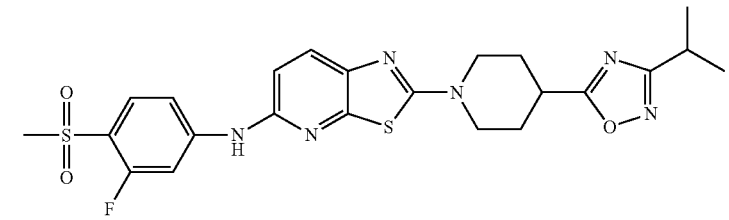 [SMILES: CC(C)c1noc(C2CCN(c3nc4ccc(Nc5ccc(S(C)(=O)=O)c(F)c5)nc4s3)CC2)n1] |

TABLE 1-continued

Illustrative compounds of present invention

| Compound No. | IUPAC name |
|---|---|
| 1026 | 5-(4-(methylsulfonyl)phenyl)-2-(1-tosyl-1,2,3,6-tetrahydropyridin-4-yl)thiazolo[5,4-b]pyridine |
| 1027 | N,N-dimethyl-4-(5-(4-(methylsulfonyl)phenyl)thiazolo[5,4-b]pyridin-2-yl)-5,6-dihydropyridine-1(2H)-carboxamide |
| 1028 | N,N-dimethyl-4-(5-(4-(methylsulfonyl)phenyl)thiazolo[5,4-b]pyridin-2-yl)piperidine-1-carboxamide |
| 1029 | (4-(2-(4-(3-isopropyl-1,2,4-oxadiazol-5-yl)piperidin-1-yl)thiazolo[5,4-b]pyridin-5-yl)phenyl)(morpholino)methanone |
| 1030 | N,N-diisopropyl-4-(5-(4-(methylsulfonyl)phenyl)thiazolo[5,4-b]pyridin-2-yl)-5,6-dihydropyridin-1(2H)-carboxamide |
| 1031 | (S)-3-isopropyl-5-(4-(1-((5-(4-(methylsulfonyl)phenyl)thiazolo[5,4-b]pyridin-2-yl)oxy)ethyl)piperidin-1-yl)-1,2,4-oxadiazole |

TABLE 1-continued

Illustrative compounds of present invention

| Compound No. | IUPAC name |
|---|---|
| 1032 | (R)-3-isopropyl-5-(4-(1-((5-(4-(methylsulfonyl)phenyl)thiazolo[5,4-b]pyridin-2-yl)oxy)ethyl)piperidin-1-yl)-1,2,4-oxadiazole |
| 1033 | 3-cyclopropyl-5-(4-((5-(4-(methylsulfonyl)phenyl)thiazolo[5,4-b]pyridin-2-yl)oxy)piperidin-1-yl)-1,2,4-oxadiazole |
| 1034 | isopropyl 4-(2-((5-(4-(methylsulfonyl)phenyl)thiazolo[5,4-b]pyridin-2-yl)oxy)ethyl)-5,6-dihydropyridine-1(2H)-carboxylate |
| 1035 | 3-isopropyl-5-(4-(2-((5-(4-(methylsulfonyl)phenyl)thiazolo[5,4-b]pyridin-2-yl)oxy)ethyl)-5,6-dihydropyridin-1(2H)-yl)-1,2,4-oxadiazole |
| 1036 | 3-isopropyl-5-(4-(2-methoxy-1-((5-(4-(methylsulfonyl)phenyl)thiazolo[5,4-b]pyridin-2-yl)oxy)ethyl)piperidin-1-yl)-1,2,4-oxadiazole |

TABLE 1-continued

Illustrative compounds of present invention

| Compound No. | IUPAC name |
|---|---|
| 1037 | 3-isopropyl-5-(4-(1-((7-methyl-5-(4-(methylsulfonyl)phenyl)thiazolo[5,4-b]pyridin-2-yl)oxy)ethyl)piperidin-1-yl)-1,2,4-oxadiazole |
| 1038 | 3-isopropyl-5-(4-(((7-methyl-5-(4-(methylsulfonyl)phenyl)thiazolo[5,4-b]pyridin-2-yl)oxy)methyl)piperidin-1-yl)-1,2,4-oxadiazole |
| 1039 | 3-isopropyl-5-(4-(1-((6-methyl-5-(4-(methylsulfonyl)phenyl)thiazolo[5,4-b]pyridin-2-yl)oxy)ethyl)piperidin-1-yl)-1,2,4-oxadiazole |
| 1040 | 5-(4-(cyclopropyl((5-(4-(methylsulfonyl)phenyl)thiazolo[5,4-b]pyridin-2-yl)oxy)methyl)piperidin-1-yl)-3-isopropyl-1,2,4-oxadiazole |
| 1041 | 3-isopropyl-5-(4-(2-((5-(4-(methylsulfonyl)phenyl)thiazolo[5,4-b]pyridin-2-yl)oxy)ethylidene)piperidin-1-yl)-1,2,4-oxadiazole |
| 1042 | 3-isopropyl-5-(4-(2-((5-(4-(methylsulfonyl)phenyl)thiazolo[5,4-b]pyridin-2-yl)oxy)ethyl)piperidin-1-yl)-1,2,4-oxadiazole |

TABLE 1-continued

Illustrative compounds of present invention

| Compound No. | IUPAC name | Structure |
|---|---|---|
| 1043 | 3-isopropyl-5-(4-(2-((5-(4-(methylsulfonyl)phenyl)thiazolo[5,4-b]pyridin-2-yl)oxy)propyl)piperidin-1-yl)-1,2,4-oxadiazole | 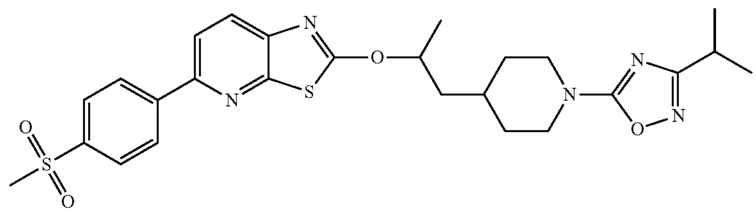 [SMILES: CC(CC1CCN(c2nc(C(C)C)no2)CC1)Oc1nc2ccc(-c3ccc(S(C)(=O)=O)cc3)nc2s1] |
| 1044 | 3-isopropyl-5-(4-(2-((5-(4-(methylsulfonyl)phenyl)thiazolo[5,4-b]pyridin-2-yl)oxy)propylidene)piperidin-1-yl)-1,2,4-oxadiazole | 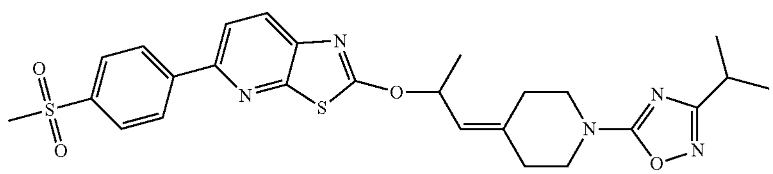 [SMILES: CC(C=C1CCN(c2nc(C(C)C)no2)CC1)Oc1nc2ccc(-c3ccc(S(C)(=O)=O)cc3)nc2s1] |
| 1045 | (S)-4-(2-(1-(1-(3-isopropyl-1,2,4-oxadiazol-5-yl)piperidin-4-yl)ethoxy)thiazolo[5,4-b]pyridin-5-yl)-N,N-dimethylbenzamide | 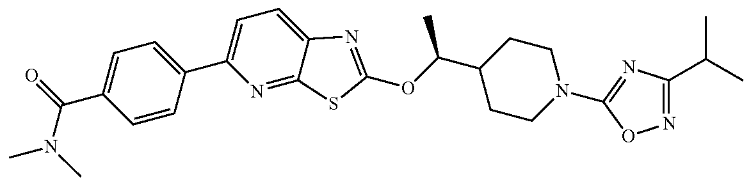 [SMILES: CC(C)c1noc(N2CCC([C@H](C)Oc3nc4ccc(-c5ccc(C(=O)N(C)C)cc5)nc4s3)CC2)n1] |
| 1046 | 3-fluoro-4-(2-(1-(1-(3-isopropyl-1,2,4-oxadiazol-5-yl)piperidin-4-yl)ethoxy)thiazolo[5,4-]pyridin-5-yl)-N,N-dimethylbenzamide | 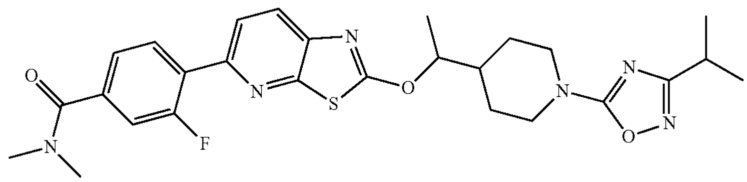 [SMILES: CC(C)c1noc(N2CCC(C(C)Oc3nc4ccc(-c5ccc(C(=O)N(C)C)cc5F)nc4s3)CC2)n1] |
| 1047 | 2-fluoro-4-(2-(1-(1-(3-isopropyl-1,2,4-oxadiazol-5-yl)piperidin-4-yl)ethoxy)thiazolo[5,4-b]pyridin-5-yl)-N,N-dimethylbenzamide | 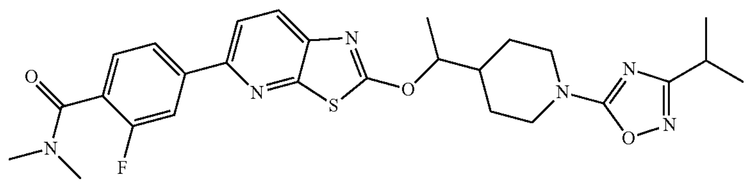 [SMILES: CC(C)c1noc(N2CCC(C(C)Oc3nc4ccc(-c5ccc(C(=O)N(C)C)c(F)c5)nc4s3)CC2)n1] |
| 1048 | 3-cyclopropyl-5-(4-(1-((5-(4-(methylsulfonyl)phenyl)thiazolo[5,4-b]pyridin-2-yl)oxy)ethyl)piperidin-1-yl)-1,2,4-oxadiazole | 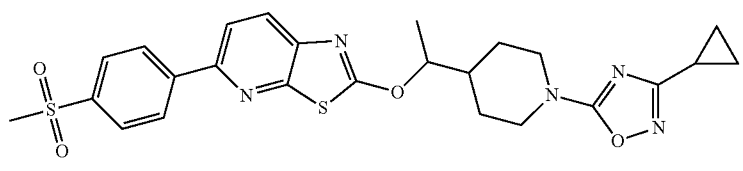 [SMILES: CC(Oc1nc2ccc(-c3ccc(S(C)(=O)=O)cc3)nc2s1)C1CCN(c2nc(C3CC3)no2)CC1] |
| 1049 | N-cyclopropyl-4-(2-(1-(1-(3-isopropyl-1,2,4-oxadiazol-5-yl)piperidin-4-yl)ethoxy)thiazolo[5,4-b]pyridin-5-yl)benzamide | 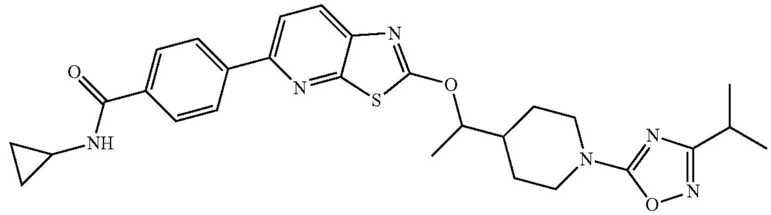 [SMILES: CC(C)c1noc(N2CCC(C(C)Oc3nc4ccc(-c5ccc(C(=O)NC6CC6)cc5)nc4s3)CC2)n1] |

TABLE 1-continued

Illustrative compounds of present invention

| Compound No. | IUPAC name | Structure |
|---|---|---|
| 1050 | 4-(2-(1-(1-(3-isopropyl-1,2,4-oxadiazol-5-yl)piperidin-4-yl)ethoxy)thiaozlo[5,4-b]pyridin-5-yl)-N-(2-methoxyethyl)benzamide | 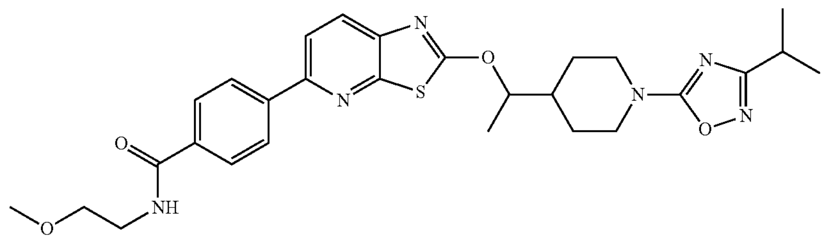 [SMILES: COCCNC(=O)c1ccc(-c2ccc3nc(OC(C)C4CCN(c5nc(C(C)C)no5)CC4)sc3n2)cc1] |
| 1051 | (4-(2-(1-(1-(3-isopropyl-1,2,4-oxadiazol-5-yl)piperidin-4-yl)ethoxy)thiazolo[5,4-b]pyridin-5-yl)phenyl)(morpholino)methanone | 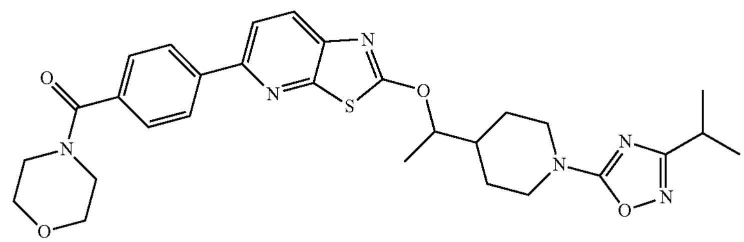 [SMILES: CC(C)c1noc(N2CCC(C(C)Oc3nc4ccc(-c5ccc(C(=O)N6CCOCC6)cc5)nc4s3)CC2)n1] |
| 1052 | N-cyclopropyl-4-(2-(1-(1-(3-isopropyl-1,2,4-oxadiazol-5-yl)piperidin-4-yl)ethoxy)thiazolo[5,4-b]pyridin-5-yl)-N-methyl-benzamide | 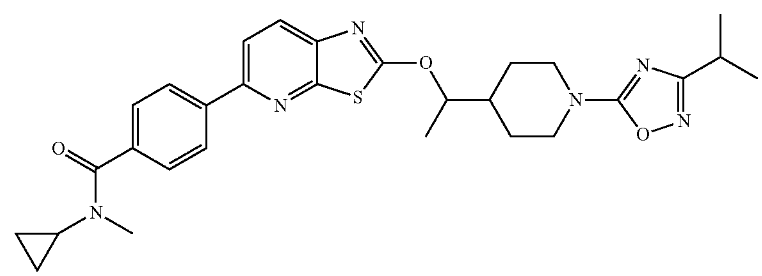 [SMILES: CC(C)c1noc(N2CCC(C(C)Oc3nc4ccc(-c5ccc(C(=O)N(C)C6CC6)cc5)nc4s3)CC2)n1] |
| 1053 | 5-(4-(methyslulfonyl)phenyl)-2-(1-(1-(5-propylpyrimidin-2-yl)piperidin-4-yl)ethoxy)thiazolo[5,4-b]pyridine | 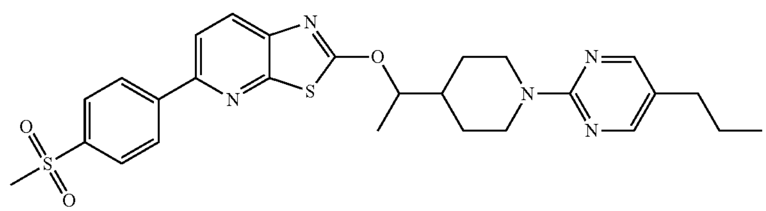 [SMILES: CCCc1cnc(N2CCC(C(C)Oc3nc4ccc(-c5ccc(S(C)(=O)=O)cc5)nc4s3)CC2)nc1] |
| 1054 | 3-isopropyl-5-(4-(1-((5-(pyridin-3-yl)thiazolo[5,4-b]pyridin-2-yl)oxy)ethyl)piperidin-1-yl)-1,2,4-oxadiazole | 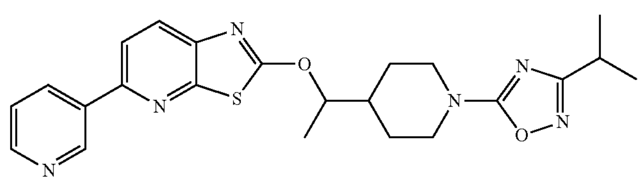 [SMILES: CC(C)c1noc(N2CCC(C(C)Oc3nc4ccc(-c5cccnc5)nc4s3)CC2)n1] |
| 1055 | 2-(1-(1-(5-ethylpyrimidin-2-yl)piperidin-4-yl)ethoxy)-5-(4-(methylsulfonyl)phenyl)thiazolo[5,4-b]pyridine | 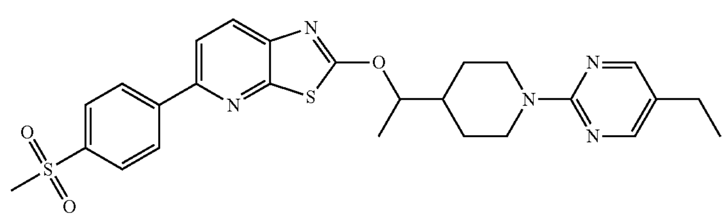 [SMILES: CCc1cnc(N2CCC(C(C)Oc3nc4ccc(-c5ccc(S(C)(=O)=O)cc5)nc4s3)CC2)nc1] |

TABLE 1-continued

Illustrative compounds of present invention

| Compound No. | IUPAC name |
|---|---|
| 1056 | isopropyl 4-(1-((5-(4-(methyl-sulfonyl)phenyl)thiazolo[5,4-b]pyridin-2-yl)oxy)ethyl) piperidine-1-carboxylate |
| 1057 | 3-isopropyl-5-(4-(1-((5-(4-((methyl sulfonyl)methyl) phenyl)thiazolo[5,4-b]pyridin-2-yl)oxy)ethyl)piperidin-1-yl)-1,2,4-oxadiazole |
| 1058 | 5-isopropyl-3-(4-(1-((5-(4-(methyl-sulfonyl)phenyl)thiazolo[5,4-b]pyridin-2-yl)oxy)ethyl) piperidin-1-yl)-1,2,4-oxadiazole |
| 1059 | 3-isopropyl-5-(4-(1-((5-(4-(methyl-sulfonyl)phenyl)thiazolo[5,4-b]pyridin-2-yl)oxy)ethyl)phenyl)-1,2,4-oxadiazole |
| 1060 | 5-(3-fluoro-4-((5-(4-(methyl-sulfonyl)phenyl)thiazolo[5,4-b]pyridin-2-yl)oxy)piperidin-1-yl)-3-isopropyl-1,2,4-oxadiazole |
| 1061 | 4-(2-(1-(1-(3-isopropyl-1,2,4-oxadiazol-5-yl)piperidin-4-yl) ethoxy)thiazolo[5,4-b]pyridin-5-yl)-N-methylbenzenesulfonamide |
| 1062 | 5-(4-(1-((5-(4-(ethylsulfonyl) phenyl)thiazolo[5,4-b]pyridin-2-yl)oxy)ethyl)piperidin-1-yl)-3-isopropyl-1,2,4-oxadiaozle |
| 1063 | 5-(4-(1-((5-(4-(cyclopropyl-sulfonyl)phenyl)thiazolo[5,4-b]pyridin-2-yl)oxy)ethyl) piperidin-1-yl)-3-isopropyl-1,2,4-oxadiazole |

TABLE 1-continued

Illustrative compounds of present invention

| Compound No. | IUPAC name |
|---|---|
| 1064 | 5-(4-(1-((5-(4-(cyclopropyl-sulfinyl)phenyl)thiazol[5,4-b]pyridin-2-yl)oxy)ethyl)piperidin-1-yl)-3-isopropyl-1,2,4-oxadiazole |
| 1065 | 4-(2-(1-(1-(3-isopropyl-1,2,4-oxadiazol-5-yl)piperidin-4-yl)ethoxy)thiazolo[5,4-b]pyridin-5-yl)benzonitrile |
| 1066 | 4-(2-(1-(1-(3-isopropyl-1,2,4-oxadiazol-5-yl)piperidin-4-yl)ethoxy)thiazolo[5,4-b]pyridin-5-yl)-N-(2-methoxyethyl)benzenesulfonamide |
| 1067 | 3-isopropyl-5-(4-(1-((5-(4-((2-methoxyethyl)sulfonyl)phenyl)thiazolo[5,4-b]pyridin-2-yl)oxy)ethyl)piperidin-1-yl)-1,2,4-oxadiazole |
| 1068 | 3-isopropyl-5-(4-(1-((5-(4-((2-methoxyethyl)sulfinyl)phenyl)thiazolo[5,4-b]pyridin-2-yl)oxy)ethyl)piperidin-1-yl)-1,2,4-oxadiazole |
| 1069 | 3-isopropyl-5-(4-(1-((5-(6-(methylsulfonyl)pyridin-3-yl)thiazolo[5,4-b]pyridin-2-yl)oxy)ethyl)piperidin-1-yl)-1,2,4-oxadiazole |
| 1070 | (R)-3-isopropyl-5-(4-(1-((5-(pyridin-4-yl)thiazolo[5,4-b]pyridin-2-yl)oxy)ethyl)piperidin-1-yl)-1,2,4-oxadiazole |

TABLE 1-continued

Illustrative compounds of present invention

| Compound No. | IUPAC name |
|---|---|
| 1071 | (R)-4-(2-(1-(1-(3-isopropyl-1,2,4-oxadiazol-5-yl)piperidin-4-yl)ethoxy)thiazolo[5,4-b]pyridin-5-yl)-1-methylpyridin-1-ium |
| 1072 | 4-(2-(4-(3-isopropyl-1,2,4-oxadiazol-5-yl)piperidin-1-yl)thiazolo[5,4-b]pyridin-5-yl)-N-methylbenzenesulfonamide |
| 1073 | 4-(2-(4-(3-isopropyl-1,2,4-oxadiazol-5-yl)piperidin-1-yl)thiazolo[5,4-b]pyridin-5-yl)-N-(2-methoxyethyl)benzene sulphonamide |
| 1074 | N-(4-(2-(1-(1-(3-isopropyl-1,2,4-oxadiazol-5-yl)piperidin-4-yl)ethoxy)thiazolo[5,4-b]pyridin-5-yl)phenyl)methanesulfonamide |
| 1075 | 2-(1-(1-(1-methyl-1H-tetrazol-5-yl)piperidin-4-yl)ethoxy)-5-(4-(methylsulfonyl)phenyl)thiazolo[5,4-b]pyridine |
| 1076 | (S)-5-(4-(1-((5-(3-fluoropyridin-4-yl)thiazolo[5,4-b]pyridin-2-yl)oxy)ethyl)piperidin-1-yl)-3-isopropyl-1,2,4-oxadiazole |

TABLE 1-continued

Illustrative compounds of present invention

| Compound No. | IUPAC name | Structure |
|---|---|---|
| 1077 | 3-isopropyl-5-(1-(5-(pyridin-4-yl)thiazolo[5,4-b]pyridin-2-yl)piperidin-4-yl)-1,2,4-oxadiazole | 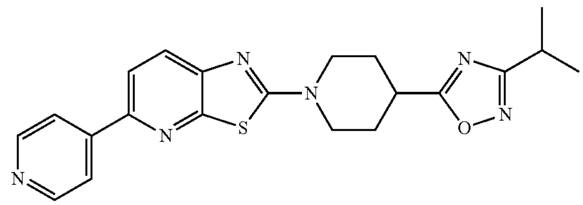 [SMILES: CC(C)c1noc(C2CCN(c3nc4ccc(-c5ccncc5)nc4s3)CC2)n1] |
| 1078 | 3-isopropyl-5-(1-(5-(4-((2-methoxyethyl)sulfonyl)phenyl)thiazolo[5,4-b]pyridin-2-yl)piperidin-4-yl)-1,2,4-oxadiazole | 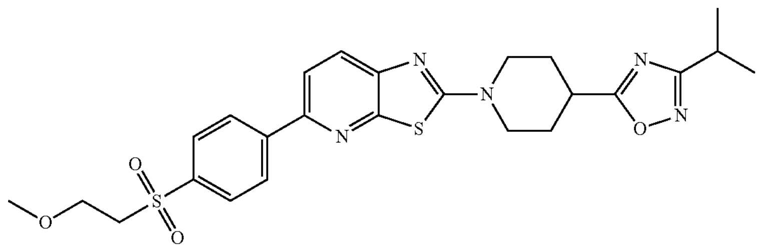 [SMILES: COCCS(=O)(=O)c1ccc(-c2ccc3nc(N4CCC(c5nc(C(C)C)no5)CC4)sc3n2)cc1] |
| 1079 | 5-(4-(1-((5-(4-(1H-tetrazol-1-yl)phenyl)thiazolo[5,4-b]pyridin-2-yl)oxy)ethyl)piperidin-1-yl)-3-isopropyl-1,2,4-oxadiazole | 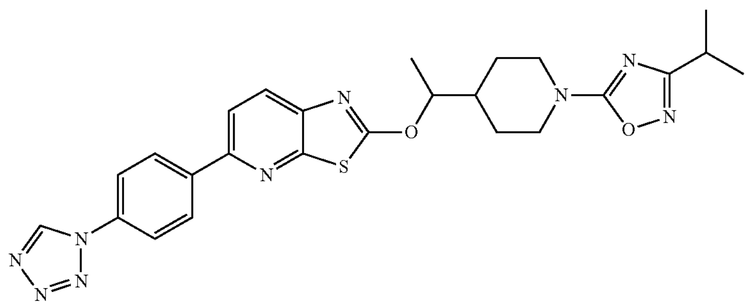 [SMILES: CC(C)c1noc(N2CCC(C(C)Oc3nc4ccc(-c5ccc(-n6cnnn6)cc5)nc4s3)CC2)n1] |
| 1080 | 3-isopropyl-5-(1-(5-(6-(methylsulfonyl)pyridin-3-yl)thiazolo[5,4-b]pyridin-2-yl)piperidin-4-yl)-1,2,4-oxadiazole | 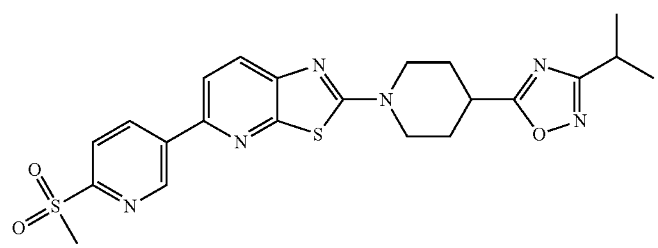 [SMILES: CC(C)c1noc(C2CCN(c3nc4ccc(-c5ccc(S(C)(=O)=O)nc5)nc4s3)CC2)n1] |
| 1081 | 5-(4-(1-((5-(2-fluoropyridin-4-yl)thiazolo[5,4-b]pyridin-2-yl)oxy)ethyl)piperidin-1-yl)-3-isopropyl-1,2,4-oxadiazole | 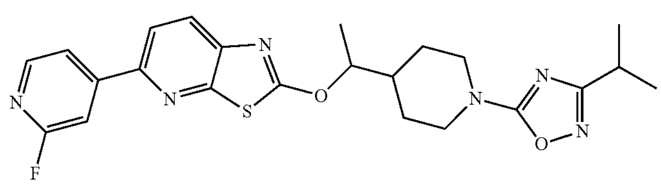 [SMILES: CC(C)c1noc(N2CCC(C(C)Oc3nc4ccc(-c5ccnc(F)c5)nc4s3)CC2)n1] |
| 1082 | (S)-3-isopropyl-5-(4-(1-((5-(6-(methylsulfonyl)pyridin-3-yl)thiazolo[5,4-b]pyridin-2-yl)oxy)ethyl)piperidin-1-yl)-1,2,4-oxadiazole | 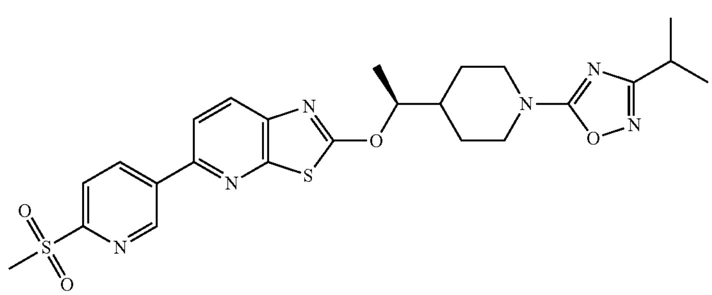 [SMILES: CC(C)c1noc(N2CCC([C@H](C)Oc3nc4ccc(-c5ccc(S(C)(=O)=O)nc5)nc4s3)CC2)n1] |

TABLE 1-continued

Illustrative compounds of present invention

| Compound No. | IUPAC name |
|---|---|
| 1083 | 3-isopropyl-5-(4-(((5-(pyridin-4-yl)thiazolo[5,4-b]pyridin-2-yl)oxy)methyl)piperidin-1-yl)-1,2,4-oxadiazole |
| 1084 | 5-(4-(((5-(3-fluoropyridin-4-yl)thiazolo[5,4-b]pyridin-2-yl)oxy)methyl)piperidin-1-yl)-3-isopropyl-1,2,4-oxadiazole |
| 1085 | 5-(4-(((5-(4-(1H-tetrazol-1-yl)phenyl)thiazolo[5,4-b]pyridin-2-yl)oxy)methyl)piperidin-1-yl)-3-isopropyl-1,2,4-oxadiazole |
| 1086 | 5-(4-(((5-(2-fluoropyridin-4-yl)thiazolo[5,4-b]pyridin-2-yl)oxy)methyl)piperidin-1-yl)-3-isopropyl-1,2,4-oxadiazole |
| 1087 | 2-(1-(1-(5-ethylpyridin-2-yl)piperidine-4-yl)ethoxy)-5-(4-(methylsulfonyl)phenyl)thiazolo[5,4-b]pyridine |
| 1088 | 5-(4-(methylsulfonyl)phenyl)-2-(1-(1-(5-vinylpyridin-2-yl)piperidin-4-yl)ethoxy)thiazolo[5,4-b]pyridine |
| 1089 | (S)-5-(4-(methylsulfonyl)phenyl)-2-(1-(1-(5-propylpyrimidin-2-yl)piperidin-4-yl)ethoxy)thiazolo[5,4-b]pyridine |

TABLE 1-continued

Illustrative compounds of present invention

| Compound No. | IUPAC name |
|---|---|
| 1090 | (R)-5-(4-(methylsulfonyl)phenyl)-2-(1-(1-(5-propylpyrimidin-2-yl)piperidin-4-yl)ethoxy)thiazolo[5,4-b]pyridine |
| 1091 | 3-isopropyl-5-(4-(((5-(6-(methylsulfonyl)pyridin-3-yl)thiazolo[5,4-b]pyridin-2-yl)oxy)methyl)piperidin-1-yl)-1,2,4-oxadiazole |
| 1092 | (S)-3-isopropyl-5-(4-(1-((5-(pyridin-4-yl)thiazolo[5,4-b]pyridin-2-yl)oxy)ethyl)piperidin-1-yl)-1,2,4-oxadiazole |
| 1093 | (S)-5-(4-(1-((5-(2-fluoropyridin-4-yl)thiazolo[5,4-b]pyridin-2-yl)oxy)ethyl)piperidin-1-yl)-3-isopropyl-1,2,4-oxadiazole |
| 1094 | 3-isopropyl-5-(4-(2,2,2-trifluoro-1-((5-(4-(methysulfonyl)phenyl)thiazolo[5,4-b]pyridin-2-yl)oxy)ethyl)piperidin-1-yl)-1,2,4-oxadiazole |
| 1095 | (S)-5-(4-(1-((5-(4-(cyclopropyl-sulfonyl)phenyl)thiazolo[5,4-b]pyridin-2-yl)oxy)ethyl)piperidin-1-yl)-3-isopropyl-1,2,4-oxadiazole |
| 1096 | (S)-5-(4-(1-((5-(3-fluoropyridin-4-yl)thiazolo[5,4-b]pyridin-2-yl)oxy)ethyl)piperidin-1-yl)-3-isopropyl-1,2,4-oxadiazole |
| 1097 | 2-isopropyl-5-(4-(1-((5-(4-(methylsulfonyl)phenyl)thiazolo[5,4-b]pyridin-2-yl)oxy)ethyl)piperidin-1-yl)-1,3,4-oxadiazole |

US 10,526,345 B2

TABLE 1-continued

Illustrative compounds of present invention

| Compound No. | IUPAC name | Structure |
|---|---|---|
| 1098 | 4-(2-(1-(1-(3-isopropyl-1,2,4-oxadiazol-5-yl)piperidin-4-yl)ethoxy)thiazolo[5,4-b]pyridin-5-yl)pyridine 1-oxide | 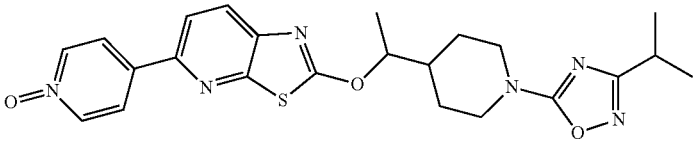 [SMILES: CC(C)c1noc(N2CCC(C(C)Oc3nc4ccc(-c5cc[n+]([O-])cc5)nc4s3)CC2)n1] |
| 1099 | (S)-5-(6-(methylsulfonyl)pyridin-3-yl)-2-(1-(1-(5-propylpyrimidin-2-yl)piperidin-4-yl)ethoxy)thiazolo[5,4-b]pyridine | 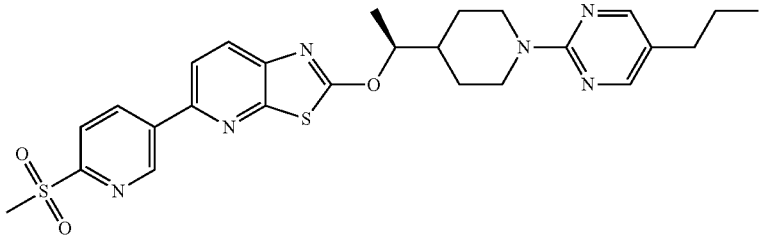 [SMILES: CCCc1cnc(N2CCC([C@H](C)Oc3nc4ccc(-c5ccc(S(C)(=O)=O)nc5)nc4s3)CC2)nc1] |
| 1100 | 5-(4-(1-((5-(3-fluoro-4-(methylsulfonyl)phenyl)thiazolo[5,4-b]pyridin-2-yl)oxy)ethyl)piperidin-1-yl)-3-isopropyl-1,2,4-oxadiazole | 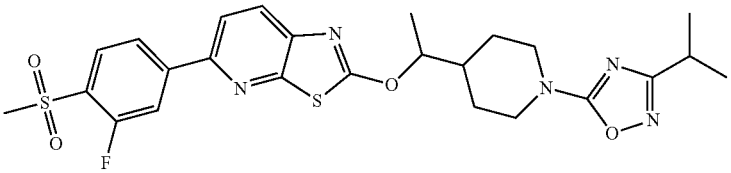 [SMILES: CC(C)c1noc(N2CCC(C(C)Oc3nc4ccc(-c5ccc(S(C)(=O)=O)c(F)c5)nc4s3)CC2)n1] |
| 1101 | (S)-5-2-fluoropyridin-4-yl)-2-(1-(1-(5-propylpyrimidin-2-yl)piperidin-4-yl)ethoxy)thiazolo[5,4-b]pyridine | 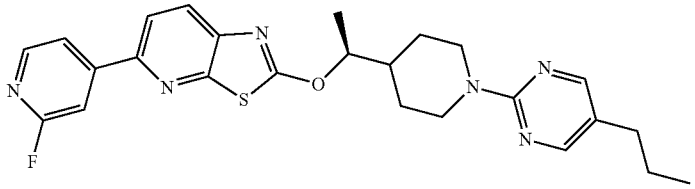 [SMILES: CCCc1cnc(N2CCC([C@H](C)Oc3nc4ccc(-c5ccnc(F)c5)nc4s3)CC2)nc1] |
| 1102 | 3-isopropyl-5-(4-(2,2,2-trifluoro-1-((5-(6-(methylsulfonyl)pyridin-3-yl)thiazolo[5,4-b]pyridin-2-yl)oxy)ethyl)piperidin-1-yl)-1,2,4-oxadiazole | 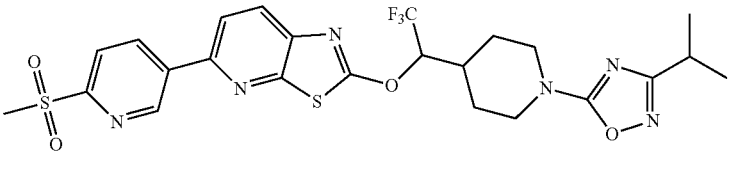 |
| 1103 | 3-isopropyl-5-(4-(2,2,2-trifluoro-1-((5-(2-fluoropyridin-4-yl)thiazolo[5,4-b]pyridin-2-yl)oxy)ethyl)piperidin-1-yl)-1,2,4-oxadiazole | 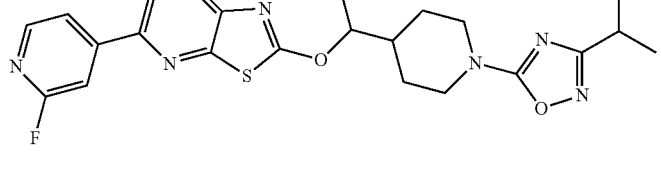 |
| 1104 | (S)-2-(1-(1-(5-ethylpyrimidin-2-yl)piperidin-4-yl)ethoxy)-5-(2-fluoropyridin-4-yl)thiazolo[5,4-b]pyridine | 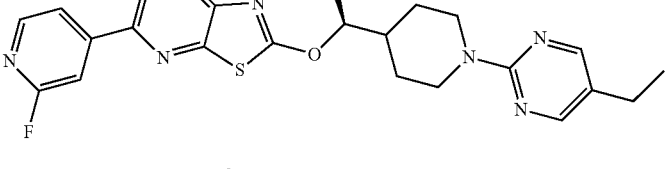 |
| 1105 | 3-isopropyl-5-(4-(1-((5-(4-(methylsulfonyl)phenyl)thiazolo[5,4-b]pyridin-2-yl)oxy)ethyl)cyclohexyl)-1,2,4-oxadiazole | 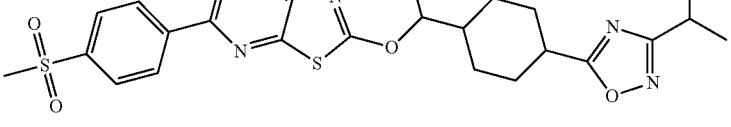 |

TABLE 1-continued

Illustrative compounds of present invention

| Compound No. | IUPAC name | Structure |
|---|---|---|
| 1106 | (S)-2-(1-(1-(5-ethylpyrimidin-2-yl)piperidin-4-yl)ethoxy)-5-(6-(methylsulfonyl)pyridin-3-yl)thiazolo[5,4-b]pyridine | 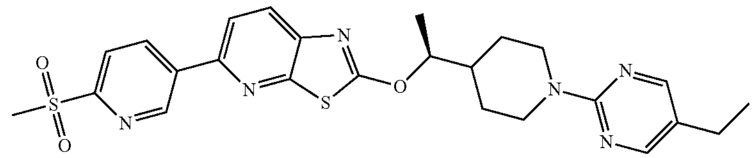 [SMILES: CCc1cnc(N2CCC([C@H](C)Oc3nc4ccc(-c5ccc(S(C)(=O)=O)nc5)nc4s3)CC2)nc1] |
| 1107 | 2-(1-(1-(3-isopropyl-1,2,4-thiadiazol-5-yl)piperidin-4-yl)ethoxy)-5-(4-(methylsulfonyl)phenyl)thiazolo[5,4-b]pyridine | 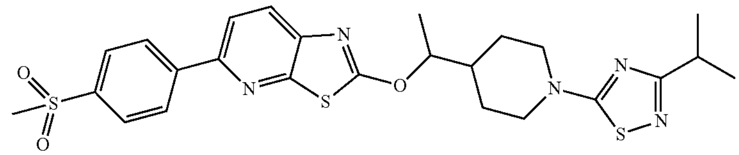 [SMILES: CC(C)c1nsc(N2CCC(C(C)Oc3nc4ccc(-c5ccc(S(C)(=O)=O)cc5)nc4s3)CC2)n1] |
| 1108 | 3-isopropyl-5-(4-(1-((6-(4-(methylsulfonyl)phenyl)thiazolo[4,5-b]pyrazin-2-yl)oxy)ethyl)piperidin-1-yl)-1,2,4-oxadiazole | 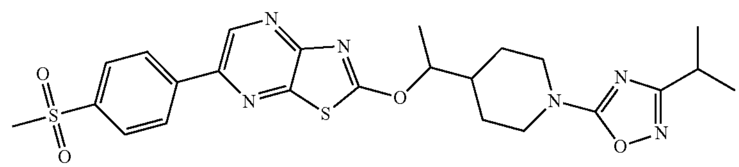 [SMILES: CC(C)c1noc(N2CCC(C(C)Oc3nc4ncc(-c5ccc(S(C)(=O)=O)cc5)nc4s3)CC2)n1] |
| 1109 | 2-(1-(1-(cyclopropylsulfonyl)piperidin-4-yl)ethoxy)-5-(4-(methyl sulfonyl)phenyl)thiazolo[5,4-b]pyridine | 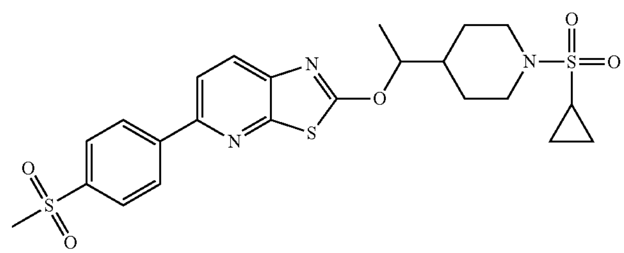 [SMILES: CC(Oc1nc2ccc(-c3ccc(S(C)(=O)=O)cc3)nc2s1)C1CCN(S(=O)(=O)C2CC2)CC1] |
| 1110 | 6-(4-(methylsulfonyl)phenyl)-2-(1-(1-(5-propylpyrimidin-2-yl)piperidin-4-yl)ethoxy)thiazolo[4,5-b]pyrazine | 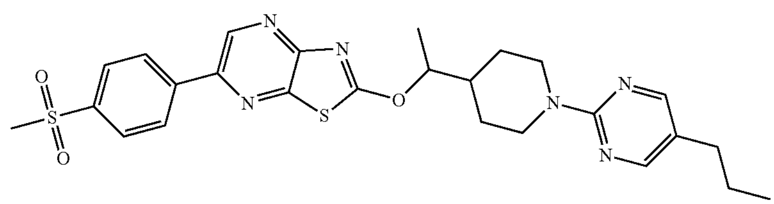 [SMILES: CCCc1cnc(N2CCC(C(C)Oc3nc4ncc(-c5ccc(S(C)(=O)=O)cc5)nc4s3)CC2)nc1] |
| 1111 | 5-(4-(1-((5-(2-fluoro-4-(methylsulfonyl)phenyl)thiazolo[5,4-b]pyridin-2-yl)oxy)ethyl)piperidin-1-yl)-3-isopropyl-1,2,4-oxadiazole | 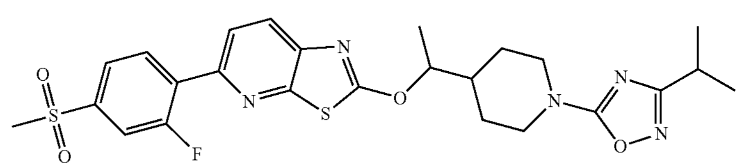 [SMILES: CC(C)c1noc(N2CCC(C(C)Oc3nc4ccc(-c5ccc(S(C)(=O)=O)cc5F)nc4s3)CC2)n1] |
| 1112 | 5-(3-fluoro-4-(1-((5-(4-(methylsulfonyl)phenyl)thiazolo[5,4-b]pyridin-2-yl)oxy)ethyl)piperidin-1-yl)-3-isopropyl-1,2,4-oxadiazole | 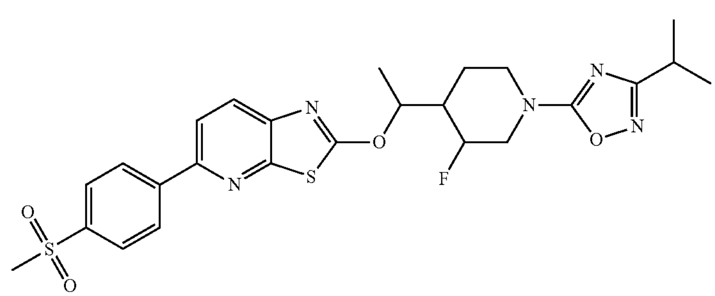 [SMILES: CC(C)c1noc(N2CCC(C(C)Oc3nc4ccc(-c5ccc(S(C)(=O)=O)cc5)nc4s3)C(F)C2)n1] |

TABLE 1-continued

Illustrative compounds of present invention

| Compound No. | IUPAC name |
|---|---|
| 1113 | 2-(1-(1-(5-isopropylpyrimidin-2-yl)piperidin-4-yl)ethoxy)-5-(4-(methylsulfonyl)phenyl)thiazolo[5,4-b]pyridine |
| 1114 | (S)-3-isopropyl-5-(4-(1-((6-(6-(methylsulfonyl)pyridin-3-yl)thiazolo[4,5-b]pyrazin-2-yl)oxy)ethyl)piperidin-1-yl)-1,2,4-oxadiazole |
| 1115 | 5-(4-(methylsulfonyl)phenyl)-2-(1-(1-(propylsulfonyl)piperidin-4-yl)ethoxy)thiazolo[5,4-b]pyridine |
| 1116 | 5-(4-(1-((5-(2-chloropyrimidin-5-yl)thiazolo[5,4-b]pyridin-2-yl)oxy)ethyl)piperidin-1-yl)-3-isopropyl-1,2,4-oxadiazole |
| 1117 | 1-methylcyclopropyl 4-(1-((5-(4-(methylsulfonyl)phenyl)thiazolo[5,4-b]pyridin-2-yl)oxy)ethyl)piperidine-1-carboxylate |
| 1118 | 5-(4-(methylsulfonyl)phenyl)-2-(1-(1-(5-(prop-1-en-2-yl)pyrimidin-2-yl)piperidin-4-yl)ethoxy)thiazolo[5,4-b]pyridine |

TABLE 1-continued

Illustrative compounds of present invention

| Compound No. | IUPAC name |
|---|---|
| 1119 | (S)-5-(4-(1-((5-(2-chloropyrimidin-5-yl)thiazolo[5,4-b]pyridin-2-yl)oxy)ethyl)piperidin-1-yl)-3-isopropyl-1,2,4-oxadiazole |
| 1120 | 2-(1-(1-(5-chloropyrimidin-2-yl)piperidin-4-yl)ethoxy)-5-(4-(methylsulfonyl)phenyl)thiazolo[5,4-b]pyridine |
| 1121 | 3-isopropyl-5-(4-(1-((5-(thiazol-5-yl)thiazolo[5,4-b]pyridin-2-yl)oxy)ethyl)piperidin-1-yl)-1,2,4-oxadiazole |
| 1122 | 3-isopropyl-5-(4-(1-((5-(isoxazol-4-yl)thiazolo[5,4-b]pyridin-2-yl)oxy)ethyl)piperidin-1-yl)-1,2,4-oxadiazole |
| 1123 | 3-isopropyl-5-(4-(1-((5-(2-methylpyridin-4-yl)thiazolo[5,4-b]pyridin-2-yl)oxy)ethyl)piperidin-1-yl)-1,2,4-oxadiazole |
| 1124 | 3-isopropyl-5-(4-(1-((5-(isothiazol-4-yl)thiazolo[5,4-b]pyridin-2-yl)oxy)ethyl)piperidin-1-yl)-1,2,4-oxadiazole |
| 1125 | 3-isopropyl-5-(4-(1-((5-(3-methylisothiazol-4-yl)thiazolo[5,4-b]pyridin-2-yl)oxy)ethyl)piperidin-1-yl)-1,2,4-oxadiazole |
| 1126 | 4-(2-(1-(1-(3-isopropyl-1,2,4-oxadiazol-5-yl)piperidin-4-yl)ethoxy)thiazolo[5,4-b]pyridin-5-yl)pyridin-2(1H)-one |

TABLE 1-continued

Illustrative compounds of present invention

| Compound No. | IUPAC name | Structure |
|---|---|---|
| 1127 | 4-(2-(1-(1-(3-isopropyl-1,2,4-oxadiazol-5-yl)piperidin-4-yl)ethoxy)thiazolo[5,4-b]pyridin-5-yl)-1-methylpyridin-2(1H)-one | 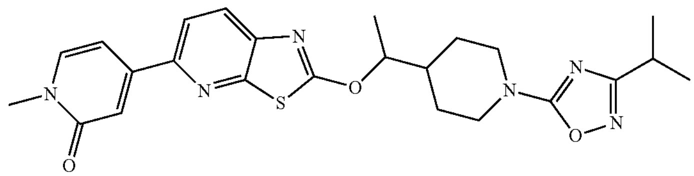 [SMILES: CC(C)c1noc(N2CCC(C(C)Oc3nc4ccc(-c5ccn(C)c(=O)c5)nc4s3)CC2)n1] |
| 1128 | 5-((3R,4S)-3-fluoro-4-(((5-(4-(methylsulfonyl)phenyl)thiazolo[5,4-b]pyridin-2-yl)oxy)methyl)piperidin-1-yl)-3-isopropyl-1,2,4-oxadiazole | 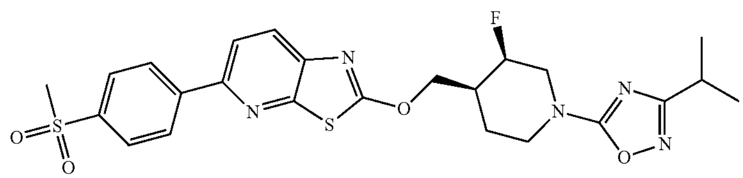 [SMILES: CC(C)c1noc(N2CC[C@@H](COc3nc4ccc(-c5ccc(S(C)(=O)=O)cc5)nc4s3)[C@@H](F)C2)n1] |
| 1129 | 5-((3S,4S)-3-fluoro-4-(((5-(4-(methylsulfonyl)phenyl)thiazolo[5,4-b]pyridin-2-yl)oxy)methyl)piperidin-1-yl)-3-isopropyl-1,2,4-oxadiazole | 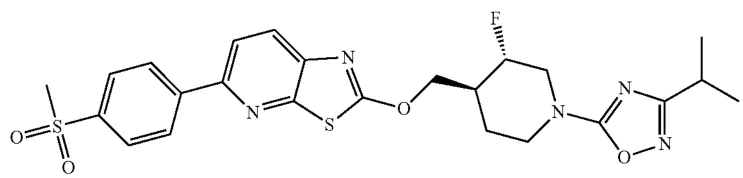 [SMILES: CC(C)c1noc(N2CC[C@@H](COc3nc4ccc(-c5ccc(S(C)(=O)=O)cc5)nc4s3)[C@H](F)C2)n1] |
| 1130 | 3-isopropyl-5-(4-(1-(5-(4-(methylsulfonyl)phenyl)thiazolo[5,4-b]pyridin-2-yl)ethoxy)piperidin-1-yl)-1,2,4-oxadiazole | 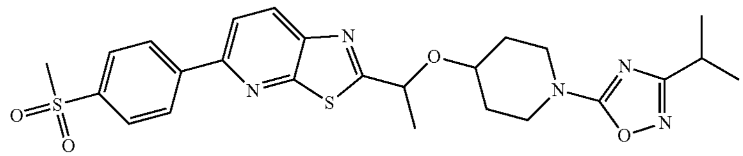 [SMILES: CC(C)c1noc(N2CCC(OC(C)c3nc4ccc(-c5ccc(S(C)(=O)=O)cc5)nc4s3)CC2)n1] |
| 1131 | 5-(4-(1-((5-(4-(methylsulfonyl)phenyl)thiazolo[5,4-b]pyridin-2-yl)oxy)ethyl)piperidin-1-yl)-3-(trifluoromethyl)-1,2,4-oxadiazole | 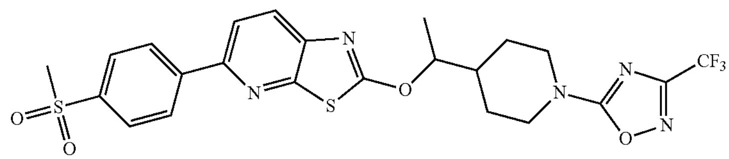 [SMILES: CC(Oc1nc2ccc(-c3ccc(S(C)(=O)=O)cc3)nc2s1)C1CCN(c2nc(C(F)(F)F)no2)CC1] |
| 1132 | 5-(4-(1-((5-(2-chloropyridin-4-yl)thiazolo[5,4-b]pyridin-2-yl)oxy)ethyl)piperidin-1-yl)-3-isopropyl-1,2,4-oxadiazole | 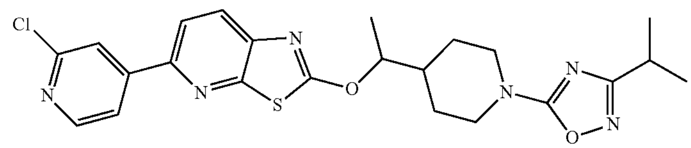 [SMILES: CC(C)c1noc(N2CCC(C(C)Oc3nc4ccc(-c5ccnc(Cl)c5)nc4s3)CC2)n1] |
| 1133 | 3-isopropyl-5-(4-(1-((5-(2-(methylsulfonyl)pyrimidin-5-yl)thiazolo[5,4-b]pyridin-2-yl)oxy)ethyl)piperidin-1-yl)-1,2,4-oxadiazole | 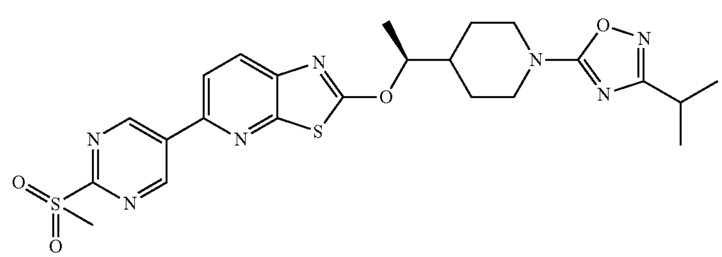 [SMILES: CC(C)c1noc(N2CCC([C@H](C)Oc3nc4ccc(-c5cnc(S(C)(=O)=O)nc5)nc4s3)CC2)n1] |
| 1134 | 3-isopropyl-5-(4-(1-((5-(pyridazin-4-yl)thiazolo[5,4-b]pyridin-2-yl)oxy)ethyl)piperidin-1-yl)-1,2,4-oxadiazole | 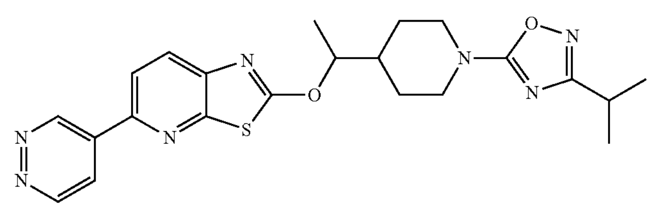 [SMILES: CC(C)c1noc(N2CCC(C(C)Oc3nc4ccc(-c5ccnnc5)nc4s3)CC2)n1] |

TABLE 1-continued

Illustrative compounds of present invention

| Compound No. | IUPAC name |
|---|---|
| 1135 | 2-((S)-1-(1-(5-ethylpyrimidin-2-yl)piperidin-4-yl)ethoxy)-5-(2-chloropyrimidin-5-yl)thiazolo[5,4-b]pyridine |
| 1136 | 2-((S)-1-(1-(5-chloropyrimidin-2-yl)piperidin-4-yl)ethoxy)-5-(6-(methylsulfonyl)pyridin-3-yl)thiazolo[5,4-b]pyridine |
| 1137 | 2-(1-(1-(5-cyclopropylpyrimidin-2-yl)piperidin-4-yl)ethoxy)-5-(6-(methylsulfonyl)pyridin-3-yl)thiazolo[5,4-b]pyridine |
| 1138 | 2-((S)-1-(1-(3-isopropyl-1,2,4-oxadiazol-5-yl)piperidin-4-yl)ethoxy)-5-(2-(methylsulfinyl)pyrimidin-5-yl)thiazolo[5,4-b]pyridine |
| 1139 | N-(5-(2-(1-(1-(3-isopropyl-1,2,4-oxadiazol-5-yl)piperidin-4-yl)ethoxy)thiazolo[5,4-b]pyridin-5-yl)pyrimidin-2-yl)-N-methylacetamide |
| 1140 | 2-((R)-1-(1-(3-isopropyl-1,2,4-oxadiazol-5-yl)pyrrolidin-3-yl)ethoxy)-5-(6-(methylsulfonyl)pyridin-3-yl)thiazolo[5,4-b]pyridine |

TABLE 1-continued

Illustrative compounds of present invention

| Compound No. | IUPAC name |
|---|---|
| 1141 | 2-((S)-1-(-(3-isopropyl-1,2,4-oxadiazol-5-yl)pyrrolidin-3-yl)ethoxy)-5-(6-(methylsulfonyl)pyridin-3-yl)thiazolo[5,4-b]pyridine |
| 1142 | 2-(1-(1-(3-isopropyl-1,2,4-oxadiazol-5-yl)piperidin-4-yl)ethoxy)-5-(6-chloropyridin-3-yl)thiazolo[5,4-b]pyridine |
| 1143 | 2-((S)-1-(1-(3-isopropyl-1,2,4-oxadiazol-5-yl)piperidin-4-yl)ethoxy)-5-(2-chloropyridin-4-yl)thiazolo[5,4-b]pyridine |
| 1144 | 1-(5-(2-(1-(1-(3-isopropyl-1,2,4-oxadiazol-5-yl)piperidin-4-yl)ethoxy)thiazolo[5,4-b]pyridin-5-yl)pyridin-2-yl)imidazolidin-2-one |
| 1145 | 2-((S)-1-(1-(3-(trifluoromethyl)-1,2,4-oxadiazol-5-yl)piperidin-4-yl)ethoxy)-5-(6-(methylsulfonyl)pyridin-3-yl)thiazolo[5,4-b]pyridine |

TABLE 1-continued

Illustrative compounds of present invention

| Compound No. | IUPAC name | Structure |
|---|---|---|
| 1146 | 1-(5-(2-(1-(1-(3-isopropyl-1,2,4-oxadiazol-5-yl)piperidin-4-yl)ethoxy)thiazolo[5,4-b]pyridin-5-yl)pyridin-2-yl)pyrrolidin-2-one | 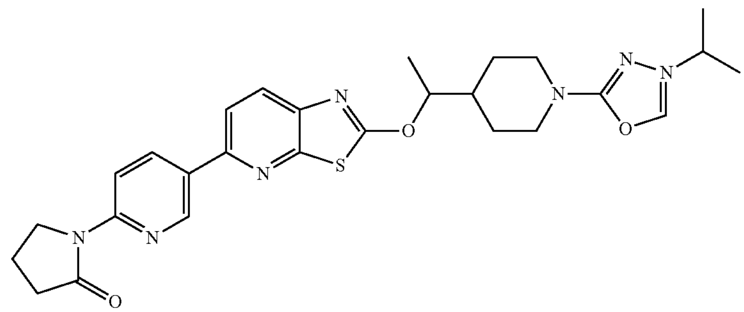 |
| 1147 | 2-(1-(1-(3-isopropyl-1,2,4-oxadiazol-5-yl)piperidin-4-yl)ethoxy)-5-(6-(trifluoromethyl)pyridin-3-yl)thiazolo[5,4-b]pyridine | 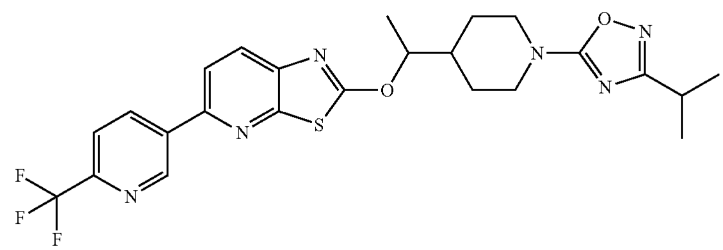 [SMILES: CC(C)c1noc(N2CCC(C(C)Oc3nc4ccc(-c5ccc(C(F)(F)F)nc5)nc4s3)CC2)n1] |
| 1148 | 2-(1-(1-(5-chloropyrazin-2-yl)piperidin-4-yl)ethoxy)-5-(4-(methylsulfonyl)phenyl)thiazolo[5,4-b]pyridine | 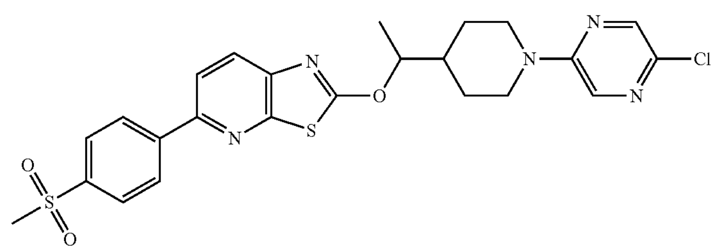 [SMILES: CC(Oc1nc2ccc(-c3ccc(S(C)(=O)=O)cc3)nc2s1)C1CCN(c2cnc(Cl)cn2)CC1] |
| 1149 | 2-(1-(1-(5-ethylpyrimidin-2-yl)piperidin-4-yl)ethoxy)-5-(pyridin-4-yl)thiazolo[5,4-b]pyridine | 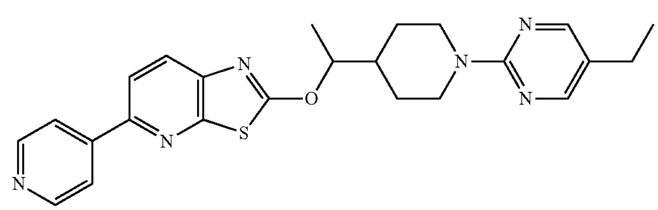 [SMILES: CCc1cnc(N2CCC(C(C)Oc3nc4ccc(-c5ccncc5)nc4s3)CC2)nc1] |
| 1150 | 2-(1-(1-(5-propylpyrimidin-2-yl)piperidin-4-yl)ethoxy)-5-(pyridin-4-yl)thiazolo[5,4-b]pyridine | 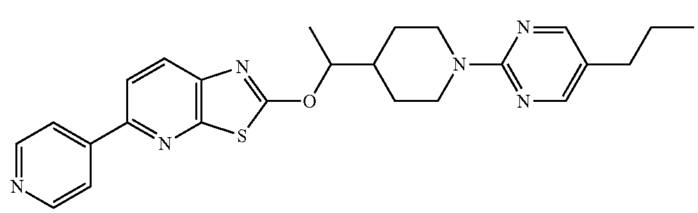 [SMILES: CCCc1cnc(N2CCC(C(C)Oc3nc4ccc(-c5ccncc5)nc4s3)CC2)nc1] |

TABLE 1-continued

Illustrative compounds of present invention

| Compound No. | IUPAC name |
|---|---|
| 1151 | 2-(1-(1-(5-chloropyrazin-2-yl)piperidin-4-yl)ethoxy)-5-(6-(methylsulfonyl)pyridin-3-yl)thiazolo[5,4-b]pyridine |
| 1152 | 2-((S)-1-(1-(3-isopropyl-1,2,4-oxadiazol-5-yl)piperidin-4-yl)ethoxy)-5-(6-(trifluoromethyl)pyridin-3-yl)thiazolo[5,4-b]pyridine |
| 1153 | 2-((S)-1-(1-(5-propylpyrimidin-2-yl)piperidin-4-yl)ethoxy)-5-(pyridin-4-yl)thiazolo[5,4-b]pyridine |
| 1154 | 2-((S)-1-(1-(5-ethylpyrimidin-2-yl)piperidin-4-yl)ethoxy)-5-(6-(trifluoromethyl)pyridin-3-yl)thiazolo[5,4-b]pyridine |
| 1155 | 2-((S)-1-(1-(3-isopropyl-1,2,4-oxadiazol-5-yl)piperidin-4-yl)ethoxy)-5-(3-fluoro-4-(methylsulfonyl)phenyl)thiazolo[5,4-b]pyridine |
| 1156 | 2-(1-(1-(3-ethyl-1,2,4-oxadiazol-5-yl)piperidin-4-yl)ethoxy)-5-(6-(methylsulfonyl)pyridin-3-yl)thiazolo[5,4-b]pyridine |

TABLE 1-continued

Illustrative compounds of present invention

| Compound No. | IUPAC name |
|---|---|
| 1157 | 2-(1-(1-(5-methylpyrimidin-2-yl)piperidin-4-yl)ethoxy)-5-(6-(methylsulfonyl)pyridin-3-yl)thiazolo[5,4-b]pyridine |
| 1158 | 2-(1-(1-(3-isopropyl-1,2,4-oxadiazol-5-yl)piperidin-4-yl)ethoxy)-5-(5-(methylsulfonyl)pyrazin-2-yl)thiazolo[5,4-b]pyridine |
| 1159 | 2-(1-(1-(5-(trifluoromethyl)pyrimidin-2-yl)piperidin-4-yl)ethoxy)-5-(6-(methylsulfonyl)pyridin-3-yl)thiazolo[5,4-b]pyridine |
| 1160 | 2-((S)-1-(1-(3-ethyl-1,2,4-oxadiazol-5-yl)piperidin-4-yl)ethoxy)-5-(6-(methylsulfonyl)pyridin-3-yl)thiazolo[5,4-b]pyridine |
| 1161 | 2-(1-(1-(3-isopropyl-1,2,4-oxadiazol-5-yl)piperidin-4-yl)ethoxy)-5-(5-(methylsulfonyl)pyridin-2-yl)thiazolo[5,4-b]pyridine |
| 1162 | 2-(1-(1-(3-isopropyl-1,2,4-oxadiazol-5-yl)piperidin-4-yl)ethoxy)-5-(6-(methylsulfonyl)pyridin-3-yl)thiazolo[5,4-d]pyrimidine |

TABLE 1-continued

Illustrative compounds of present invention

| Compound No. | IUPAC name | Structure |
|---|---|---|
| 1163 | 2-(1-(1-(5-(methoxymethyl)pyrimidin-2-yl)piperidin-4-yl)ethoxy)-5-(6-(methylsulfonyl)pyridin-3-yl)thiazolo[5,4-b]pyridine | 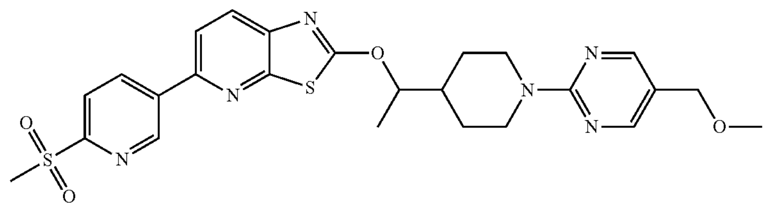 |
| 1164 | 2-((R)-1-(1-(3-isopropyl-1,2,4-oxadiazol-5-yl)piperidin-4-yl)ethoxy)-5-(6-(cyclopropylsulfonyl)pyridin-3-yl)thiazolo[5,4-b]pyridine | 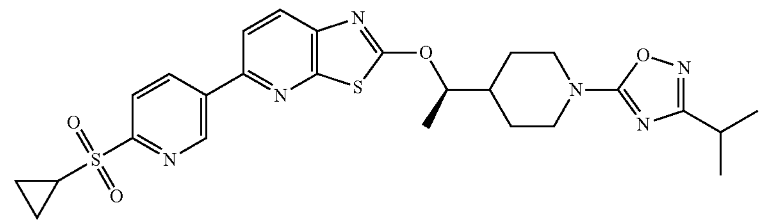 [SMILES: CC(C)c1noc(N2CCC([C@@H](C)Oc3nc4ccc(-c5ccc(S(=O)(=O)C6CC6)nc5)nc4s3)CC2)n1] |
| 1165 | 2-((R)-1-(1-(5-(methoxymethyl)pyrimidin-2-yl)piperidin-4-yl)ethoxy)-5-(6-(methylsulfonyl)pyridin-3-yl)thiazolo[5,4-b]pyridine | 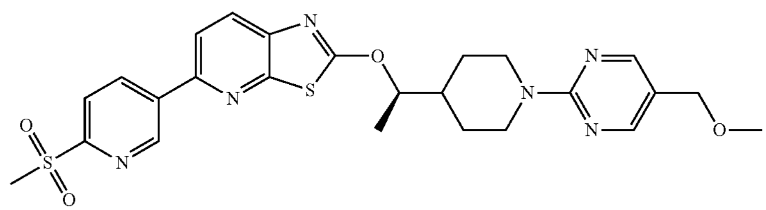 |
| 1166 | 2-((S)-1-(1-(5-(trifluoromethyl)pyrimidin-2-yl)piperidin-4-yl)ethoxy)-5-(6-(methylsulfonyl)pyridin-3-yl)thiazolo[5,4-b]pyridine | 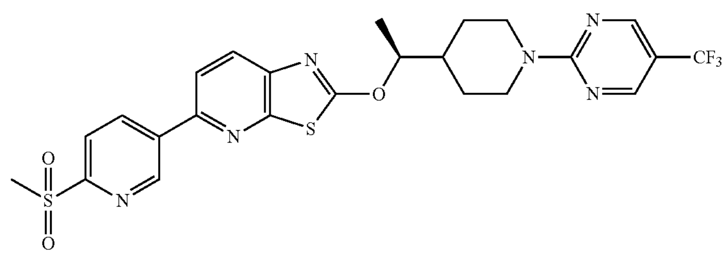 [SMILES: C[C@H](Oc1nc2ccc(-c3ccc(S(C)(=O)=O)nc3)nc2s1)C1CCN(c2ncc(C(F)(F)F)cn2)CC1] |
| 1167 | 2-((S)-1-(1-(3-isopropyl-1,2,4-oxadiazol-5-yl)piperidin-4-yl)ethoxy)-5-(2-fluoro-6-(methylsulfonyl)pyridin-3-yl)thiazolo[5,4-b]pyridine | 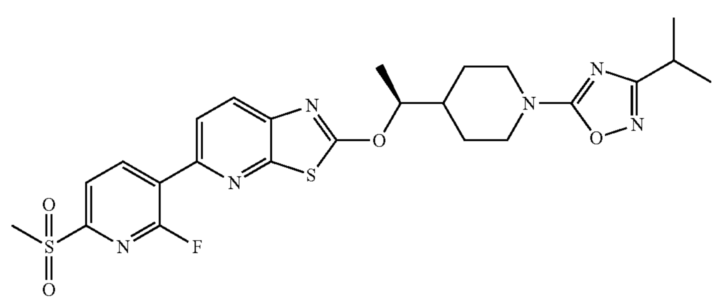 [SMILES: CC(C)c1noc(N2CCC([C@H](C)Oc3nc4ccc(-c5ccc(S(C)(=O)=O)nc5F)nc4s3)CC2)n1] |
| 1168 | 2-((R)-1-(1-(3-isopropyl-1,2,4-oxadiazol-5-yl)piperidin-4-yl)ethoxy)-5-(2-methyl-6-(methylsulfonyl)pyridin-3-yl)thiazolo[5,4-b]pyridine | 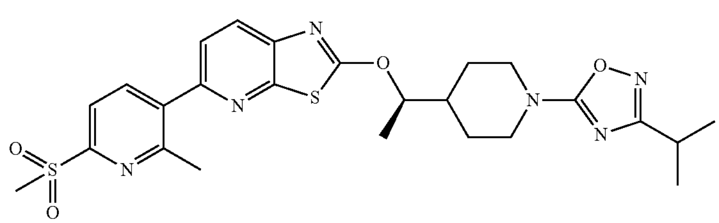 [SMILES: Cc1nc(S(C)(=O)=O)ccc1-c1ccc2nc(O[C@H](C)C3CCN(c4nc(C(C)C)no4)CC3)sc2n1] |

TABLE 1-continued

Illustrative compounds of present invention

| Compound No. | IUPAC name | Structure |
|---|---|---|
| 1169 | 2-((R)-1-(1-(3-isopropyl-1,2,4-oxadiazol-5-yl)piperidin-4-yl)ethoxy)-5-(2-methyl-4-(methylsulfonyl)phenyl)thiazolo[5,4-b]pyridine | 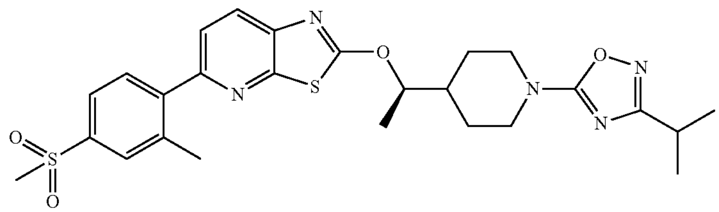 [SMILES: Cc1cc(S(C)(=O)=O)ccc1-c1ccc2nc(O[C@H](C)C3CCN(c4nc(C(C)C)no4)CC3)sc2n1] |

The present invention also provides for compounds of formula (I) as below:

i. 3-isopropyl-5-(1-(5-(4-(methylsulfonyl)phenoxy)thiazolo[5,4-b]pyridin-2-yl)piperidin-4-yl)-1,2,4-oxadiazole
ii. 3-isopropyl-5-(4-(((5-(4-(methylsulfonyl)phenoxy)thiazolo[5,4-b]pyridin-2-yl)oxy)methyl)piperidin-1-yl)-1,2,4-oxadiazole
iii. 3-isopropyl-5-(1-(2-(4-(methylsulfonyl)phenyl)thiazolo[5,4-b]pyridin-5-yl)piperidin-4-yl)-1,2,4-oxadiazole
iv. 3-isopropyl-5-(1-(5-(4-(methylsulfonyl)phenyl)thiazolo[5,4-b]pyridin-2-yl)piperidin-4-yl)-1,2,4-oxadiazole
v. 3-isopropyl-5-(4-((5-(4-(methylsulfonyl)phenoxy)thiazolo[5,4-b]pyridin-2-yl)oxy)piperidin-1-yl)-1,2,4-oxadiazole
vi. 3-isopropyl-5-(4-(((5-(4-(methylsulfonyl)phenyl)thiazolo[5,4-b]pyridin-2-yl)oxy)methyl)piperidin-1-yl)-1,2,4-oxadiazole
vii. 3-isopropyl-5-(4-((5-(4-(methylsulfonyl)phenyl)thiazolo[5,4-b]pyridin-2-yl)oxy)piperidin-1-yl)-1,2,4-oxadiazole
viii. 2-(4-(5-ethylpyrimidin-2-yl)piperazin-1-yl)-5-(4-(methylsulfonyl)phenyl)thiazolo[5,4-b]pyridine
ix. 5-((1-benzylpiperidin-4-yl)methoxy)-2-(4-(methylsulfonyl)phenyl)thiazolo[5,4-b]pyridine
x. 2-(4-(5-ethylpyrimidin-2-yl)piperazin-1-yl)-5-(4-(methylsulfonyl)phenoxy)thiazolo[5,4-b]pyridine
xi. isopropyl 4-(5-(4-(methylsulfonyl)phenyl)thiazolo[5,4-b]pyridin-2-yl)-5,6-dihydropyridine-1(2H)-carboxylate
xii. isopropyl4-(5-(4-(methylsulfonyl)phenyl)thiazolo[5,4-b]pyridin-2-yl) piperazine-1-carboxylate
xiii. isopropyl-4-(5-(4-(methylsulfonyl)phenyl)thiazolo[5,4-b]pyridin-2-yl) piperidine-1-carboxylate
xiv. 1-(5-ethylpyrimidin-2-yl)-N-(5-(4-(methylsulfonyl)phenyl)thiazolo[5,4-b]pyridin-2-yl)piperidine-4-carboxamide
xv. 2-(4-(5-(4-(methylsulfonyl)phenyl)thiazolo[5,4-b]pyridin-2-yl)-5,6-dihydropyridin-1(2H)-yl)ethanol
xvi. isopropyl-4-(methyl(5-(4-(methylsulfonyl)phenyl)thiazolo[5,4-b]pyridin-2-yl)amino)piperidine-1-carboxylate
xvii. N-(1-(5-ethylpyrimidin-2-yl)piperidin-4-yl)-N-methyl-5-(4-(methylsulfonyl)phenyl) thiazolo[5,4-b]pyridin-2-amine
xviii. isopropyl 4-((5-(4-(dimethyl carbamoyl)phenyl)thiazolo[5,4-b]pyridin-2-yl)(methyl)amino)piperidine-1-carboxylate
xix. isopropyl (5-(4-(methylsulfonyl)phenyl)thiazolo[5,4-b]pyridin-2-yl) carbonate
xx. 3-isopropyl-5-(4-(1-((5-(4-(methylsulfonyl)phenyl)thiazolo[5,4-b]pyridin-2-yl)oxy)ethyl)piperidin-1-yl)-1,2,4-oxadiazole
xxi. 3-isopropyl-5-(1-(5-(4-(methylsulfonyl)phenyl)thiazolo[5,4-b]pyridin-2-yl)pyrrolidin-3-yl)-1,2,4-oxadiazole
xxii. 4-(2-(4-(3-isopropyl-1,2,4-oxadiazol-5-yl)piperidin-1-yl)thiazolo[5,4-b]pyridin-5-yl)-N,N-dimethylbenzamide
xxiii. N-(1-(3-isopropyl-1,2,4-oxadiazol-5-yl)piperidin-4-yl)-N-methyl-5-(4-(methylsulfonyl)phenyl)thiazolo[5,4-b]pyridin-2-amine
xxiv. 4-(2-(4-(3-isopropyl-1,2,4-oxadiazol-5-yl)piperidin-1-yl)thiazolo[5,4-b]pyridin-5-yl)-N-(2-methoxyethyl)benzamide
xxv. N-(3-fluoro-4-(methylsulfonyl)phenyl)-2-(4-(3-isopropyl-1,2,4-oxadiazol-5-yl)piperidin-1-yl)thiazolo[5,4-b]pyridin-5-amine
xxvi. 5-(4-(methylsulfonyl)phenyl)-2-(1-tosyl-1,2,3,6-tetrahydropyridin-4-yl)thiazolo[5,4-b]pyridine
xxvii. N,N-dimethyl-4-(5-(4-(methylsulfonyl)phenyl)thiazolo[5,4-b]pyridin-2-yl)-5,6-dihydropyridine-1(2H)-carboxamide
xxviii. N,N-dimethyl-4-(5-(4-(methylsulfonyl)phenyl)thiazolo[5,4-b]pyridin-2-yl)piperidine-1-carboxamide
xxix. (4-(2-(4-(3-isopropyl-1,2,4-oxadiazol-5-yl)piperidin-1-yl)thiazolo[5,4-b]pyridin-5-yl)phenyl)(morpholino)methanone
xxx. N,N-diisopropyl-4-(5-(4-(methylsulfonyl)phenyl)thiazolo[5,4-b]pyridin-2-yl)-5,6-dihydropyridine-1(2H)-carboxamide
xxxi. (S)-3-isopropyl-5-(4-(1-((5-(4-(methylsulfonyl)phenyl)thiazolo[5,4-b]pyridin-2-yl)oxy)ethyl)piperidin-1-yl)-1,2,4-oxadiazole
xxxii. (R)-3-isopropyl-5-(4-(1-((5-(4-(methylsulfonyl)phenyl)thiazolo[5,4-b]pyridin-2-yl)oxy)ethyl)piperidin-1-yl)-1,2,4-oxadiazole
xxxiii. 3-cyclopropyl-5-(4-((5-(4-(methylsulfonyl)phenyl)thiazolo[5,4-b]pyridin-2-yl)oxy)piperidin-1-yl)-1,2,4-oxadiazole
xxxiv. isopropyl 4-(2-((5-(4-(methyl sulfonyl)phenyl)thiazolo[5,4-b]pyridin-2-yl)oxy)ethyl)-5,6-dihydropyridine-1(2H)-carboxylate
xxxv. 3-isopropyl-5-(4-(2-((5-(4-(methyl sulfonyl)phenyl)thiazolo[5,4-b]pyridin-2-yl)oxy)ethyl)-5,6-dihydropyridin-1(2H)-yl)-1,2,4-oxadiazole
xxxvi. 3-isopropyl-5-(4-(2-methoxy-1-((5-(4-(methylsulfonyl) phenyl)thiazolo[5,4-b]pyridin-2-yl)oxy)ethyl)piperidin-1-yl)-1,2,4-oxadiazole
xxxvii. 3-isopropyl-5-(4-(1-((7-methyl-5-(4-(methylsulfonyl)phenyl)thiazolo[5,4-b]pyridin-2-yl)oxy)ethyl)piperidin-1-yl)-1,2,4-oxadiazole
xxxviii. 3-isopropyl-5-(4-(((7-methyl-5-(4-(methylsulfonyl) phenyl)thiazolo[5,4-b]pyridin-2-yl)oxy)methyl)piperidin-1-yl)-1,2,4-oxadiazole xxxix. 3-isopropyl-5-(4-(1-((6-methyl-5-(4-(methylsulfonyl)phenyl)thiazolo[5,4-b]pyridin-2-yl)oxy)ethyl)piperidin-1-yl)-1,2,4-oxadiazole
xl. 5-(4-(cyclopropyl((5-(4-(methylsulfonyl)phenyl)thiazolo[5,4-b]pyridin-2-yl)oxy)methyl)piperidin-1-yl)-3-isopropyl-1,2,4-oxadiazole
xli. 3-isopropyl-5-(4-(2-((5-(4-(methylsulfonyl)phenyl)thiazolo[5,4-b]pyridin-2-yl)oxy)ethylidene) piperidin-1-yl)-1,2,4-oxadiazole
xlii. 3-isopropyl-5-(4-(2-((5-(4-(methylsulfonyl)phenyl)thiazolo[5,4-b]pyridin-2-yl)oxy)ethyl)piperidin-1-yl)-1,2,4-oxadiazole
xliii. 3-isopropyl-5-(4-(2-((5-(4-(methylsulfonyl)phenyl)thiazolo[5,4-b]pyridin-2-yl)oxy)propyl) piperidin-1-yl)-1,2,4-oxadiazole
xliv. 3-isopropyl-5-(4-(2-((5-(4-(methylsulfonyl)phenyl)thiazolo[5,4-b]pyridin-2-yl)oxy)propylidene) piperidin-1-yl)-1,2,4-oxadiazole
xlv. (S)-4-(2-(1-(1-(3-isopropyl-1,2,4-oxadiazol-5-yl)piperidin-4-yl)ethoxy)thiazolo[5,4-b]pyridin-5-yl)-N,N-dimethylbenzamide
xlvi. 3-fluoro-4-(2-(1-(1-(3-isopropyl-1,2,4-oxadiazol-5-yl)piperidin-4-yl)ethoxy)thiazolo[5,4-b]pyridin-5-yl)-N,N-dimethylbenzamide
xlvii. 2-fluoro-4-(2-(1-(1-(3-isopropyl-1,2,4-oxadiazol-5-yl)piperidin-4-yl)ethoxy)thiazolo[5,4-b]pyridin-5-yl)-N,N-dimethylbenzamide
xlviii. 3-cyclopropyl-5-(4-(1-((5-(4-(methylsulfonyl)phenyl)thiazolo[5,4-b]pyridin-2-yl)oxy)ethyl)piperidin-1-yl)-1,2,4-oxadiazole
xlix. N-cyclopropyl-4-(2-(1-(1-(3-isopropyl-1,2,4-oxadiazol-5-yl)piperidin-4-yl)ethoxy)thiazolo [5,4-b]pyridin-5-yl)benzamide
l. 4-(2-(1-(1-(3-isopropyl-1,2,4-oxadiazol-5-yl)piperidin-4-yl)ethoxy)thiazolo[5,4-b]pyridin-5-yl)-N-(2-methoxyethyl)benzamide
li. (4-(2-(1-(1-(3-isopropyl-1,2,4-oxadiazol-5-yl)piperidin-4-yl) ethoxy)thiazolo[5,4-b]pyridin-5-yl)phenyl)(morpholino)methanone
lii. N-cyclopropyl-4-(2-(1-(1-(3-isopropyl-1,2,4-oxadiazol-5-yl)piperidin-4-yl)ethoxy)thiazolo [5,4-b]pyridin-5-yl)-N-methylbenzamide
liii. 5-(4-(methylsulfonyl)phenyl)-2-(1-(1-(5-propylpyrimidin-2-yl) piperidine-4-yl)ethoxy)thiazolo [5,4-b]pyridine
liv. 3-isopropyl-5-(4-(1-((5-(pyridin-3-yl)thiazolo[5,4-b]pyridin-2-yl)oxy) ethyl)piperidin-1-yl)-1,2,4-oxadiazole
lv. 2-(1-(1-(5-ethylpyrimidin-2-yl)piperidin-4-yl)ethoxy)-5-(4-(methylsulfonyl)phenyl)thiazolo[5,4-b]pyridine
lvi. isopropyl-4-(1-((5-(4-(methylsulfonyl)phenyl)thiazolo[5,4-b]pyridin-2-yl)oxy)ethyl)piperidine-1-carboxylate
lvii. 3-isopropyl-5-(4-(1-((5-(4-((methylsulfonyl)methyl)phenyl)thiazolo[5,4-b]pyridin-2-yl)oxy)ethyl)piperidin-1-yl)-1,2,4-oxadiazole
lviii. 5-isopropyl-3-(4-(1-((5-(4-(methylsulfonyl)phenyl)thiazolo[5,4-b]pyridin-2-yl)oxy)ethyl)piperidin-1-yl)-1,2,4-oxadiazole
lix. 3-isopropyl-5-(4-(1-((5-(4-(methylsulfonyl)phenyl)thiazolo[5,4-b]pyridin-2-yl)oxy)ethyl)phenyl)-1,2,4-oxadiazole
lx. 5-(3-fluoro-4-((5-(4-(methylsulfonyl)phenyl)thiazolo[5,4-b]pyridin-2-yl)oxy)piperidin-1-yl)-3-isopropyl-1,2,4-oxadiazole
lxi. 4-(2-(1-(1-(3-isopropyl-1,2,4-oxadiazol-5-yl)piperidin-4-yl)ethoxy)thiazolo[5,4-b]pyridin-5-yl)-N-methylbenzenesulfonamide
lxii. 5-(4-(1-((5-(4-(ethylsulfonyl)phenyl)thiazolo[5,4-b]pyridin-2-yl)oxy)ethyl)piperidin-1-yl)-3-isopropyl-1,2,4-oxadiazole
lxiii. 5-(4-(1-((5-(4-(cyclopropylsulfonyl)phenyl)thiazolo[5,4-b]pyridin-2-yl)oxy)ethyl)piperidin-1-yl)-3-isopropyl-1,2,4-oxadiazole
lxiv. 5-(4-(1-((5-(4-(cyclopropylsulfinyl)phenyl)thiazolo[5,4-b]pyridin-2-yl)oxy)ethyl)piperidin-1-yl)-3-isopropyl-1,2,4-oxadiazole
lxv. 4-(2-(1-(1-(3-isopropyl-1,2,4-oxadiazol-5-yl)piperidin-4-yl)ethoxy)thiazolo[5,4-b]pyridin-5-yl)benzonitrile
lxvi. 4-(2-(1-(1-(3-isopropyl-1,2,4-oxadiazol-5-yl)piperidin-4-yl)ethoxy)thiazolo[5,4-b]pyridin-5-yl)-N-(2-methoxyethyl)benzene sulfonamide
lxvii. 3-isopropyl-5-(4-(1-((5-(4-((2-methoxyethyl)sulfonyl)phenyl)thiazolo[5,4-b]pyridin-2-yl)oxy)ethyl) piperidin-1-yl)-1,2,4-oxadiazole
lxviii. 3-isopropyl-5-(4-(1-((5-(4-((2-methoxyethyl)sulfinyl)phenyl)thiazolo[5,4-b]pyridin-2-yl)oxy)ethyl) piperidin-1-yl)-1,2,4-oxadiazole
lxix. 3-isopropyl-5-(4-(1-((5-(6-(methylsulfonyl)pyridin-3-yl)thiazolo[5,4-b]pyridin-2-yl)oxy)ethyl)piperidin-1-yl)-1,2,4-oxadiazole
lxx. (R)-3-isopropyl-5-(4-(1-((5-(pyridin-4-yl)thiazolo[5,4-b]pyridin-2-yl)oxy)ethyl)piperidin-1-yl)-1,2,4-oxadiazole
lxxi. (R)-4-(2-(1-(1-(3-isopropyl-1,2,4-oxadiazol-5-yl)piperidin-4-yl)ethoxy)thiazolo[5,4-b]pyridin-5-yl)-1-methylpyridin-1-ium
lxxii. N,N-dimethyl-4-(2-(1-(1-(5-propylpyrimidin-2-yl)piperidin-4-yl)ethoxy)imidazo[2,1-b][1,3,4] thiadiazol-6-yl)benzamide
lxxiii. 4-(2-(4-(3-isopropyl-1,2,4-oxadiazol-5-yl)piperidin-1-yl)thiazolo[5,4-b]pyridin-5-yl)-N-methylbenzenesulfonamide
lxxiv. 4-(2-(4-(3-isopropyl-1,2,4-oxadiazol-5-yl)piperidin-1-yl)thiazolo[5,4-b]pyridin-5-yl)-N-(2-methoxyethyl) benzenesulfonamide
lxxv. N-(4-(2-(1-(1-(3-isopropyl-1,2,4-oxadiazol-5-yl)piperidin-4-yl)ethoxy)thiazolo[5,4-b]pyridin-5-yl)phenyl) methanesulfonamide
lxxvi. 2-(1-(1-(1-methyl-1H-tetrazol-5-yl)piperidin-4-yl)ethoxy)-5-(4-(methylsulfonyl)phenyl)thiazolo[5,4-b] pyridine
lxxvii. (S)-5-(4-(1-((5-(3-fluoropyridin-4-yl)thiazolo[5,4-b]pyridin-2-yl)oxy)ethyl)piperidin-1-yl)-3-isopropyl-1,2,4-oxadiazole
lxxviii. 3-isopropyl-5-(1-(5-(pyridin-4-yl)thiazolo[5,4-b]pyridin-2-yl)piperidin-4-yl)-1,2,4-oxadiazole
lxxix. 3-isopropyl-5-(1-(5-(4-((2-methoxyethyl)sulfonyl)phenyl)thiazolo[5,4-b]pyridin-2-yl)piperidin-4-yl)-1,2,4-oxadiazole
lxxx. 5-(4-(1-((5-(4-(1H-tetrazol-1-yl)phenyl)thiazolo[5,4-b]pyridin-2-yl)oxy)ethyl)piperidin-1-yl)-3-isopropyl-1,2,4-oxadiazole
lxxxi. 3-isopropyl-5-(1-(5-(6-(methylsulfonyl)pyridin-3-yl)thiazolo[5,4-b]pyridin-2-yl)piperidin-4-yl)-1,2,4-oxadiazole
lxxxii. 5-(4-(1-((5-(2-fluoropyridin-4-yl)thiazolo[5,4-b]pyridin-2-yl)oxy)ethyl)piperidin-1-yl)-3-isopropyl-1,2,4-oxadiazole
lxxxiii. (S)-3-isopropyl-5-(4-(1-((5-(6-(methylsulfonyl)pyridin-3-yl)thiazolo[5,4-b]pyridin-2-yl)oxy)ethyl)piperidin-1-yl)-1,2,4-oxadiazole
lxxxiv. 3-isopropyl-5-(4-(((5-(pyridin-4-yl)thiazolo[5,4-b]pyridin-2-yl)oxy)methyl)piperidin-1-yl)-1,2,4-oxadiazole lxxxv. 5-(4-(((5-(3-fluoropyridin-4-yl)thiazolo[5,4-b]pyridin-2-yl)oxy)methyl)piperidin-1-yl)-3-isopropyl-1,2,4-oxadiazole lxxxvi. 5-(4-(((5-(4-(1H-tetrazol-1-yl)phenyl)thiazolo[5,4-b]pyridin-2-yl)oxy)methyl)piperidin-1-yl)-3-isopropyl-1,2,4-oxadiazole lxxxvii. 5-(4-(((5-(2-fluoropyridin-4-yl)thiazolo[5,4-b]pyridin-2-yl)oxy)methyl)piperidin-1-yl)-3-isopropyl-1,2,4-oxadiazole lxxxviii. 2-(1-(1-(5-ethylpyridin-2-yl)piperidine-4-yl)ethoxy)-5-(4-(methylsulfonyl)phenyl)thiazolo[5,4-b]pyridine lxxxix. 5-(4-(methylsulfonyl)phenyl)-2-(1-(1-(5-vinylpyridin-2-yl)piperidin-4-yl)ethoxy)thiazolo[5,4-b]pyridine xc. (S)-5-(4-(methylsulfonyl)phenyl)-2-(1-(1-(5-propylpyrimidin-2-yl)piperidin-4-yl)ethoxy)thiazolo [5,4-b]pyridine xci. (R)-5-(4-(methylsulfonyl)phenyl)-2-(1-(1-(5-propylpyrimidin-2-yl)piperidin-4-yl)ethoxy)thiazolo [5,4-b]pyridine xcii. 3-isopropyl-5-(4-(((5-(6-(methylsulfonyl)pyridin-3-yl)thiazolo[5,4-b]pyridin-2-yl)oxy)methyl)piperidin-1-yl)-1,2,4-oxadiazole xciii. (S)-3-isopropyl-5-(4-(1-(5-(pyridin-4-yl)thiazolo[5,4-b]pyridin-2-yl)oxy)ethyl)piperidin-1-yl)-1,2,4-oxadiazole xciv. (S)-5-(4-(1-(5-(2-fluoropyridin-4-yl)thiazolo[5,4-b]pyridin-2-yl)oxy)ethyl)piperidin-1-yl)-3-isopropyl-1,2,4-oxadiazole xcv. 3-isopropyl-5-(4-(2,2,2-trifluoro-1-((5-(4-(methylsulfonyl)phenyl) thiazolo[5,4-b]pyridin-2-yl)oxy)ethyl)piperidin-1-yl)-1,2,4-oxadiazole xcvi. (S)-5-(4-(1-(5-(4-(cyclopropylsulfonyl)phenyl)thiazolo[5,4-b]pyridin-2-yl)oxy)ethyl)piperidin-1-yl)-3-isopropyl-1,2,4-oxadiazole xcvii. (S)-5-(4-(1-(5-(3-fluoropyridin-4-yl)thiazolo[5,4-b]pyridin-2-yl)oxy)ethyl)piperidin-1-yl)-3-isopropyl-1,2,4-oxadiazole xcviii. 2-isopropyl-5-(4-(1-(5-(4-(methylsulfonyl)phenyl)thiazolo[5,4-b]pyridin-2-yl)oxy)ethyl)piperidin-1-yl)-1,3,4-oxadiazole xcix. 4-(2-(1-(1-(3-isopropyl-1,2,4-oxadiazol-5-yl)piperidin-4-yl) ethoxy)thiazolo[5,4-b]pyridin-5-yl)pyridine 1-oxide c. (S)-5-(6-(methylsulfonyl)pyridin-3-yl)-2-(1-(1-(5-propylpyrimidin-2-yl)piperidin-4-yl)ethoxy)thiazolo [5,4-b]pyridine ci. 5-(4-(1-(5-(3-fluoro-4-(methylsulfonyl)phenyl)thiazolo[5,4-b]pyridin-2-yl)oxy)ethyl)piperidin-1-yl)-3-isopropyl-1,2,4-oxadiazole cii. (S)-5-(2-fluoropyridin-4-yl)-2-(1-(1-(5-propylpyrimidin-2-yl)piperidin-4-yl)ethoxy)thiazolo[5,4-b]pyridine ciii. 3-isopropyl-5-(4-(2,2,2-trifluoro-1-((5-(6-(methylsulfonyl)pyridin-3-yl)thiazolo[5,4-b]pyridin-2-yl)oxy) ethyl) piperidin-1-yl)-1,2,4-oxadiazole civ. 3-isopropyl-5-(4-(2,2,2-trifluoro-1-(5-(2-fluoropyridin-4-yl)thiazolo [5,4-b]pyridin-2-yl)oxy)ethyl) piperidin-1-yl)-1,2,4-oxadiazole cv. (S)-2-(1-(1-(5-ethylpyrimidin-2-yl)piperidin-4-yl)ethoxy)-5-(2-fluoropyridin-4-yl)thiazolo[5,4-b]pyridine cvi. 3-isopropyl-5-(4-(1-((5-(4-(methylsulfonyl)phenyl)thiazolo[5,4-b]pyridin-2-yl)oxy)ethyl) cyclohexyl)-1,2,4-oxadiazole cvii. (S)-2-(1-(1-(5-ethylpyrimidin-2-yl)piperidin-4-yl)ethoxy)-5-(6-(methylsulfonyl)pyridin-3-yl) thiazolo[5,4-b]pyridine cviii. 2-(1-(1-(3-isopropyl-1,2,4-thiadiazol-5-yl)piperidin-4-yl)ethoxy)-5-(4-(methyl sulfonyl)phenyl)thiazolo[5,4-b]pyridine cix. 3-isopropyl-5-(4-(1-((6-(4-(methylsulfonyl)phenyl)thiazolo[4,5-b] pyrazin-2-yl)oxy)ethyl)piperidin-1-yl)-1,2,4-oxadiazole cx. 2-(1-(1-(cyclopropylsulfonyl)piperidin-4-yl)ethoxy)-5-(4-(methyl sulfonyl)phenyl)thiazolo[5,4-b] pyridine cxi. 6-(4-(methylsulfonyl)phenyl)-2-(1-(1-(5-propylpyrimidin-2-yl)piperidin-4-yl)ethoxy)thiazolo[4,5-b]pyrazine cxii. 5-(4-(1-(5-(2-fluoro-4-(methylsulfonyl)phenyl)thiazolo[5,4-b]pyridin-2-yl)oxy)ethyl)piperidin-1-yl)-3-isopropyl-1,2,4-oxadiazole cxiii. 5-(3-fluoro-4-(1-((5-(4-(methylsulfonyl)phenyl)thiazolo[5,4-b]pyridin-2-yl)oxy)ethyl)piperidin-1-yl)-3-isopropyl-1,2,4-oxadiazole cxiv. 2-(1-(1-(5-isopropylpyrimidin-2-yl)piperidin-4-yl)ethoxy)-5-(4-(methylsulfonyl)phenyl)thiazolo[5,4-b] pyridine cxv. (S)-3-isopropyl-5-(4-(1-((6-(6-(methylsulfonyl)pyridin-3-yl)thiazolo[4,5-b]pyrazin-2-yl)oxy) ethyl)piperidin-1-yl)-1,2,4-oxadiazole cxvi. 5-(4-(methylsulfonyl)phenyl)-2-(1-(1-(propylsulfonyl)piperidin-4-yl)ethoxy)thiazolo[5,4-b]pyridine cxvii. 5-(4-(1-((5-(2-chloropyrimidin-5-yl)thiazolo[5,4-b]pyridin-2-yl) oxy)ethyl)piperidin-1-yl)-3-isopropyl-1,2,4-oxadiazole cxviii. 1-methylcyclopropyl 4-(1-((5-(4-(methylsulfonyl)phenyl)thiazolo[5,4-b]pyridin-2-yl)oxy)ethyl) piperidine-1-carboxylate cxix. 5-(4-(methylsulfonyl)phenyl)-2-(1-(1-(5-(prop-1-en-2-yl)pyrimidin-2-yl)piperidin-4-yl)ethoxy)thiazolo [5,4-b]pyridine cxx. (S)-5-(4-(1-((5-(2-chloropyrimidin-5-yl)thiazolo[5,4-b]pyridin-2-yl)oxy)ethyl)piperidin-1-yl)-3-isopropyl-1,2,4-oxadiazole cxxi. 2-(1-(1-(5-chloropyrimidin-2-yl)piperidin-4-yl)ethoxy)-5-(4-(methylsulfonyl)phenyl)thiazolo[5,4-b] pyridine cxxii. 3-isopropyl-5-(4-(1-((5-(thiazol-5-yl)thiazolo[5,4-b]pyridin-2-yl)oxy)ethyl)piperidin-1-yl)-1,2,4-oxadiazole cxxiii. 3-isopropyl-5-(4-(1-((5-(isoxazol-4-yl)thiazolo[5,4-b]pyridin-2-yl)oxy)ethyl)piperidin-1-yl)-1,2,4-oxadiazole cxxiv. 3-isopropyl-5-(4-(1-((5-(2-methylpyridin-4-yl)thiazolo[5,4-b]pyridin-2-yl)oxy)ethyl)piperidin-1-yl)-1,2,4-oxadiazole cxxv. 3-isopropyl-5-(4-(1-((5-(isothiazol-4-yl)thiazolo[5,4-b]pyridin-2-yl)oxy)ethyl)piperidin-1-yl)-1,2,4-oxadiazole cxxvi. 3-isopropyl-5-(4-(1-((5-(3-methylisothiazol-4-yl)thiazolo[5,4-b]pyridin-2-yl)oxy)ethyl)piperidin-1-yl)-1,2,4-oxadiazole cxxvii. 4-(2-(1-(1-(3-isopropyl-1,2,4-oxadiazol-5-yl)piperidin-4-yl)ethoxy)thiazolo[5,4-b]pyridin-5-yl)pyridin-2(1H)-one cxxviii. 4-(2-(1-(1-(3-isopropyl-1,2,4-oxadiazol-5-yl)piperidin-4-yl)ethoxy)thiazolo[5,4-b]pyridin-5-yl)-1-methylpyridin-2(1H)-one cxxix. 5-((3R,4S)-3-fluoro-4-(((5-(4-(methylsulfonyl)phenyl)thiazolo[5,4-b]pyridin-2-yl)oxy)methyl)piperidin-1-yl)-3-isopropyl-1,2,4-oxadiazole cxxx. 5-((3S,4S)-3-fluoro-4-(((5-(4-(methylsulfonyl)phenyl)thiazolo[5,4-b]pyridin-2-yl)oxy)methyl) piperidin-1-yl)-3-isopropyl-1,2,4-oxadiazole cxxxi. 3-isopropyl-5-(4-(1-(5-(4-(methylsulfonyl)phenyl)thiazolo[5,4-b]pyridin-2-yl)ethoxy)piperidin-1-yl)-1,2,4-oxadiazole cxxxii. 5-(4-(1-((5-(4-(methylsulfonyl)phenyl)thiazolo[5,4-b]pyridin-2-yl)oxy)ethyl)piperidin-1-yl)-3-(trifluoromethyl)-1,2,4-oxadiazole cxxxiii. 5-(4-(1-((5-(2-chloropyridin-4-yl)thiazolo[5,4-b]pyridin-2-yl)oxy)ethyl)piperidin-1-yl)-3-isopropyl-1,2,4-oxadiazole cxxxiv. 3-isopropyl-5-(4-(1-((5-(2-(methylsulfonyl)pyrimidin-5-yl)thiazolo[5,4-b]pyridin-2-yl)oxy)ethyl)piperidin-1-yl)-1,2,4-oxadiazole cxxxv. 3-isopropyl-5-(4-(1-((5-(pyridazin-4-yl)thiazolo[5,4-b]pyridin-2-yl)oxy)ethyl)piperidin-1-yl)-1,2,4-oxadiazole cxxxvi. 3-isopropyl-5-(4-(1-((5-(pyridazin-4-yl)thiazolo[5,4-b]pyridin-2-yl)oxy)ethyl)piperidin-1-yl)-1,2,4-oxadiazole cxxxvii. 2-((S)-1-(1-(5-ethylpyrimidin-2-yl)piperidin-4-yl)ethoxy)-5-(2-chloropyrimidin-5-yl)thiazolo[5,4-b]pyridine cxxxviii. 2-((S)-1-(1-(5-chloropyrimidin-2-yl)piperidin-4-yl)ethoxy)-5-(6-(methylsulfonyl)pyridin-3-yl)thiazolo[5,4-b]pyridine cxxxix. 2-(1-(1-(5-cyclopropylpyrimidin-2-yl)piperidin-4-yl)ethoxy)-5-(6-(methylsulfonyl)pyridin-3-yl)thiazolo[5,4-b]pyridine cxl. 2-((S)-1-(1-(3-isopropyl-1,2,4-oxadiazol-5-yl)piperidin-4-yl)ethoxy)-5-(2-(methylsulfinyl)pyrimidin-5-yl)thiazolo[5,4-b]pyridine cxli. N-(5-(2-(1-(1-(3-isopropyl-1,2,4-oxadiazol-5-yl)piperidin-4-yl)ethoxy)thiazolo[5,4-b]pyridin-5-yl)pyrimidin-2-yl)-N-methylacetamide cxlii. 2-((R)-1-(1-(3-isopropyl-1,2,4-oxadiazol-5-yl)pyrrolidin-3-yl)ethoxy)-5-(6-(methylsulfonyl)pyridin-3-yl)thiazolo[5,4-b]pyridine cxliii. 2-((S)-1-(1-(3-isopropyl-1,2,4-oxadiazol-5-yl)pyrrolidin-3-yl)ethoxy)-5-(6-(methylsulfonyl)pyridin-3-yl)thiazolo[5,4-b]pyridine cxliv. 2-(1-(1-(3-isopropyl-1,2,4-oxadiazol-5-yl)piperidin-4-yl)ethoxy)-5-(6-chloropyridin-3-yl)thiazolo[5,4-b]pyridine cxlv. 2-((S)-1-(1-(3-isopropyl-1,2,4-oxadiazol-5-yl)piperidin-4-yl)ethoxy)-5-(2-chloropyridin-4-yl)thiazolo[5,4-b]pyridine cxlvi. 1-(5-(2-(1-(1-(3-isopropyl-1,2,4-oxadiazol-5-yl)piperidin-4-yl)ethoxy)thiazolo[5,4-b]pyridin-5-yl)pyridin-2-yl)imidazolidin-2-one cxlvii. 2-((S)-1-(1-(3-(trifluoromethyl)-1,2,4-oxadiazol-5-yl)piperidin-4-yl)ethoxy)-5-(6-(methylsulfonyl)pyridin-3-yl)thiazolo[5,4-b]pyridine cxlviii. 1-(5-(2-(1-(1-(3-isopropyl-1,2,4-oxadiazol-5-yl)piperidin-4-yl)ethoxy)thiazolo[5,4-b]pyridin-5-yl)pyridin-2-yl)pyrrolidin-2-one cxlix. 2-(1-(1-(3-isopropyl-1,2,4-oxadiazol-5-yl)piperidin-4-yl)ethoxy)-5-(6-(trifluoromethyl)pyridin-3-yl)thiazolo[5,4-b]pyridine cl. 2-(1-(1-(5-chloropyrazin-2-yl)piperidin-4-yl)ethoxy)-5-(4-(methylsulfonyl)phenyl)thiazolo[5,4-b]pyridine cli. 2-(1-(1-(5-ethylpyrimidin-2-yl)piperidin-4-yl)ethoxy)-5-(pyridin-4-yl)thiazolo[5,4-b]pyridine clii. 2-(1-(1-(5-propylpyrimidin-2-yl)piperidin-4-yl)ethoxy)-5-(pyridin-4-yl)thiazolo[5,4-b]pyridine cliii. 2-(1-(1-(5-chloropyrazin-2-yl)piperidin-4-yl)ethoxy)-5-(6-(methylsulfonyl)pyridin-3-yl)thiazolo[5,4-b]pyridine cliv. 2-((S)-1-(1-(3-isopropyl-1,2,4-oxadiazol-5-yl)piperidin-4-yl)ethoxy)-5-(6-(trifluoromethyl)pyridin-3-yl)thiazolo[5,4-b]pyridine clv. 2-((S)-1-(1-(5-propylpyrimidin-2-yl)piperidin-4-yl)ethoxy)-5-(pyridin-4-yl)thiazolo[5,4-b]pyridine clvi. 2-((S)-1-(1-(5-ethylpyrimidin-2-yl)piperidin-4-yl)ethoxy)-5-(6-(trifluoromethyl)pyridin-3-yl)thiazolo[5,4-b]pyridine clvii. 2-((S)-1-(1-(3-isopropyl-1,2,4-oxadiazol-5-yl)piperidin-4-yl)ethoxy)-5-(3-fluoro-4-(methylsulfonyl)phenyl)thiazolo[5,4-b]pyridine clviii. 2-(1-(1-(3-ethyl-1,2,4-oxadiazol-5-yl)piperidin-4-yl)ethoxy)-5-(6-(methylsulfonyl)pyridin-3-yl)thiazolo[5,4-b]pyridine clix. 2-(1-(1-(5-methylpyrimidin-2-yl)piperidin-4-yl)ethoxy)-5-(6-(methylsulfonyl)pyridin-3-yl)thiazolo[5,4-b]pyridine clx. 2-(1-(1-(3-isopropyl-1,2,4-oxadiazol-5-yl)piperidin-4-yl)ethoxy)-5-(5-(methylsulfonyl)pyrazin-2-yl)thiazolo[5,4-b]pyridine clxi. 2-(1-(1-(5-(trifluoromethyl)pyrimidin-2-yl)piperidin-4-yl)ethoxy)-5-(6-(methylsulfonyl)pyridin-3-yl)thiazolo[5,4-b]pyridine clxii. 2-((S)-1-(1-(3-ethyl-1,2,4-oxadiazol-5-yl)piperidin-4-yl)ethoxy)-5-(6-(methylsulfonyl)pyridin-3-yl)thiazolo[5,4-b]pyridine clxiii. 2-(1-(1-(3-isopropyl-1,2,4-oxadiazol-5-yl)piperidin-4-yl)ethoxy)-5-(5-(methylsulfonyl)pyridin-2-yl)thiazolo[5,4-b]pyridine clxiv. 2-(1-(1-(3-isopropyl-1,2,4-oxadiazol-5-yl)piperidin-4-yl)ethoxy)-5-(6-(methylsulfonyl)pyridin-3-yl)thiazolo[5,4-d]pyrimidine clxv. 2-(1-(1-(5-(methoxymethyl)pyrimidin-2-yl)piperidin-4-yl)ethoxy)-5-(6-(methylsulfonyl)pyridin-3-yl)thiazolo[5,4-b]pyridine clxvi. 2-((R)-1-(1-(3-isopropyl-1,2,4-oxadiazol-5-yl)piperidin-4-yl)ethoxy)-5-(6-(cyclopropylsulfonyl)pyridin-3-yl)thiazolo[5,4-b]pyridine clxvii. 2-((R)-1-(1-(5-(methoxymethyl)pyrimidin-2-yl)piperidin-4-yl)ethoxy)-5-(6-(methylsulfonyl)pyridin-3-yl)thiazolo[5,4-b]pyridine clxviii. 2-((S)-1-(1-(5-(trifluoromethyl)pyrimidin-2-yl)piperidin-4-yl)ethoxy)-5-(6-(methylsulfonyl)pyridin-3-yl)thiazolo[5,4-b]pyridine clxix. 2-((S)-1-(1-(3-isopropyl-1,2,4-oxadiazol-5-yl)piperidin-4-yl)ethoxy)-5-(2-fluoro-6-(methylsulfonyl)pyridin-3-yl)thiazolo[5,4-b]pyridine clxx. 2-((R)-1-(1-(3-isopropyl-1,2,4-oxadiazol-5-yl)piperidin-4-yl)ethoxy)-5-(2-methyl-6-(methylsulfonyl)pyridin-3-yl)thiazolo[5,4-b]pyridine clxxi. 2-((R)-1-(1-(3-isopropyl-1,2,4-oxadiazol-5-yl)piperidin-4-yl)ethoxy)-5-(2-methyl-4-(methylsulfonyl)phenyl)thiazolo[5,4-b]pyridine B. Synthesis of Compounds of the Present Invention The present invention also relates to a process of preparing the compounds of formula (I). The compounds of present invention may be prepared by the schemes as here below:

Synthetic Scheme 1:
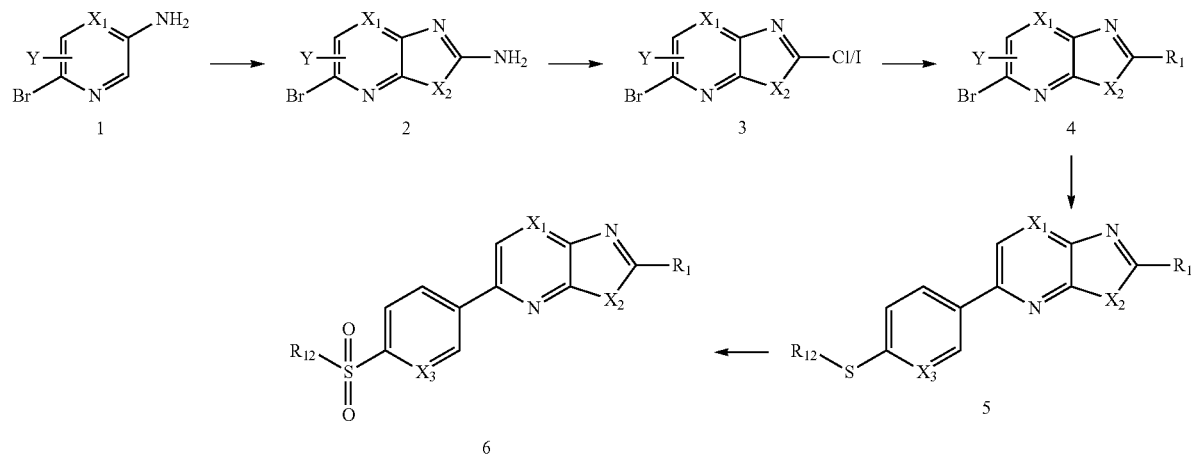
Wherein,
X₁, X₂ and X₃ is CH, N, O, S;
R1 is

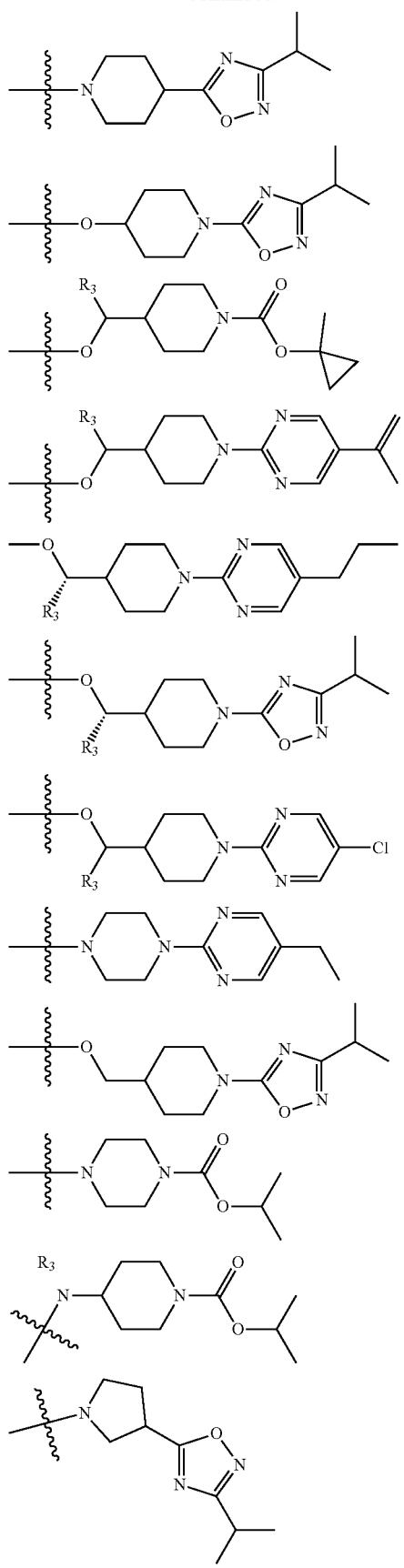
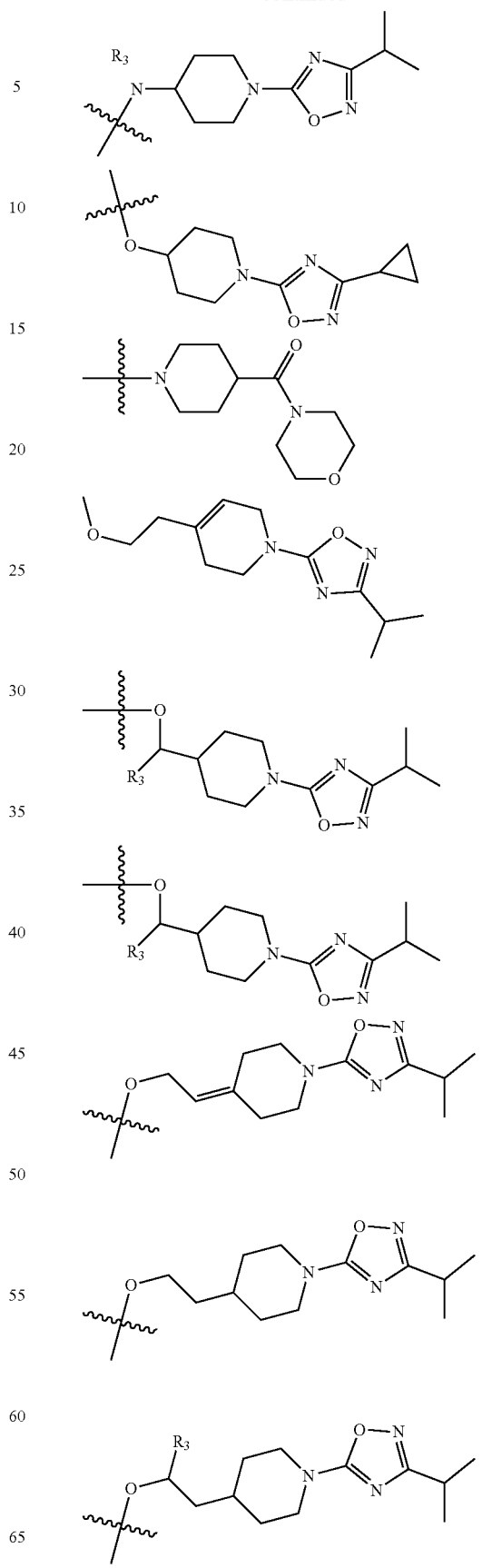

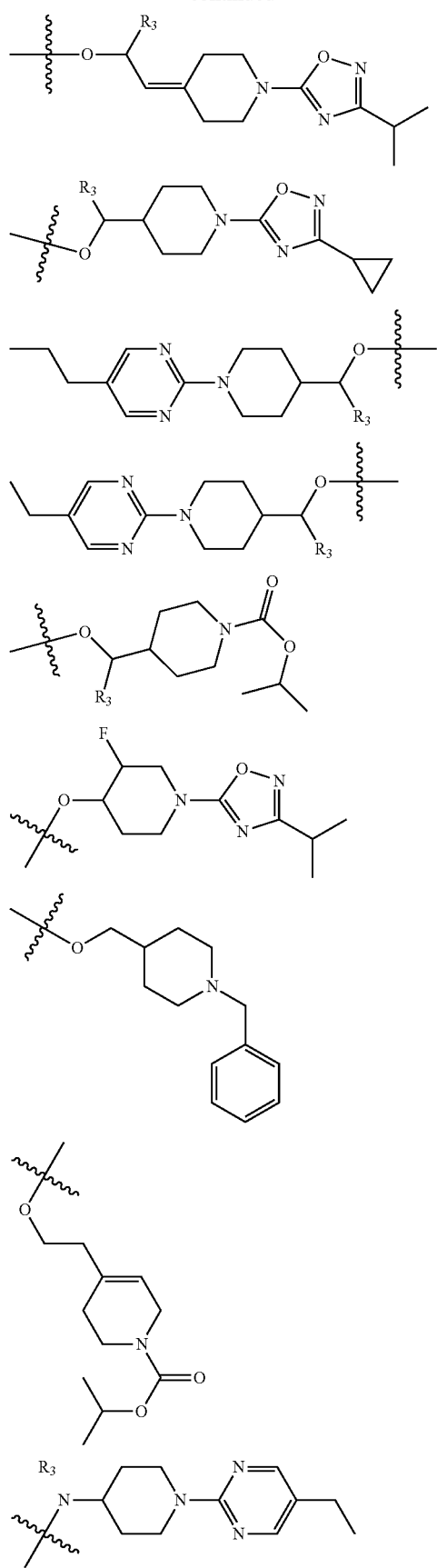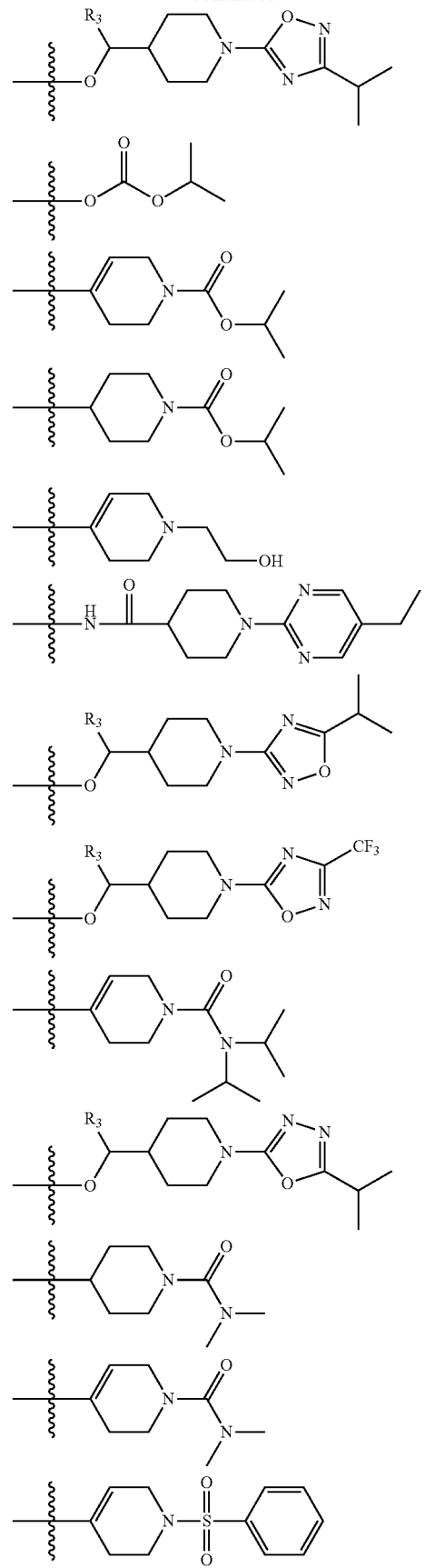

-continued

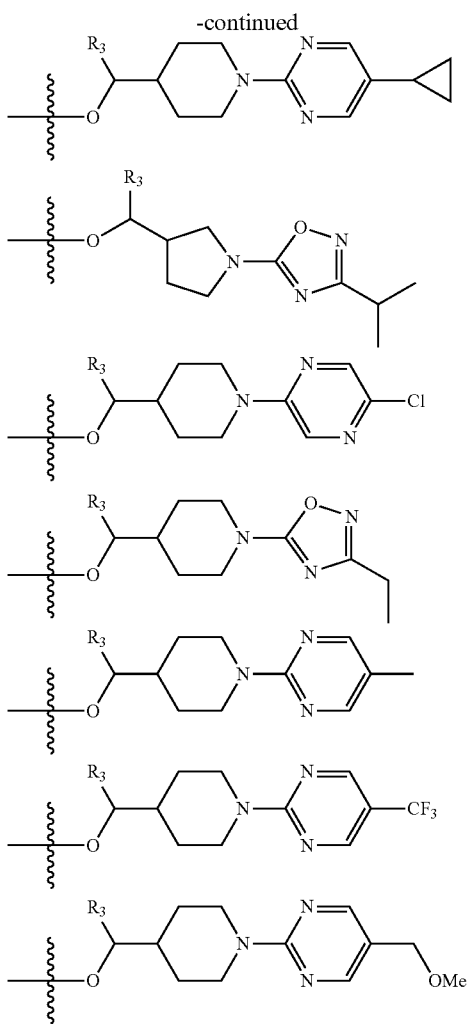

$R_3$ is selected from H, OH, halogen, $C_{1-6}$ alkyl, $C_{1-6}$alkoxy, —$(CH_2)n$, amino, —CO, —CONH, —NH(Alkyl), —N(Alkyl)$_2$, —NH-aralkyl, —CF3, —OCH(CH$_3$),

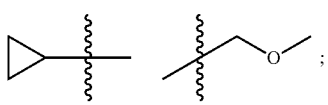

Y is selected from H, OH, halogen, $C_{1-6}$ alkyl, $C_{1-6}$alkoxy, —$(CH_2)n$, amino, —CO, —CONH, —NH(Alkyl), —N(Alkyl)$_2$, —NH-aralkyl, —OCH(CH$_3$));

$R_{12}$ is selected from H, OH, halogen, $C_{1-6}$ alkyl, $C_{1-6}$alkoxy, —$(CH_2)n$, amino, —CO, —CONH, —NH(Alkyl), —N(Alkyl)$_2$, —NH-aralkyl, —NH—$(CH_2)n$-O—$(CH_2)n$, —$(CH_2)n$-O—$CH_3$, OCH(CH$_3$),

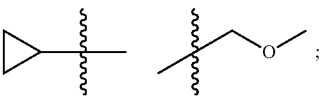

n is 0, 1, 2 or 3;

Synthetic Scheme 2:

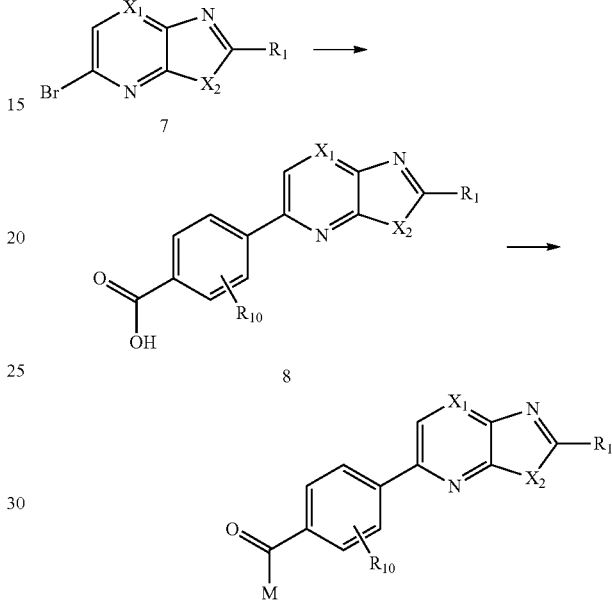

Wherein,
$X_1$, $X_2$, $X_3$, $R_1$ is as illustrated above;
M is H, OH, halogen, $C_{1-6}$ alkyl, $C_{1-6}$alkoxy, —$(CH_2)n$, amino, —CO, —CONH, —NH(Alkyl), —N(Alkyl)$_2$, —NH-aralkyl, —NH—$(CH_2)n$-O—$(CH_2)n$, —$(CH_2)n$-O—$CH_3$, OCH(CH$_3$),

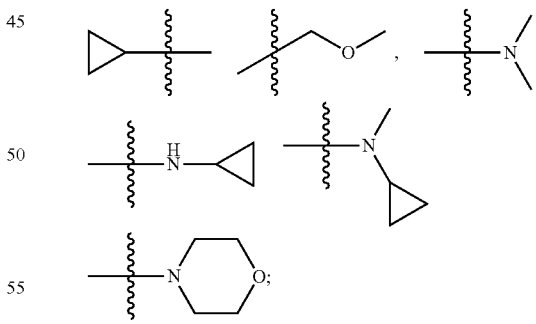

Synthetic Scheme 3:
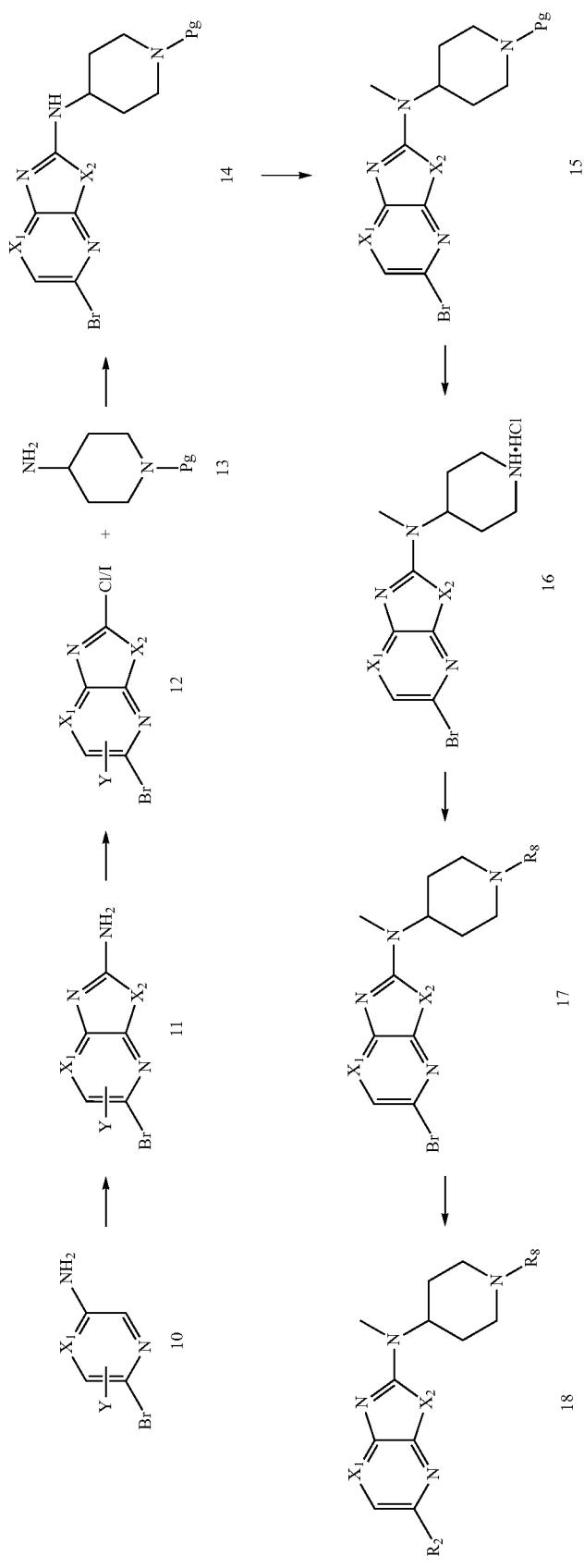

Wherein,
$X_1$, $X_2$ and Y is as illustrated above;
$R_2$ is selected from
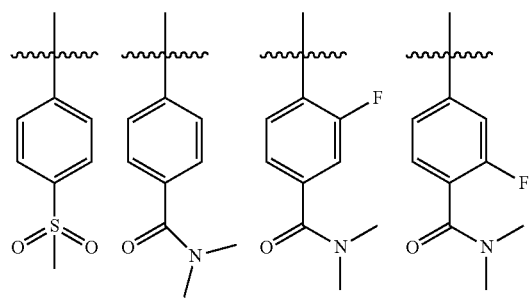
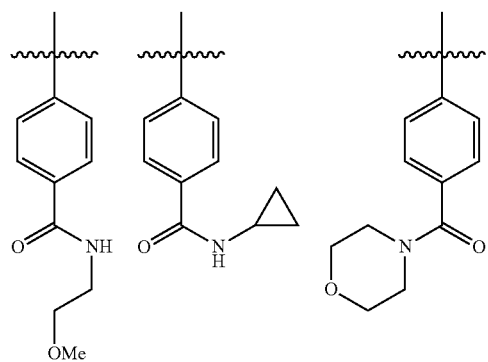
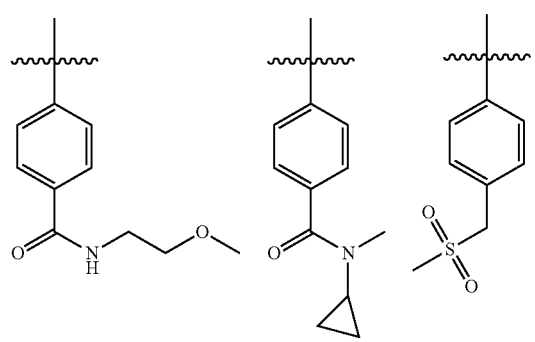
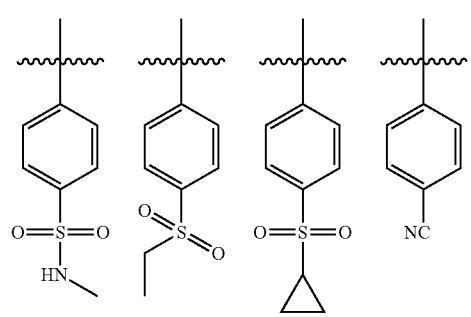
-continued
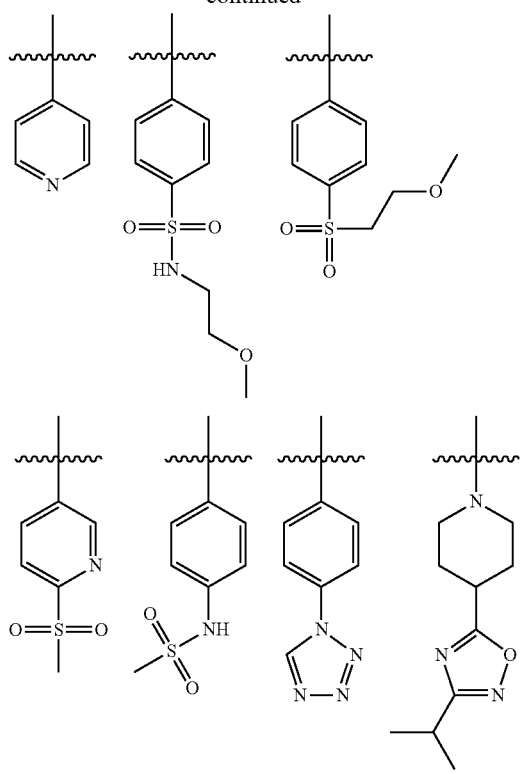
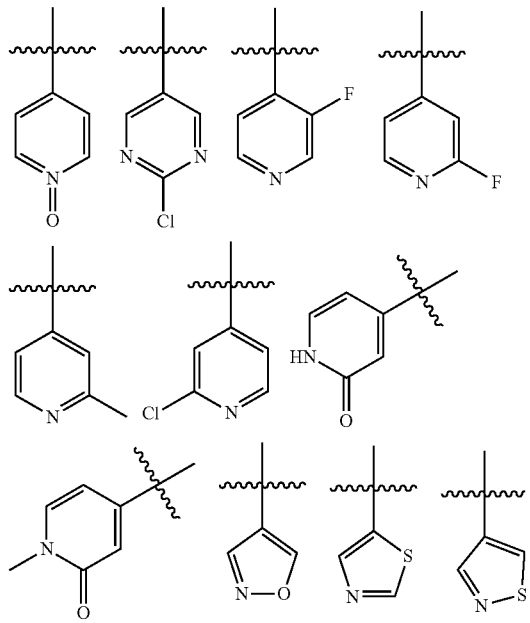
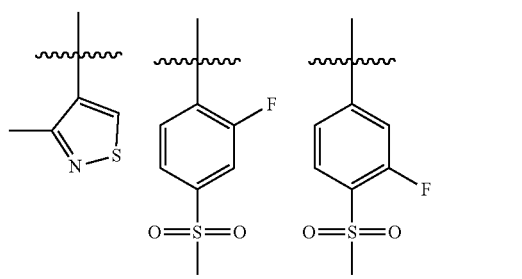

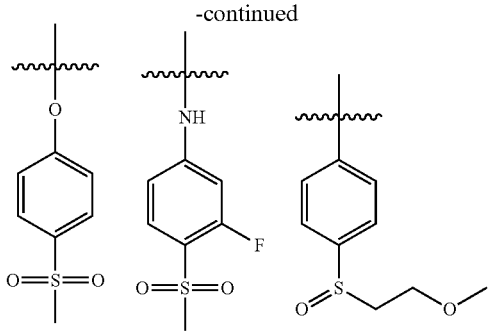
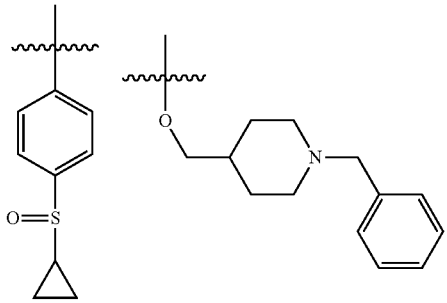
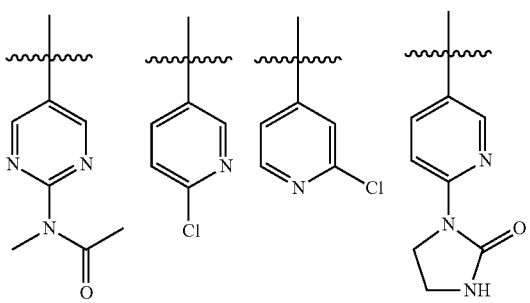
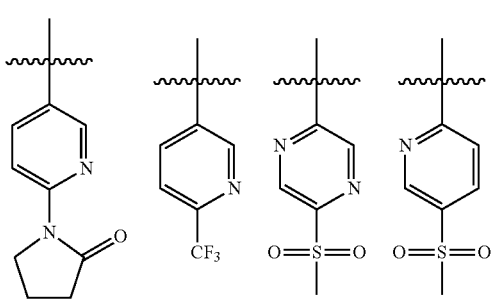
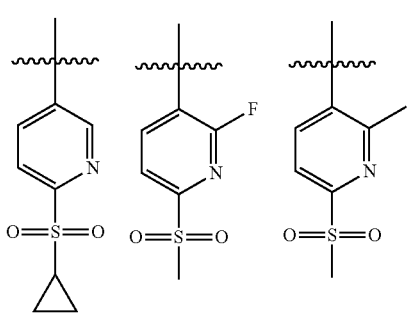

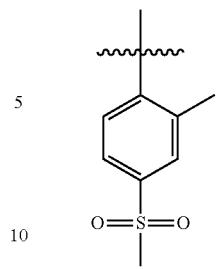

R8 is

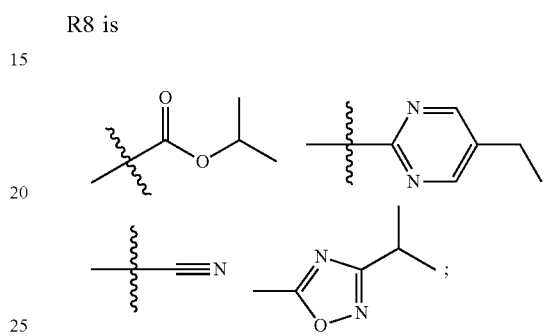

C. Salts and Isomers and Counter Ions

The present invention includes within its scope the salts and isomers. Compounds of the present invention after being novel may in some cases form salts which are also within the scope of this invention. The term "salt(s)", as employed herein, denotes acidic and/or basic salts formed with inorganic and/or organic acids and bases.

All stereoisomer's of the present compounds, such as those which may exist due to asymmetric carbons on the R substituents of the compound, including enantiomeric and diastereomeric forms, are contemplated within the scope of this invention.

The Compounds of the present invention may be present in their enantiomeric pure forms or their mixtures.

D. Methods of Use and Pharmaceutical Composition Containing the Novel Entities of the Invention The invention thus provides the use of the novel compounds as defined herein for use in human or veterinary medicine. The compounds of the present invention may be used in the prevention and treatment of metabolic disorders. Particularly, the compounds of the present invention are effective in the treatment of type I and type II diabetes mellitus, obesity and related disorders. The compounds of present invention activates the GPR119 which increases the intracellular accumulation of cAMP, leading to enhanced glucose-dependent insulin secretion from pancreatic β-cells and increased release of the gut peptides GLP-1 (glucagon like peptide 1), GIP (glucose-dependent insulinotropic peptide) and PYY (polypeptide YY) and thus acts as GPR119 agonists.

In an aspect, the compounds of the present invention may be used either alone or in combination with DPP IV inhibitors.

The compound for use as a pharmaceutical may be presented as a pharmaceutical composition. The invention therefore provides in a further aspect a pharmaceutical composition comprising the novel compounds of the invention along with pharmaceutically acceptable excipients/carriers thereof and optionally other therapeutic and/or prophylactic ingredients. The excipients/carriers must be "acceptable" in the sense of being compatible with the other ingredients of the composition and not deleterious to the recipient thereof. Suitably the pharmaceutical composition will be in an appropriate formulation.

The pharmaceutical formulations may be any formulation and include those suitable for oral, intranasal, or parenteral (including intramuscular and intravenous) administration. The formulations may, where appropriate, be conveniently presented in discrete dosage units and may be prepared by any of the methods well known in the art of pharmacy. All methods include the step of bringing into association the active compound with liquid carriers or finely divided solid carriers or both, and then, if necessary, shaping the product into the desired formulation.

For these purposes the compounds of the present invention may be administered orally, topically, intranasally, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasteral injection or infusion techniques. In addition to the treatment of warm-blooded animals such as mice, rats, horses, dogs, cats, etc. The compounds of the present invention are effective in the treatment of humans.

In an aspect, compound of the present invention may be administered in a dose ranging from 0.1 to 100 mg/kg body weight per day. The compounds of the present invention are useful for the prevention and treatment of metabolic disorders and may be used as GPR119 agonist.

Without being limited by theory, it is submitted that the novel compounds of the present invention exhibit substantially different pharmacokinetic and pharmacodynamic profiles. The invention is described in detail herein below with respect to the following examples which are provided merely for illustration. However, these examples may not be construed to restrict the scope of the invention. Any embodiments that may be apparent to a person skilled in the art are deemed to fall within the scope of present invention.

EXPERIMENTALS

Example 1: 3-isopropyl-5-(1-(5-(4-(methylsulfonyl)phenoxy)thiazolo[5,4-b]pyridin-2-yl)piperidin-4-yl)-1,2,4-oxadiazole [1001]

Step 1: Synthesis of 5-(4-(methylsulfonyl)phenoxy)-2-(4-(3-isopropyl-1,2,4-oxadiazol-5-yl)piperidin-1-yl)thiazolo[5,4-b]pyridine

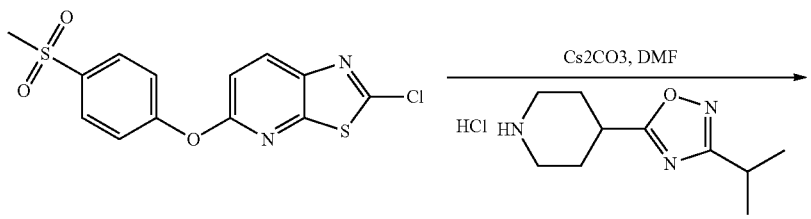

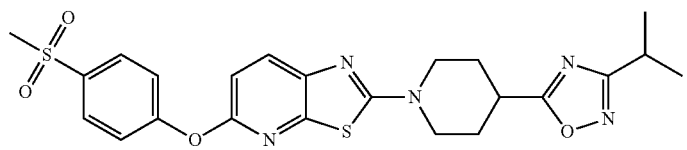

To a stirred solution of 5-(4-(methylsulfonyl)phenoxy)-2-chlorothiazolo[5,4-b]pyridine (0.075 g, 0.22 mmol) and compound 4-(3-isopropyl-1,2,4-oxadiazol-5-yl)piperidine HCl salt (0.06 g, 0.26 mmol) in DMF (5 ml) was added Cs$_2$CO$_3$ (0.215 g, 0.66 mmol) and reaction heated at 70° C. for 90 min. Reaction was monitored by TLC. On completion reaction mixture was quenched with water and extracted with ethylacetate. The organic layer was washed with water, brine, dried over sodium sulphate and concentrated under reduced pressure to give crude desired product that was purified by silica gel (100 to 200 Mesh) column chromatography: eluent 30% EtOAc in Hexane to obtain 5-(4-(methylsulfonyl)phenoxy)-2-(4-(3-isopropyl-1,2,4-oxadiazol-5-yl)piperidin-1-yl)thiazolo[5,4-b]pyridine (0.012 g, 11.36%) as off white powder. MS: 500.11 [M$^+$+1]

Example 2: 3-isopropyl-5-(1-(2-(4-(methylsulfonyl)phenyl)thiazolo[5,4-b]pyridin-5-yl)piperidin-4-yl)-1,2,4-oxadiazole [1002]

Step 1: 5-bromothiazolo[5,4-b]pyridin-2-amine

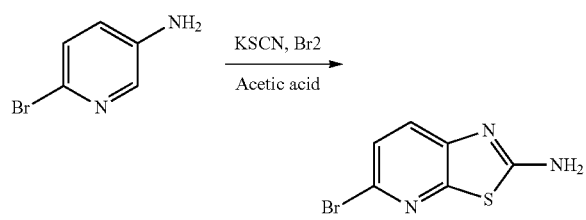

To a suspension of KSCN (2.2 g, 22.83 mmol) in acetic acid (10 ml) was added 6-bromopyridin-3-amine (1 g, 5.78 mmol) and the mixture was stirred at room temperature for 15 min. A solution of bromine (0.38 ml 7.51 mmol) in acetic acid (10 ml) was added dropwise to the obtained solution at room temperature for 15 min. After the completion of dropwise addition the mixture was stirred at room temperature for 3 h. Reaction was monitored by TLC. On completion to the reaction mixture was added water (25 ml); the solid so precipitated was filtered out. The filtrate was concentrated under reduced pressure; the residue was neutralised to pH=7 with aq. sol. of NaHCO$_3$ and extracted with mixture of THF:ethyl acetate (1:1). The organic layer was dried over sodium sulphate, concentrated under reduced pressure to afford 5-bromothiazolo[5,4-b]pyridin-2-amine (0.910 g, 68.93%) as reddish brown solid. MS: 231.86 [M$^+$+1]

Step 2: Synthesis of 5-bromo-2-chlorothiazolo[5,4-b]pyridine

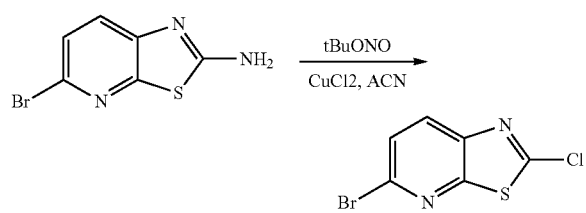

To a stirred solution of 5-bromothiazolo[5,4-b]pyridin-2-amine (0.5 g, 2.17 mmol) in ACN (8 ml) was added CuCl$_2$ (0.432 g, 3.21 mmol) at 0° C. reaction allowed to run at 0° C. for 15 min. After 15 min. tBuONO (0.38 mL, 3.21 mmol) dissolved in ACN (2 ml) was added to reaction mixture at 0° C., its stir at room temperature for 16 h. Reaction was monitored of TLC. On completion reaction mixer was concentrated under reduced pressure. To the residue was added water and reaction mixer extracted with ethyl acetate. The organic layer was washed with water, saturated aq. sol. of NaHCO3 brine, dried over sodium sulphate and concentrated under reduced pressure to afford of 5-bromo-2-chlorothiazolo[5,4-b]pyridine (0.470 g, 87.03%) as yellow solid.
MS: 250.74 [M$^+$+1]

Step 3: Synthesis of 5-bromo-2-(4-(methylsulfonyl)phenyl)thiazolo[5,4-b]pyridine

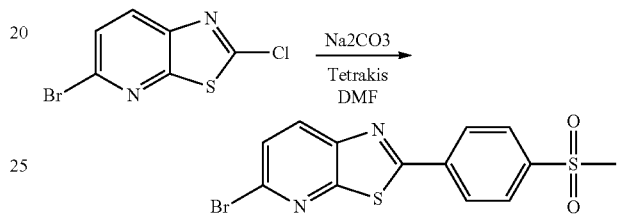

To a stirred solution of 5-bromo-2-chlorothiazolo[5,4-b]pyridine (0.3 g, 1.3 mmol) and 4-(methylsulfonyl)phenylboronic acid (0.289 g, 1.44 mmol) in DMF (5 mL) was added Na$_2$CO$_3$ (0.278 g, 2.63 mmol) dissolved in water (1 mL) and reaction purged with nitrogen for 30 min. After 30 min Tetrakis (0.151 g, 0.13 mmol) was added to the reaction mixture and reaction heated at 100° C. for 16 h. Reaction was monitored by TLC. On completion reaction was quenched with water and extracted with ethyl acetate. The organic layer was concentrated reduced pressure to give crude which was purified by silica gel (100 to 200 Mesh) column chromatography; eluant 35% ethyl acetate/hexane to afford of 5-bromo-2-(4-(methylsulfonyl)phenyl)thiazolo[5,4-b]pyridine (0.199 g, 41.6%) as brown solid.
MS: 370.91 [M$^+$+1]

Step 4: Synthesis of 5-(4-(3-isopropyl-1,2,4-oxadiazol-5-yl)piperidin-1-yl)-2-(4-(methylsulfonyl)phenyl)thiazolo[5,4-b]pyridine

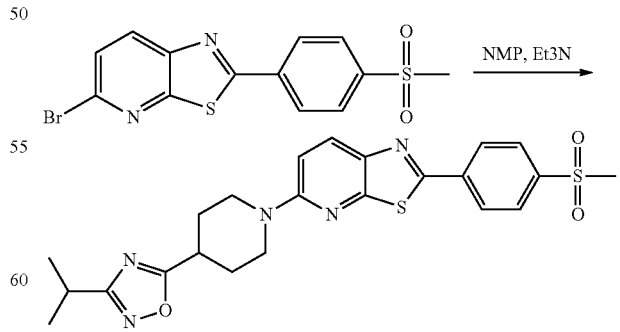

To stirred solution of 5-bromo-2-(4-(methylsulfonyl)phenyl)thiazolo[5,4-b]pyridine (0.05 g, 0.13 mmol) and 4-(3-isopropyl-1,2,4-oxadiazol-5-yl)piperidine HCl salt (0.079 g, 0.4 mmol) in NMP (2 ml) was added Et3N (0.08 mL, 0.54 mmol) and reaction heated in seal tube at 140° C. for 2 hours. Reaction was monitored by MS. On completion reaction was quenched with water and extracted with ethyl acetate. The organic layer was washed with water (3 times), brine (1 time) dried over sodium sulphate and concentrated under reduced pressure to give crude which was purified by silica gel (100 to 200 Mesh) column chromatography; eluant 40% ethyl acetate in hexane to obtained 5-(4-(3-isopropyl-1,2,4-oxadiazol-5-yl)piperidin-1-yl)-2-(4-(methylsulfonyl) phenyl)thiazolo[5,4-b]pyridine (0.0132 g, 20.2%) as pale yellow solid.

MS: 484.22 [M$^+$+1]

Example 3: 3-isopropyl-5-(4-((5-(4-(methylsulfonyl) phenoxy)thiazolo[5,4-b]pyridin-2-yl)oxy)piperidin-1-yl)-1,2,4-oxadiazole [1005]

Step 1 Synthesis of 2-(4-(methylsulfonyl)phenoxy)-5-nitropyridine

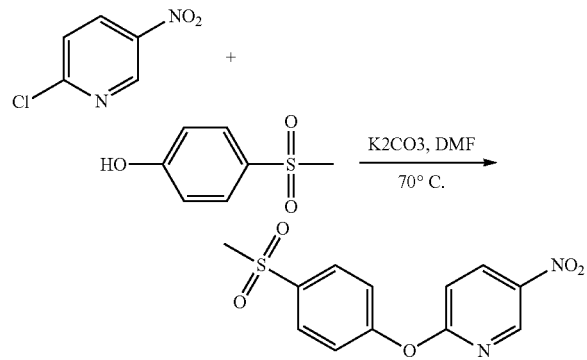

To a stirred solution of 4-(methylsulfonyl)phenol (0.6 g, 348 mmol) in DMF (4 mL) was added to K$_2$CO$_3$ (0.873 g, 6.32 mmol) and reaction allowed to stir at room temperature for 15 min. After 15 min 2-chloro-5-nitropyridine (0.5 g, 3.16 mmol) in DMF (1 mL) was added to reaction mixture, and reaction heated at 70° C. for 1 hr. Reaction was monitored by TLC. On completion of reaction was quenched by 15 ml water, extracted with ethyl acetate. The combined organic layer was washed with water, dried over sodium sulphate and concentrated under reduced pressure to obtained 2-(4-(methylsulfonyl)phenoxy)-5-nitropyridine (0.650 g, 69.89%) as yellowish orange solid.

MS: 295.03 [M$^+$+1]

Step 2: Synthesis of 6-(4-(methylsulfonyl)phenoxy)pyridin-3-amine

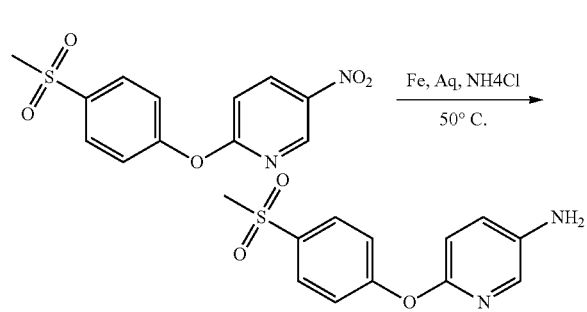

To a stirred solution of 2-(4-(methylsulfonyl)phenoxy)-5-nitropyridine (0.5 g, 1.70 mmol) in EtOH (8 mL) was added iron power (0.374 g, 6.80 mmol), followed by addition of saturated aq. sol. of NH$_4$Cl (5 mL) and reaction was heated at 50° C. for 90 min. Reaction was monitored by TLC. On completion reaction mixture was filtered through celite bed and celite bed was washed with ethylacetate. The filtrate was washed with water, brine dried over sodium sulphate and concentrated under reduced pressure to afford 6-(4-(methylsulfonyl)phenoxy)pyridin-3-amine (0.39 g, 87.05%) as off white solid.

MS: 264.88 [M$^+$+1]

Step 3: Synthesis of 5-(4-(methylsulfonyl)phenoxy) thiazolo[5,4-b]pyridin-2-amine

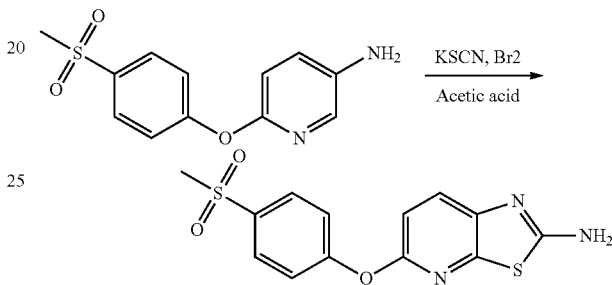

To a Stirred solution of KSCN (0.219 g, 2.24 mmol) in acetic acid (2 mL) was added 6-(4-(methylsulfonyl)phenoxy)pyridin-3-amine (0.150 g, 0.56 mmol) dissolved in acetic acid (1 mL) and reaction was allowed to stir at room temperature for 15 min. Bromine (0.03 mmol) dissolved in acetic acid (2 mL) was added to reaction drop wise. Reaction was allowed to stir at room temperature for 1 h. Reaction was monitored by TLC & MS. On completion water was added to reaction mixture. The solid precipitated was filtered out and filtrate was concentrated under reduced pressure to give residue. Residue was extracted with ethylacetate. The organic layer was washed with aq. sol. of NaHCO3 (3×50 mL), brine, dried over sodium sulphate and concentrated under reduced pressure to afford 5-(4-(methylsulfonyl)phenoxy)thiazolo[5,4-b]pyridin-2-amine (0.1 g, 54.94%) as off white solid.

MS: 322.06 [M$^+$+1]

Step 4: Synthesis of 5-(4-(methylsulfonyl)phenoxy)-2-chlorothiazolo[5,4-b]pyridine

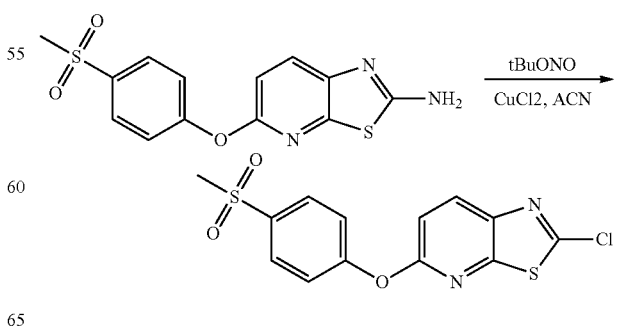

To a stirred solution of 5-(4-(methylsulfonyl)phenoxy) thiazolo[5,4-b]pyridin-2-amine (1.0 g, 3.10 mmol) in ACN (10 mL) was added CuCl$_2$ (0.617 g, 4.59 mmol) at 0° C. After 15 min tBuONO (0.55 mL) was added to reaction mixture dissolved in ACN (1 mL) and reaction allowed to stir at room temperature for overnight. Reaction was monitored by TLC. On completion reaction mixture was concentrated under reduced pressure and to the residue was added water, extracted with ethyl acetate, dried over sodium sulphate and concentrated under reduced pressure to give crude desired product that was purified by silica gel (100-200 Mesh) column chromatography eluent 30% ethylacetate in hexane to afford 5-(4-(methylsulfonyl)phenoxy)-2-chlorothiazolo[5,4-b]pyridine (0.710 g, 67.04%) as yellow solid. MS: 340.96 [M$^+$+1]

Step 5: Synthesis of 2-(1-(3-isopropyl-1,2,4-oxadiazol-5-yl)piperidin-4-yloxy)-5-((methylsulfonyl)phenoxy)thiazolo[5,4-b]pyridine

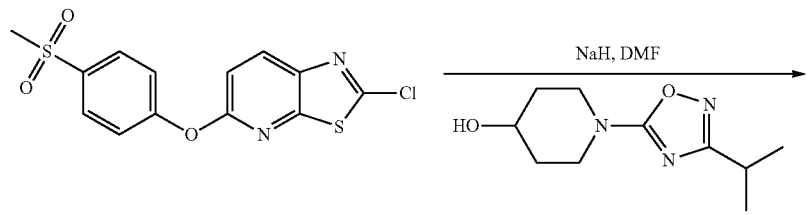

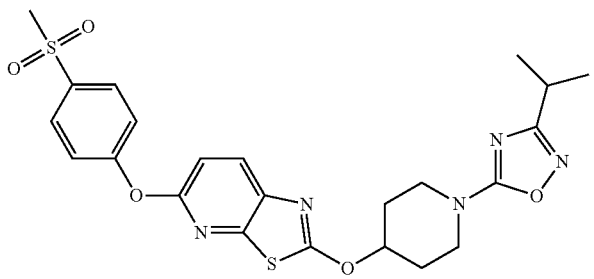

To a stirred solution of 1-(3-isopropyl-1,2,4-oxadiazol-5-yl)piperidin-4-ol (37 mg, 0.17 mmol) in DMF (1 ml) was added sodium hydride (8 mg, 0.22 mmol) at 0° C. and reaction allowed to run at 0° C. for 15 min. After 15 min 5-(4-(methylsulfonyl)phenoxy)-2-chlorothiazolo[5,4-b] pyridine (37 mg, 0.17 mmol) dissolved in DMF was added to reaction mixture and reaction stirred at room temperature for 1 hr. Reaction was monitored by TLC. On completion reaction was quenched with ice cold water extracted with ethylacetate. The organic layer was washed with water, brine, dried over sodium sulphate and concentrated under reduced pressure to give crude desired product that was purified by silica gel (100 to 200 Mesh) column chromatography, eluant 35% ethyl acetate in hexane to afford 2-(1-(3-isopropyl-1,2,4-oxadiazol-5-yl)piperidin-4-yloxy)-5-((methylsulfonyl)phenoxy)thiazolo[5,4-b]pyridine (0.015 g, 20.4%) as off white solid. MS: 516.18 [M$^+$+1]

Example 4: 5-((1-benzylpiperidin-4-yl)methoxy)-2-(4-(methylsulfonyl)phenyl) thiazolo[5,4-b]pyridine
[1009]

Step 1: Synthesis of 1-benzylpiperidin-4-yl)methanol

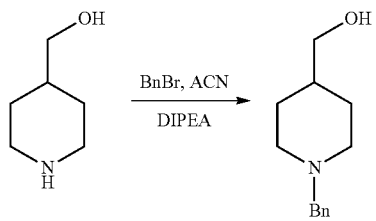

To a stirred solution of (piperidin-4-yl)methanol (1 g, 8.68 mmol) in ACN (10 mL) was added DIPEA (3.02 mL, 1.36 mmol) followed by addition of benzyl bromide (1.2 mL, 17.36 mmol) and reaction heated at 60° C. for overnight. Reaction was monitored by TLC. On completion reaction mixture was concentrated under reduced pressure to give crude that was purified by combiflash chromatography, eluent 1% CH$_3$OH/DCM to afford (1-benzylpiperidin-4-yl) methanol (1.40 g, 78.65%) as off white solid.
MS: 206.42 [M$^+$+1]

Step 2: Synthesis of 2-((1-benzylpiperidin-4-yl)methoxy)-5-nitropyridine

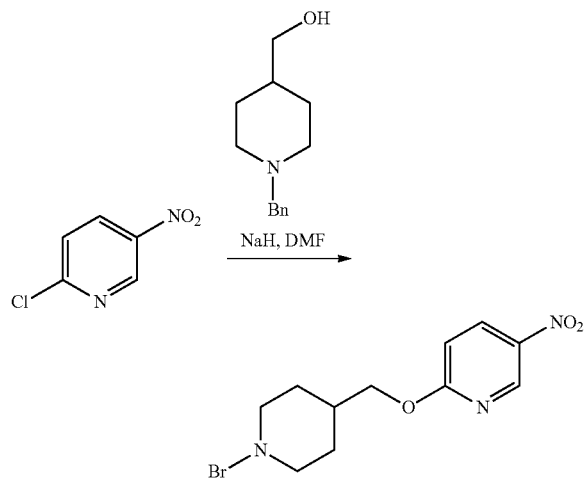

To a stirred solution of (1-benzylpiperidin-4-yl)methanol (1.29 g, 0.6.32 mmol) in DMF (5 mL) was added NaH (189 mg, 4.74 mmol) at 0° C. and reaction allowed to stir for 15 min. After 15 min. 2-chloro-5-nitropyridine (0.5 g, 03.16 mmol) was added to reaction mixture and reaction allowed to run for 2 h. Reaction was monitored by TLC. Reaction was quenched with ice cold water, extracted with ethyl acetate. The organic layer washed with water, brine dried over sodium sulphate and concentrated under reduced pressure to give crude. Crude was purified by silica gel (100-200 Mesh) column chromatography eluent 50% EA/Hexane to afford 2-((1-benzylpiperidin-4-yl)methoxy)-5-nitropyridine (0.4 g, 38.38%) as off white solid.
MS: 328.49 [M$^+$+1]

Step 3: Synthesis of 6-((1-benzylpiperidin-4-yl)methoxy)pyridin-3-amine

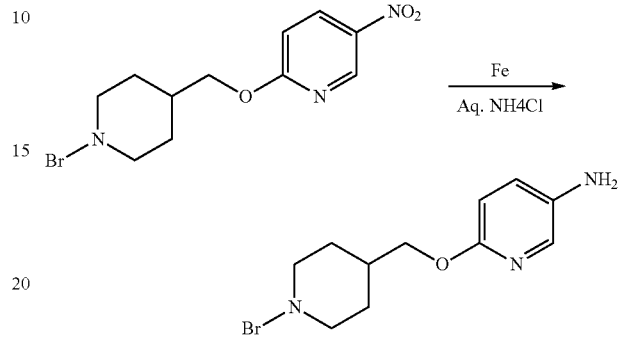

To a stirred solution of 2-((1-benzylpiperidin-4-yl) methoxy)-5-nitropyridine (0.4 g, 1.22 mmol) in EtOH (5 mL) was added iron power (0.269 g, 4.89 mmol), followed by addition of saturated aq. Solution of NH$_4$Cl (5 mL) and reaction was heated at 50° C. for 4 h. Reaction was monitored by TLC. On completion reaction mixture was filtered through celite bed with ethyl acetate. The filtrate was washed with water, brine dried over sodium sulphate and concentrated under reduced pressure to afford 6-((1-benzylpiperidin-4-yl)methoxy)pyridin-3-amine (0.32 g, 84.21%) as yellow solid. MS: 298.2 [M$^+$+1]

Step 4: Synthesis of 5-((1-benzylpiperidin-4-yl)methoxy)thiazolo[5,4-b]pyridin-2-amine

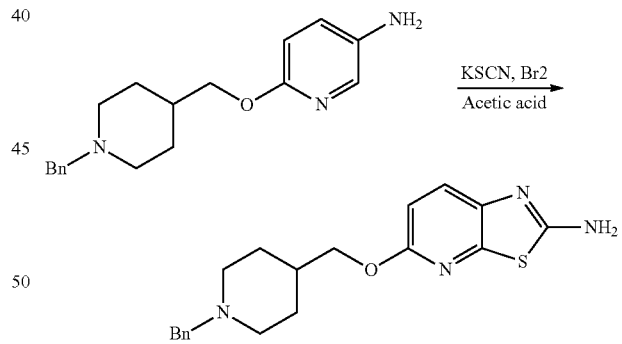

To a suspension of KSCN (0.065 g, 0.66 mmol) in acetic acid (4 mL) was added 6-((1-benzylpiperidin-4-yl)methoxy) pyridin-3-amine (0.05 g, 0.168 mmol) dissolved in acetic acid (1 mL) and reaction was allowed to stir at room temperature for 15 min. After for 15 min. bromine (0.01 mL, 0.21 mmol) dissolved in acetic acid (1 mL) was added to reaction drop wise at room temperature and reaction allowed to run at room temperature for 1 h. Reaction was monitored by TLC & MS. On completion water was added to reaction mixture. The solid so precipitated was filtered out, filtrate was concentrated under reduced pressure to give residue. Residue was extracted with ethylacetate. The organic layer was washed with aq. sol. of NaHCO3 (3×20 mL)), brine, dried over sodium sulphate and concentrated under reduced pressure to afford of 5-((1-benzylpiperidin-4-yl)methoxy)thiazolo[5,4-b]pyridin-2-amine (0.040 g, 67.67%) as red solid.

MS: 354.0 [M++1]

Step 5: Synthesis of 5-((1-benzylpiperidin-4-yl)methoxy)thiazolo[5,4-b]pyridin-2-amine

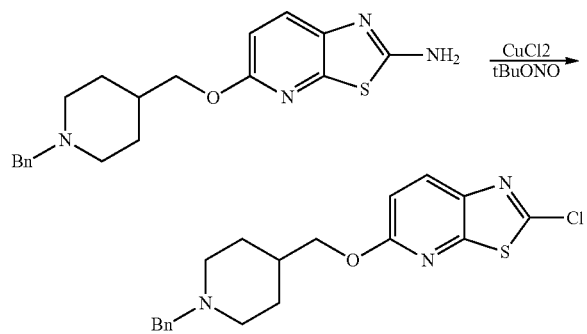

To a stirred solution of 5-((1-benzylpiperidin-4-yl)methoxy)thiazolo[5,4-b]pyridin-2-amine (0.3 g, 0.86 mmol) in ACN (4 ml) was added CuCl2 (169 mg, 1.27 mmol) at 0° C. After 15 min ᵗBuONO (0.15 ml, 1.27 mmol) was added to reaction mixture dissolved in CAN and reaction allowed to stir at room temperature for overnight. Reaction was monitored by TLC. On completion reaction mixture was concentrated under reduced pressure, added water, extracted with ethyl acetate. The organic layer was concentrated under reduced pressure to Afford 5-((1-benzylpiperidin-4-yl)methoxy)-2-chlorothiazolo[5,4-b]pyridine (0.8 g, 25.25%) as off white solid.

MS: 374.11 [M++1]

Step 6: Synthesis of 5-((1-benzylpiperidin-4-yl)methoxy)-2-(4-(methylsulfonyl)phenyl)thiazolo[5,4-b]pyridine

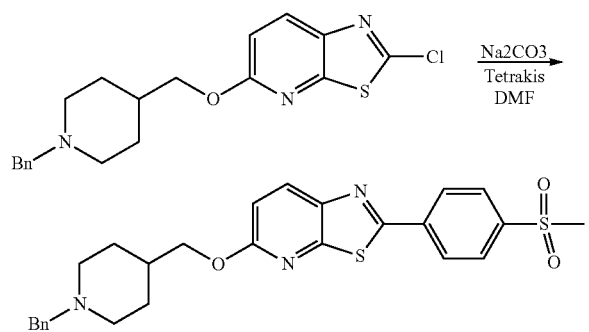

To a stirred solution of 5-((1-benzylpiperidin-4-yl)methoxy)-2-chlorothiazolo[5,4-b]pyridine (0.03 g, 0.08 mmol) and 4-(methylsulfonyl)phenylboronic acid (0.017 g, 0.08 mmol) in DMF (3 mL) was added Na₂CO₃ (0.025 g, 0.24 mmol) dissolved in water (1 mL), purged with nitrogen for 30 min. After 30 min Tetrakis (0.009 g, 0.008 mmol) was added to the reaction mixture then heated at 100° C. for overnight. Reaction was monitored by TLC. On completion reaction was quenched with water, extracted with ethyl acetate. The organic layer was concentrated reduced pressure to give crude which was purified by silica gel (100 to 200 mesh) column chromatography; eluant 5% CH₃OH/DCM to afford 5-((1-benzylpiperidin-4-yl)methoxy)-2-(4-(methylsulfonyl)phenyl)thiazolo[5,4-b]pyridine (0.0014 g, 3.58%) as pale yellow oily compound.

MS: 494.21 [M++1]

Example 5: isopropyl 4-(5-(4-(methylsulfonyl)phenyl)thiazolo[5,4-b]pyridin-2-yl) piperazine-1-carboxylate [1012]

Step-1 Synthesis of t-butyl 4-(5-bromothiazolo[5,4-b]pyridin-2-yl)piperazine-1-carboxylate

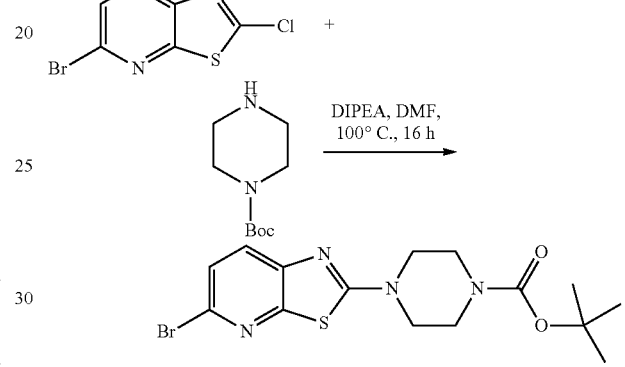

To a stirred solution of t-butyl piperazine-1-carboxylate (0.074 g, 0.400 mmol) in DMF (5 mL) was added DIPEA (0.155 g, 1.202 mmol) and stir at room temperature for 30 min. Then 5-bromo-2-chlorothiazolo[5,4-b]pyridine (0.1 g, 0.400 mmol) was added and stir at 120° C. for 16 h. Reaction was monitored by TLC. Reaction was quenched ice cold water, extracted with ethyl acetate. The organic layer was washed with brine, dried over sodium sulphate, concentrated under reduced pressure obtained crude which was purified by Silica (100-200 Mesh) column chromatography; eluent 15% EtOAc/Hexane to afford t-butyl 4-(5-bromothiazolo[5,4-b]pyridin-2-yl)piperazine-1-carboxylate (0.110 g, 68.75%) as off white solid.

MS: 399.02 [M++1]

Step-2 Synthesis of 5-bromo-2-(piperazin-1-yl)thiazolo[5,4-b]pyridine hydrochloride

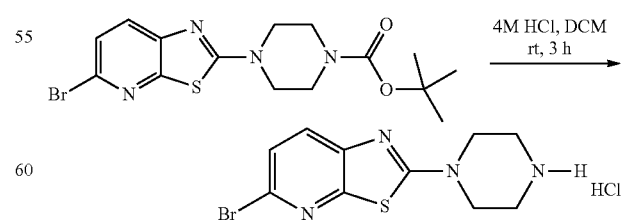

To a stirred solution of t-butyl 4-(5-bromothiazolo[5,4-b]pyridin-2-yl)piperazine-1-carboxylate (0.1 g, 0.250 mmol) in DCM (10 mL) was added 4M HCl in Dioxane (0.5 mL) and reaction allowed to stir at room temperature for 3 h.

Reaction was monitored by TLC. On completion reaction mixture was concentrated under reduced pressure to obtained 5-bromo-2-(piperazin-1-yl)thiazolo[5,4-b]pyridine hydrochloride (0.080 g, 95.23%) as off white solid.

MS: 299.2 [M$^+$+1]

Step-3 Synthesis of isopropyl 4-(5-bromothiazolo[5,4-b]pyridin-2-yl)piperazine-1-carboxylate

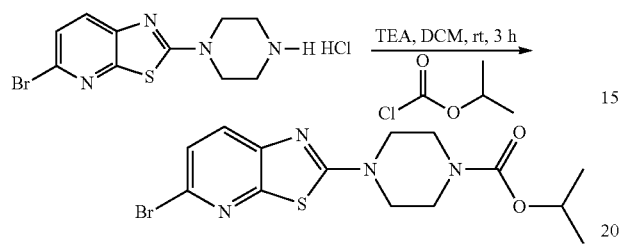

To a stirred solution of 5-bromo-2-(piperazin-1-yl)thiazolo[5,4-b]pyridine hydrochloride (0.08 g, 0.238 mmol) in DCM (10 mL) was added TEA (0.06 mL, 0.476 mmol) at 0° C. and reaction allowed to stir for 30 min. After 30 min Isopropyl chloroformate (2 M in toluene) (0.179 mL, 0.358 mmol) was added to it, stirred for 2 h. Reaction was monitored by TLC. On completion reaction was quenched with ice cold water, extracted with DCM. The organic layer was washed with water, brine, dried over Na$_2$SO$_4$, evaporated under reduced pressure obtained isopropyl 4-(5-bromothiazolo[5,4-b]pyridin-2-ylcarbamoyl)piperidine-1-carboxylate (0.050 g, 54.94%) as yellow solid.

MS: 385.03 [M$^+$+1]

Step-4 Synthesis of isopropyl 4-(5-(4-(methylsulfonyl)phenyl)thiazolo[5,4-b]pyridin-2-yl)piperazine-1-carboxylate

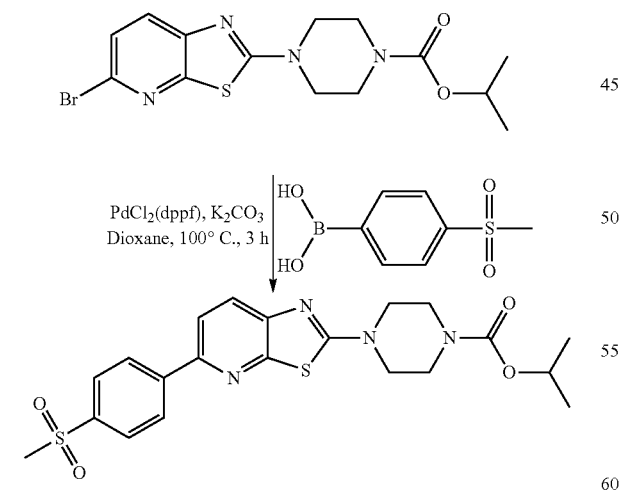

To a stirred solution of isopropyl 4-(5-bromothiazolo[5,4-b]pyridin-2-yl)piperazine-1-carboxylate (0.05 g, 0.129 mmol) and 4-(methylsulfonyl)phenylboronic acid (0.031 g, 0.155 mmol) in Dioxane (10 mL) was added K$_2$CO$_3$ (0.053 g, 0.389 mmol) in water (2 mL) and reaction mass was purged with nitrogen for 30 min. Then PdCl$_2$(dppf) (0.009 g, 0.0129 mmol) was added to it and stir at 100° C. for 3 h. Reaction was monitored by TLC. On completion reaction mass was concentrated under reduced pressure obtained crude which was purified by Neutral alumina column chromatography; eluent 30% EtOAc/Hexane to afford isopropyl 4-(5-(4-(methylsulfonyl)phenyl)thiazolo[5,4-b]pyridin-2-yl)piperazine-1-carboxylate (0.042 g, 70.00%) as off white solid.

MS: 460.2 [M$^+$+1]

Example 6: Isopropyl (5-(4-(methylsulfonyl)phenyl) thiazolo[5,4-b]pyridin-2-yl) carbonate [1019]

Step 1: Synthesis of t-butyl 4-formylpiperidine-1-carboxylate

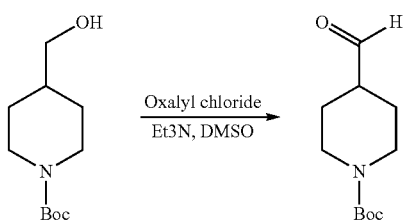 [SMILES: CC(C)(C)OC(=O)N1CCC(CO)CC1 ; CC(C)(C)OC(=O)N1CCC(C=O)CC1]

To a stirred solution of DCM (5 mL) was added oxalyl chloride (0.59 mL, 6.97 mmol) at –78° C. and reaction allowed to stir at –78° C. for 15 min. After 15 min DMSO (0.75 mL, 10.69 mmol) was added slowly dropwise then reaction allowed to stir at –78° C. for 15 min. After 15 min. t-butyl 4-(hydroxymethyl)piperidine-1-carboxylate (1.0 g, 4.65 mmol) was added to reaction mixture dissolved in DCM (5 mL) at –78° C. and reaction allowed to stir at this temp. For 30 min. After 30 min TEA (3.2 mL, 23.25 mmol) was added to reaction mixture then stir at –78° C. for 30 min. Reaction was monitored by TLC. Reaction was quenched with water, extracted DCM. The organic layer was washed with brine, dried over sodium sulphate and concentrated under reduced pressure to afford of t-butyl 4-formylpiperidine-1-carboxylate (0.99 g, 98.98%) as off white solid. MS: 214.2 [M$^+$+1]

Step 2: Synthesis of t-butyl 4-(1-hydroxyethyl)piperidine-1-carboxylat

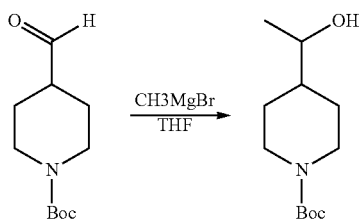

To a stirred solution of t-butyl 4-formylpiperidine-1-carboxylate (0.5 g, 2.34 mmol) in THF (10 mL) was added MeMgBr (1.5M in THF) (3 mL, 4.68 mmol at 0° C. and reaction allowed to stir at room temperature for 1 h. Reaction was monitored by TLC. Reaction was quenched with aq. NH$_4$Cl, extracted with ethyl acetate. The organic layer was washed with brine, dried over sodium sulphate and concentrated under reduced pressure to give 525 mg (97.7%) of t-butyl 4-(1-hydroxyethyl)piperidine-1-carboxylate. MS: 230.2 [M⁺+1]

Step 3: Synthesis of t-butyl 4-(1-(5-bromothiazolo [5,4-b]pyridin-2-yloxy)ethyl)piperidine-1-carboxylate

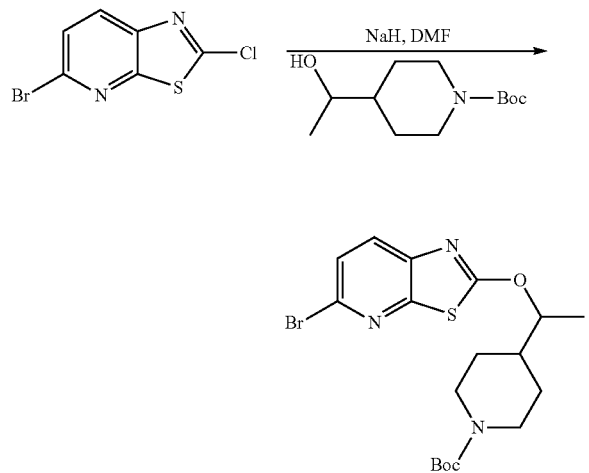

To a stirred solution of t-butyl 4-(1-hydroxyethyl)piperidine-1-carboxylate (0.520 g, 2.27 mmol) in DMF (5 mL) was added sodium hydride (0.113 g, 2.84 mmol) at 0° C. and reaction allowed to stir at room temperature for 30 min. After 30 min 5-bromo-2-chlorothiazolo[5,4-b]pyridine (0.470 g, 1.89 mmol) dissolved in DMF (2 mL) was added to the reaction mixture at 0° C. and reaction allowed to stir at room temperature for 2 hr. Reaction was monitored by TLC. On completion reaction was quenched with ice cold water extracted with ethylacetate. Organic layer was washed with water, brine dried over sodium sulphate and concentrated under reduced pressure to give crude. Purification of the crude was done by silica gel (100-200 mesh) column chromatography; eluant 25% EA/hexane to afford t-butyl 4-(1-(5-bromothiazolo[5,4-b]pyridin-2-yloxy)ethyl)piperidine-1-carboxylate (0.25 g, 29.90%) as pale yellow solid. MS: 442.2 [M⁺+1]

Step 4: Synthesis of t-butyl 4-(1-(5-(4-(methylsulfonyl)phenyl)thiazolo[5,4-b]pyridin-2-yloxy)ethyl) piperidine-1-carboxylate

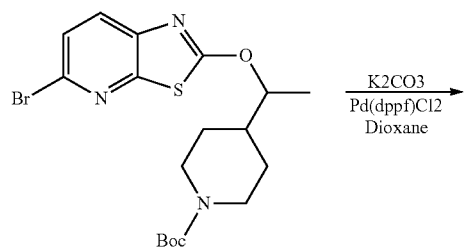

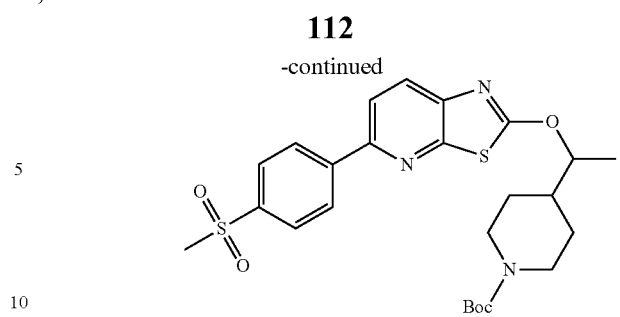

To a stirred solution of t-butyl 4-(1-(5-bromothiazolo[5,4-b]pyridin-2-yloxy)ethyl)piperidine-1-carboxylate (0.150 g, 0.346 mmol) and 4-(methylsulfonyl)phenylboronic acid (0.074 g, 0.37 mmol) in dioxane (6 mL) was added K₂CO₃ (0.093 g, 0.62 mmol) dissolved in water (1.5 mL) and reaction was purged with nitrogen for 30 min. After 30 min Pd(dppf)Cl₂ (0.012 g, 0.017 mmol) was added to reaction mixture then heated at 100° C. for 1 hrs. Reaction was monitored by MS. On completion reaction was quenched with water, extracted with ethyl acetate. Organic layer was washed with water, brine dried over sodium sulphate and concentrated under reduced pressure to give crude. Purification of the crude was done by silica gel (100-200 mesh) column chromatography; eluant 30% ethyl acetate/hexane to obtained t-butyl 4-(1-(5-(4-(methylsulfonyl)phenyl)thiazolo [5,4-b]pyridin-2-yloxy)ethyl)piperidine-1-carboxylate (0.090 g, 51.4%) as pale yellow solid. MS: 518.2 [M⁺+1]

Step 5: Synthesis of 5-(4-(methylsulfonyl)phenyl) thiazolo[5,4-b]pyridin-2-ol hydrochloride

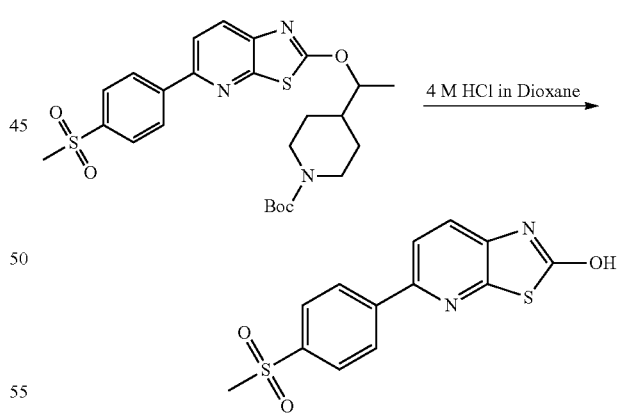

To a stirred solution of 4-(1-(5-(4-(methylsulfonyl)phenyl)thiazolo[5,4-b]pyridin-2-yloxy)ethyl)piperidine-1-carboxylate (0.09 g, 0.17 mmol) in DCM (3 mL) was added 4 M HCl in Dioxane (2 mL) then stir at room temperature for 1 hr. Reaction was monitored by TLC. On completion reaction mixture was concentrated under reduced pressure to afford 5-(4-(methylsulfonyl)phenyl)thiazolo[5,4-b]pyridin-2-ol hydrochloride (0.059 g, 84.70%) as off white solid. MS: 307.2 [M⁺+1]

Step 6: synthesis of isopropyl 5-(4-(methylsulfonyl)phenyl)thiazolo[5,4-b]pyridin-2-yl carbonate

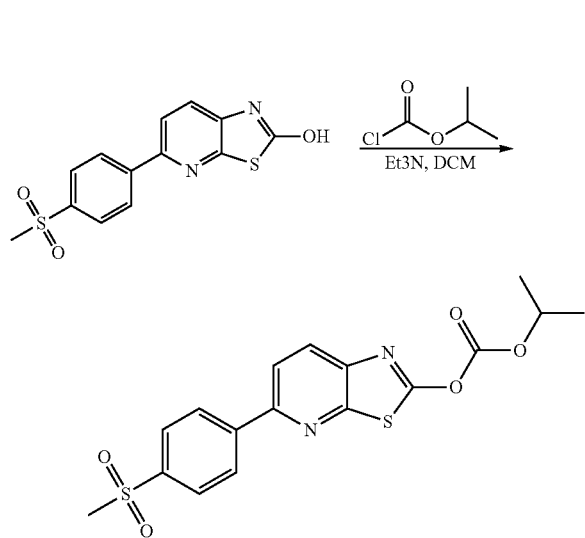

To a stirred solution of 5-(4-(methylsulfonyl)phenyl)thiazolo[5,4-b]pyridin-2-ol hydrochloride (0.030 g, 0.09 mmol) DCM (5 mL) was added Et3N (0.04 mL, 0.29 mmol) at 0° C. and reaction allowed to stir at room temperature for 15 min. After 15 min Ethyl chloroformate (0.023 g, 0.18 mmol) was added to reaction mixture then stir at room temperature for 30 min. On completion reaction was quenched with extracted with DCM. Organic layer was washed with water, brine dried over sodium sulphate and concentrated under reduced pressure to give crude. Purification of the crude was done by silica gel (100-200 mesh) column chromatography eluent 40% ethyl acetate/hexane to obtained isopropyl 5-(4-(methylsulfonyl)phenyl)thiazolo[5,4-b]pyridin-2-yl carbonate (0.0056 g, 14.73%) as off white solid. MS: 393.02 [M$^+$+1]

Example 7: 4-(2-(4-(3-isopropyl-1,2,4-oxadiazol-5-yl)piperidin-1-yl)thiazolo[5,4-b]pyridin-5-yl)-N,N-dimethylbenzamide [1022]

Step 1: Synthesis of 5-bromo-2-(4-(3-isopropyl-1,2,4-oxadiazol-5-yl)piperidin-1-yl)thiazolo[5,4-b]pyridine

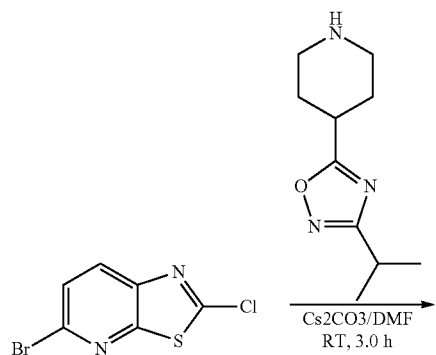

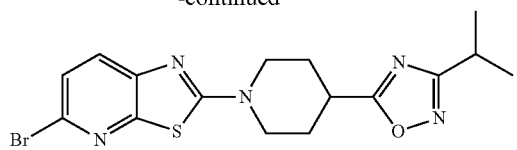

To a stirred soln. of 4-(3-isopropyl-1,2,4-oxadiazol-5-yl)piperidine (0.13 gm, 0.65 mmol) in DMF (6 ml), Cs2CO3 (0.631 gm, 1.94 mmol) at 0° C. was added and reaction allowed to run at 0° C. for 30.0 min. then 5-bromo-2-chlorothiazolo[5,4-b]pyridine (0.16 gm, 0.65 mmol) was added to reaction mixture and reaction warmed up to RT for next 3.0 h. Reaction was monitored by TLC. On completion reaction mixture was quenched with ice cold water and compound was extracted with ethyl acetate. The organic layer was washed with water, brine, dried over sodium sulphate and concentrated under reduced pressure to give crude desired product that was purified by silica gel (100-200 mess) column chromatography, compound was eluted in 20% ethyl acetate in hexane that was concentrated to get compound 5-bromo-2-(4-(3-isopropyl-1,2,4-oxadiazol-5-yl)piperidin-1-yl)thiazolo[5,4-b]pyridine (0.16 gm, 60.89%) as light yellow semisolid.

MS: 408.04 [M$^+$+1].

Step 2: Synthesis of 4-(2-(4-(3-isopropyl-1,2,4-oxadiazol-5-yl)piperidin-1-yl)thiazolo[5,4-b]pyridin-5-yl)benzoic Acid

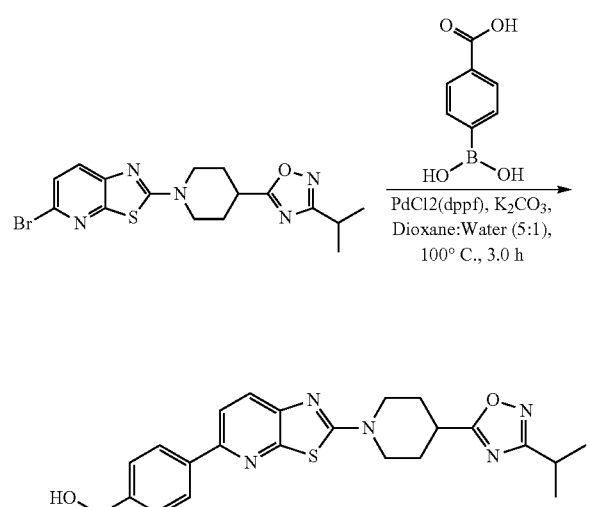

To a stirred soln. of 5-bromo-2-(4-(3-isopropyl-1,2,4-oxadiazol-5-yl)piperidin-1-yl)thiazolo[5,4-b]pyridine (0.1 gm, 0.25 mmol) and corresponding Boronic acid (0.045 gm, 0.27 mmol) in Dioxane (5 ml), K₂CO₃ (0.102 gm, 0.74 mmol) dissolved in water (1 ml) was added and reaction purged with nitrogen for 30 min. After 30 min Pd(dppf)Cl2 (0.009 mg, 0.01 mmol) was added to the reaction mixture and reaction heated at 100° C. for 3.0 h. Progress of reaction was monitored by TLC. On completion reaction was quenched with water and extracted with ethyl acetate. The organic layer was concentrated under reduced pressure to give crude desired compound. Purification of the compound was done by silica gel (100-200 mess) column chromatography using 35% ethyl acetate in hexane that was concentrated to get compound 4-(2-(4-(3-isopropyl-1,2,4-oxadiazol-5-yl)piperidin-1-yl)thiazolo[5,4-b]pyridin-5-yl)benzoic acid (0.06 gm, 54.38%) as white solid.

MS: 450.15 [M⁺+1].

Step 3: Synthesis of 4-(2-(4-(3-isopropyl-1,2,4-oxadiazol-5-yl)piperidin-1-yl)thiazolo[5,4-b]pyridin-5-yl)-N,N-dimethylbenzamide (1022)

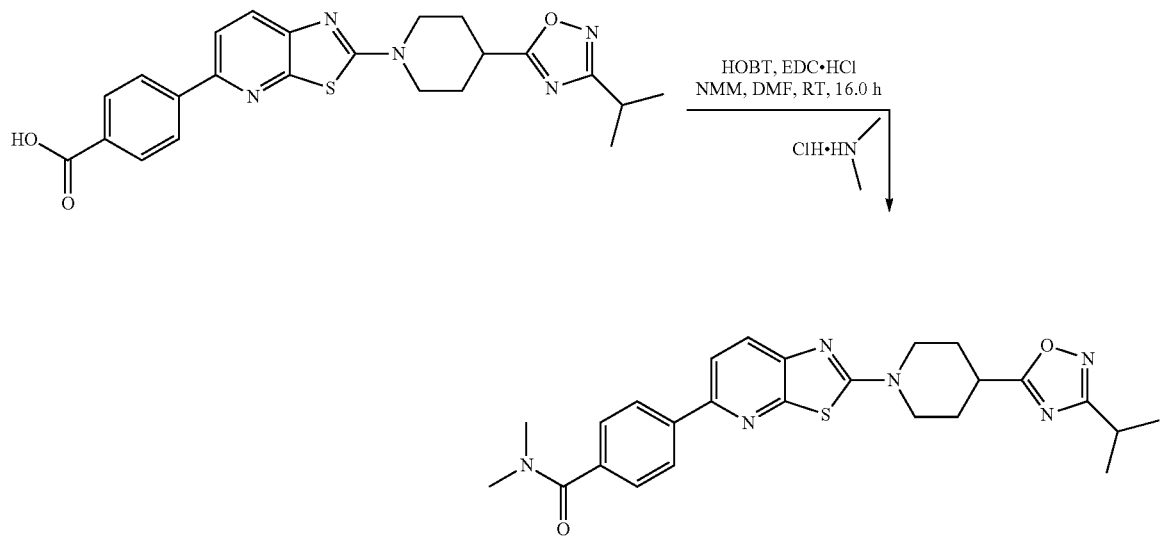

To a stirred soln. of 4-(2-(4-(3-isopropyl-1,2,4-oxadiazol-5-yl)piperidin-1-yl)thiazolo[5,4-b]pyridin-5-yl)benzoic acid (0.03 gm, 0.07 mmol) and dimethylamine hydrochloride (0.008 gm, 0.10 mmol) in DMF (5.0 ml), HOBT (0.015 gm, 0.10 mmol), EDC.HCl (0.019 gm, 0.10 mmol) and NMM (0.04 ml, 0.33 mmol) were added and reaction allowed to run at RT for 16.0 h. Progress of reaction was monitored by TLC. On completion reaction mixture was quenched with chilled water and compound was extracted with ethyl acetate. The organic layer was concentrated under reduced pressure to give crude compound. Purification of the crude was done by silica gel (100-200 mess) column chromatography; eluent 15% ethyl acetate in hexane that was concentrated to get compound 4-(2-(4-(3-isopropyl-1,2,4-oxadiazol-5-yl)piperidin-1-yl)thiazolo[5,4-b]pyridin-5-yl)-N,N-dimethylbenzamide MKP10052.01 (0.02 gm, 62.87%) as white solid.

MS: 477.20 [M⁺+1].

Example 8: N-(3-fluoro-4-(methylsulfonyl)phenyl)-2-(4-(3-isopropyl-1,2,4-oxadiazol-5-yl)piperidin-1-yl)thiazolo[5,4-b]pyridin-5-amine [1025]

Step 1: Synthesis of N-(3-fluoro-4-(methylsulfonyl)phenyl)-5-nitropyridin-2-amine

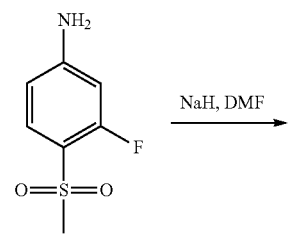

-continued

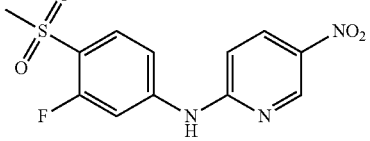

To a stirred solution of 3-fluoro-4-(methylsulfonyl)benzenamine (0.051 g, 0.27 mmol) in DMF (2 mL) was added NaH (0.019 g, 0.49 mmol) at 0° C. and reaction allowed to stir for 15 min. After 15 min. 2-bromo-5-nitropyridine (50 mg, 0.24 mmol) was added to reaction mixture and then to stir at room temperature for 1 h. Reaction was monitored by TLC. Reaction was quenched with ice cold water, extracted with ethyl acetate. The organic layer washed with water, brine dried over sodium sulphate and concentrated under reduced pressure to give crude. Crude was diluted with ethylacetate and organic layer washed with cold 1N HCl solution several times. The organic layer was dried over sodium sulphate and concentrated under reduced pressure to obtained of N-(3-fluoro-4-(methylsulfonyl)phenyl)-5-nitropyridin-2-amine (0.035 g, 46.05%) as off white solid.

MS: 311.93 [M⁺+1]

Step 2: Synthesis of 6-(3-fluoro-4-(methylsulfonyl)phenoxy)pyridin-3-amine

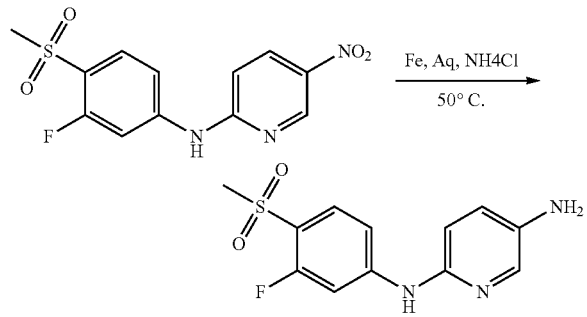

To a stirred solution of N-(3-fluoro-4-(methylsulfonyl)phenyl)-5-nitropyridin-2-amine (0.350 g, 1.12 mmol) in EtOH (10 mL) was added iron power (0.310 g, 5.64 mmol), followed by addition of saturated aq. sol. of NH₄Cl (5 mL) then heated at 50° C. for 2 h. Reaction was monitored by TLC. On completion reaction mixture was filtered through celite bed with ethylacetate. The filtrate was washed with water, brine dried over sodium sulphate and concentrated under reduced pressure to obtained 6-(3-fluoro-4-(methylsulfonyl)phenoxy)pyridin-3-amine (0.290 g, 91.40%) as brown solid.

MS: 283.1 [M⁺+1]

Step 3: Synthesis of N-5-(3-fluoro-4-(methylsulfonyl)phenyl)thiazolo[5,4-b]pyridine-2,5-diamine

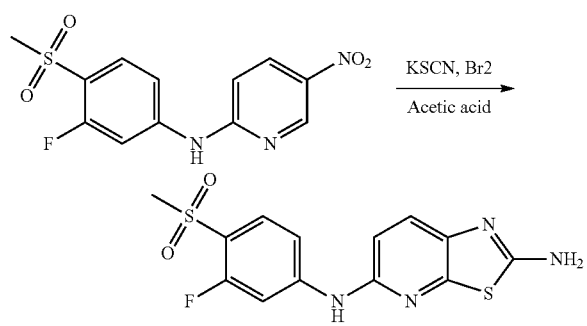

To a suspended of KSCN (0.274 g, 2.81 mmol) in acetic acid (4 mL) was added 6-(3-fluoro-4-(methylsulfonyl)phenoxy)pyridin-3-amine (0.020 g, 0.71 mmol) dissolved in acetic acid (1 mL) and reaction was allowed to stir at room temperature for 15 min. After for 15 min. Bromine (0.04 mL, 0.92 mmol) dissolved in acetic acid (1 mL) was added to reaction drop wise at −20° C. Reaction was allowed to stir at −20° C. for 15 min. After 15 min. it was brought to room temperature then stir at room temperature for 1 h. Reaction was monitored by TLC & MS. On completion water was added to reaction mixture. The solid so precipitated was filtered out, filtrate was concentrated under reduced pressure to give residue. Residue was extracted with ethylacetate. The organic layer was washed with aq. sol. of NaHCO₃ (3×50 ml), brine, dried over sodium sulphate and concentrated under reduced pressure to afford N-5-(3-fluoro-4-(methylsulfonyl)phenyl)thiazolo[5,4-b]pyridine-2,5-diamine (0.15 g, 62.5%) as brown solid.

MS: 340.0 [M⁺+1]

Step 4: Synthesis of 2-chloro-N-(3-fluoro-4-(methylsulfonyl)phenyl) thiazolo[5,4-b]pyridin-5-amine

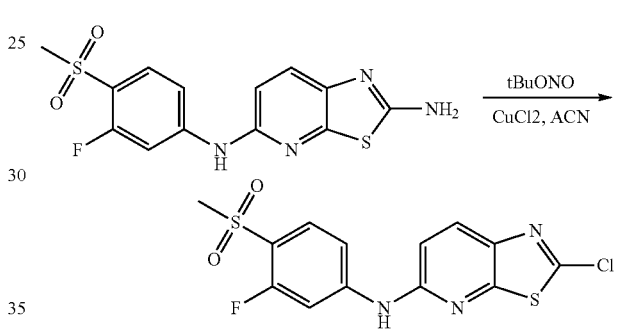

To a stirred solution of N-5-(3-fluoro-4-(methylsulfonyl)phenyl)thiazolo[5,4-b]pyridine-2,5-diamine (0.075 g, 0.22 mmol) in ACN (3 mL) was added CuCl₂ (0.044 g, 4.59 mmol) at 0° C. After 15 min ᵗBuONO (0.03 mL, 0.32 mmol) was added to reaction mixture dissolved in ACN, reaction allowed to stir at room temperature for overnight. Reaction was monitored by TLC. On completion reaction mixture was concentrated under reduced pressure added water, extracted with ethyl acetate. The organic layer was concentrated under reduced pressure to give crude desired product that was purified by silica gel (100-200 mesh) column chromatography eluent 15% ethylacetate/hexane to afford 2-chloro-N-(3-fluoro-4-(methylsulfonyl)phenyl)thiazolo[5,4-b]pyridin-5-amine (0.035 g, 44.8%) as white solid.

MS: 358.0 [M⁺+1]

Step 5: Synthesis of N-(3-fluoro-4-(methylsulfonyl)phenyl)-2-(4-(3-isopropyl-1,2,4-oxadiazol-5-yl)piperidin-1-yl)thiazolo[5,4-b]pyridin-5-amine

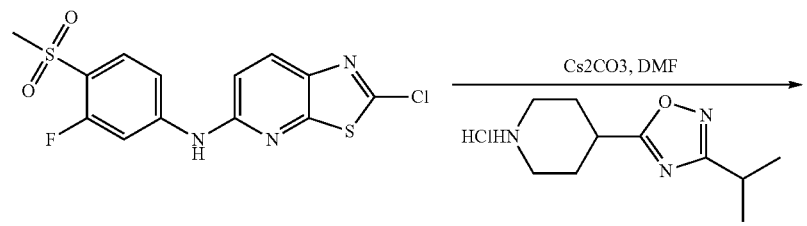

-continued

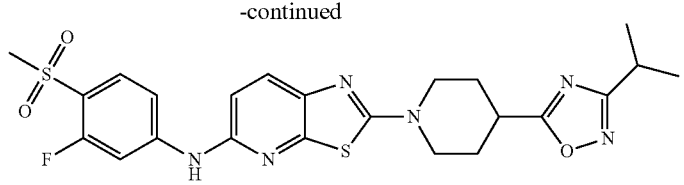

To mixture of 2-chloro-N-(3-fluoro-4-(methylsulfonyl) phenyl)thiazolo[5,4-b]pyridin-5-amine (0.030 g, 0.08 mmol) and 4-(3-isopropyl-1,2,4-oxadiazol-5-yl)piperidine HCl salt (0.021 g, 0.09 mmol) in DMF (2 mL) Cs$_2$CO$_3$ (0.081 g, 0.25 mmol) was added followed by heating at 70° C. for overnight. Reaction was monitored by TLC. On completion reaction mixture was quenched with water, extracted with ethyl acetate. The organic layer was washed with water, brine, dried over sodium sulphate and concentrated under reduced pressure to give crude desired product that was purified by silica gel (100 to 200 Mesh column) chromatography; eluent 22% acetone/hexane to afford N-(3-fluoro-4-(methylsulfonyl)phenyl)-2-(4-(3-isopropyl-1,2,4-oxadiazol-5-yl)piperidin-1-yl)thiazolo[5,4-b]pyridin-5-amine (0.0028 g, 6.5%) as off white solid.

MS: 517.1 [M$^+$+1]

Example 9: N,N-dimethyl-4-(5-(4-(methylsulfonyl) phenyl)thiazolo[5,4-b]pyridin-2-yl)piperidine-1-carboxamide [1028]

Step 1: Synthesis of 5-(4-(methylsulfonyl)phenyl)-2-(piperidin-4-yl)thiazolo[5,4-b]pyridine hydrochloride

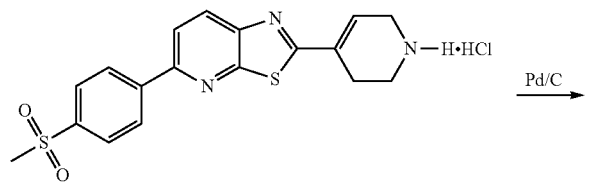

To a stirred solution of 2-(1,2,3,6-tetrahydropyridin-4-yl)-5-(4-(methylsulfonyl)phenyl)thiazolo[5,4-b]pyridine hydrochloride (0.02 g, 0.049 mmol) in methanol (3 mL) was added Pd/C (0.006 g, 0.3% wt/wt) and hydrogenated with hydrogen bladder for 30 min. Progress of the reaction was monitored by TLC. After reaction completion reaction mass filtered through celite and filtrate was evaporated under reduced pressure to give 5-(4-(methylsulfonyl)phenyl)-2-(piperidin-4-yl)thiazolo[5,4-b]pyridine hydrochloride (0.02 g, 100%) as white solid.

MS: 410.9 [M$^+$+1]

Step 2: Synthesis of N,N-dimethyl-4-(5-(4-(methylsulfonyl)phenyl)thiazolo[5,4-b]pyridin-2-yl)piperidine-1-carboxamide

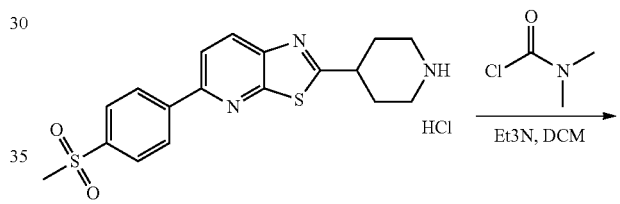

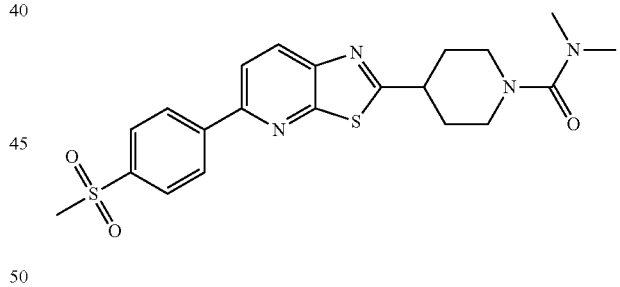

To a stirred solution of 2-(1,2,3,6-tetrahydropyridin-4-yl)-5-(4(methylsulfonyl) phenyl)thiazolo[5,4-b]pyridine hydrochloride (0.02 g, 0.049 mmol) in DCM (3 mL) was added Et3N (0.02 mL, 0.146 mmol) at 0° C. and reaction allowed to stir at room temperature for 15 min. After 15 min dimethylcarbamic chloride (0.056 g, 0.053 mmol) was added to reaction mixture and reaction allowed to stir at room temperature for 4 h. Progress of the reaction was monitored by TLC. After reaction completion reaction was quenched with water and extracted with DCM. Organic layer was washed with water, brine, dried over sodium sulphate and concentrated under reduced pressure to give crude. Crude was purified by silica gel (100-200 mesh) column chromatography using 40% ethyl acetate in hexane as eluent to give N,N-dimethyl-4-(5-(4-(methylsulfonyl) phenyl)thiazolo[5,4-b]pyridin-2-yl)piperidine-1-carboxamide (0.01 g, 46%) as white solid. MS: 445.5 [M$^+$+1]

Example 10: 3-cyclopropyl-5-(4-((5-(4-(methylsulfonyl)phenyl)thiazolo[5,4-b]pyridin-2-yl)oxy)piperidin-1-yl)-1,2,4-oxadiazole [1033]

Step 1: Synthesis of 1-(3-cyclopropyl-1,2,4-oxadiazol-5-yl)piperidin-4-one

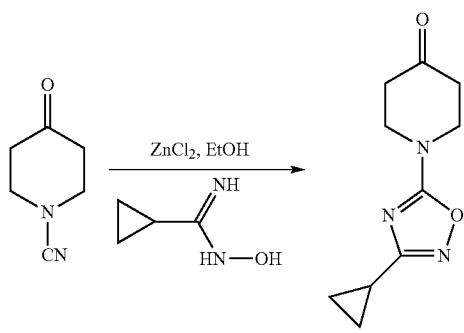

To a solution of 4-oxopiperidine-1-carbonitrile (0.15 g, 0.24 mmol) and N-hydroxycyclopropane carboxamidine (0.15 g, 0.29 mmol) in ethanol (10 mL) was added zinc chloride (0.094 g, 0.29 mmol) and the mixture was stirred at room temperature for 3 h. Conc. HCl (0.6 mL, 0.717 mmol) was then added to it and heated at 60° C. for 16 h. Progress of reaction was monitored by TLC. After reaction completion solvents were removed under reduced pressure to dryness. Residue was dissolved in sat. aq. NaHCO$_3$ solution, extracted with ethyl acetate. Combined organic layer was washed with brine, dried over sodium sulphate and concentrated under reduced pressure to give 1-(3-cyclopropyl-1,2,4-oxadiazol-5-yl)piperidin-4-one (0.13 g, 52%) as yellow oil.

MS: 208.23 [M$^+$+1]

Step 2: Synthesis of 1-(3-cyclopropyl-1,2,4-oxadiazol-5-yl)piperidin-4-ol

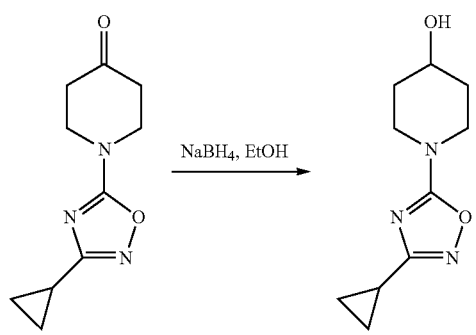 [SMILES: O=C1CCN(c2nc(C3CC3)no2)CC1 ; OC1CCN(c2nc(C3CC3)no2)CC1]

To a stirred solution of 1-(3-cyclopropyl-1,2,4-oxadiazol-5-yl)piperidin-4-one (0.13 g, 0.62 mmol) in ethanol (2 mL) was added sodiumborohydride (0.014 g, 0.376 mmol) and the mixture was stirred at room temperature for 3 h. Progress of reaction was monitored by TLC. After reaction completion water (5 mL) was added to the reaction mixture and the product extracted with ethyl acetate. The organic layer was dried over sodium sulphate, concentrated under reduced pressure to give 1-(3-cyclopropyl-1,2,4-oxadiazol-5-yl)piperidin-4-ol (0.09 g, 68.93%) as reddish brown solid. MS: 210.24 [M$^+$+1]

Step 3: Synthesis of 2-(1-(3-cyclopropyl-1,2,4-oxadiazol-5-yl)piperidin-4-yloxy)-5-bromothiazolo[5,4-b]pyridine

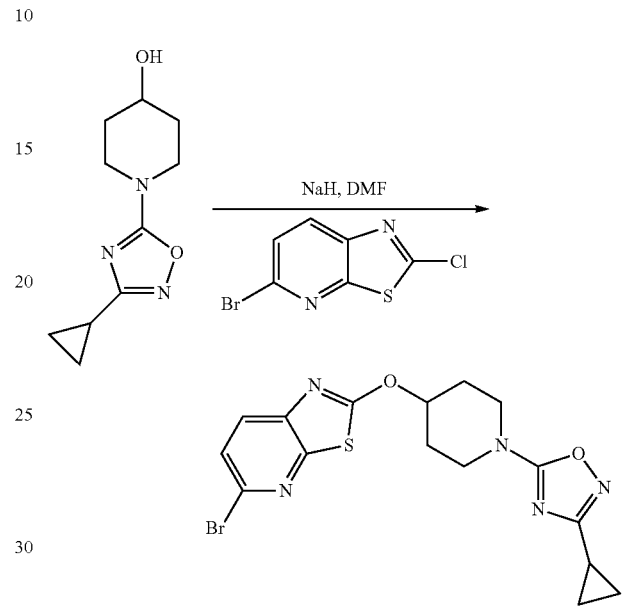

To a stirred solution of solution of compound 1-(3-cyclopropyl-1,2,4-oxadiazol-5-yl)piperidin-4-ol (0.09 g, 0.04 mmol) in DMF (1 mL) was added sodium hydride (0.019 g, 0.08 mmol) at 0° C. and reaction allowed to stir for 30 min at room temperature. After 30 min solution of 5-bromo-2-chlorothiazolo[5,4-b]pyridine (0.089 g, 0.044 mmol) in DMF (1 mL) was added to the reaction mixture and stirred for 1 h at room temperature. Progress of reaction was monitored by TLC. After reaction completion reaction mass was quenched with ice cold water and extracted with ethyl acetate. The organic layer was washed with water, brine, dried over sodium sulphate, concentrated under reduced pressure to give 2-(1-(3-cyclopropyl-1,2,4-oxadiazol-5-yl)piperidin-4-yloxy)-5-bromothiazolo[5,4-b]pyridine (0.07 g, 46%) as brown solid.

MS: 423.3 [M$^+$+1]

Step 4: Synthesis of 2-(1-(3-cyclopropyl-1,2,4-oxadiazol-5-yl)piperidin-4-yloxy)-5-(4-(methylsulfonyl)phenyl)thiazolo[5,4-b]pyridine

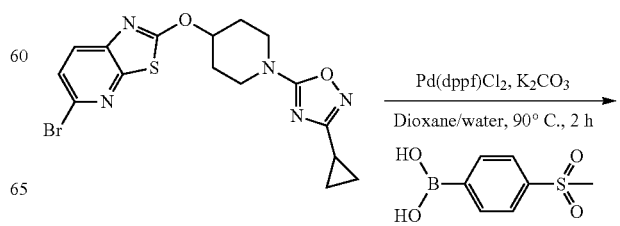

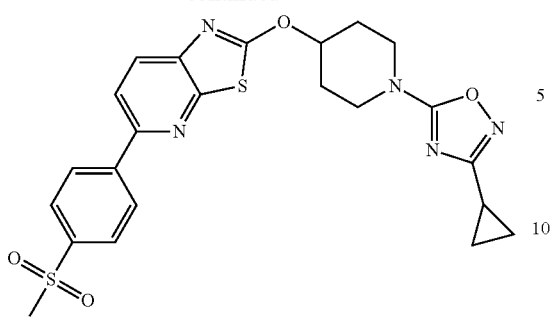

To a stirred solution of 2-(1-(3-cyclopropyl-1,2,4-oxadiazol-5-yl)piperidin-4-yloxy)-5-bromothiazolo[5,4-b]pyridine (0.025 g, 0.0592 mmol) and 4-(methylsulfonyl)phenylboronic acid (0.013 g, 0.0651 mmol) in dioxane (4 mL) was added solution of $K_2CO_3$ (0.016 g, 0.118) in water (1 mL) and the resulting mixture was purged with nitrogen for 30 min. After 30 min Pd(dppf)Cl$_2$ (0.002 g, 0.0029 mmol) was added to it and the mixture was heated at 90° C. for 2 h. Progress of reaction was monitored by TLC. After reaction completion reaction mass was diluted with water and extracted with ethyl acetate. The organic layer was washed with brine, dried over sodium sulphate and concentrated under reduced pressure to give crude product. Crude was purified by silica gel (100-200#) column chromatography using 30-40% ethyl acetate in hexane as eluent to yield 2-(1-(3-cyclopropyl-1,2,4-oxadiazol-5-yl)piperidin-4-yloxy)-5-(4-(methylsulfonyl)phenyl) thiazolo[5,4-b]pyridine (0.004 g, 13.6%) as white solid.

MS: 498.59 [M$^+$+1]

Example 11: 3-isopropyl-5-(4-(2-methoxy-1-((5-(4-(methylsulfonyl)phenyl) thiazolo[5,4-b]pyridin-2-yl)oxy)ethyl)piperidin-1-yl)-1,2,4-oxadiazole [1036]

Step-1: Synthesis of ethyl piperidine-4-carboxylate hydrochloride

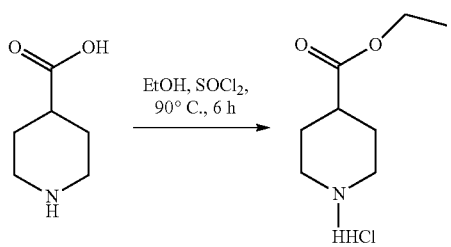

To a stirred solution of piperidine-4-carboxylic acid (10.0 g) in ethanol (500 mL), added SOCl$_2$ dropwise at 0° C., then reaction mixture was heated at 90° C. for 6 h, Reaction was monitored by TLC. On completion all volatiles were evaporated obtained sticky mass, triturated with pentane, Solid ppt out which was filtered off, solid dried under vacuum to afford ethyl piperidine-4-carboxylate hydrochloride (12.0 g, 80.05%) as off white solid.

MS: 158.11 [M$^+$+1]

Step-2: Synthesis of t-butyl ethyl piperidine-1,4-dicarboxylate

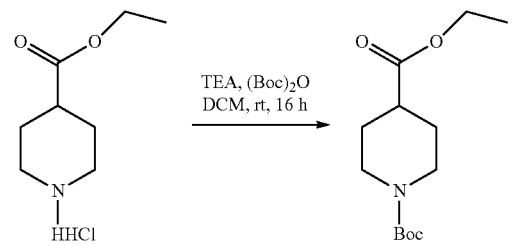

To a stirred solution of ethyl piperidine-4-carboxylate hydrochloride (12.0 g, 62.33 mmol) in DCM (200 mL) was added TEA (18.92 g, 187.01 mmol) dropwise at room temperature and reaction allowed to stir for 15 min. After 15 min Boc anhydride (20.40 g, 93.50 mmol) was added it and stirred for 16 h. Reaction was monitored by TLC. On completion reaction was quenched with water, extracted with DCM. The organic layer was washed with water, NaHCO$_3$, brine, dried over Na$_2$SO$_4$, evaporated under reduced pressure obtained t-butyl ethyl piperidine-1,4-dicarboxylate (20.15 g, 92.98%) as white solid.

MS: 258.16 [M$^+$+1]

Step-3: Synthesis of t-butyl 4-(hydroxymethyl)piperidine-1-carboxylate

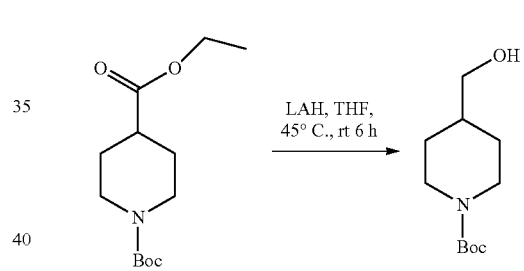

To a stirred solution of t-butyl ethyl piperidine-1,4-dicarboxylate (20 g, 77.72 mmol) in THF (200 mL) was added LAH (14.74 g, 0.926 mmol) at 0° C. and reaction allowed to stir at 45° C. for 6 h. Reaction was monitored by TLC. On completion reaction mass was diluted with EtOAc, water and extracted with EtOAc. The organic layer was washed with water, brine, dried over Na$_2$SO$_4$, and evaporated under reduced pressure obtained t-butyl 4-(hydroxymethyl) piperidine-1-carboxylate (12.15 g, 72.53%) as white solid.

MS: 216.15 [M$^+$+1]

Step-4: Synthesis of (piperidin-4-yl)methanol hydrochloride

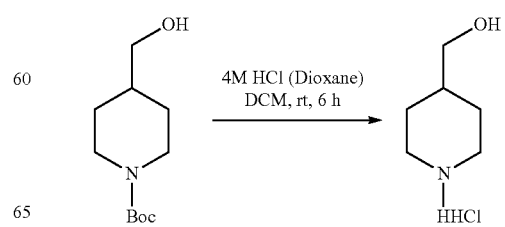

To a stirred solution of t-butyl 4-(hydroxymethyl) piperidine-1-carboxylate (12 g, 0.439 mmol) in DCM (10 mL) was added 4 M HCl in Dioxane (50 mL) and reaction allowed to stir at room temperature for 6 h. Reaction was monitored by TLC. On completion reaction mixture was concentrated under reduced pressure obtained (piperidin-4-yl) methanol hydrochloride (6.2 g, 77.00%) as white solid.
MS: 116.2 [M++1]

Step-5: 4-(hydroxymethyl) piperidine-1-carbonitrile

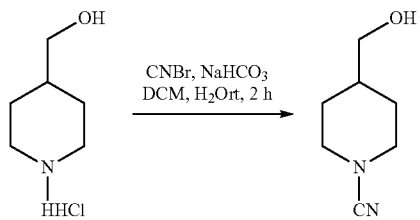

To a stirred solution of c (piperidin-4-yl) methanol hydrochloride (3.2 g, 21.09 mmol) in DCM (100 ml) was added NaHCO$_3$ (5.31 g, 63.29 mmol) in water (2 mL) at room temperature and reaction allowed to stir for 15 min. After 15 min CNBr (2.68 g, 25.31 mmol) was added to reaction mass and stirred for 2 h. Reaction was monitored by TLC. On completion, reaction was quenched with water, extracted with DCM. The organic layer was washed with water, brine, dried over Na$_2$SO$_4$, evaporated under reduced pressure obtained 4-(hydroxymethyl) piperidine-1-carbonitrile (2.8 g, 96.55% yield) as light yellow sticky mass.
MS: 141.18 [M++1]

Step-6: (1-(3-isopropyl-1,2,4-oxadiazol-5-yl)piperidin-4-yl)methanol

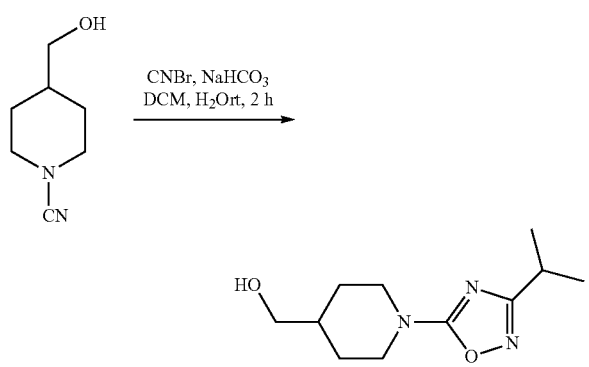

To a stirred solution of 4-(hydroxymethyl)piperidine-1-carbonitrile (2.8 g, 19.97 mmol) and N-hydroxyisobutyramidine (2.03 g, 19.97 mmol) in ethanol (150 mL) was added ZnCl$_2$ (4.08 g, 29.961 mmol) suspended in 10 mL ethanol and reaction allowed to stir at room temperature for 2 h. After 2 h (intermediate confirmed by TLC) Conc. HCl (20 mL) was added to it and heated at 50° C. for 16 h. On completion, reaction mixture was concentrated under reduced pressure. To the residue was added aq. Sol. Of NaHCO$_3$, extracted with ethyl acetate. The organic layer was concentrated under reduced pressure. Purification of the compound was done by silica gel (100-200 Mesh) column chromatography eluent 1% MeOH/DCM obtained (1-(3-isopropyl-1,2,4-oxadiazol-5-yl) piperidin-4-yl) methanol (2.5 g, 55.67%) as yellow oil.
MS: 226.29 [M++1]

Step-7: Synthesis of 1-(3-isopropyl-1,2,4-oxadiazol-5-yl)piperidine-4-carbaldehyde

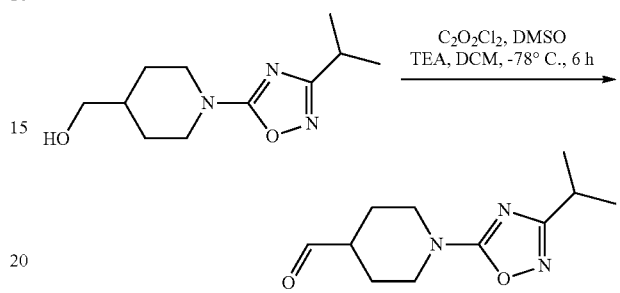

To DCM (50 mL) was added oxalyl chloride (3.35 g, 2.643 mmol) at −78° C. and reaction allowed to stir for 15 min. After 15 min. DMSO (3.44 g, 44.05 mmol) was added slowly dropwise to reaction mass and stir for 2 h at same temperature. Then (1-(3-isopropyl-1,2,4-oxadiazol-5-yl) piperidin-4-yl) methanol (2.0 g, 8.810 mmol) in DCM (5 mL) was added to reaction mass at −78° C. and reaction allowed to stir at same temp for 2 h. After 2 h, TEA (6.24 g, 61.67 mmol) was added to reaction mass and allowed to run at −78° C. for 30 min. Reaction was monitored by TLC. Reaction was quenched with water, extracted with DCM. The organic layer was washed with brine, dried over sodium sulphate, concentrated under reduced pressure obtained crude which was purified by silica gel (100-200 Mesh) column chromatography eluent 1% MeOH/DCM to afford 1-(3-isopropyl-1,2,4-oxadiazol-5-yl)piperidine-4-carbaldehyde (1.5 g, 55.67%) as off yellow oil.
MS: 223.13 [M++1]

Step-8: Synthesis of 1-(3-isopropyl-1,2,4-oxadiazol-5-yl)-4-(oxiran-2-yl)piperidine

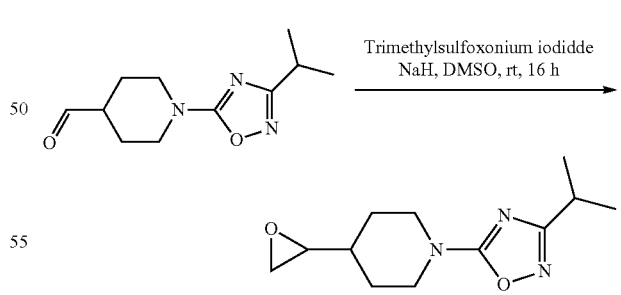

To a solution of trimethylsulfoxonium iodide (0.1 g, 0.447 mmol) in DMSO (10 mL) was added NaH (0.017 g, 0.447 mmol) at room temperature and stir for 30 min. After 30 min 1-(3-isopropyl-1,2,4-oxadiazol-5-yl)piperidine-4-carbaldehyde (0.1 g, 0.447 mmol) was added to reaction mass and stirred for 16 h. Reaction was monitored by TLC. On completion reaction was quenched with water, extracted with DCM. The organic layer was washed with water, brine, dried over Na$_2$SO$_4$, evaporated under reduced pressure obtained 1-(3-isopropyl-1,2,4-oxadiazol-5-yl)-4-(oxiran-2-yl)piperidine (0.102 g, 96.22% Yield) as light yellow sticky mass.

MS: 238.15 [M⁺+1]

Step-9: Synthesis of 1-(1-(3-isopropyl-1,2,4-oxadiazol-5-yl)piperidin-4-yl)-2-methoxyethanol

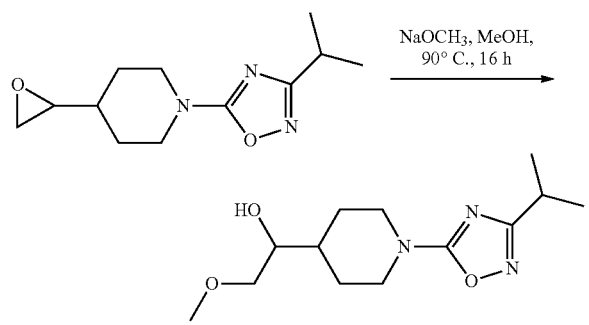

To a stirred solution of 1-(3-isopropyl-1,2,4-oxadiazol-5-yl)-4-(oxiran-2-yl)piperidine (0.1 g, 0.420 mmol) in MeOH (15 mL) was added NaOCH₃ (0.022 g, 0.420 mmol) at room temperature and reaction allowed to stir at 90° C. for 16 h. Reaction was monitored by TLC. On completion reaction was quenched with water, extracted with EtOAc. The organic layer was washed with water, brine, dried over Na₂SO₄, evaporated under reduced pressure obtained 1-(1-(3-isopropyl-1,2,4-oxadiazol-5-yl)piperidin-4-yl)-2-methoxyethanol (0.1 g, 88.49% yield) as light yellow solid.

MS: 269.17 [M⁺+1]

Step-10: Synthesis of 2-(1-(1-(3-isopropyl-1,2,4-oxadiazol-5-yl) piperidin-4-yl)-2-methoxyethoxy)-5-(4-(methylsulfonyl)phenyl) thiazolo [5,4-b] pyridine

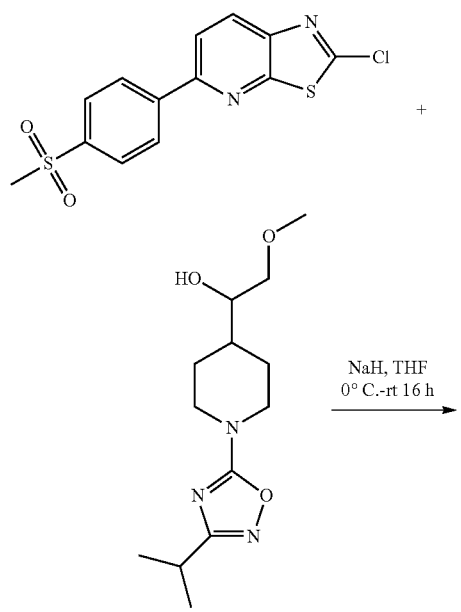

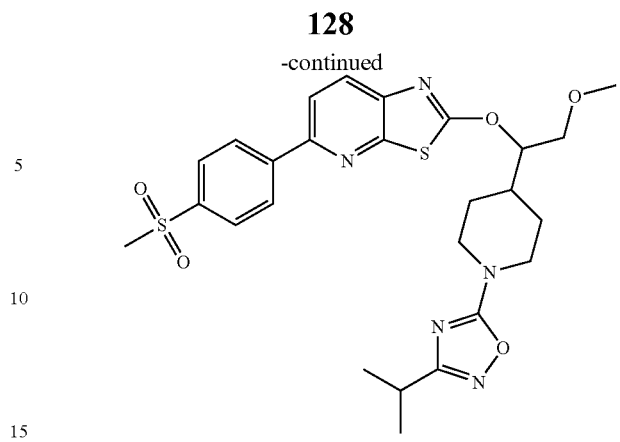

To a stirred solution of 1-(1-(3-isopropyl-1,2,4-oxadiazol-5-yl)piperidin-4-yl)-2-methoxyethanol (0.03 g, 0.092 mmol) in THF (10 mL) was added sodium hydride (0.0055 g, 0.138 mmol) at 0° C. and reaction allowed to stir for 30 min. After 30 min 2-chloro-5-(4-(methylsulfonyl)phenyl)thiazolo[5,4-b]pyridine (0.03 g, 0.092 mmol) in DMF (1 mL) was added to it and stirred for 16 h. Reaction was monitored by TLC. On completion reaction was quenched with ice cold water, extracted with ethyl acetate. The organic layer was washed with water, brine, dried over sodium sulphate, concentrated under reduced pressure obtained crude desired product that was purified by Neutral alumina chromatography, eluent 30% EtOAc/Hexane to afford 2-(1-(1-(3-isopropyl-1,2,4-oxadiazol-5-yl)piperidin-4-yl)-2-methoxyethoxy)-5-(4-(methylsulfonyl)phenyl)thiazolo[5,4-b]pyridine (0.015 g, 29.41%) as off white solid.

MS: 558.1 [M⁺+1]

Example 12: 5-(4-(cyclopropyl((5-(4-(methylsulfonyl)phenyl)thiazolo[5,4-b] pyridin-2-yl)oxy)methyl) piperidin-1-yl)-3-isopropyl-1,2,4-oxadiazole [1040]

Step-1: Synthesis of cyclopropyl (1-(3-isopropyl-1,2,4-oxadiazol-5-yl) piperidin-4-yl) methanol

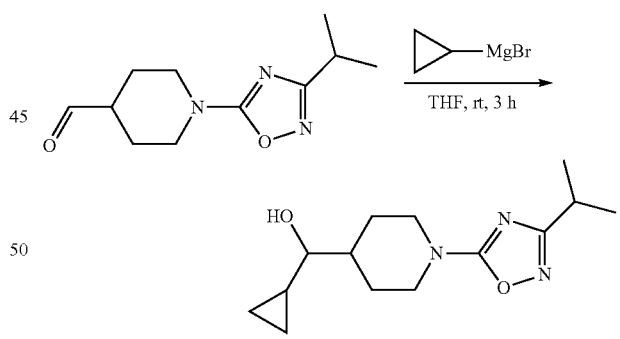

To a stirred solution of 1-(3-isopropyl-1,2,4-oxadiazol-5-yl)piperidine-4-carbaldehyde (0.1 g, 0.447 mmol) in THF (10 mL) was added Cyclopropyl magnesium bromide (0.7 M in THF) (1.91 mL, 1.34 mmol) at 0° C. and reaction allowed to stir at room temperature for 3 h. Reaction was monitored by TLC. Reaction was quenched with aq. NH4Cl, extracted with ethyl acetate. The organic layer was washed with brine, dried over sodium sulphate and concentrated under reduced pressure obtained crude which was purified by silica gel (100-200 Mesh) column chromatography eluent 30% EtOAc/Hexane to afford cyclopropyl (1-(3-isopropyl-1,2,4-oxadiazol-5-yl) piperidin-4-yl) methanol (0.0645 g, 55.67%) as colourless oil.

MS: 266.2 [M⁺+1]

Step-2: Synthesis of 5-bromo-2-(cyclopropyl(1-(3-isopropyl-1,2,4-oxadiazol-5-yl)piperidin-4-yl)methoxy)thiazolo[5,4-b]pyridine

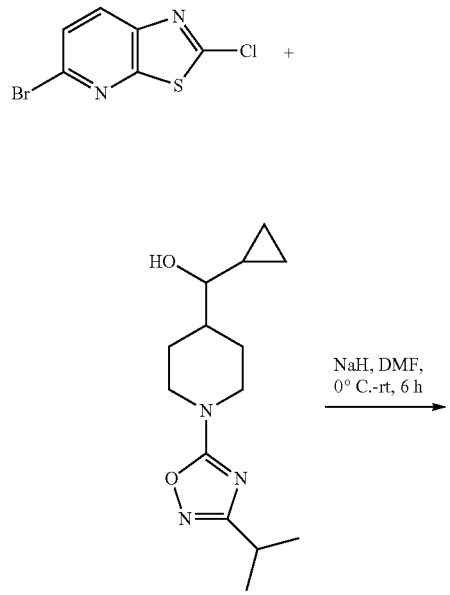

Step-3: Synthesis of 2-(cyclopropyl(1-(3-isopropyl-1,2,4-oxadiazol-5-yl)piperidin-4-yl)methoxy)-5-(4-(methylsulfonyl)phenyl)thiazolo[5,4-b]pyridine

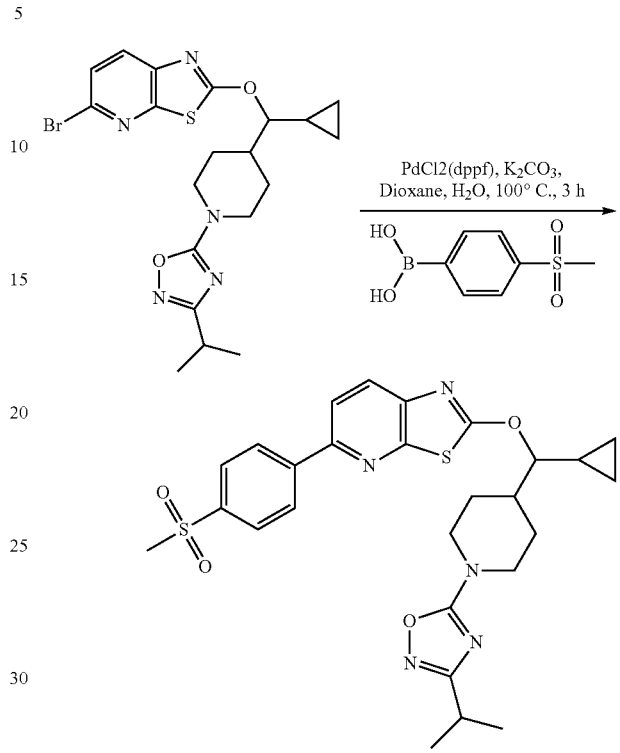

To a stirred solution of cyclopropyl(1-(3-isopropyl-1,2,4-oxadiazol-5-yl)piperidin-4-yl)methanol (0.046 g, 0.176 mmol) in DMF (5 mL) was added sodium hydride (0.0057 g, 0.240 mmol) at 0° C. and stir at 0° C. for 1 h. After 1 h, 5-bromo-2-chlorothiazolo[5,4-b]pyridine (0.04 g, 0.160 mmol) in DMF (1 mL) was added to reaction mass and stirred at room temperature for 16 h. Reaction was monitored by TLC. On completion reaction was quenched with ice cold water, extracted with ethyl acetate. The organic layer was washed with water, brine, dried over sodium sulphate, concentrated under reduced pressure obtained crude desired product which was purified by silica gel (100-200 Mesh) column chromatography eluent 10% EtOAc/Hexane obtained 5-bromo-2-(cyclopropyl(1-(3-isopropyl-1,2,4-oxadiazol-5-yl)piperidin-4-yl)methoxy)thiazolo[5,4-b]pyridine (0.03 g, 39.47%) as white solid.

MS: 478.08 [M$^+$+1]

To a stirred solution of 5-bromo-2-(cyclopropyl(1-(3-isopropyl-1,2,4-oxadiazol-5-yl)piperidin-4-yl)methoxy)thiazolo[5,4-b]pyridine (0.025 g, 0.052 mmol) and 4-(methylsulfonyl)phenylboronic acid (0.012 g, 0.062 mmol) in Dioxane (5 mL) was added K$_2$CO$_3$ (0.021 g, 0.156 mmol) in water (2 mL) and reaction mass was purged with nitrogen for 30 min. After 30 min PdCl$_2$(dppf) (0.0019 g, 0.0026 mmol) was added to it and stir at 100° C. for 3 h. Reaction was monitored by TLC. On completion reaction mass was concentrated under reduced pressure obtained crude which was purified by Neutral alumina column chromatography; eluent 35% EtOAc/Hexane obtained 2-(cyclopropyl(1-(3-isopropyl-1,2,4-oxadiazol-5-yl)piperidin-4-yl)methoxy)-5-(4-(methylsulfonyl)phenyl)thiazolo[5,4-b]pyridine (0.016 g, 57.14%) as off white solid.

MS: 548.2 [M$^+$+1]

Example 13: 3-fluoro-4-(2-(1-(1-(3-isopropyl-1,2,4-oxadiazol-5-yl)piperidin-4-yl)ethoxy)thiazolo[5,4-b]pyridin-5-yl)-N,N-dimethylbenzamide [1047]

Step 1: Synthesis of 2-(1-(1-(3-isopropyl-1,2,4-oxadiazol-5-yl) piperidin-4-yl) ethoxy)-5-bromothiazolo [5,4-b]pyridine

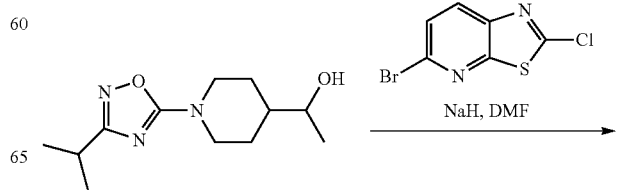

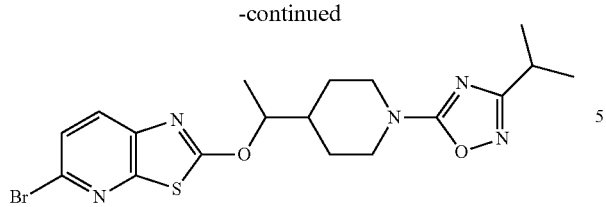

To a suspension of NaH (0.0062 g, 0.26 mmol) in DMF (3 mL) was added 1-(1-(3-isopropyl-1,2,4-oxadiazol-5-yl) piperidin-4-yl)ethanol (0.040 g, 0.192 mmol) solution in DMF (1 mL) at 0° C. over a period of 15 min and stir at room temperature for 1.5 h. To resultant reaction mixture, 5-bromo-2-chlorothiazolo [5,4-b]pyridine (0.062 g, 0.24 mmol) was added and allowed to stir at room temperature for 3 h. Reaction progress was monitored on TLC for its completion. On completion, reaction mixture was quenched with ice chilled water and extracted with ethyl acetate. The organic layer was washed with water, saturated aq. sol. of NaHCO$_3$ and brine. Now organic layer dried over sodium sulphate and concentrated under reduced pressure to give 0.040 g (52.63%) 2-(1-(1-(3-isopropyl-1,2,4-oxadiazol-5-yl) piperidin-4-yl) ethoxy)-5-bromothiazolo [5,4-b] pyridine as yellow oily gummy mass.

MS: 452.37 [M+1]$^+$

Step 2: Synthesis of 4-(2-(1-(1-(3-isopropyl-1,2,4-oxadiazol-5-yl)piperidin-4-yl)ethoxy)thiazolo[5,4-b]pyridin-5-yl)-3-fluorobenzoic Acid

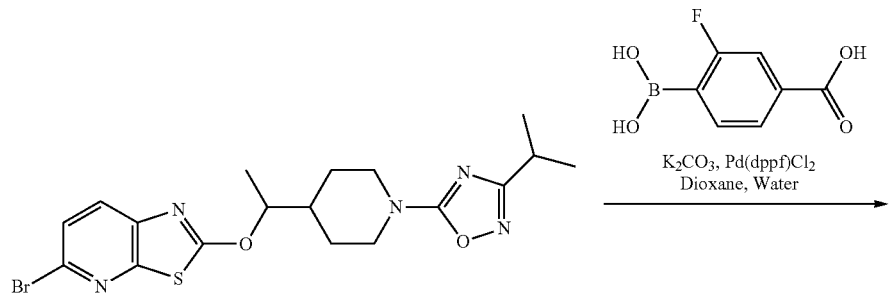

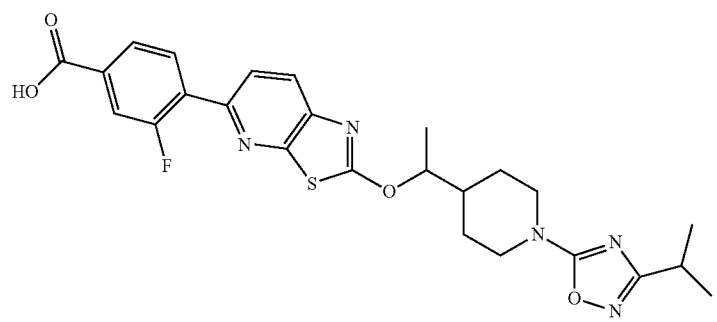

To a solution of 2-(1-(1-(3-isopropyl-1,2,4-oxadiazol-5-yl) piperidin-4-yl) ethoxy)-5-bromothiazolo [5,4-b] pyridine (0.040 g, 0.000089 mol) and 2-Fluoro 4-carboxy phenylboronic acid (0.023 g, 0.11 mmol) in Dioxane (4 mL), K₂CO₃ (0.032 g, 0.23 mmol) (dissolved in water 1 mL) was added and reaction mixture purged with nitrogen for 30 min. To it, Pd(dppf)Cl₂ (0.0065 g, 0.09 mmol) was added and again purged with nitrogen for 15 min. Now reaction mixture was heated at 100° C. for 2 h. Reaction progress was monitored on TLC for its completion. On completion, reaction mixture was quenched with water and extracted with ethyl acetate. The organic layer was concentrated under reduced pressure to give crude reaction mass. Purification of the compound was done by silica gel (100-200#) column chromatography and desired product staroom temperature eluting at 1.3-1.6% acetone in MDC, giving 0.014 g (30.95%) of 4-(2-(1-(1-(3-isopropyl-1,2,4-oxadiazol-5-yl)piperidin-4-yl)ethoxy)thiazolo[5,4-b]pyridin-5-yl)-3-fluorobenzoic acid as off white grey solid.

MS: 511.57 [M⁺+1]

Step 3: Synthesis of 4-(2-(1-(1-(3-isopropyl-1,2,4-oxadiazol-5-yl)piperidin-4-yl)ethoxy)thiazolo[5,4-b]pyridin-5-yl)-3-fluoro-N,N-dimethylbenzamide

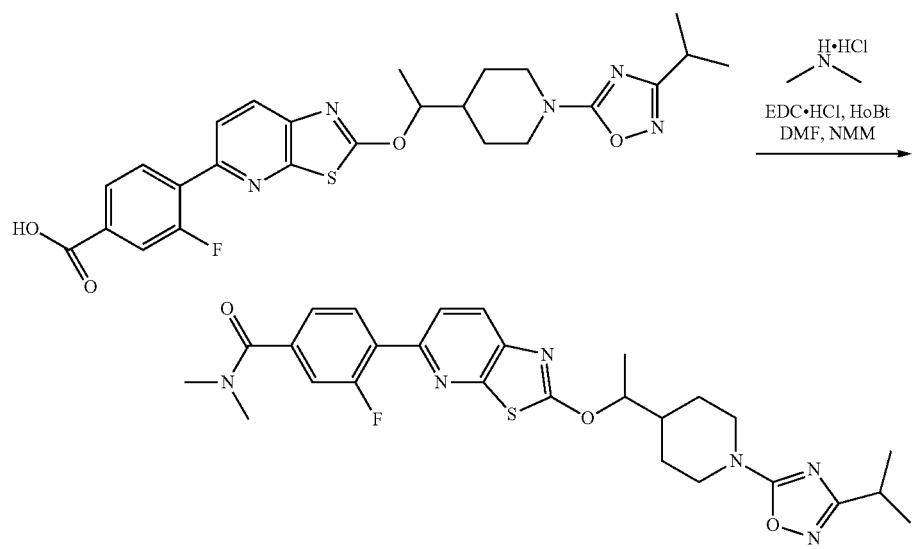

To a stirred solution of 4-(2-(1-(1-(3-isopropyl-1,2,4-oxadiazol-5-yl)piperidin-4-yl)ethoxy)thiazolo[5,4-b]pyridin-5-yl)-3-fluorobenzoic acid (0.30 g, 0.058 mmol) and dimethyl amine hydrochloride (0.71 g, 0.0088 mmol) in DMF (2 mL) were added EDC.HCl (0.017 g, 0.088 mmol), HoBt (0.018 g, 0.132 mmol) and NMM (0.017 g). Then reaction mixture was stirred at room temperature for 16 h. Reaction was monitored by TLC. On completion, reaction mixture was quenched with water, extracted with ethyl acetate. Organic layer was washed with water, brine, dried over sodium sulphate and evaporated under reduced pressure to give crude product. Purification of the crude was done by silica gel (100-200 Mesh) column chromatography; eluent 3% MeOH in DCM to obtain 0.03 g (95%) 4-(2-(1-(1-(3-isopropyl-1,2,4-oxadiazol-5-yl)piperidin-4-yl)ethoxy)thiazolo[5,4-b]pyridin-5-yl)-3-fluoro-N,N-dimethylbenzamide as light yellow solid.

MS: 539.1 [M+1]⁺ (CM1001600201)
1H NMR: CM1001600201

Example 14: 5-(4-(methylsulfonyl)phenyl)-2-(1-(1-(5-propylpyrimidin-2-yl) piperidine-4-yl)ethoxy) thiazolo [5,4-b]pyridine [1054]

Step-1: Synthesis of t-butyl 4-formylpiperidine-1-carboxylate

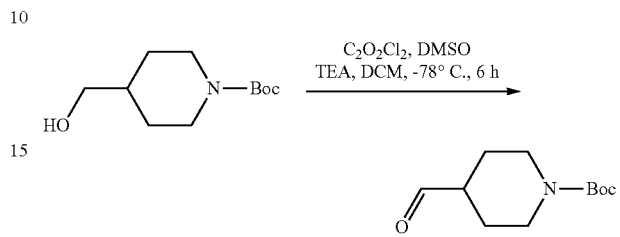

To DCM (50 mL) was added oxalyl chloride (7.07 g, 55.74 mmol) at −78° C. and reaction allowed to stir at −78° C. for 15 min. After 15 min. DMSO (5.27 g, 74.32 mmol) was added slowly dropwise and stir at −78° C. for 2 h. After 2 h t-butyl 4-(hydroxymethyl)piperidine-1-carboxylate (4.0 g, 18.58 mmol) in DCM (10 mL) was added to reaction mass at −78° C. and stir 2 h. Then, TEA (6.24 g, 61.67 mmol) was added to it and stir at −78° C. for 30 min. Reaction was monitored by TLC. Reaction was quenched with water, extracted with DCM. The organic layer was washed with brine, dried over sodium sulphate, concentrated under reduced pressure obtained t-butyl 4-formylpiperidine-1-carboxylate (4.0 g, %) of as yellow oil. MS: 214.14 [M⁺+1]

Step-2: Synthesis of t-butyl 4-(1-hydroxyethyl)piperidine-1-carboxylate

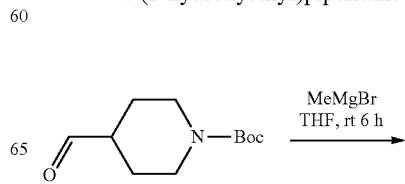

-continued

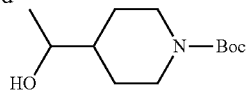

To a stirred solution of t-butyl 4-(1-hydroxyethyl)piperidine-1-carboxylate (4 g, 18.75 mmol) in THF (200 mL) was added MeMgBr (2M in THF) (46.88 mL, 93.77 mmol) at 0° C. and reaction allowed to stir at room temperature for 3 h. Reaction was monitored by TLC. Reaction was quenched with aq. NH$_4$Cl, and extracted with ethyl acetate. The organic layer was washed with brine, dried over sodium sulphate, concentrated under reduced pressure obtained crude which was purified by silica gel (100-200 Mesh) column chromatography eluent 25% EtOAc/Hexane to afford t-butyl 4-(1-hydroxyethyl)piperidine-1-carboxylate (2.6 g, 60.46%) as yellow oil. MS: 230.1 [M$^+$+1]

Step-3: Synthesis of 1-(piperidin-4-yl)ethanol hydrochloride

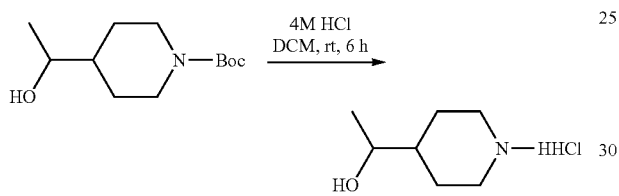

To a stirred solution of t-butyl 4-(1-hydroxyethyl) piperidine-1-carboxylate (2.5 g, 10.90 mmol) in DCM (50 mL) was added 4 M HCl in Dioxane (13.62 mL, 54.50 mmol) and reaction allowed to stir at room temperature for 6 h. Reaction was monitored by TLC. On completion all volatiles were evaporated under reduced pressure obtained 1-(piperidin-4-yl)ethanol hydrochloride (1.5 g, 83.79%) as off white solid. MS: 130.2 [M$^+$+1]

Step-4: Synthesis of 1-(1-(5-propylpyrimidin-2-yl) piperidin-4-yl)ethanol

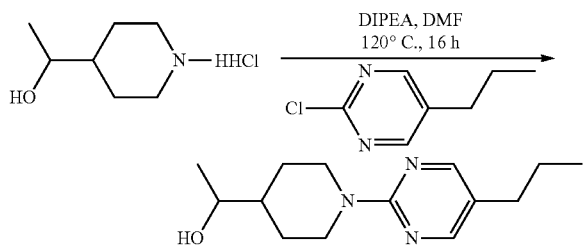

To a stirred solution of 1-(piperidin-4-yl) ethanol hydrochloride (0.1 g, 0.606 mmol) in DMF (5 mL) was added DIPEA (0.15 g, 1.21 mmol) and reaction allowed to stir at room temperature for 30 min. Then 2-chloro-5-propylpyrimidine (0.113 g, 0.727 mmol) was added to it and stir at 120° C. for 16 h. Reaction was monitored by TLC. Reaction was quenched with ice cold water, extracted with ethyl acetate. The organic layer was washed with brine, dried over sodium sulphate, concentrated under reduced pressure obtained crude which was purified by combiflesh (Lumen) chromatography eluent 30% EtOAc/Hexane obtained 1-(1-(5-propylpyrimidin-2-yl)piperidin-4-yl)ethanol (0.06 g, 39.73%) as yellow oil. MS: 250.1 [M$^+$+1]

Step-5: Synthesis of 2-(1-(1-(5-propylpyrimidin-2-yl) piperidin-4-yl)ethoxy)-5-bromothiazolo[5,4-b] pyridine

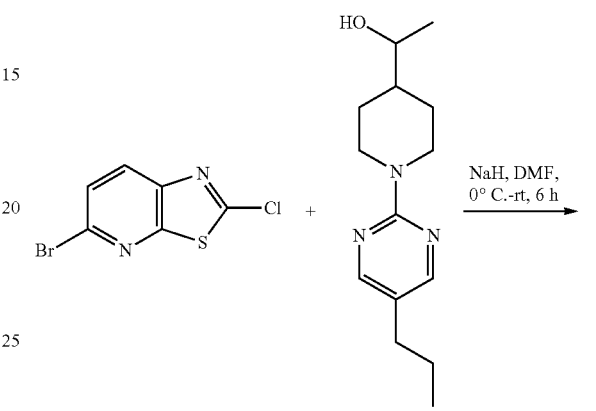

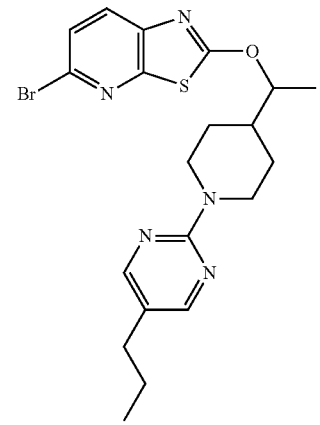

To a stirred solution of 1-(1-(5-propylpyrimidin-2-yl) piperidin-4-yl)ethanol (0.032 g, 0.132 mmol) in DMF (5 mL) was added sodium hydride (0.0072 g, 0.180 mmol) at 0° C. and stir for 30 min. After 30 min 5-bromo-2-chlorothiazolo[5,4-b]pyridine (0.03 g, 0.120 mmol) in DMF (1 mL) was added to reaction mass and stir at room temperature for 6 h. Reaction was monitored by TLC. On completion reaction was quenched with ice cold water, extracted with ethyl acetate. The organic layer was washed with water, brine, dried over sodium sulphate, concentrated under reduced pressure obtained crude desired product which was purified by silica gel (100-200 Mesh) column chromatography eluent 10% EtOAc/Hexane to afford 2-(1-(1-(5-propylpyrimidin-2-yl)piperidin-4-yl)ethoxy)-5-bromothiazolo [5,4-b]pyridine (0.040 g, 64.28%) as white solid. MS: 462.08 [M$^+$+1]

Step-6: Synthesis of 2-(1-(1-(5-propylpyrimidin-2-yl)piperidin-4-yl)ethoxy)-5-(4-(methylsulfonyl)phenyl)thiazolo[5,4-b]pyridine

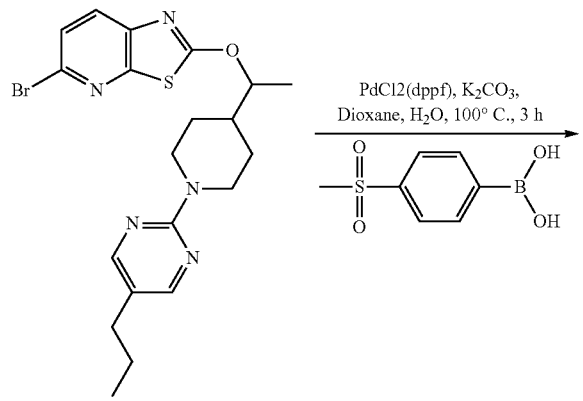

To a stirred solution of 2-(1-(1-(5-propylpyrimidin-2-yl)piperidin-4-yl)ethoxy)-5-bromothiazolo[5,4-b]pyridine (0.04 g, 0.086 mmol) and 4-(methylsulfonyl)phenylboronic acid (0.020 g, 0.103 mmol) in Dioxane (10 mL) was added K$_2$CO$_3$ (0.035 g, 0. 0.259 mmol in water (2 mL) and reaction mass was purged with nitrogen for 30 min. After 30 min PdCl$_2$(dppf) (0.0031 g, 0.004 mmol) was added to reaction mass and stir at 100° C. for 3 h. Reaction was monitored by TLC. On completion all volatiles were under reduced pressure obtained crude which was purified by Neutral alumina column chromatography; eluent 30% EtOAc/Hexane to afford 2-(1-(1-(5-propylpyrimidin-2-yl)piperidin-4-yl)ethoxy)-5-(4-(methylsulfonyl)phenyl)thiazolo[5,4-b]pyridine (0.028 g, 60.86%) as off white solid. MS: 538.2 [M$^+$+1]

Example 15: Isopropyl 4-(1-((5-(4-(methylsulfonyl)phenyl)thiazolo[5,4-b]pyridin-2-yl)oxy)ethyl)piperidine-1-carboxylate[1057]

Step-1: Synthesis of isopropyl 4-(1-hydroxyethyl)piperidine-1-carboxylate

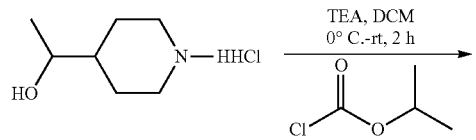

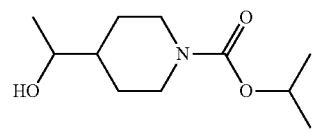

To a stirred solution of 1-(piperidin-4-yl) ethanol hydrochloride (0.05 g, 0.301 mmol) in DCM (10 mL) was added TEA (0.061 g, 0.603 mmol) and stir at 0° C. for 30 min. Then Isopropylchloroformate (2M in toluene) (0.166 ml, 0.332 mmol) was added, stirred at 0° C.-25° C. for 2 h. Reaction was monitored by TLC. Reaction was quenched with ice cold water, extracted with ethyl acetate. The organic layer was washed with brine, dried over sodium sulphate, concentrated under reduced pressure obtained Isopropyl 4-(1-hydroxyethyl) piperidine-1-carboxylate (0.07 g, 97.22%) as yellow oil. MS: 216.2 [M$^+$+1]

Step-2: Synthesis of Isopropyl 4-(1-(5-bromothiazolo[5,4-b]pyridin-2-yloxy)ethyl)piperidine-1-carboxylate

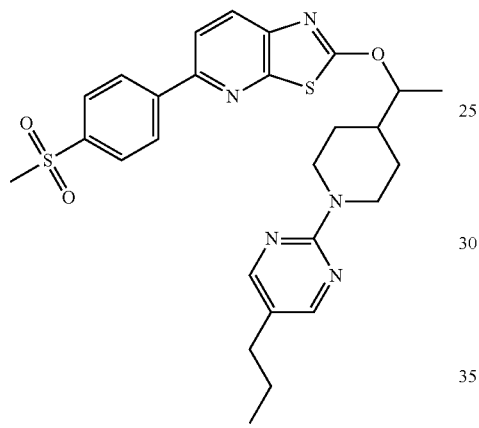

To a stirred solution of isopropyl 4-(1-hydroxyethyl) piperidine-1-carboxylate (0.043 g, 0.200 mmol) in DMF (5 mL) was added sodium hydride (0.012 g, 0.300 mmol) at 0° C. and stir for 30 min. After 30 min 5-bromo-2-chlorothiazolo [5,4-b]pyridine (0.05 g, 0.200 mmol) in DMF (1 mL) was added to it and stirred at room temperature for 6 h. Reaction was monitored by TLC. On completion reaction was quenched with ice cold water, extracted with ethyl acetate. The organic layer was washed with water, brine, dried over sodium sulphate, concentrated under reduced pressure obtained crude desired product which was purified by silica gel (100-200 Mesh) column chromatography eluent 10% EtOAc/Hexane to afford Isopropyl 4-(1-(5-bromothiazolo[5,4-b]pyridin-2-yloxy)ethyl)piperidine-1-carboxylate (0.045 g, 52.94%) as off white solid.

MS: 428.06 [M$^+$+1]

Step-3: Synthesis of Isopropyl 4-(1-(5-(4-(methylsulfonyl)phenyl)thiazolo[5,4-b]pyridin-2-yloxy)ethyl)piperidine-1-carboxylate

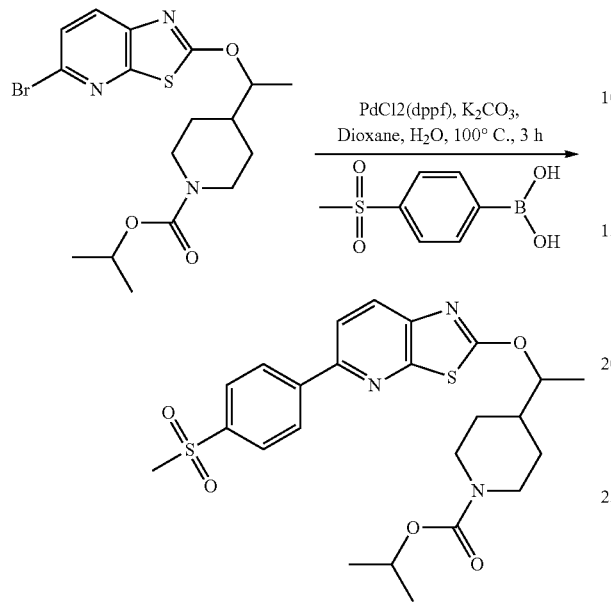

To a stirred solution of Isopropyl 4-(1-(5-bromothiazolo[5,4-b]pyridin-2-yloxy)ethyl)piperidine-1-carboxylate (0.04 g, 0.0933 mmol) and 4-(methylsulfonyl)phenylboronic acid (0.037 g, 0.186 mmol) in Dioxane (10 mL) was added $K_2CO_3$ (0.038 g, 0. 0.280 mmol) in water (2 mL) and reaction mass was purged with nitrogen for 30 min. After 30 min $PdCl_2$(dppf) (0.0034 g, 0.0046 mmol) was added to it and stir at 100° C. for 3 h. Reaction was monitored by TLC. On completion all volatiles were evaporated under reduced pressure obtained crude which was purified by Neutral alumina column chromatography; eluent 30% EtOAc/Hexane to afford Isopropyl 4-(1-(5-(4-(methylsulfonyl) phenyl) thiazolo [5,4-b]pyridin-2-yloxy)ethyl)piperidine-1-carboxylate (0.007 g, 14.89%) as off white solid. MS: 504.15 [M$^+$+1]

Example 16: 4-(2-(1-(1-(3-isopropyl-1,2,4-oxadiazol-5-yl)piperidin-4-yl) ethoxy)thiazolo[5,4-b]pyridin-5-yl)-N-methylbenzenesulfonamide [1062]

Step 1: Synthesis 4-bromobenzene-1-sulfonyl chloride

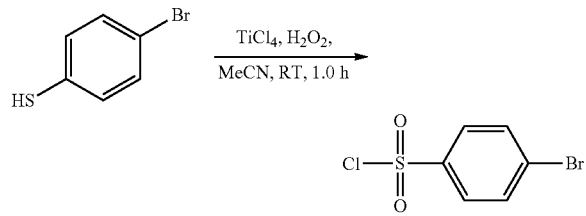

To a stirred solution of compound 4-bromobenzenethiol (0.5 g, 2.66 mmol) in ACN (10 mL), 30% $H_2O_2$ (0.9 mL, 7.98 mmol) and titanium tetrachloride (0.29 mL, 2.66 mmol) were added at 25° C. and allowed to stir room temperature for 1 h. Reaction was monitored by TLC. On completion, reaction was quenched with water and compound was extracted with ethyl acetate, organic layer was concentrated under reduced pressure to give compound 4-bromobenzene-1-sulfonyl chloride (0.410 g, 60.69%) as white solid.

MS: 254.88 [M$^+$+1].

Step 2: Synthesis of 1-bromo-4-(methylaminosulfonyl)benzene

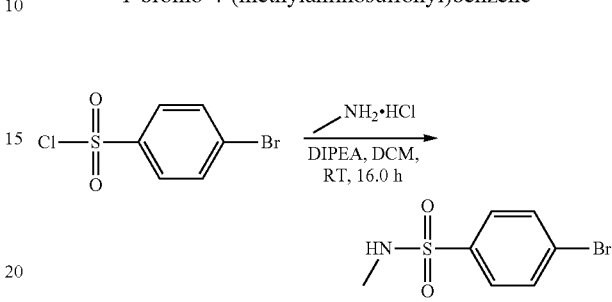

To a stirred solution of Methyl amine hydrochloride salt (0.13 g, 1.97 mmol) in DCM, DIPEA (0.52 mL, 2.95 mmol) and 4-bromobenzene-1-sulfonyl chloride (0.25 g, 0.98 mmol) were added and reaction allowed to stir at RT for 16 h. Progress of reaction was monitored by TLC. On completion, reaction mixture was quenched with water and extracted with DCM. The organic layer was dried on sodium sulfate and concentrated under reduced pressure to 1-bromo-4-(methylaminosulfonyl)benzene (0.220 g, 89.74%) as yellow semisolid.

MS: 248.0 [M$^-$–1].

Step 3: Synthesis of 2-(4-(methylaminosulfonyl)phenyl)-4,4,5,5-tetramethyl-1,3,2-dioxaborolane

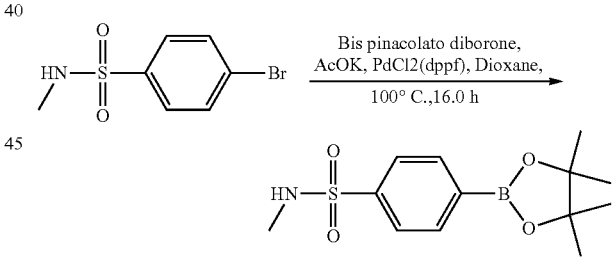

To a stirred 1-bromo-4-(methylaminosulfonyl)benzene (0.22 g, 0.88 mmol) and Bispinacolatodiboron (0.27 g, 1.06 mmol) in Dioxane (7.0 mL), Potassium acetate (0.26 g, 2.65 mmol) was added and reaction mixture degassed with nitrogen gas for 30 min. Then to it, PdCl2(dppf) (0.033 g, 0.05 mmol) was added and allowed to stir at 100° C. for 16 h. Progress of reaction was monitored by TLC. On completion, Dioxane was evaporated from reaction mixture and residue quenched with water, compound was extracted with ethyl acetate. The organic layer was concentrated under reduced pressure to give crude compound which was purified by Combi-flash column chromatography (4.0 g column); eluted in 15% ethyl acetate in hexane to give 2-(4-(methylaminosulfonyl)phenyl)-4,4,5,5-tetramethyl-1,3,2-dioxaborolane (0.120 g, 45.70%) as white solid.

MS: 298.12 [M$^+$+1].

Step 4: Synthesis of 2-(1-(1-(3-isopropyl-1,2,4-oxadiazol-5-yl)piperidin-4-yl)ethoxy)-5-(4-(methylaminosulfonyl)phenyl)thiazolo[5,4-b]pyridine

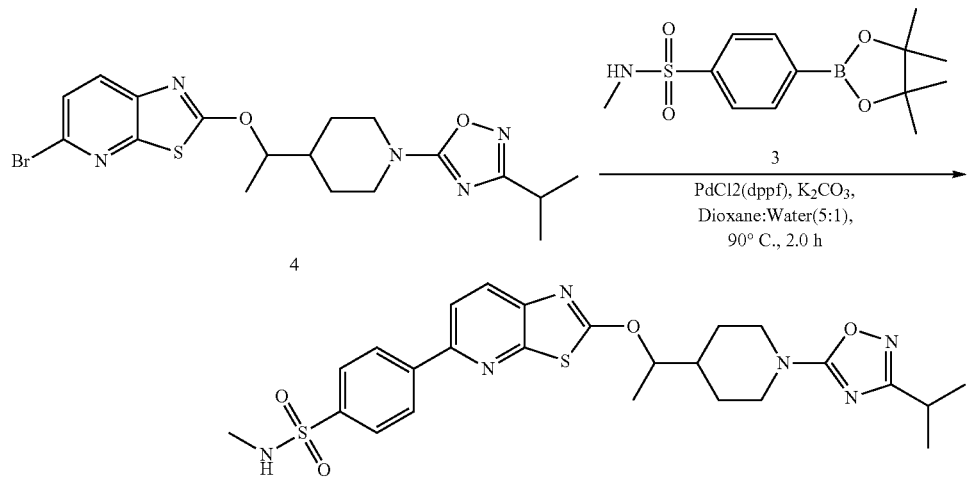

To a stirred solution of 2-(1-(1-(3-isopropyl-1,2,4-oxadiazol-5-yl)piperidin-4-yl)ethoxy)-5-bromothiazolo[5,4-b]pyridine (0.03 g, 0.06 mmol) and 2-(4-(methylaminosulfonyl)phenyl)-4,4,5,5-tetramethyl-1,3,2-dioxaborolane (0.02 g, 0.07 mmol) in Dioxane (5.0 mL), K$_2$CO$_3$ (0.02 g, 0.17 mmol) dissolved in water (1.0 mL) was added and reaction purged with nitrogen for 30 min. After 30 min, Pd(dppf)Cl2 (0.002 g, 0.003 mmol) was added to the reaction mixture and heated at 90° C. for 2 h. Progress of reaction was monitored by TLC. On completion, reaction was quenched with water and extracted with ethyl acetate. The organic layer was concentrated under reduced pressure to give crude compound. Purification of the compound was done by silica gel (100-200 mesh) column chromatography using 50% ethyl acetate in hexane to give compound 2-(1-(1-(3-isopropyl-1,2,4-oxadiazol-5-yl)piperidin-4-yl)ethoxy)-5-(4-(methylaminosulfonyl)phenyl)thiazolo[5,4-b]pyridine (0.007 g, 19.41%) as white solid.
MS: 543.2 [M$^+$+1].

Example 17: (R)-3-isopropyl-5-(4-(1-((5-(pyridin-4-yl)thiazolo[5,4-b]pyridin-2-yl)oxy)ethyl)piperidin-1-yl)-1,2,4-oxadiazole [1071]

Step 1: Synthesis of 2-((S)-1-(1-(3-isopropyl-1,2,4-oxadiazol-5-yl)piperidin-4-yl)ethoxy)-5-bromothiazolo[5,4-b]pyridine

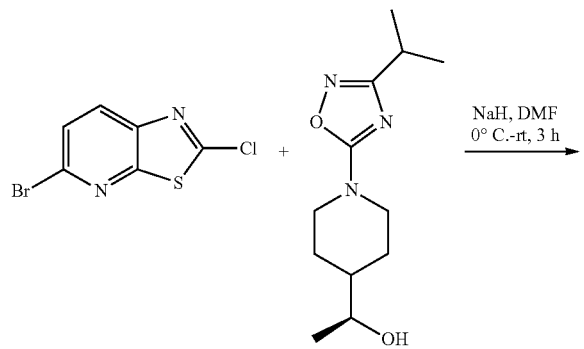

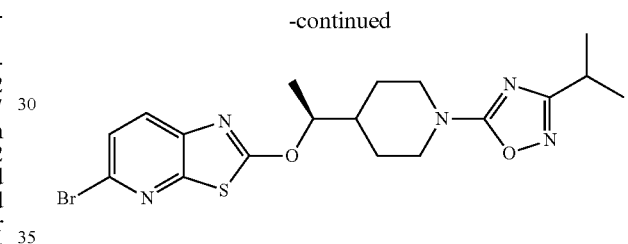

To a stirred solution of (S)-1-(1-(3-isopropyl-1,2,4-oxadiazol-5-yl)piperidin-4-yl)ethanol (0.03 g, 0.12 mmol) in DMF (1 mL) was added sodium hydride (0.008 g, 0.18 mmol) at 0° C. and allowed to stir at 0° C. for 30 min. After 30 min, 5-bromo-2-chlorothiazolo [5,4-b] pyridine (0.037 g, 0.15 mmol) in DMF (1 mL) was added to reaction mixture and allowed to stir at room temperature for 3 h. Reaction was monitored by TLC. On completion, reaction was quenched with ice cold water, extracted with ethyl acetate. The organic layer was washed with water, brine, dried over sodium sulphate and concentrated under reduced pressure to give crude desired product that was purified by silica gel (100 to 200 Mesh) chromatography, eluent 20% EtOAc:Hexane to obtain 2-((S)-1-(1-(3-isopropyl-1,2,4-oxadiazol-5-yl)piperidin-4-yl)ethoxy)-5-bromothiazolo[5,4-b]pyridine (0.04 g, 71%) as light yellow sticky mass.
MS: 452.37 [M$^+$+1]

Step 2: Synthesis of 2-((S)-1-(1-(3-isopropyl-1,2,4-oxadiazol-5-yl)piperidin-4-yl)ethoxy)-5-(pyridin-4-yl)thiazolo[5,4-b]pyridine

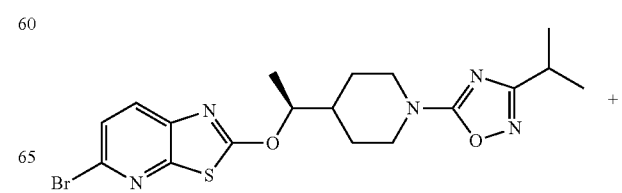

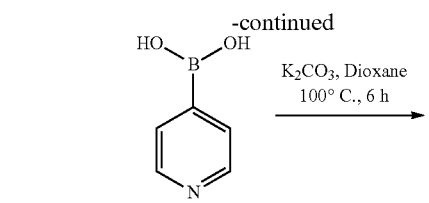

K₂CO₃, Dioxane
100° C., 6 h

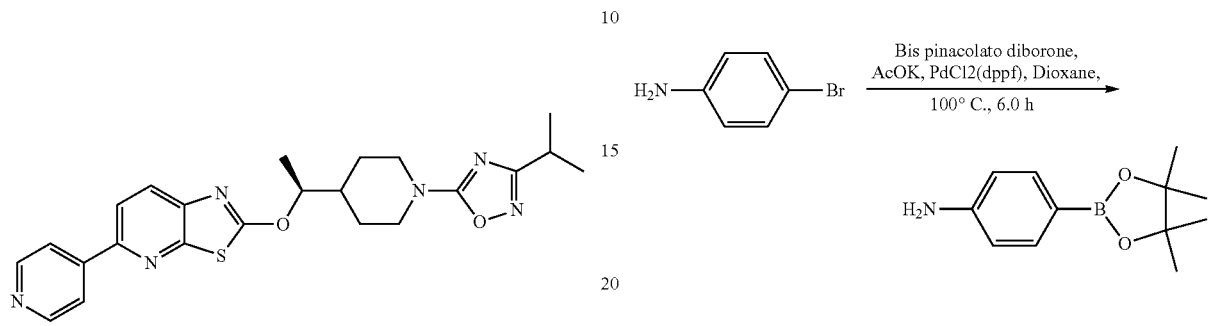

To a stirred solution of 2-((S)-1-(1-(3-isopropyl-1,2,4-oxadiazol-5-yl)piperidin-4-yl)ethoxy)-5-bromothiazolo[5,4-b]pyridine (0.04 g, 0.688 mmol) and pyridin-4-yl-4-boronic acid (0.013 g, 0.10 mmol) in Dioxane:water (10 mL). To it, K₂CO₃ (0.037 g, 0.26 mmol) was added and purged with nitrogen for 30 min. After 30 min, Pd (dppf)Cl₂ (0.003 g, 0.004 mmol) was added to reaction mixture and heated at 100° C. for 6 h. Reaction was monitored by TLC. On completion, reaction was quenched with water, extracted with ethyl acetate. Organic layer was washed with water, brine, dried over Na₂SO₄, evaporated under reduced pressure to give crude. Purification of crude was done by silica gel (100-200 Mesh) column chromatography; eluent 1.5% MeOH:DCM obtain 2-((S)-1-(1-(3-isopropyl-1,2,4-oxadiazol-5-yl)piperidin-4-yl)ethoxy)-5-(pyridin-4-yl)thiazolo[5,4-b]pyridine (0.02 g, 50%) as off white solid.

MS: 451.18 [M⁺+1]

Example 18: N-(4-(2-(1-(1-(3-isopropyl-1,2,4-oxadiazol-5-yl)piperidin-4-yl)ethoxy)thiazolo[5,4-b]pyridin-5-yl)phenyl)methanesulfonamide [1075]

Step 1: Synthesis of 4-(4,4,5,5-tetramethyl-1,3,2-dioxaborolan-2-yl)benzenamine

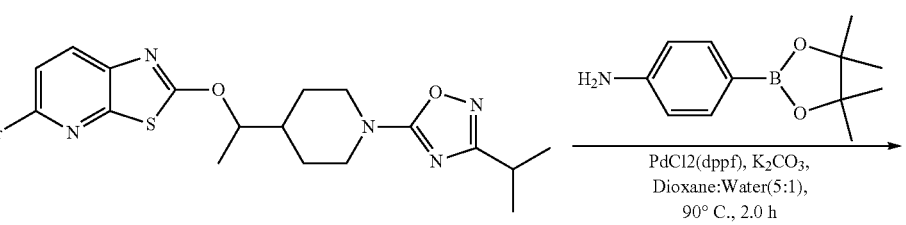

To a stirred solution of 4-bromobenzenamine (1.0 g, 5.8 mmol) and Bispinacolatodiboron (1.78 g, 7.0 mmol) in Dioxane (15.0 mL), Potassium acetate (1.71 g, 17.4 mmol) was added. Reaction mixture degassed with nitrogen gas for 30.0 min and added PdCl2(dppf) (0.21 g, 0.3 mmol). Allowed the reaction to stir at 100° C. for 6 h. Progress of reaction was monitored by TLC. On completion, Dioxane was evaporated from reaction mixture and residue quenched with water, compound was extracted with ethyl acetate. The organic layer was concentrated under reduced pressure to give crude compound which was purified by Combi-Flash™ column chromatography (4.0 g column); eluted in 20% ethyl acetate in hexane to give 4-(4,4,5,5-tetramethyl-1,3,2-dioxaborolan-2-yl) benzenamine (0.65 g, 50.78%) as light yellow solid.

MS: 220.20 [M⁺+1].

Step 2: Synthesis of 4-(2-(1-(1-(3-isopropyl-1,2,4-oxadiazol-5-yl)piperidin-4-yl)ethoxy)thiazolo[5,4-b]pyridin-5-yl)benzenamine

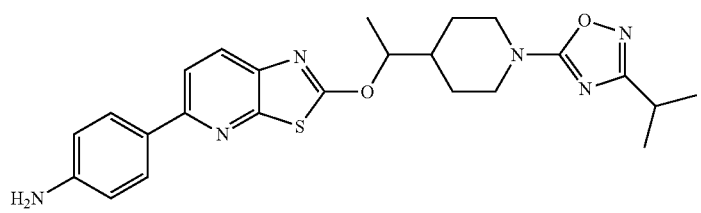

To a stirred solution of 2-(1-(1-(3-isopropyl-1,2,4-oxadiazol-5-yl)piperidin-4-yl)ethoxy)-5-bromothiazolo[5,4-b]pyridine (0.05 g, 0.11 mmol) and 4-(4,4,5,5-tetramethyl-1,3,2-dioxaborolan-2-yl)benzenamine (0.65 g, 50.78%) (0.03 g, 0.13 mmol) in Dioxane (5.0 mL), $K_2CO_3$ (0.05 g, 0.33 mmol) dissolved in water (1.0 mL) was added and reaction purged with nitrogen for 30 min. After 30 min, Pd(dppf)Cl2 (0.005 mg, 0.006 mmol) was added to the reaction mixture and reaction heated at 90° C. for 2 h. Progress of reaction was monitored by TLC. On completion, reaction was quenched with water and extracted with ethyl acetate. The organic layer was concentrated under reduced pressure to give crude compound. Purification of the compound was done by silica gel (100-200 mesh) column chromatography using 50% ethyl acetate in hexane to give 4-(2-(1-(1-(3-isopropyl-1,2,4-oxadiazol-5-yl)piperidin-4-yl)ethoxy)thiazolo[5,4-b]pyridin-5-yl)benzenamine (0.04 g, 77.73%) as yellow semisolid.

MS: 465.20 [M$^+$+1].

Step 3: Synthesis of 2-(1-(1-(3-isopropyl-1,2,4-oxadiazol-5-yl)piperidin-4-yl)ethoxy)-5-(4-((methylsulfonyl)amino)phenyl)thiazolo[5,4-b]pyridine

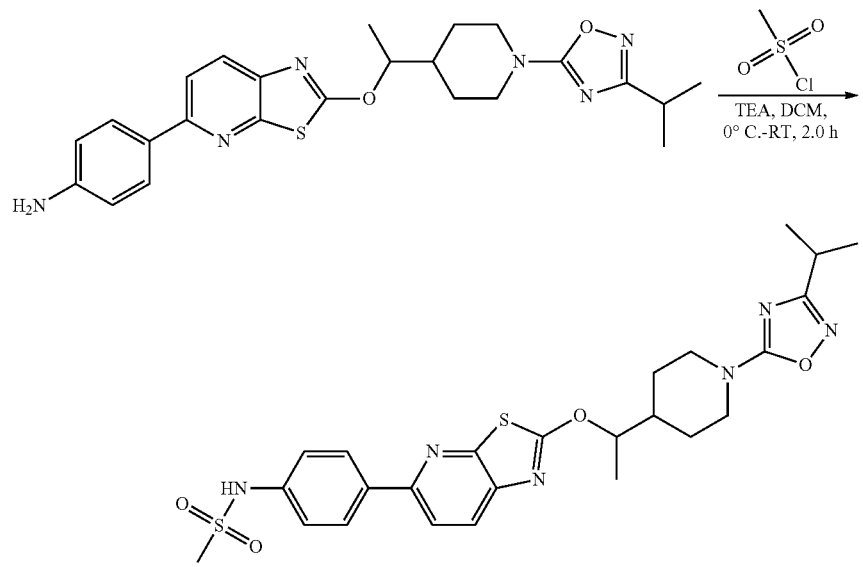

To a stirred solution of 4-(2-(1-(1-(3-isopropyl-1,2,4-oxadiazol-5-yl)piperidin-4-yl)ethoxy)thiazolo[5,4-b]pyridin-5-yl)benzenamine (0.02 g, 0.04 mmol) in DCM (4.0 mL), TEA (0.01 mL, 0.09 mmol) and methanesulfonyl chloride (0.01 mL, 0.05 mmol) at 0° C. were added and reaction allowed to stir at RT for 2 h. Progress of reaction was monitored by TLC. On completion, reaction mixture was quenched with water and compound was extracted with DCM. The organic layer was dried on sodium sulphate and concentrated under reduced pressure to give crude compound. Purification of the compound was done by silica gel (100-200 mesh) column chromatography using 50% ethyl acetate in hexane to give 2-(1-(1-(3-isopropyl-1,2,4-oxadiazol-5-yl)piperidin-4-yl)ethoxy)-5-(4-((methylsulfonyl)amino)phenyl)thiazolo[5,4-b]pyridine (0.015 g, 64.21%) as white solid.

MS: 541.20 [M$^-$−1].

Example 19: 5-(4-(methylsulfonyl)phenyl)-2-(1-(1-(5-vinylpyridin-2-yl)piperidin-4-yl)ethoxy)thiazolo[5,4-b]pyridine [1089]

Step 1: Synthesis of 2-(1-(1-(5-vinylpyridin-2-yl)piperidin-4-yl)ethoxy)-5-bromothiazolo[5,4-b]pyridine

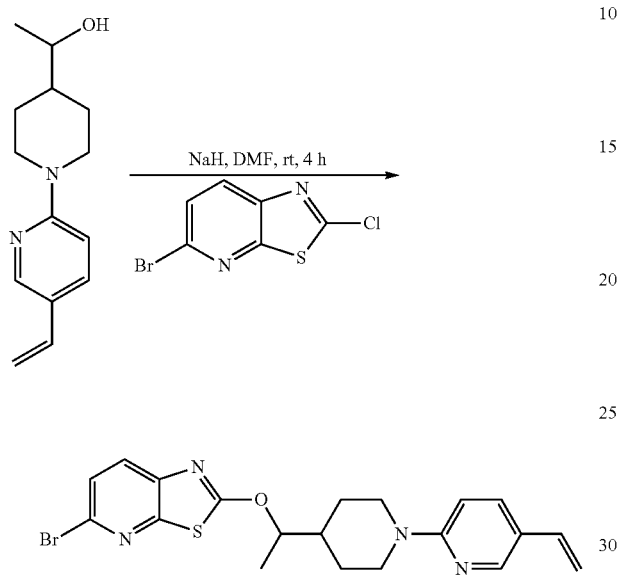

To a stirred solution of 1-(1-(5-vinylpyridin-2-yl)piperidin-4-yl)ethanol (0.046 g, 0.1983 mmol) in DMF (6 mL) was added sodium hydride (0.014 g, 0.3607 mmol) at 0° C. and stirred for 30 min at room temperature. After 30 min solution of 5-bromo-2-chlorothiazolo[5,4-b]pyridine (0.045 g, 0.1803 mmol) in DMF (4 mL) was added to it and stirred for 4 h. Progress of reaction was monitored by TLC. After completion, reaction mass was quenched with ice cold water and extracted with ethyl acetate. The organic layer was washed with water, brine, dried over sodium sulphate and concentrated under reduced pressure to give crude product. Crude was purified by silica gel (100-200 mesh) column chromatography using 15% ethyl acetate in hexane as eluent to give 2-(1-(1-(5-vinylpyridin-2-yl)piperidin-4-yl)ethoxy)-5-bromothiazolo[5,4-b]pyridine (0.03 g, 37.5%) as yellow oil.

MS: 445.0 [M+1]

Step 2: Synthesis of 2-(1-(1-(5-vinylpyridin-2-yl)piperidin-4-yl)ethoxy)-5-(4-(methylsulfonyl)phenyl)thiazolo[5,4-b]pyridine

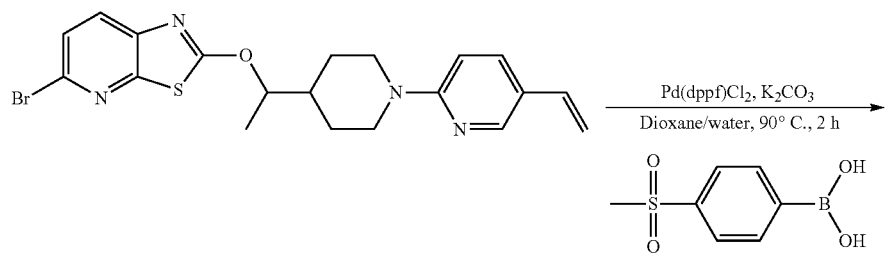

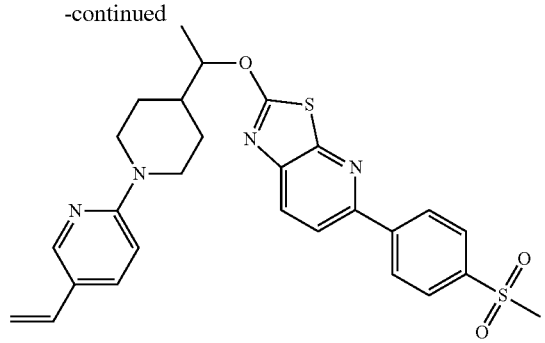

To a stirred solution of 2-(1-(1-(5-vinylpyridin-2-yl)piperidin-4-yl)ethoxy)-5-bromothiazolo[5,4-b]pyridine (0.03 g, 0.0675 mmol) and 4-(methylsulfonyl)phenylboronic acid (0.016 g, 0.810 mmol) in dioxane (5 mL) was added solution of $K_2CO_3$ (0.028 g, 0.2027 mmol) in water (1 mL) and the resulting mixture was purged with nitrogen for 30 min. After 30 min Pd(dppf)Cl$_2$ (0.0025 g, 0.00337 mmol) was added to the reaction mixture and heated at 90° C. for 2 h. Progress of reaction was monitored by TLC. After reaction completion reaction mass was diluted with water and extracted with ethyl acetate. The organic layer was washed with brine, dried over sodium sulphate and concentrated under reduced pressure to give crude product. Crude was purified by silica gel (100-200 mesh) column chromatography using 40% ethyl acetate in hexane as eluent to give 2-(1-(1-(5-vinylpyridin-2-yl)piperidin-4-yl)ethoxy)-5-(4-(methylsulfonyl)phenyl) thiazolo[5,4-b]pyridine (0.016 g, 45.5%) as white solid.

MS: 521.2 [M+1]

Example 20: 5-(4-(1-((5-(3-fluoro-4-(methylsulfonyl)phenyl)thiazolo[5,4-b]pyridin-2-yl)oxy)ethyl)piperidin-1-yl)-3-isopropyl-1,2,4-oxadiazole [1101]

Step 1: Synthesis of (4-bromo-2-fluorophenyl)(methyl) sulfane

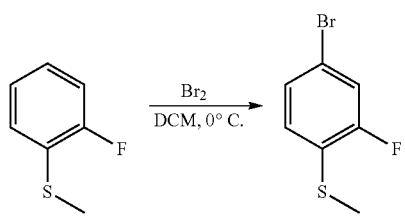

To a stirred solution of (2-fluorophenyl) (methyl) sulfane (0.5 g, 3.516 mmol) in DCM (15 ml) at 0° C., Br$_2$ (0.18 mL, 0.559 g, 3.516 mmol) in DCM (1.0 mL) was added drop wise. Allowed the reaction mixture to stir at 0° C. for 1 h. Reaction was monitored by TLC. On completion, the reaction mixture was partitioned between saturated solution of NaHCO$_3$ (30.0 mL) and ethyl acetate (2×30 mL). Combined both organic layers, dried over sodium sulphate, concentrated under vacuo. Obtained Crude was purified by column chromatography (silica gel, 100-200 mesh, 0-8% DCM in hexane as eluent) to give 0.300 g (38.58%) of (4-bromo-2-fluorophenyl) (methyl) sulfane as yellow liquid.

Mass: 217.0, 219.1 [M$^+$+1]

Step 2: Synthesis of 2-(3-fluoro-4-(methylthio)phenyl)-4,4,5,5-tetramethyl-1,3,2-dioxaborolane

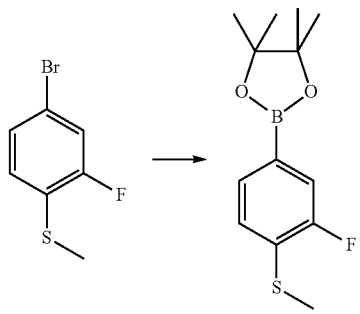

(4-bromo-2-fluorophenyl)(methyl) sulfane (0.200 g, 0.904 mmol), Potassium Acetate (0.266 g, 2.714 mmol) and Bispinacoletodiboron (0.298 g, 1.175 mmol) were dissolved in 1,4-Dioxan (15.0 mL). Degassed the reaction using N$_2$ for 30 min. To it, PdCl$_2$dppf (0.044 g, 0.060 mmol) was added and heated at 100° C. for 4 h. Reaction was monitored by TLC. On completion, reaction mass was filtered through celite pad and washed with EtOAc (2×30 mL). Filtrate was evaporated to give crude product which was purified by column chromatography using (Silica gel 100-200 mesh, 0-3% EtOAc in hexane as eluent) to give 0.062 g of 2-(3-fluoro-4-(methylthio)phenyl)-4,4,5,5-tetramethyl-1,3,2-dioxaborolane as colourless gum.

Mass: 271.2, 272.2 [M$^+$+1]

Step-3: Synthesis of 2-(1-(1-(3-isopropyl-1,2,4-oxadiazol-5-yl)piperidin-4-yl)ethoxy)-5-(3-fluoro-4-(methylthio)phenyl) thiazolo[5,4-b]pyridine

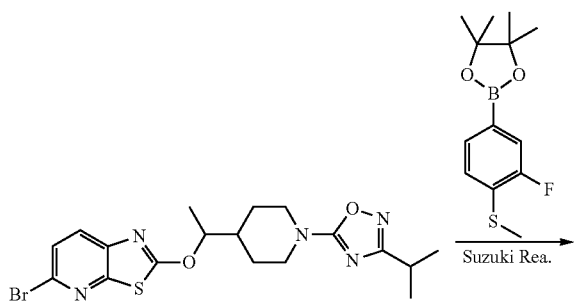

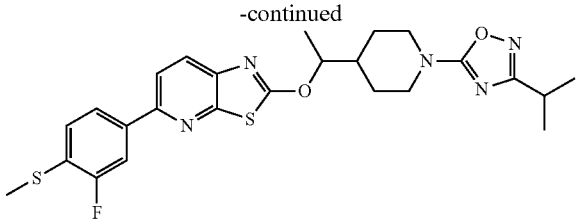

To a stirred solution of 2-(1-(1-(3-isopropyl-1,2,4-oxadi-azol-5-yl)piperidin-4-yl)ethoxy)-5-bromothiazolo[5,4-b]pyridine (0.080 g, 0.177 mmol) and 2-(3-fluoro-4-(methyl-thio)phenyl)-4,4,5,5-tetramethyl-1,3,2-dioxaborolane (0.060 g, 0.221 mmol) in dioxan (10 mL), $K_2CO_3$ (0.073 g, 0.531 mmol) in water (2 mL) was added at room temperature. Reaction was purged with nitrogen for 30 min. Then to it, $PdCl_2$(dppf) (0.0064 g, 0.0088 mmol) was added and heated at 100° C. for 3 h. Reaction was monitored by TLC. On completion, D.M. water (30 mL) was added to reaction mixture and extracted with ethyl acetate (2×30 mL). Organic layer was combined, dried over sodium sulphate and concentrated under reduced pressure to give crude product. Crude product was purified by column chromatography using (silica gel, 100-200 mesh, 0-30% ethyl acetate in hexane as eluent) to give 0.049 g (53.96%) of 2-(1-(1-(3-isopropyl-1,2,4-oxadiazol-5-yl)piperidin-4-yl)ethoxy)-5-(3-fluoro-4-(methylthio)phenyl) thiazolo[5,4-b]pyridine as yellow gum.

Mass: 514.2 [M$^+$+1]

Step-4: 2-(1-(1-(3-isopropyl-1,2,4-oxadiazol-5-yl)piperidin-4-yl)ethoxy)-5-(3-fluoro-4-(methylsulfonyl)phenyl)thiazolo[5,4-b]pyridine

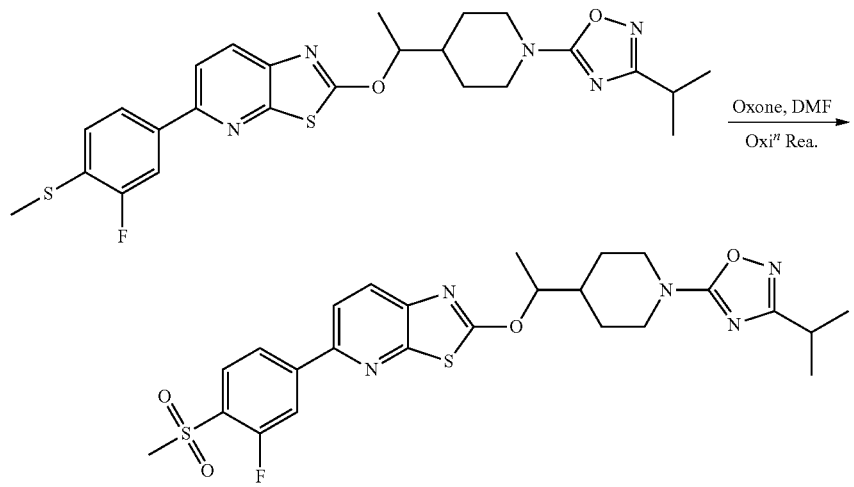

To a stirred solution of 2-(1-(1-(3-isopropyl-1,2,4-oxadi-azol-5-yl)piperidin-4-yl)ethoxy)-5-(3-fluoro-4-(methylthio)phenyl)thiazolo[5,4-b]pyridine (0.048 g, 0.0934 mmol) in Acetone (10 mL), Oxone (0.057 g, 0.186 mmol) in water (2.0 mL) was added at room temperature. Allowed the reaction mixture to stir at room temperature for 16 h. Then again oxone (0.029 g, 0.0943 mmol) was added and allowed to heat the reaction at 40° C. for 16 h. Reaction was monitored by TLC. On completion, D.M. water (50 mL) was added to reaction mixture and extracted with ethyl acetate (2×50 mL). Organic layers were combined, dried over sodium sulphate and concentrated under reduced pressure to give crude product. Crude product was purified by column chromatography using (silica gel, 100-200 mesh, 0-50% ethyl acetate in hexane as eluent) again purified in (neutral alumina, 0-40% ethyl acetate in hexane as eluent) to give 0.020 g (39.76%) of 2-(1-(1-(3-isopropyl-1,2,4-oxadiazol-5-yl)piperidin-4-yl)ethoxy)-5-(3-fluoro-4-(methylsulfonyl)phenyl)thiazolo[5,4-b]pyridine as white solid.

Mass: 546.2, 222.2 [M$^+$+1]
HPLC: (98.99%)

Example 21: 5-(4-(1-((5-(2-fluoro-4-(methylsulfo-nyl)phenyl)thiazolo[5,4-b]pyridin-2-yl)oxy)ethyl)piperidin-1-yl)-3-isopropyl-1,2,4-oxadiazole [1112]

Step 1: Synthesis of 4-bromo-3-fluorobenzenethiol

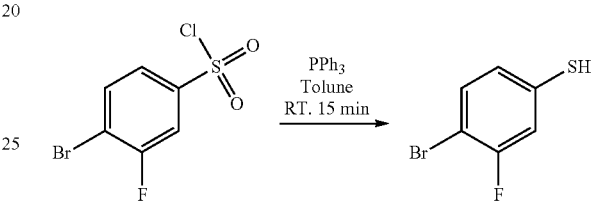

To a stirred solution of 4-bromo-3-fluorobenzene-1-sul-fonyl chloride (1 g, 0.088 mmol) in toluene (15 mL) PPh3 (4.3 g, 0.097 mmol) was added and reaction was stirred at room temperature below 50° C. for 15 min. Progress of reaction was monitored by TLC. On completion reaction was quenched with water (5 mL) and reaction mass was stirred for 10 min then aqueous layer was discarded and organic layer was extracted with 10% NaOH solution, this alkaline extract was washed with toluene and acidified with dilute HCL and extracted with DCM. The organic layer was concentrated under reduced pressure to give crude desired compound. Purification of the compound was done by silica gel (100-200 mesh) column chromatography using 10% ethyl acetate in hexane as eluent which was concentrated to afford 4-bromo-3-fluorobenzenethiol (0.5 g, 71%) as colourless oil.

MS: 207.1 [M$^+$+1].

Step 2: Synthesis of (4-bromo-3-fluorophenyl) (Methyl) sulfane

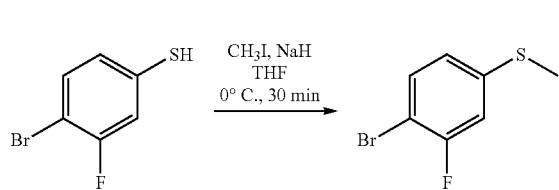

To a stirred solution of 4-bromo-3-fluorobenzenethiol (0.5 g., 2.4 mmol) in THF (5 mL) was added sodium hydride (0.146 g., 3.6 mmol) at 0° C. and reaction allowed to stir at 0° C. for 30 min. After 30 min methyl Iodide (0.380 g, 2.6 mmol) in THF (2 mL) was added to reaction mixture and stirred at room temperature for 1 h. Reaction was monitored by TLC. On completion reaction mass was quenched with ice cold water and extracted with ethyl acetate. The organic layer was washed with water, brine, dried over sodium sulphate and concentrated under reduced pressure to give crude desired product which was purified by silica gel (100-200 mesh) column chromatography using 10% ethyl acetate in hexane as eluent to afford (4-bromo-3-fluorophenyl)(Methyl) sulfane (0.450 g, 45%) as colourless oil.

MS: 222.2 [M⁺+1]

Step 3: Synthesis of 2-(2-fluoro-4-(methylthio) phenyl)-4,4,5,5-tetramethyl-1,3,2-dioxaborolane

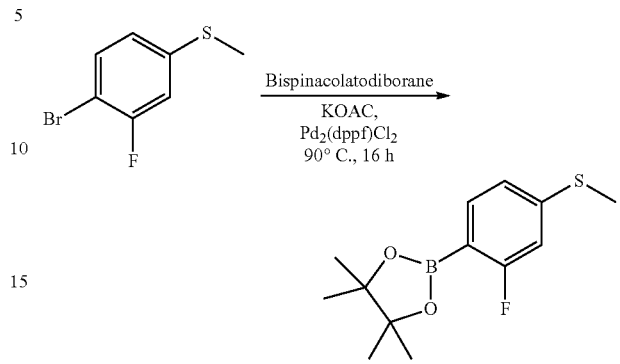

To a stirred solution of (4-bromo-3-fluorophenyl) (Methyl) sulfane (0.2 g, 0.904 mmol), Potassium acetate (0.266 g, 2.714 mmol) and Bispinacolatodiboron (298.38 g., 1.175 mmol) in dioxan (15 mL). Degassed the reaction mass with N₂ for 30 min. To it, PdCl₂dppf (0.033.3 g, 0.060 mmol) was added and heated at 90° C. for 4 h. Reaction was monitored by TLC. On completion, reaction mass was filtered through celite pad and washed with EtOAc (2×30 mL). Filtrate was evaporated to give crude product which was purified by column chromatography using (Silica gel 100-200 mesh) 0-3% EtOAc in hexane as eluent) to give of 2-(2-fluoro-4-(methylthio)phenyl)-4,4,5,5-tetramethyl-1,3,2-dioxaborolane (0.24 g,) as colourless sticky mass. MS: 269.2 [M⁺+1]

Step 4: Synthesis of 2-(1-(1-(3-isopropyl-1,2,4-oxadiazol-5-yl)piperidin-4-yl)ethoxy)-5-(2-fluoro-4-(methylthio)phenyl)thiazolo[5,4-b]pyridine

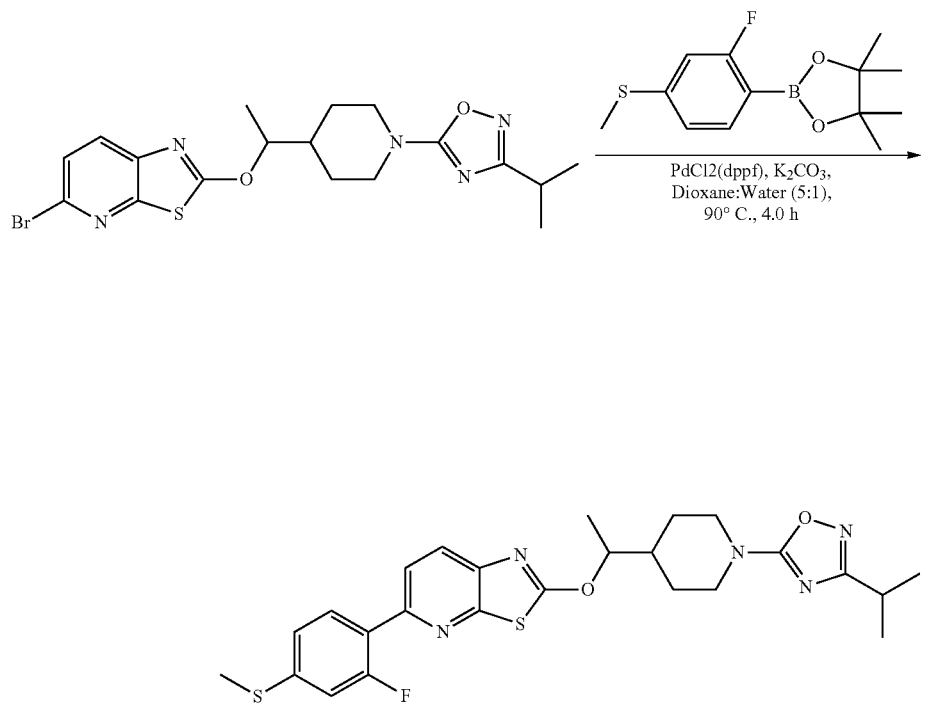

To a stirred solution of 2-(1-(1-(3-isopropyl-1,2,4-oxadiazol-5-yl)piperidin-4-yl)ethoxy)-5-bromothiazolo[5,4-b]pyridine (0.04 g, 0.088 mmol) and 2-(2-fluoro-4-(methylthio)phenyl)-4,4,5,5-tetramethyl-1,3,2-dioxaborolane (0.035 g, 0.133 mmol) in Dioxane (5 mL), $K_2CO_3$ (0.036 g, 0.26 mmol) in water (1 mL) was added and reaction mass purged with nitrogen for 30 min. After 30 min. Pd (dppf) $Cl_2$ (0.004 g, 0.004 mmol) was added to it and heated at 90° C. for 4 h. Progress of reaction was monitored by TLC. On completion reaction mass was quenched with water and extracted with ethyl acetate. The organic layer was concentrated under reduced pressure to give crude desired compound. Purification of the compound was done by silica gel (100-200 mesh) column chromatography using 30% ethyl acetate in hexane to obtain 2-(1-(1-(3-isopropyl-1,2,4-oxadiazol-5-yl)piperidin-4-yl)ethoxy)-5-(2-fluoro-4-(methylthio)phenyl)thiazolo[5,4-b]pyridine (0.009 g, 12%) as off white solid.

MS: 514.2 [$M^+$+1].

Step 5: Synthesis of 2-(1-(1-(3-isopropyl-1,2,4-oxadiazol-5-yl)piperidin-4-yl)ethoxy)-5-(2-fluoro-4-(methylsulfonyl)phenyl)thiazolo[5,4-b]pyridine

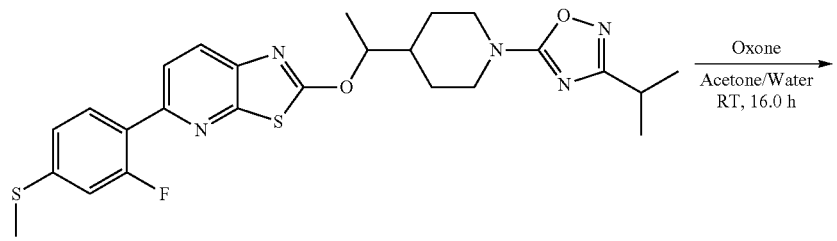

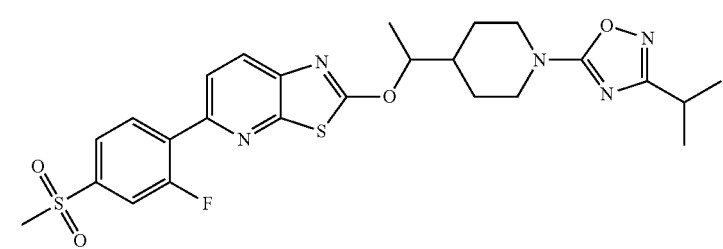

To a stirred solution of 2-(1-(1-(3-isopropyl-1,2,4-oxadiazol-5-yl)piperidin-4-yl)ethoxy)-5-(2-fluoro-4-(methylthio)phenyl)thiazolo[5,4-b]pyridine (0.009 g, 0.017 mmol) in acetone (5 mL), Oxone (0.010 g, 0.035 mmol) in water (1.5 mL) was added and reaction mass was stir for 16 h at room temperature. Progress of reaction was monitored by TLC. On completion acetone was evaporated and residue was quenched with water, compound was extracted with ethyl acetate. The organic layer was concentrated under reduced pressure to give crude desired compound. Purification of the compound was done by silica gel (100-200 mesh) column chromatography using 2% methanol in DCM to obtain 2-(1-(1-(3-isopropyl-1,2,4-oxadiazol-5-yl)piperidin-4-yl)ethoxy)-5-(2-fluoro-4-(methylsulfonyl)phenyl)thiazolo[5,4-b]pyridine (0.02 g, 62%) as white solid.

MS: 546.2 [M$^+$+1].

Example 22: Synthesis of 2-(1-(1-(3-isopropyl-1,2,4-oxadiazol-5-yl)piperidin-4-yl)ethoxy)-5-(isothiazol-4-yl)thiazolo[5,4-b]pyridine[1124]

Step 1: Synthesis of 4-(4,4,5,5-tetramethyl-1,3,2-dioxaborolan-2-yl)isothiazole

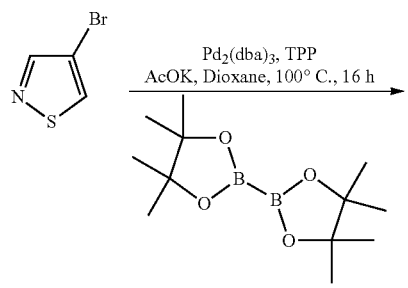
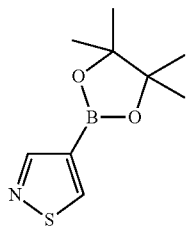

To a stirred solution of 4-bromoisothiazole (0.2 g, 1.21 mmol) and Bis(pinacolato)diboron (0.464 g, 1.81 mmol) in Dioxane (10 mL) was added AcOK (0.358 g, 3.61 mmol) along with TPP (0.032 g, 0.12 mmol) and reaction mass was purged with nitrogen for 30 min. Then, Pd$_2$(dba)$_3$ (0.056 g, 0.061 mmol) was added to it and stirred at 100° C. for 16 h. Reaction was monitored by TLC. On completion reaction mass was concentrated under reduced pressure and extracted with ethyl acetate. The organic layer was washed with water, brine, dried over sodium sulphate, concentrated under reduced pressure obtained crude which was purified column chromatography; eluent 3% EtOAc/Hexane to afford 4-(4,4,5,5-tetramethyl-1,3,2-dioxaborolan-2-yl)isothiazole (0.07 g, 27%) as yellow solid.

MS: 212.1 [M$^+$+1]

Step 2: Synthesis of 2-(1-(1-(3-isopropyl-1,2,4-oxadiazol-5-yl)piperidin-4-yl)ethoxy)-5-(isothiazol-4-yl)thiazolo[5,4-b]pyridine

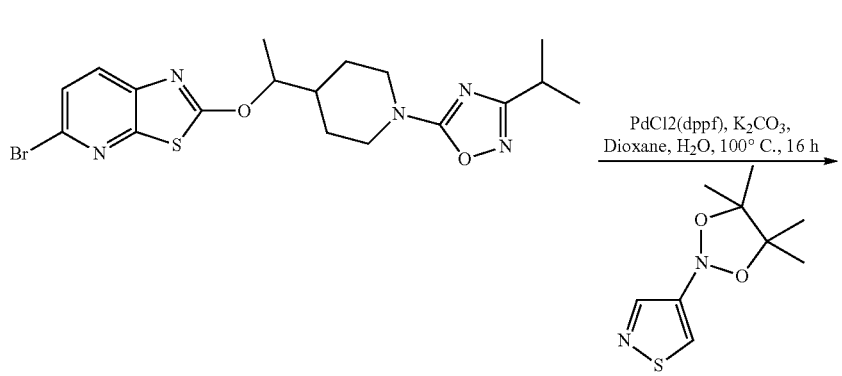
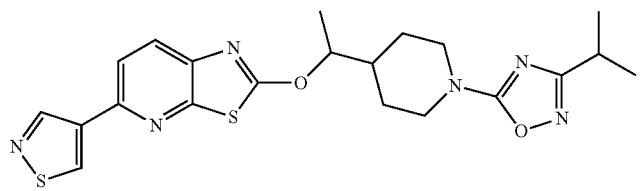

To a stirred solution of 2-(1-(1-(3-isopropyl-1,2,4-oxadiazol-5-yl)piperidin-4-yl)ethoxy)-5-bromothiazolo[5,4-b]pyridine (0.03 g, 0.0663 mmol) and 4-(4,4,5,5-tetramethyl-1,3,2-dioxaborolan-2-yl)isothiazole (0.017 g, 0.071 mmol) in Dioxane (10 mL) was added $K_2CO_3$ (0.028 g, 0.19 mmol) in water (2 mL) and reaction mass was purged with nitrogen for 30 min. Then, $PdCl_2$(dppf) (0.003 g, 0.0031 mmol) was added to it and stirred at 100° C. for 16 h. Reaction was monitored by TLC. On completion reaction was concentrated under reduced pressure obtained crude which was purified by column chromatography (100-200 Mesh); eluent 30% EtOAc/Hexane to afford 2-(1-(1-(3-isopropyl-1,2,4-oxadiazol-5-yl)piperidin-4-yl)ethoxy)-5-(isothiazol-4-yl)thiazolo[5,4-b]pyridine (0.011 g, 36%) as light yellow solid.

MS: 457.1 [M$^+$+1]

Example 23: 2-(1-(1-(3-isopropyl-1,2,4-oxadiazol-5-yl)piperidin-4-yl)ethoxy)-5-(2-chloropyridin-4-yl)thiazolo[5,4-b]pyridine [1132]

Step 1: Synthesis of 2-(1-(1-(3-isopropyl-1,2,4-oxadiazol-5-yl)piperidin-4-yl)ethoxy)-5-(2-chloropyridin-4-yl)thiazolo[5,4-b]pyridine

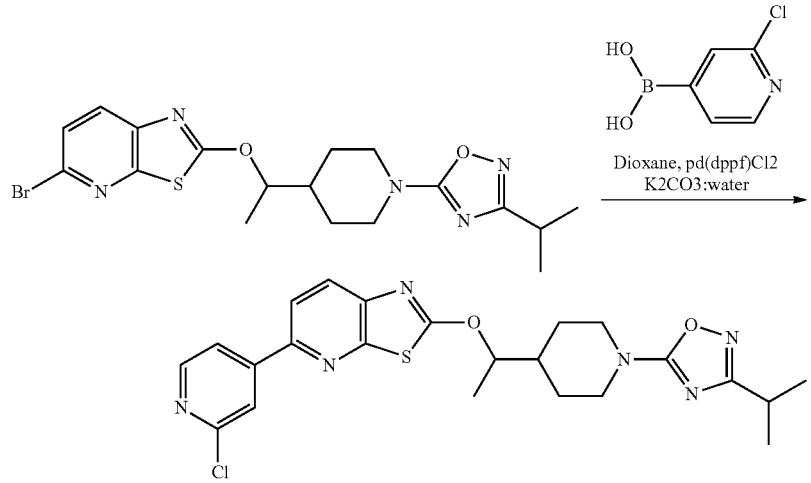

To a solution of 2-(1-(1-(3-isopropyl-1,2,4-oxadiazol-5-yl)piperidin-4-yl)ethoxy)-5-bromothiazolo[5,4-b]pyridine (0.040 g, 0.000089 mol) and 2-chloropyridin-4-yl-4-boronic acid (0.023 g, 0.11 mmol) in Dioxane (4 mL), $K_2CO_3$ (0.032 g, 0.23 mmol) (dissolved in water 1 mL) was added and reaction mixture purged with nitrogen for 30 min. To it, Pd(dppf)Cl$_2$ (0.0065 g, 0.09 mmol) was added and again purged with nitrogen for 15 min. Now reaction mixture was heated at 100° C. for 2 h. Reaction progress was monitored on TLC for its completion. On completion, reaction mixture was quenched with water and extracted with ethyl acetate. The organic layer was concentrated under reduced pressure to give crude reaction mass. Purification of the compound was done by silica gel (100-200#) column chromatography and desired product start eluting at 7-10% EtOAc/N-Hexane to obtained 2-(1-(1-(3-isopropyl-1,2,4-oxadiazol-5-yl)piperidin-4-yl)ethoxy)-5-(2-chloropyridin-4-yl)thiazolo[5,4-b]pyridine as white pinkish solid material.

MS: 485 [M$^+$+1]

Example 24: 2-((S)-1-(1-(3-isopropyl-1,2,4-oxadiazol-5-yl)piperidin-4-yl)ethoxy)-5-(2-(methylsulfonyl)pyrimidin-5-yl)thiazolo[5,4-b]pyridine [1133]

Step 1: Synthesis of 5-bromo-2-(methylthio)pyrimidine

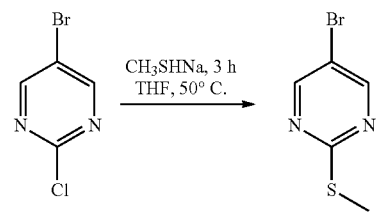

To a stirred solution of 5-bromo-2-chloropyrimidine (0.3 g, 1.563 mmol) in DMF (10 mL) was added methyl mercaptan (0.1 mL, 1.563 mmol) at room temperature and heat at 50° C. for 3 h. Completion of reaction was monitored by TLC. Reaction mixture was quenched by addition of water, extracted with EtOAc. Organic portions were combined, dried over $Na_2SO_4$, evaporated under reduced pressure to obtain crude which was purified by column chromatography using silica gel (100-200 mesh); eluent 5% ethyl acetate/hexane to obtain pure product 5-bromo-2-(methylthio)pyrimidine (0.240 g, 75%) as white solid.

MS: 205.1 [M$^+$+1]

Step 2: Synthesis of 2-(methylthio)pyrimidin-5-yl-5-boronic Acid

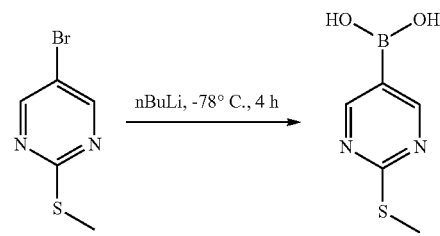

To a stirred solution of 5-bromo-2-(methylthio)pyrimidine (0.05 g, 0.241 mmol) in THF (10 mL) at −78° C. was added n-Butyl lithium (0.15 mL, 0.36 mmol, 2.5M in hexane) under nitrogen and stirred for 1 h at the same temperature. Triisopropyl borate (0.068 g, 0.361 mmol) was then added drop wise to the reaction mixture, stirred for 4 h at −78° C. Progress of reaction was monitored by TLC. After completion reaction mass was quenched with ice cold water and partitioned between saturated NH$_4$Cl solution and EtOAc. The organic layer was washed with brine, dried over sodium sulphate and concentrated under reduced pressure to give 2-(methylthio)pyrimidin-5-yl-5-boronic acid (0.03 g, 73%) as off-white solid.

MS: 171.1 [M$^+$+1]

Step 3: Synthesis of 2-((S)-1-(1-(3-isopropyl-1,2,4-oxadiazol-5-yl)piperidin-4-yl)ethoxy)-5-(2-(methylthio)pyrimidin-5-yl)thiazolo[5,4-b]pyridine

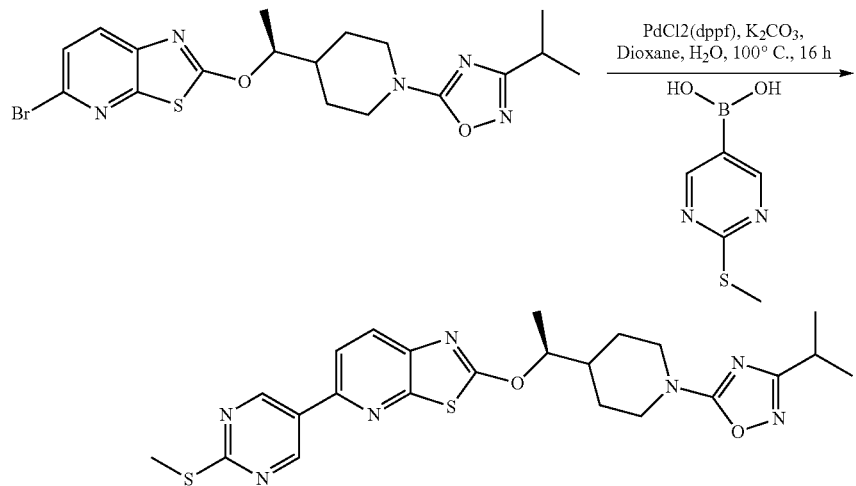

To a stirred solution of 2-((S)-1-(1-(3-isopropyl-1,2,4-oxadiazol-5-yl)piperidin-4-yl)ethoxy)-5-bromothiazolo[5,4-b]pyridine (0.06 g, 0.0663 mmol) and 2-(methylthio)pyrimidin-5-yl-5-boronic acid (0.030 g, 0.071 mmol) in Dioxane (10 mL) was added K$_2$CO$_3$ (0.073 g, 0.52 mmol) in water (2 mL) and reaction mass was purged with nitrogen for 30 min. Then, PdCl$_2$(dppf) (0.007 g, 0.0088 mmol) was added to it and stirred at 100° C. for 16 h. Reaction was monitored by TLC. On completion reaction was concentrated under reduced pressure obtained crude which was purified by column chromatography (100-200 Mesh); eluent 30% EtOAc/Hexane to afford 2-((S)-1-(1-(3-isopropyl-1,2,4-oxadiazol-5-yl)piperidin-4-yl)ethoxy)-5-(2-(methylthio)pyrimidin-5-yl)thiazolo[5,4-b]pyridine (0.030 g, 45%) as off-white solid.

MS: 498.1 [M$^+$+1]

Step 4: Synthesis of 2-((S)-1-(1-(3-isopropyl-1,2,4-oxadiazol-5-yl)piperidin-4-yl)ethoxy)-5-(2-(methylsulfonyl)pyrimidin-5-yl)thiazolo[5,4-b]pyridine

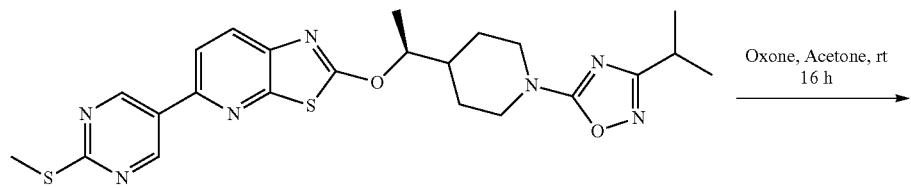

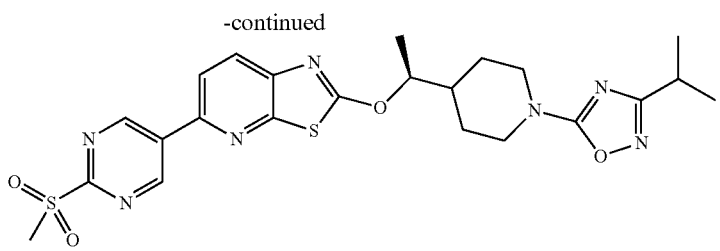

To a stirred solution of 2-((S)-1-(1-(3-isopropyl-1,2,4-oxadiazol-5-yl)piperidin-4-yl)ethoxy)-5-(2-(methylthio)pyrimidin-5-yl)thiazolo[5,4-b]pyridine (0.03 g, 0.06 mmol) in Acetone (10 mL) was added Oxone (0.037 g, 0.12 mmol) in water (2 mL) then, reaction mass was stirred at room temperature for 16 h. Reaction was monitored by TLC. On completion reaction was concentrated under reduced pressure and extracted with ethyl acetate. The organic layer was washed with water, brine, dried over sodium sulphate, concentrated under reduced pressure obtained crude which was purified column chromatography (100-200 Mesh); eluent 2% methanol/DCM to afford 2-((S)-1-(1-(3-isopropyl-1,2,4-oxadiazol-5-yl)piperidin-4-yl)ethoxy)-5-(2-(methylsulfonyl)pyrimidin-5-yl)thiazolo[5,4-b]pyridine (0.012 g, 38%) as off white solid.

MS: 530.1 [M$^+$+1]

Example 25: 2-((S)-1-(1-(5-chloropyrimidin-2-yl)piperidin-4-yl)ethoxy)-5-(6-(methylsulfonyl)pyridin-3-yl)thiazolo[5,4-b]pyridine [1136]

Step 1: Synthesis of 2-chloropyrimidin-5-yl-5-boronic Acid

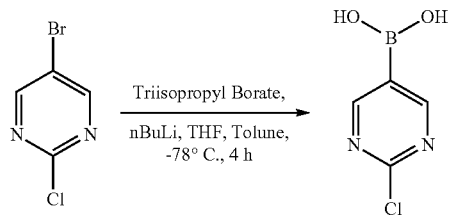 [SMILES: Clc1ncc(Br)cn1 ; OB(O)c1cnc(Cl)nc1]

To a stirred solution of 5-bromo-2-chloropyrimidine (1.0 g, 5.170 mmol) in mixture of THF:Toluene (25 mL, 4:1) was added n-BuLi (1.6M in Hexane) (3.87 mL, 5.61 mmol) dropwise at −78° C. And allowed to stir at −78° C. for 4 h. On completion, Reaction mass diluted with water and stirred at RT for 1 h, extracted with Diethyl ether. Then acidify using 1N HCl up to pH 2-3 and extracted with EtOAc. Organic portions were combined, dried over Na$_2$SO$_4$, evaporated under reduced pressure to give 2-chloropyrimidin-5-yl-5-boronic acid (0.6 g, 73.3%) as white solid.

MS: 159.3 [M$^+$+1]

Step 2: Synthesis of 2,5-dichloropyrimidine

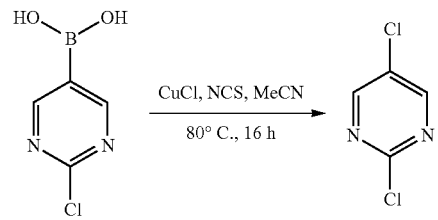

To a stirred solution of 2-chloropyrimidin-5-yl-5-boronic acid (0.5 g, 3.164 mmol) and CuCl (0.569 g, 6.329 mmol) in MeCN (20 mL) was added N-Chloro succinimide (0.084 g, 6.329 mmol) and heated at 80° C. for 16 h. Completion of reaction was monitored by TLC. Reaction was quenched with sat. Soln. Of NaHCO$_3$ up to pH-8 and extracted with Diethyl ether. The organic layer was washed with water, brine, dried over Na$_2$SO$_4$, evaporated under reduced pressure to give 2,5-dichloropyrimidine (0.2 g, 75%) as light yellow solid.

MS: 148.9 [M$^+$+1]

Step-3: Synthesis of 1-(1-(5-chloropyrimidin-2-yl)piperidin-4-yl)ethanol

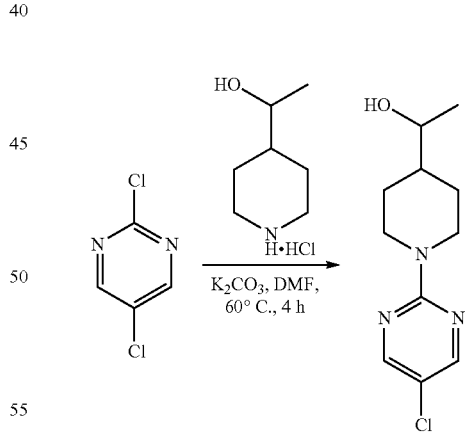

1-(piperidin-4-yl) ethanol hydrochloride (0.344 g, 2.229 mmol) was dissolved in DMF (15.0 mL). To it, K$_2$CO$_3$ (0.840 g, 6.081 mmol) was added and allowed the reaction to stir at room temperature for 30 min. Then to it, 2,5-dichloropyrimidine (0.300 g, 2.027 mmol) was added and allowed to stir at 60° C. for 4 h. Reaction was monitored by TLC. On completion, D.M. water was added to reaction mixture and extracted with EtOAc. Organic layers were combined, washed with brine solution, dried over sodium sulphate and concentrated under reduced pressure to give crude product. Crude product was purified by column chromatography using (silica gel, 100-200 mesh, 0-30% EtOAc in hexane as eluent) to give 1-(1-(5-chloropyrimidin-2-yl)piperidin-4-yl)ethanol (0.230 g, 46.9%) as off white solid.

MS: 242.1 [M$^+$+1]

Step-4: Synthesis of (2S)-1-(1-(5-chloropyrimidin-2-yl)piperidin-4-yl)ethyl 2-methoxy-2-phenyl acetate

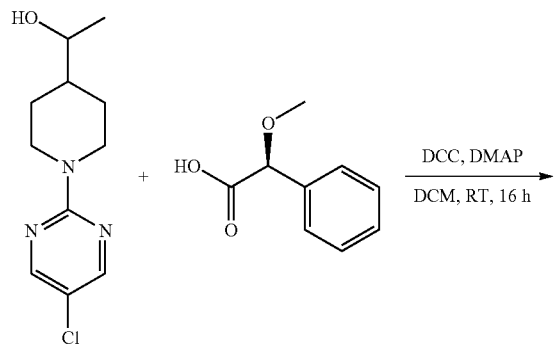

To a stirred solution of 1-(1-(5-chloropyrimidin-2-yl)piperidin-4-yl)ethanol (0.22 g, 0.913 mmol) and (S)-2-methoxy-2-phenylacetic acid (0.167 g, 1.005 mmol) in DCM (30 mL) was added DCC (0.226 g, 1.096 mmol), DMAP (0.030 g, 0.246 mmol) and stirred at room temperature for 16 h. Reaction was monitored by TLC. On completion, D.M. water (50 mL) was added to reaction mixture and extracted with DCM (2×50 mL). Organic layers were combined, washed with brine solution (50 mL), dried over sodium sulphate and concentrated under reduced pressure to give crude product. Crude product was purified by column chromatography using (silica gel, 100-200 mesh, 0-20% EtOAc in hexane as eluent) to give 1-(1-(5-propylpyrimidin-2-yl)piperidin-4-yl)ethyl 2-methoxy-2-phenylacetate (0.320 g) mixture which was separated by Prep HPLC to give (2S)—(R)-1-(1-(5-chloropyrimidin-2-yl)piperidin-4-yl)ethyl 2-methoxy-2-phenylacetate (0.035 g, 19.71%) as off white solid.

MS: 390.15 [M$^+$+1]

Step-5: Synthesis of (R)-1-(1-(5-chloropyrimidin-2-yl)piperidin-4-yl)ethanol

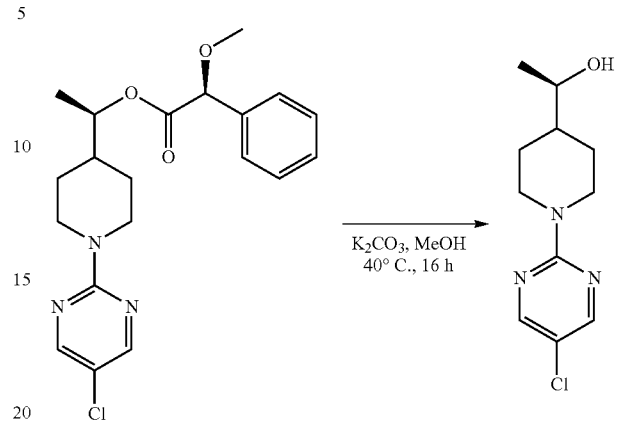

To a stirred solution of (S)-1-(1-(5-propylpyrimidin-2-yl)piperidin-4-yl)ethyl 2-methoxy-2-phenylacetate (0.035 g, 0.089 mmol) in MeOH (5 mL) was added K$_2$CO$_3$ (0.018 g, 0.134 mmol) in water (2.5 mL) at room temperature and stirred at 40° C. for 16 h. Reaction was monitored by TLC. On completion, removed all volatiles, D.M. was added to reaction mixture and extracted with EtOAc. Organic layers were combined, washed with brine solution, dried over sodium sulphate and concentrated under reduced pressure to give (R)-1-(1-(5-chloropyrimidin-2-yl)piperidin-4-yl)ethanol (0.022 g, 100%) as white solid.

MS: 242.1 [M$^+$+1]

Step-6: Synthesis of 2-(1-(1-(3-isopropyl-1,2,4-thiadiazol-5-yl)piperidin-4-yl)ethoxy)-5-bromothiazolo[5,4-b]pyridine

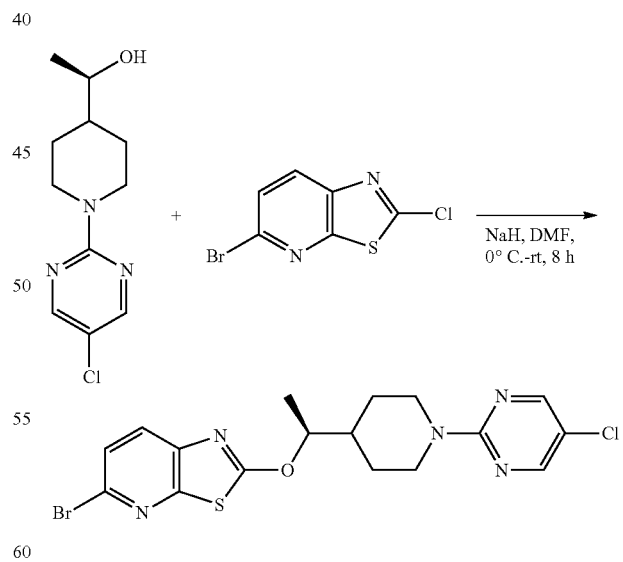

To a stirred solution of (R)-1-(1-(5-chloropyrimidin-2-yl)piperidin-4-yl)ethanol (0.020 g, 0.083 mmol) in DMF (2 mL) was added sodium hydride (0.0067 g, 0.166 mmol) at 0° C. and stirred for 30 min. After 30 min, 5-bromo-2-chlorothiazolo[5,4-b]pyridine (0.025 g, 0.099 mmol) in DMF (1 mL) was added to reaction mass and stir at room temperature for 6 h. Reaction was monitored by TLC. On completion reaction was quenched with ice cold water, extracted with ethyl acetate. The organic layer was washed with water, brine, dried over sodium sulphate, concentrated under reduced pressure to give crude product which was purified by column chromatography (silica gel, 100-200 Mesh, 0-18% EtOAc in Hexane as eluent) to give 2-((S)-1-(1-(5-chloropyrimidin-2-yl)piperidin-4-yl)ethoxy)-5-bromo thiazolo[5,4-b]pyridine (0.015 g, 37.59%) as off white gum.

MS: 454.0 [M⁺+1]

Step-7: Synthesis of 2-((S)-1-(1-(5-chloropyrimidin-2-yl)piperidin-4-yl)ethoxy)-5-(6-(methylthio)pyridin-3-yl) thiazolo[5,4-b]pyridine

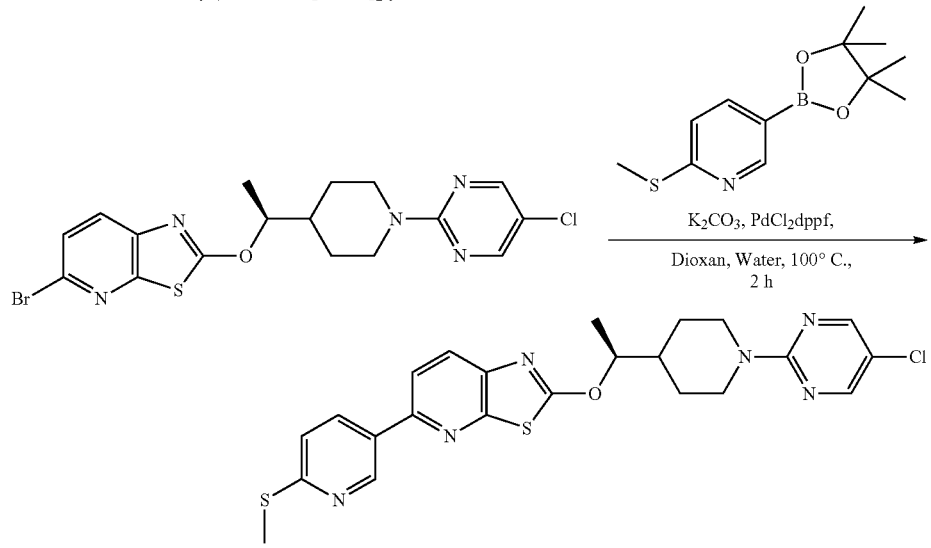

To a stirred solution of 2-((S)-1-(1-(5-chloropyrimidin-2-yl)piperidin-4-yl)ethoxy)-5-bromothiazolo [5,4-b]pyridine (0.030 g, 0.066 mmol) and 5-(4,4,5,5-tetramethyl-1,3,2-dioxaborolan-2-yl)-2-(methylthio)pyridine (0.026 g, 0.105 mmol) in dioxan (4 mL), K$_2$CO$_3$ (0.027 g, 0.198 mmol) in water (1.0 mL) was added at room temperature. Reaction was purged with nitrogen for 30 min. Then to it, PdCl$_2$(dppf) (0.0024 g, 0.0033 mmol) was added and heated at 100° C. for 2 h. Reaction was monitored by TLC. On completion, D.M. water was added to reaction mixture and extracted with ethyl acetate. Organic layers were combined, dried over sodium sulphate and concentrated under reduced pressure to give crude product. Crude product was purified by column chromatography using (silica gel, 100-200 mesh, 0-20% Acetone in hexane as eluent) to give 2-((S)-1-(1-(5-chloropyrimidin-2-yl)piperidin-4-yl)ethoxy)-5-(6-(methylthio) pyridin-3-yl)thiazolo[5,4-b]pyridine (0.015 g, 45.39%) as off white solid.

MS: 499.1 [M⁺+1]

Step 8: Synthesis of 2-((S)-1-(1-(5-chloropyrimidin-2-yl)piperidin-4-yl)ethoxy)-5-(6-(methylsulfonyl)pyridin-3-yl)thiazolo[5,4-b]pyridine

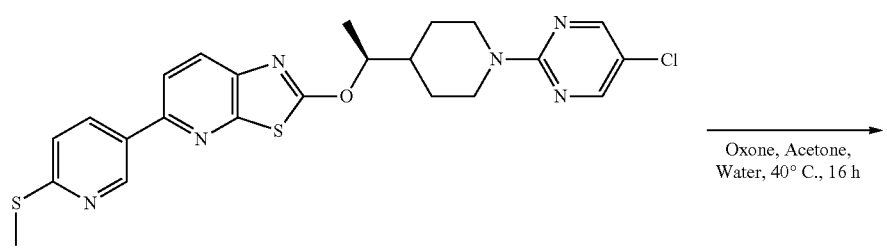

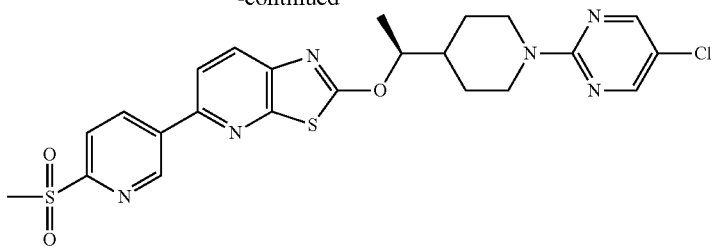

To a stirred solution of 2-((S)-1-(1-(5-chloropyrimidin-2-yl)piperidin-4-yl)ethoxy)-5-(6-(methylthio)pyridin-3-yl)thiazolo[5,4-b]pyridine (0.015 g, 0.030 mmol) in acetone (5.0 mL), Oxone (0.018 g, 0.060 mmol) in water (1 mL) was added drop wise at room temperature. Allowed the reaction to stir at 40° C. for 16 h. Completion of reaction was monitored by TLC. Reaction mass was evaporated, diluted with water, extracted with EtOAc. Organic portions were combined, dried over $Na_2SO_4$, evaporated under reduced pressure to obtain crude product. Crude product was purified by column chromatography using (Neutral alumina followed by silica gel, 100-200 mesh, 0-20% Acetone in hexane as eluent) to give 2-((S)-1-(1-(5-chloropyrimidin-2-yl)piperidin-4-yl)ethoxy)-5-(6-(methylthio)pyridin-3-yl)thiazolo[5,4-b]pyridine (0.006 g, 37.58%) as off white sticky gum.

MS: 531.1 [M$^+$+1]

Example 26: 2-(1-(1-(5-cyclopropylpyrimidin-2-yl)piperidin-4-yl)ethoxy)-5-(6-(methylsulfonyl)pyridin-3-yl)thiazolo[5,4-b]pyridine [1137]

Step 1: Synthesis of 2-chloro-5-cyclopropylpyrimidine

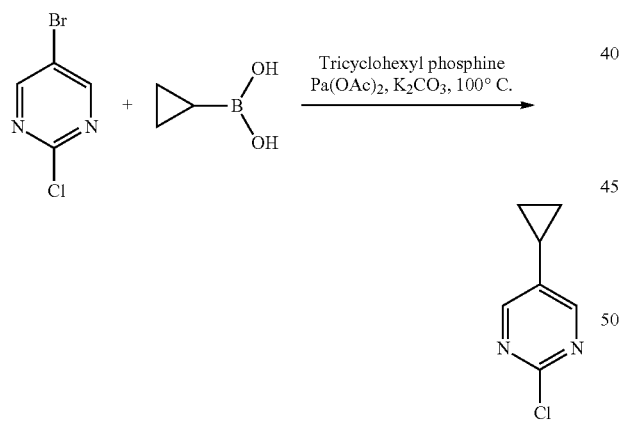

To a stirred solution of 5-bromo-2-chloropyrimidine (0.1 g, 0.521 mmol) and cyclopropylboronic acid (0.053 g, 0.625 mmol) in Dioxane (10 mL) was added $K_2CO_3$ (0.216 g, 1.563 mmol) in water (2 mL) and reaction mass was purged with nitrogen for 30 min. Then, Pd(OAc)2 (0.007 g, 0.026 mmol) along with tricyclohexyl phosphine (0.014 g, 0.051 mmol) were added to it and stirred at 100° C. for 16 h. Reaction was monitored by TLC. On completion reaction was concentrated under reduced pressure obtained crude which was purified by column chromatography (100-200 Mesh); eluent 10% EtOAc/Hexane to afford 2-chloro-5-cyclopropylpyrimidine (0.038 g, 47%) as Off-white solid.

MS: 155.1 [M$^+$+1]

Step 2: Synthesis of 1-(1-(5-cyclopropylpyrimidin-2-yl)piperidin-4-yl)ethanol

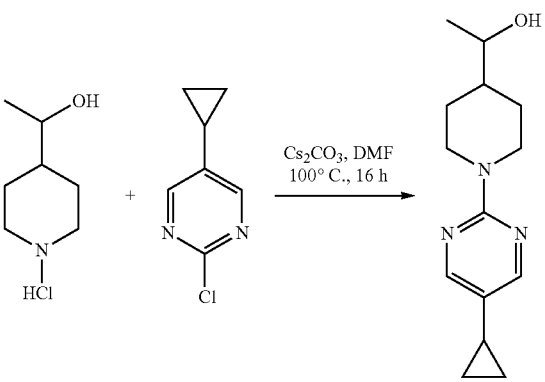

To a stirred solution of 1-(piperidin-4-yl)ethanol HCl (0.035 g, 0.212 mmol) and 2-chloro-5-cyclopropylpyrimidine (0.032 g, 0.212 mmol) in DMF (5 mL) was added cesium carbonate under nitrogen and heated 16 h at 100° C. Progress of reaction was monitored by TLC. After reaction completion reaction mass was diluted with water, extracted with ethyl acetate. The organic layer was washed with brine, dried over sodium sulphate and concentrated under reduced pressure to give crude product. Crude was purified by silica gel (100-200 mesh) column chromatography using 20% acetone in hexane as eluent to obtain 1-(1-(5-cyclopropylpyrimidin-2-yl)piperidin-4-yl)ethanol (0.046 g, 88%) as colourless oil.

MS: 248.2 [M+1]

Step 3: Synthesis of 2-(1-(1-(5-cyclopropylpyrimidin-2-yl)piperidin-4-yl)ethoxy)-5-bromothiazolo[5,4-b]pyridine

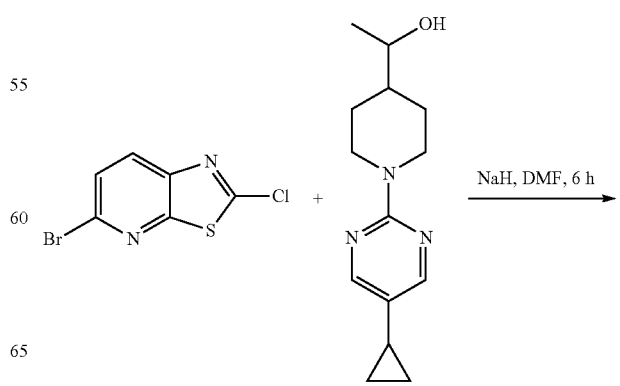

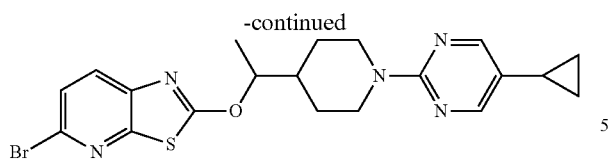

To a stirred solution of 1-(1-(5-cyclopropylpyrimidin-2-yl)piperidin-4-yl)ethanol (0.050 g, 0.200 mmol) in DMF (3 mL) was added sodium hydride (0.016 g, 0.404 mmol) at 0° C. and stirred for 30 min at room temperature. After 30 min solution of 5-bromo-2-chlorothiazolo[5,4-b]pyridine (0.075 g, 0.300 mmol) in DMF (2 mL) was added to the reaction mixture and stirred for 6 h. Progress of reaction was monitored by TLC. After completion reaction mass was quenched with ice cold water and extracted with ethyl acetate. The organic layer was washed with water, brine, dried over sodium sulphate and concentrated under reduced pressure to give crude product. Crude was purified by silica gel (100-200 mesh) column chromatography using 10% acetone in hexane as eluent to give 2-(1-(1-(5-cyclopropylpyrimidin-2-yl)piperidin-4-yl)ethoxy)-5-bromothiazolo[5,4-b]pyridine (0.046 g, 49%) as sticky solid.

MS: 461.1 [M+1]

Step 4: Synthesis of 2-(1-(1-(5-cyclopropylpyrimidin-2-yl)piperidin-4-yl)ethoxy)-5-(6-(methylthio)pyridin-3-yl)thiazolo[5,4-b]pyridine

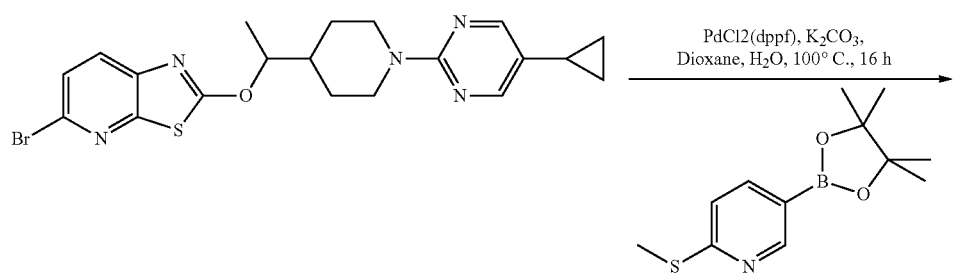

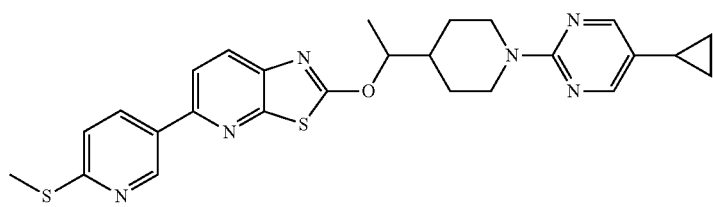

To a stirred solution of 2-(1-(1-(5-cyclopropylpyrimidin-2-yl)piperidin-4-yl)ethoxy)-5-bromothiazolo[5,4-b]pyridine (0.03 g, 0.0663 mmol) and 5-(4,4,5,5-tetramethyl-1,3,2-dioxaborolan-2-yl)-2-(methylthio)pyridine (0.019 g, 0.071 mmol) in Dioxane (10 mL) was added K$_2$CO$_3$ (0.027 g, 0.19 mmol) in water (2 mL) and reaction mass was purged with nitrogen for 30 min. Then, PdCl$_2$(dppf) (0.003 g, 0.0031 mmol) was added to it and stirred at 100° C. for 16 h. Reaction was monitored by TLC. On completion reaction was concentrated under reduced pressure obtained crude which was purified by column chromatography (100-200 Mesh); eluent 25% EtOAc/Hexane to afford 2-(1-(1-(5-cyclopropylpyrimidin-2-yl)piperidin-4-yl)ethoxy)-5-(6-(methylthio)pyridin-3-yl)thiazolo[5,4-b]pyridine (0.02 g, 62%) as light yellow sticky.

MS: 505.1 [M$^+$+1]

Step 5: Synthesis of 2-(1-(1-(5-cyclopropylpyrimidin-2-yl)piperidin-4-yl)ethoxy)-5-(6-(methylsulfonyl)pyridin-3-yl)thiazolo[5,4-b]pyridine

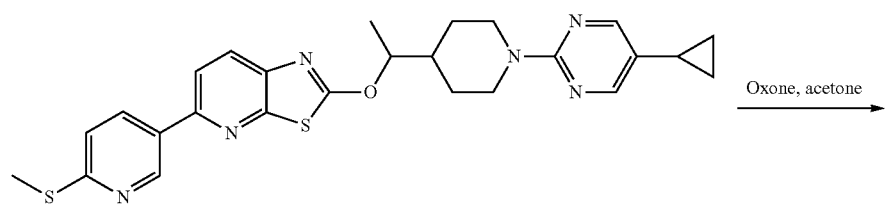

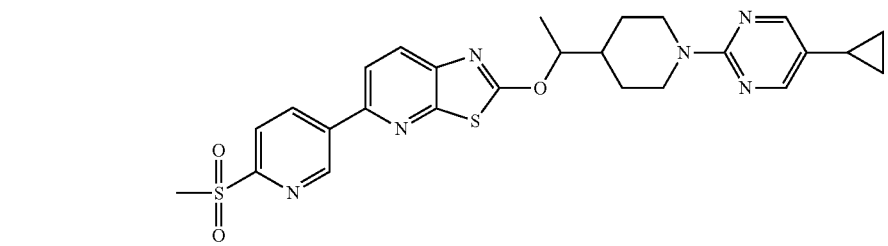

To a stirred solution of 2-(1-(1-(5-cyclopropylpyrimidin-2-yl)piperidin-4-yl)ethoxy)-5-(6-(methylthio)pyridin-3-yl)thiazolo[5,4-b]pyridine (0.03 g, 0.050 mmol) in Acetone (10 mL) was added Oxone (0.036 g, 0.11 mmol) in water (2 mL) then, reaction mass was stirred at room temperature for 16 h. Reaction was monitored by TLC. On completion reaction was concentrated under reduced pressure and extracted with ethyl acetate. The organic layer was washed with water, brine, dried over sodium sulphate, concentrated under reduced pressure obtained crude which was purified column chromatography (100-200 Mesh); eluent 25% Acetone/Hexane to afford 2-(1-(1-(5-cyclopropylpyrimidin-2-yl)piperidin-4-yl)ethoxy)-5-(6-(methylsulfonyl)pyridin-3-yl)thiazolo[5,4-b]pyridine (0.012 g, 38%) as off white solid.

MS: 538.1 [M$^+$+1]

Example 27: 1-(5-(2-(1-(1-(3-isopropyl-1,2,4-oxadiazol-5-yl)piperidin-4-yl)ethoxy)thiazolo[5,4-b]pyridin-5-yl)pyridin-2-yl)imidazolidin-2-one [1144]

Step 1: Synthesis of 1-(4-bromophenyl)imidazolidin-2-one

To a solution of 5-bromo-2-iodopyridine (0.15 g, 0.53 mmol) and imidazolidin-2-one (0.22 g, 2.65 mmol) in n-butanol (15 mL) was added copper iodide (0.01 g, 0.053 mmol) TMEDA (0.018, 0.15 mmol) and pot. Carbonate (0.22 g, 1.59 mmol) and the mixture was heated to 100° C. for 5 h. Progress of reaction was monitored by TLC. After reaction completion solvents water was added and extracted with ethyl acetate. Combined organic layer was washed with brine, dried over sodium sulphate and concentrated under reduced pressure. Crude was purified by washing with diethyl ether/hexane to give 1-(4-bromophenyl)imidazolidin-2-one (0.11 g, 89.8%) as yellow solid.

MS: 242.08 [M+1]

Step 2: Synthesis of 1-(5-(4,4,5,5-tetramethyl-1,3,2-dioxaborolan-2-yl)pyridin-2-yl)imidazolidin-2-one

Step 3: Synthesis of 1-(5-(2-(1-(1-(3-isopropyl-1,2,4-oxadiazol-5-yl)piperidin-4-yl)ethoxy)thiazolo[5,4-b]pyridin-5-yl)pyridin-2-yl)imidazolidin-2-one

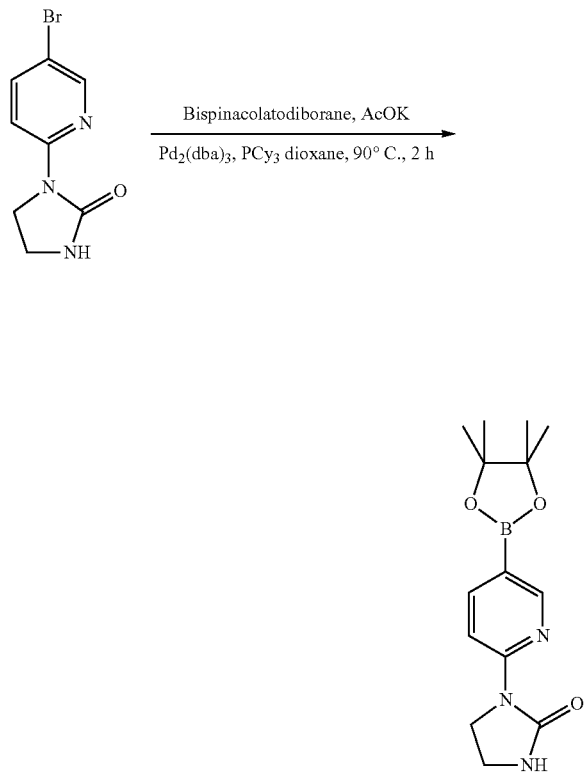

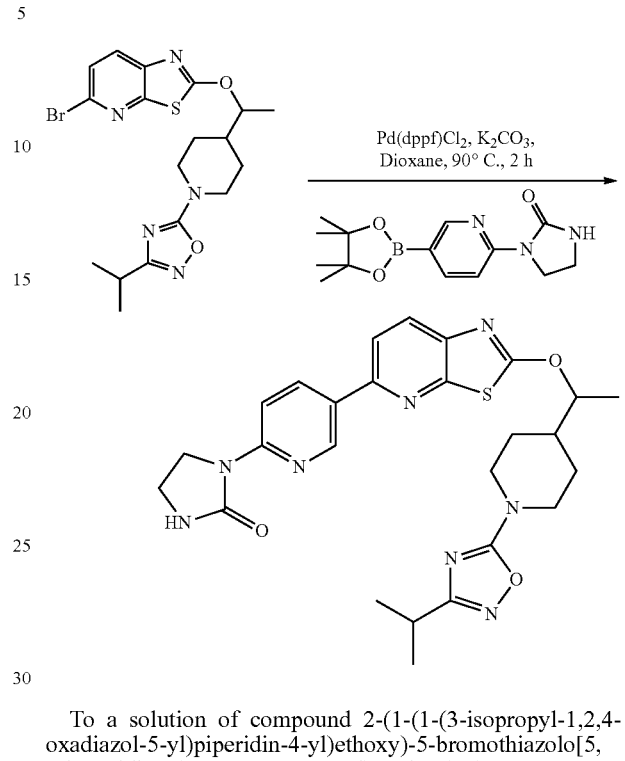

To a solution of 1-(4-bromophenyl)imidazolidin-2-one (0.05 g, 0.206 mmol) and bispinacilatodiborane (0.058 g, 0.22) in dioxane 5 mL). Pd2(dba)3 (0.09, 0.010 mmol) and tricyclohexyl phosphine (0.046, 0.016) were added after degassing the mixture for 30 min. with nitrogen. The resulting mixture was then heated to 100° C. for 2 h. Progress of reaction was monitored by TLC. After reaction completion water (5 mL) was added to the reaction mixture and the product extracted with ethyl acetate. The organic layer was dried over sodium sulphate, concentrated under reduced pressure. Crude was purified by washing with pentane to give 1-(5-(4,4,5,5-tetramethyl-1,3,2-dioxaborolan-2-yl)pyridin-2-yl)imidazolidin-2-one (0.025 g, 41.8%) as brown solid.

MS: 290.14 [M+1]

To a solution of compound 2-(1-(1-(3-isopropyl-1,2,4-oxadiazol-5-yl)piperidin-4-yl)ethoxy)-5-bromothiazolo[5,4-b]pyridine (0.03 g, 0.06 mmol) and 1-(5-(4,4,5,5-tetramethyl-1,3,2-dioxaborolan-2-yl)pyridin-2-yl)imidazolidin-2-one (0.023 g, 0.079 mmol) in dioxane (5 mL) and water (1 mL) was added potassium carbonate (0.027 g, 0.199 mmol). Pd(dppf)Cl$_2$ was added after degassing the mixture for 30 min. with nitrogen. The resulting mixture was then heated to 90° C. for 3 h. Progress of reaction was monitored by TLC. After reaction completion reaction mass was quenched with water and extracted with ethyl acetate. The organic layer was washed with water, brine, dried over sodium sulphate, concentrated under reduced pressure. Crude was purified by neutral alumina column chromatography using ethyl acetate/hexane (50%) as eluent to give 1-(5-(2-(1-(1-(3-isopropyl-1,2,4-oxadiazol-5-yl)piperidin-4-yl)ethoxy)thiazolo[5,4-b]pyridin-5-yl)pyridin-2-yl)imidazolidin-2-one (0.015 g, 42.2%) as off white solid.

MS: 535.63 [M+1]

Example 28: 2-(1-(1-(3-(trifluoromethyl)-1,2,4-oxadiazol-5-yl)piperidin-4-yl)ethoxy)-5-(6-(methylsulfonyl)pyridin-3-yl)thiazolo[5,4-b]pyridine [1145]

Step 1: Synthesis of 2-(1-(1-(3-(trifluoromethyl)-1,2,4-oxadiazol-5-yl)piperidin-4-yl)ethoxy)-5-(6-(methylthio)pyridin-3-yl)thiazolo[5,4-b]pyridine

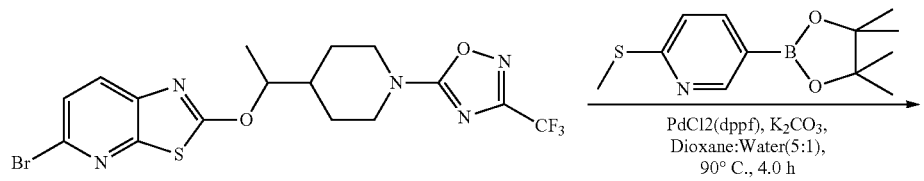

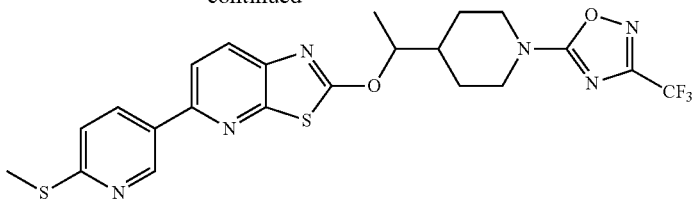

To a stirred solution of 2-(1-(1-(3-(trifluoromethyl)-1,2,4-oxadiazol-5-yl)piperidin-4-yl)ethoxy)-5-bromothiazolo[5,4-b]pyridine (0.04 gm, 0.088 mmol) and 5-(4,4,5,5-tetramethyl-1,3,2-dioxaborolan-2-yl)-2-(methylthio)pyridine (0.017 gm, 0.097 mmol) in Dioxane (5.0 mL), $K_2CO_3$ (0.036 gm, 0.26 mmol) in water (1.0 mL) was added and reaction mass purged with nitrogen for 30 min. After 30 min. Pd (dppf) Cl2 (0.004 g, 0.004 mmol) was added to the reaction mass, heated at 90° C. for 4.0 h. Progress of reaction was monitored by TLC. On completion, reaction was quenched with water, extracted with ethyl acetate, dried over $Na_2SO_4$. The organic layer was concentrated under reduced pressure to give crude desired compound. Purification of the compound was done by silica gel (100-200 mess) column chromatography: eluted 30% ethyl acetate:hexane to 2-(1-(1-(3-(trifluoromethyl)-1,2,4-oxadiazol-5-yl)piperidin-4-yl)ethoxy)-5-(6-(methylthio)pyridin-3-yl)thiazolo[5,4-b]pyridine (0.032 g, 71%) as off white solid.

MS: 522.57 [M$^+$+1]

Step 2: Synthesis of 2-(1-(1-(3-(trifluoromethyl)-1,2,4-oxadiazol-5-yl)piperidin-4-yl)ethoxy)-5-(6-(methylsulfonyl)pyridin-3-yl)thiazolo[5,4-b]pyridine

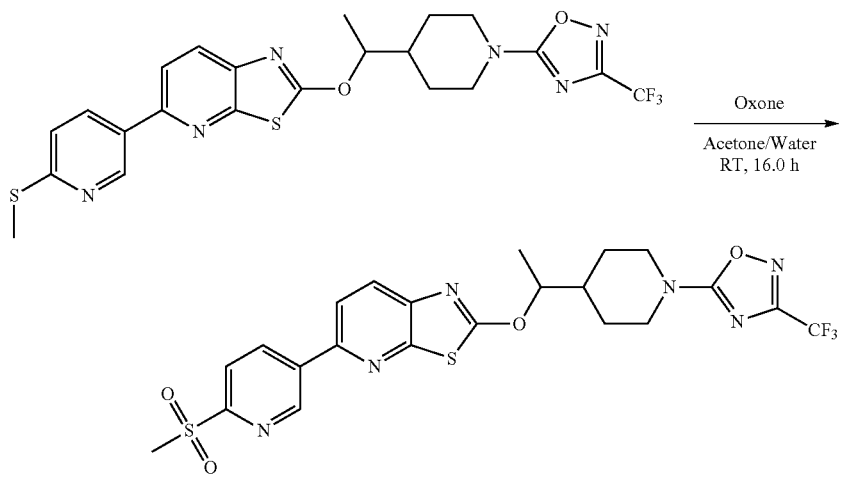

To a stirred solution of 2-(1-(1-(3-(trifluoromethyl)-1,2,4-oxadiazol-5-yl)piperidin-4-yl)ethoxy)-5-(6-(methylthio)pyridin-3-yl)thiazolo[5,4-b]pyridine (0.032 gm, 0.062 mmol) in Acetone (5.0 mL), Oxone (0.019 gm, 0.12 mmol) in Water (1.5 mL) was added, reaction mass Stirred at room temperature for 16 h. Progress of reaction was monitored by TLC. On completion, reaction mass was concentrated, quenched with water, extracted with ethyl acetate, dried over $Na_2SO_4$, concentrated under reduced pressure to give crude. Purification of the compound was done by silica gel (100-200 mess) column chromatography using 2% methanol: DCM to afford 2-(1-(1-(3-(trifluoromethyl)-1,2,4-oxadiazol-5-yl)piperidin-4-yl)ethoxy)-5-(6-(methylsulfonyl)pyridin-3-yl)thiazolo[5,4-b]pyridine (0.02 g, 62%) as off white solid.

MS: 554.57 [M$^+$+1].

Example 29: 2-(1-(1-(5-chloropyrazin-2-yl)piperidin-4-yl)ethoxy)-5-(4-(methylsulfonyl)phenyl)thiazolo[5,4-b]pyridine [1148]

Step 1: Synthesis of 5-chloropyrazin-2-amine

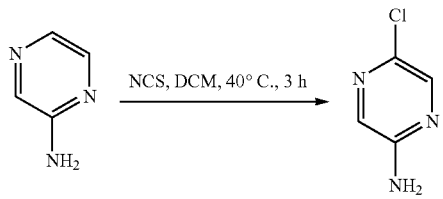 [SMILES: Nc1cnccn1 ; Nc1cnc(Cl)cn1]

To a stirred solution of pyrazin-2-amine (3 g, 31.545 mmol) in anhydrous DCM (30 mL) was added NCS (4.2 g, 30.545 mmol) under nitrogen and stirred at 40° C. for 2 h. Progress of reaction was monitored by TLC. After reaction completion DCM was added and washed with water. The organic layer was dried over sodium sulphate and concentrated under reduced pressure. Crude was purified by silica gel (100-200 mesh) column chromatography using 20% ethyl acetate in hexane as eluent to yield 5-chloropyrazin-2-amine (0.59 g, 15%) as yellow solid.

MS: 242.08 [M$^+$+1]

Step 2: Synthesis of 2,5-dichloropyrazine

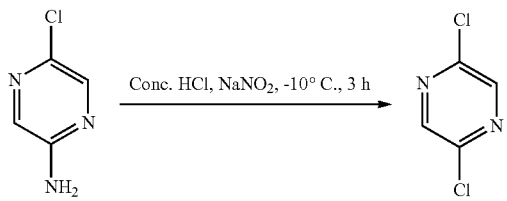 [SMILES: Nc1cnc(Cl)cn1 ; Clc1cnc(Cl)cn1]

To a stirred solution of 5-chloropyrazin-2-amine (1 g, 7.751 mmol) in conc. HCl (10 mL) was added aq. solution sodium nitrite (1.1 g, 15.89 mmol) at −10° C. over a period of 1 h, stirred for 1 h 0° C. and then at RT for 2 h. Progress of reaction was monitored by TLC. After reaction completion reaction mass neutralised with 50% NaOH solution and extracted with DCM. The organic layer was dried over sodium sulphate and concentrated under reduced pressure. Crude was purified by silica gel (100-200 mesh) column chromatography using 2% ethyl acetate in hexane as eluent to yield 2,5-dichloropyrazine (0.59 g, 15%) as colourless oil.

MS: 184.1 [M−1]

Step 3: Synthesis of 1-(1-(5-chloropyrazin-2-yl)piperidin-4-yl)ethanol

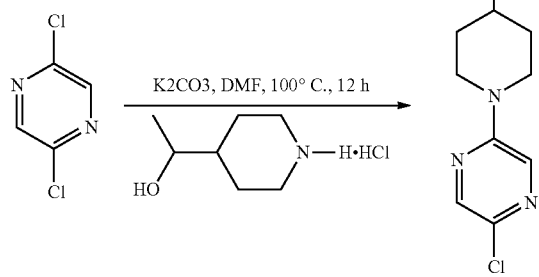

To a stirred solution of 2,5-dichloropyrazine (0.09 g, 0.608 mmol) and 1-(piperidin-4-yl)ethanol hydrochloride (0.12 g, 0.729 mmol) in DMF (5 mL) was added potassium carbonate under nitrogen and heated 12 h at 100° C. Progress of reaction was monitored by TLC. After reaction completion reaction mass was diluted with water and extracted with ethyl acetate. The organic layer was washed with brine, dried over sodium sulphate and concentrated under reduced pressure to give crude product. Crude was purified by silica gel (100-200 mesh) column chromatography using 20% ethyl acetate in hexane as eluent to obtain 1-(1-(5-chloropyrazin-2-yl)piperidin-4-yl)ethanol (0.08 g, 54.6%) as yellow oil.

MS: 242.7 [M$^+$+1]

Step 4: Synthesis of 2-(1-(1-(5-chloropyrazin-2-yl)piperidin-4-yl)ethoxy)-5-bromothiazolo[5,4-b]pyridine

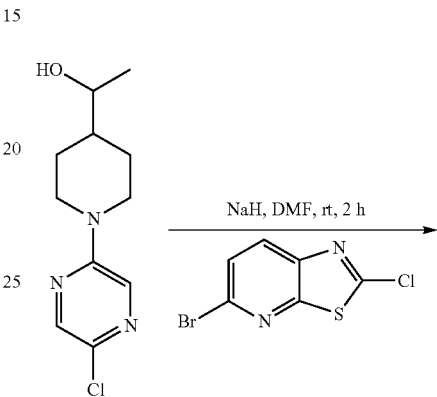

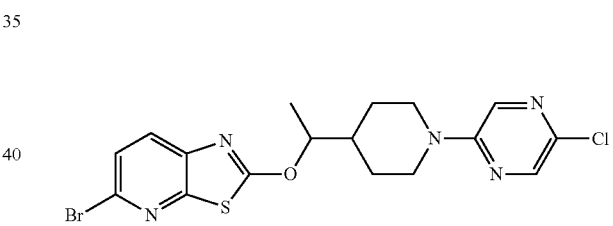

To a stirred solution of 1-(1-(5-chloropyrazin-2-yl)piperidin-4-yl)ethanol (0.03 g, 0.124 mmol) in DMF (3 mL) was added sodium hydride (0.01 g, 0.248 mmol) at 0° C. and stirred for 30 min at room temperature. After 30 min solution of 5-bromo-2-chlorothiazolo[5,4-b]pyridine (0.034 g, 0.136 mmol) in DMF (2 mL) was added to the reaction mixture and stirred for 2 h. Progress of reaction was monitored by TLC. After completion reaction mass was quenched with ice cold water and extracted with ethyl acetate. The organic layer was washed with water, brine, dried over sodium sulphate and concentrated under reduced pressure to give crude product. Crude was purified by silica gel (100-200 mesh) column chromatography using 20% ethyl acetate in hexane as eluent to give 2-(1-(1-(5-chloropyrazin-2-yl)piperidin-4-yl)ethoxy)-5-bromothiazolo[5,4-b]pyridine (0.03 g, 55.9%) as white solid.

MS: 455.7 [M$^+$+1]

Step 5: Synthesis of 2-(1-(1-(5-chloropyrazin-2-yl)piperidin-4-yl)ethoxy)-5-(4-(methylsulfonyl)phenyl)thiazolo[5,4-b]pyridine

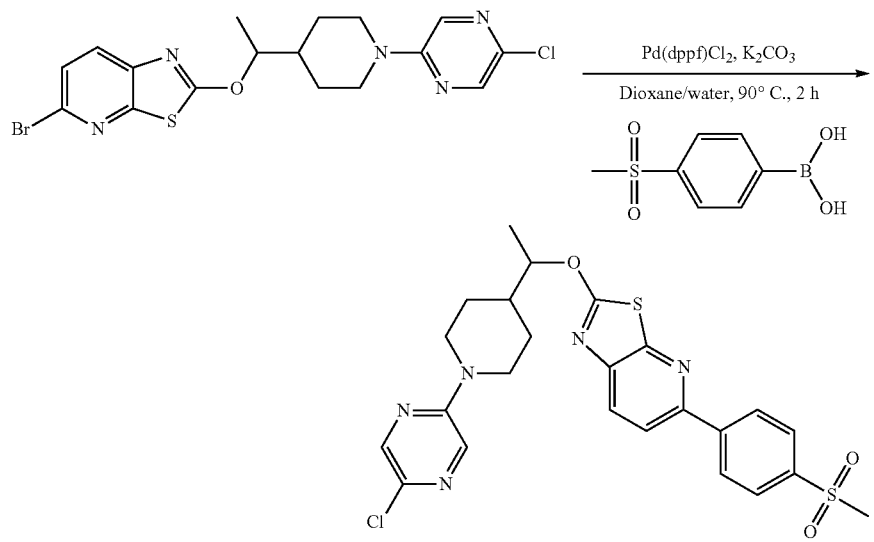

To a solution of compound 2-(1-(1-(5-chloropyrazin-2-yl)piperidin-4-yl)ethoxy)-5-bromothiazolo[5,4-b]pyridine (0.01 g, 0.022 mmol) and 4-(methylsulfonyl)phenylboronic acid (0.005 g, 0.026 mmol) in dioxane (5 mL) and water (1 mL) was added potassium carbonate (0.009 g, 0.066 mmol). Pd(dppf)Cl₂ (0.0008 g, 0.0011 mmol) was added after degassing the mixture for 30 min. with nitrogen. The resulting mixture was then heated to 90° C. for 3 h. Progress of reaction was monitored by TLC. After reaction completion reaction mass was quenched with water and extracted with ethyl acetate. The organic layer was washed with water, brine, dried over sodium sulphate, concentrated under reduced pressure. Crude was purified by neutral alumina column chromatography using ethyl acetate/hexane (40%) as eluent to give 2-(1-(1-(5-chloropyrazin-2-yl)piperidin-4-yl)ethoxy)-5-(4-(methylsulfonyl)phenyl)thiazolo[5,4-b]pyridine (0.003 g, 25.8%) as off white solid.

MS: 531.0 [M⁺+1]

Example 30: 2-(1-(1-(3-isopropyl-1,2,4-oxadiazol-5-yl)piperidin-4-yl)ethoxy)-5-(6-(trifluoromethyl)pyridin-3-yl)thiazolo[5,4-b]pyridine [1152]

Step 1: Synthesis of 5-bromo-2-(trifluoromethyl)pyridine

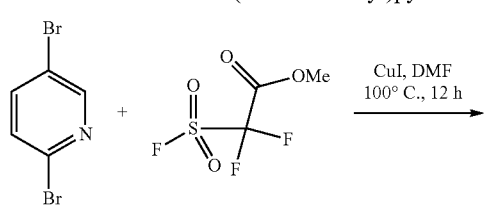

-continued

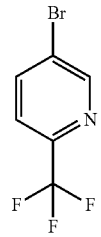

To a stirred solution of 2,5-dibromopyridine (0.1 g, 0.421 mmol) in DMF (5.0 mL) was added Methyl 2,2-difluoro-2-(fluorosulfonyl)acetate (0.405 g, 2.109 mmol) along with CuI (0.401 g, 2.109 mmol) and stirred at 100° C. for 12 h. Completion of reaction was monitored by TLC. Reaction mass was cooled to room temperature, diluted with water, extracted with EtOAc. Organic portions were combined, dried over Na₂SO₄, evaporated under reduced pressure to obtain crude product 5-bromo-2-(trifluoromethyl)pyridine (0.07 g, 73%) as light yellow oil which was directly carry forward for next step.

MS: 227.28 [M⁺+1]

Step 2: Synthesis of 6-(trifluoromethyl)pyridin-3-yl-3-boronic Acid

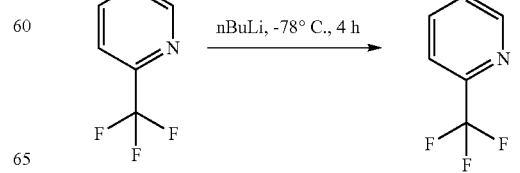

To a stirred solution of 5-bromo-2-(trifluoromethyl)pyridine (0.07 g, 0.309 mmol) in THF (10 mL) at −78° C. was added n-Butyl lithium (0.15 mL, 0.37 mmol, 2.5M in hexane) under nitrogen and stirred for 1 h at the same temperature. Triisopropyl borate (0.087 g, 0.464 mmol) was then added drop wise to the reaction mixture, stirred for 5 h at −78° C. Progress of reaction was monitored by TLC. After completion reaction mass was quenched with ice cold water and partitioned between saturated NH₄Cl solution and EtOAc. The organic layer was washed with brine, dried over sodium sulphate and concentrated under reduced pressure to give 6-(trifluoromethyl)pyridin-3-yl-3-boronic acid (0.03 g, 50%) as off-white sticky solid

MS: 192.1 [M⁺+1]

Step 3: Synthesis of 2-(1-(1-(3-isopropyl-1,2,4-oxadiazol-5-yl)piperidin-4-yl)ethoxy)-5-(6-(trifluoromethyl)pyridin-3-yl)thiazolo[5,4-b]pyridine

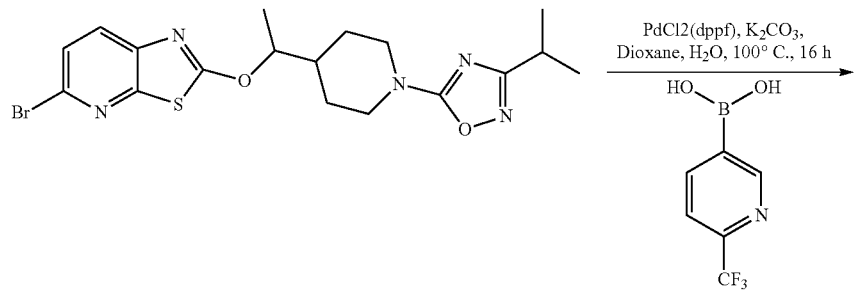

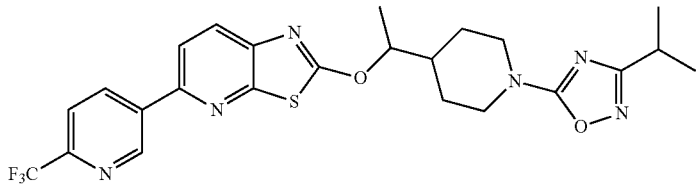

To a stirred solution of 2-(1-(1-(3-isopropyl-1,2,4-oxadiazol-5-yl)piperidin-4-yl)ethoxy)-5-bromothiazolo[5,4-b]pyridine (0.05 g, 0.11 mmol) and 6-(trifluoromethyl)pyridin-3-yl-3-boronic acid (0.025 g, 0.13 mmol) in Dioxane (10 mL) was added K₂CO₃ (0.046 g, 0.33 mmol) in water (2 mL) and reaction mass was purged with nitrogen for 30 min. Then, PdCl₂(dppf) (0.004 g, 0.055 mmol) was added to it and stirred at 100° C. for 16 h. Reaction was monitored by TLC. On completion reaction was concentrated under reduced pressure obtained crude which was purified by column chromatography (100-200 Mesh); eluent 30% EtOAc/Hexane to afford 2-(1-(1-(3-isopropyl-1,2,4-oxadiazol-5-yl)piperidin-4-yl)ethoxy)-5-(6-(trifluoromethyl)pyridin-3-yl)thiazolo[5,4-b]pyridine (0.010 g, 17%) as off-white solid.

MS: 519.1 [M⁺+1]

Example 31: (S)-2-(1-(1-(5-ethylpyrimidin-2-yl)piperidin-4-yl)ethoxy)-5-(6-(trifluoromethyl)pyridin-3-yl)thiazolo[5,4-b]pyridine [1154]

Step 1: Synthesis of (S)-2-(1-(1-(5-ethylpyrimidin-2-yl)piperidin-4-yl)ethoxy)-5-(6-(trifluoromethyl)pyridin-3-yl)thiazolo[5,4-b]pyridine

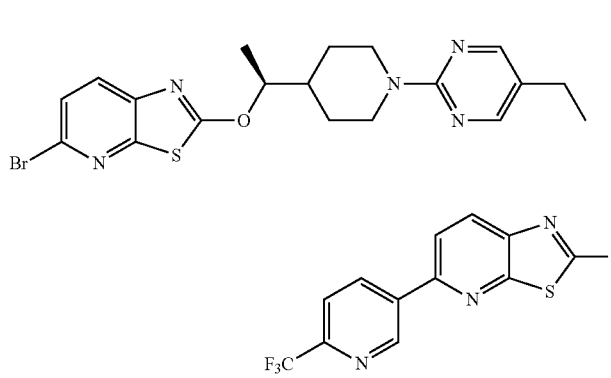

To a stirred solution of 2-((S)-1-(1-(4-ethylphenyl)piperidin-4-yl)ethoxy)-5-bromothiazolo[5,4-b]pyridine (0.04 gm, 0.088 mmol) and 2-(trifluoromethyl)-5-(4,4,5,5-tetramethyl-1,3,2-dioxaborolan-2-yl)pyridine (0.017 gm, 0.097 mmol) in Dioxane (5.0 mL), K$_2$CO$_3$ (0.036 gm, 0.26 mmol) in water (1.0 mL) was added and reaction mass purged with nitrogen for 30 min. After 30 min. Pd (dppf) Cl2 (0.004 g, 0.004 mmol) was added to the reaction mass, heated at 90° C. for 4.0 h. Progress of reaction was monitored by TLC. On completion, reaction was quenched with water, extracted with ethyl acetate, dried over Na$_2$SO$_4$. The organic layer was concentrated under reduced pressure to give crude desired compound. Purification of the compound was done by silica gel (100-200 mess) column chromatography: eluted 30% ethyl acetate:hexane to 2-((S)-1-(1-(4-ethylphenyl)piperidin-4-yl)ethoxy)-5-(6-(trifluoromethyl)pyridin-3-yl)thiazolo[5,4-b]pyridine (0.032 g, 71%) as off white solid.

MS: 513.22 [M$^+$+1]

Example 32: 2-(1-(1-(3-isopropyl-1,2,4-oxadiazol-5-yl)piperidin-4-yl)ethoxy)-5-(5-(methylsulfonyl)pyrazin-2-yl)thiazolo[5,4-b]pyridine [1158]

Step 1: Synthesis of 5-bromopyrazin-2-amine

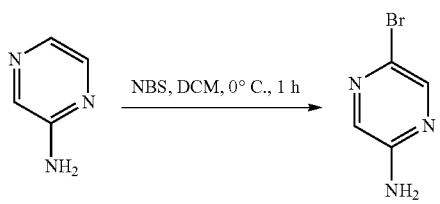 [SMILES: Nc1cnccn1 ; Nc1cnc(Br)cn1]

To a stirred solution of pyrazin-2-amine (3 g, 31.545 mmol) in anhydrous DCM (30 mL) was added NBS (5.6 g, 31.54 mmol) under nitrogen and stirred at 0° C. for 1 h. Progress of reaction was monitored by TLC. After reaction completion DCM was added and washed with water. The organic layer was dried over sodium sulphate and concentrated under reduced pressure. Crude was purified by silica gel (100-200 mesh) column chromatography using 70% DCM/hexane to 10% ethyl acetate in hexane as eluent to yield 5-bromopyrazin-2-amine (3.4 g, 62.9%) as white solid.

MS: 175.1 [M$^+$+1]

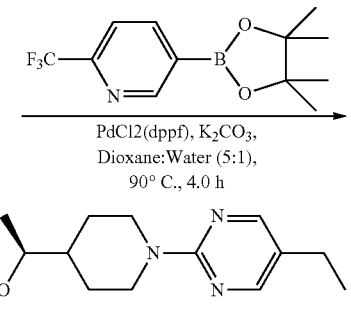

Step 2: Synthesis of 2,5-dibromopyrazine

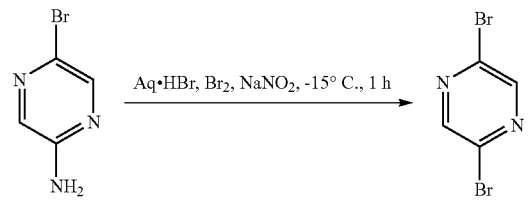

5-bromopyrazin-2-amine (3 g, 17.241 mmol) and bromine (8.2 g, 51.729 mmol) were added to aq. HBr solution at −15° C. Aq. solution of sodium nitrite (2.97 g, 43.0103 mmol) was then added to the mixture over a period of 1 h at −10° C. keeping the internal temperature below 5° C. during addition and stirred for 1 h at 0° C. Progress of reaction was monitored by TLC. After reaction completion reaction mass neutralised with 40% NaOH solution and extracted with diethyl ether. The organic layer was dried over sodium sulphate and concentrated under reduced pressure (below 30° C.) to yield 2,5-dibromopyrazine (1 g, 24.4%) as brown oil.

MS: 238.8 [M$^+$+1]

Step 3: Synthesis of 2-bromo-5-(methylthio)pyrazine

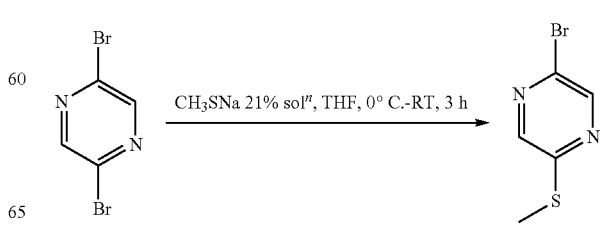

To a stirred solution of 2,5-dibromopyrazine (0.45 g, 1.892 mmol) in anhydrous THF (5 mL) was added 21% aq. solution of sodium thiomethoxide (0.94 mL g, 2.83 mmol) at 0° C. and stirred for 1 h at RT. Progress of reaction was monitored by TLC. After reaction completion DCM was added and washed with water. The organic layer was dried over sodium sulphate and concentrated under reduced pressure to yield 2-bromo-5-(methylthio)pyrazine (0.3 g, 78%) as brown oil.

MS: 206.08 [M$^+$+1]

Step 4: Synthesis of 2-(trimethylstannyl)-5-(methylthio)pyrazine

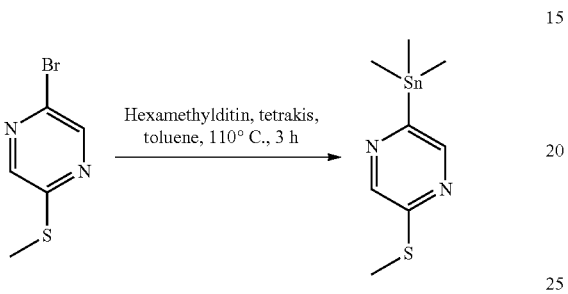

To a stirred solution of 2-bromo-5-(methylthio)pyrazine (0.3 g, 1.471 mmol) in toluene was added hexamethylditin (0.48 g, 0.1.471 mmol). Tetrakis (0.017 g, 0.014 mmol) was added after degassing the mixture for 30 min. with nitrogen. The resulting mixture was then heated to 110° C. for 3 h. Progress of reaction was monitored by TLC. After reaction completion water (5 mL) was added to the reaction mixture and the product extracted with ethyl acetate. The organic layer was dried over sodium sulphate, concentrated under reduced pressure. Crude was triturated with pentane and decanted, residue was again washed with pentane. Combined pentane layer concentrated to give 2-(trimethylstannyl)-5-(methylthio)pyrazine (0.3 g, 70.5%) as brown oil.

MS: 289.9 [M$^+$+1]

Step 5: Synthesis of 2-(1-(1-(3-isopropyl-1,2,4-oxadiazol-5-yl)piperidin-4-yl)ethoxy)-5-(5-(methylthio)pyrazin-2-yl)thiazolo[5,4-b]pyridine

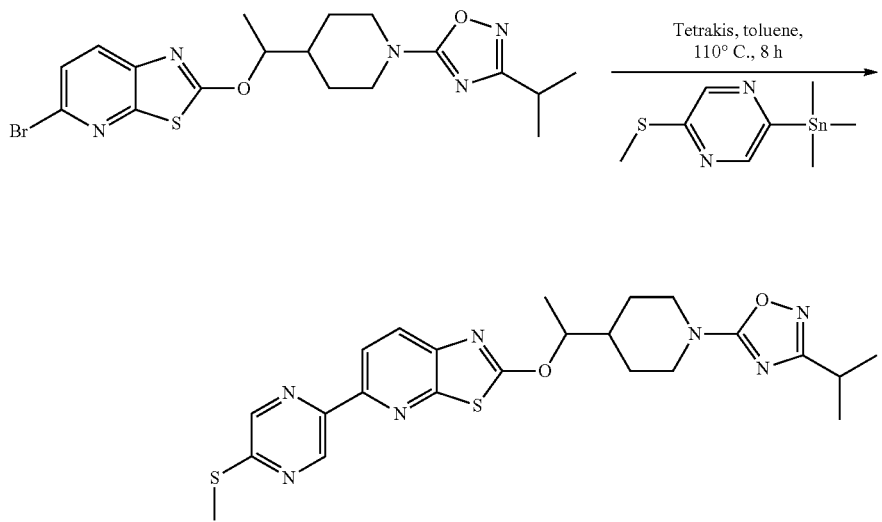

To a stirred solution of 2-(1-(1-(3-isopropyl-1,2,4-oxadiazol-5-yl)piperidin-4-yl)ethoxy)-5-bromothiazolo[5,4-b]pyridine (0.15 g, 0.332 mmol) and 2-(trimethylstannyl)-5-(methylthio)pyrazine (0.14 g, 0.498 mmol) in toluene was added tetrakis (0.0038 g, 0.00332 mmol) was added after degassing the mixture for 30 min. with nitrogen. The resulting mixture was then heated to 110° C. for 5 h. Progress of reaction was monitored by TLC. After reaction completion water (5 mL) was added to the reaction mixture and the product extracted with ethyl acetate. The organic layer was dried over sodium sulphate, concentrated under reduced pressure. Crude was purified by silica (100-200) column chromatography using 3% acetone in DCM as eluent to give 2-(1-(1-(3-isopropyl-1,2,4-oxadiazol-5-yl)piperidin-4-yl)ethoxy)-5-(5-(methylthio)pyrazin-2-yl)thiazolo[5,4-b]pyridine (0.03 g, 18.1%) as yellow solid.

MS: 498.6 [M⁺+1]

Step 6: Synthesis of 2-(1-(1-(3-isopropyl-1,2,4-oxadiazol-5-yl)piperidin-4-yl)ethoxy)-5-(5-(methylsulfonyl)pyrazin-2-yl)thiazolo[5,4-b]pyridine

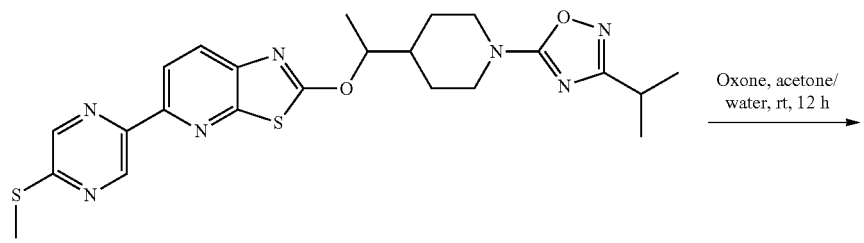

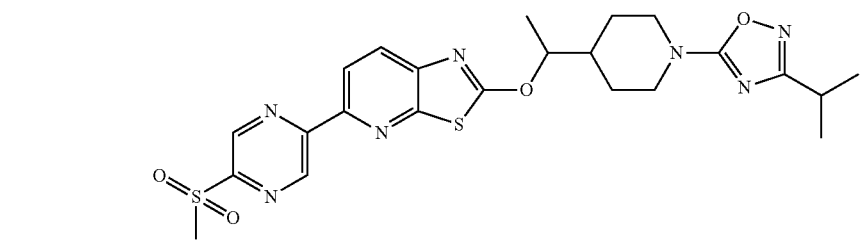

To a stirred solution of 2-(1-(1-(3-isopropyl-1,2,4-oxadiazol-5-yl)piperidin-4-yl)ethoxy)-5-(5-(methylthio)pyrazin-2-yl)thiazolo[5,4-b]pyridine (0.03 g, 0.0603 mmol) in acetone (5 mL) and water (1 mL) was added oxone (0.055 g, 0.181 mmol) and the mixture was stirred at 50° C. for 8 h. Progress of reaction was monitored by TLC. After reaction completion reaction mass was filtered, filtrate neutralised with 2M Na₂CO₃ solution and extracted with DCM. The organic layer was washed with brine, dried over sodium sulphate and concentrated under reduced pressure to give crude product. Crude was by neutral alumina column chromatography using 25% ethyl acetate in hexane as eluent to give 2-(1-(1-(3-isopropyl-1,2,4-oxadiazol-5-yl)piperidin-4-yl)ethoxy)-5-(5-(methylsulfonyl) pyrazin-2-yl)thiazolo[5,4-b]pyridine (0.01 g, 31.3%) as white solid.

MS: 530.6 [M⁺+1]

Example 33: 2-(1-(1-(3-isopropyl-1,2,4-oxadiazol-5-yl)piperidin-4-yl)ethoxy)-5-(5-(methylsulfonyl)pyridin-2-yl)thiazolo[5,4-b]pyridine [1161]

Step 1: Synthesis of 2-bromo-5-(methylthio)pyridine

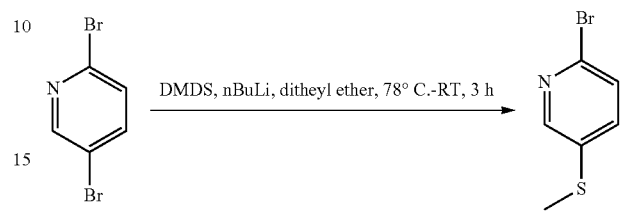

To a stirred solution of 2,5-dibromopyridine (0.4 g, 1.688 mmol) in diethyl ether (15 mL) at −78° C. was added n-Butyl lithium (2.5M in hexane) (0.8 mL, 2.026 mmol) under nitrogen and stirred for 1 h at same temperature. Solution of DMDS (1.3 mL, 16.463 mmol) in diethyl ether was then added drop wise to the reaction mixture, stirred for 1 h at −78° C. and for 1 h at RT. Progress of reaction was monitored by TLC. After reaction completion reaction mass was quenched with 1N HCl and extracted with diethyl ether. The organic layer was washed with brine, dried over sodium sulphate and concentrated under reduced pressure. Crude was purified by silica gel (100-200 mesh) column chromatography using 2% ethyl acetate in hexane as eluent to obtain 2-bromo-5-(methylthio)pyridine (0.23 g, 66.7%) as yellow oil.

MS: 205.0 [M⁺+1]

Step 2: Synthesis of 2-(tributylstannyl)-5-(methylthio)pyridine

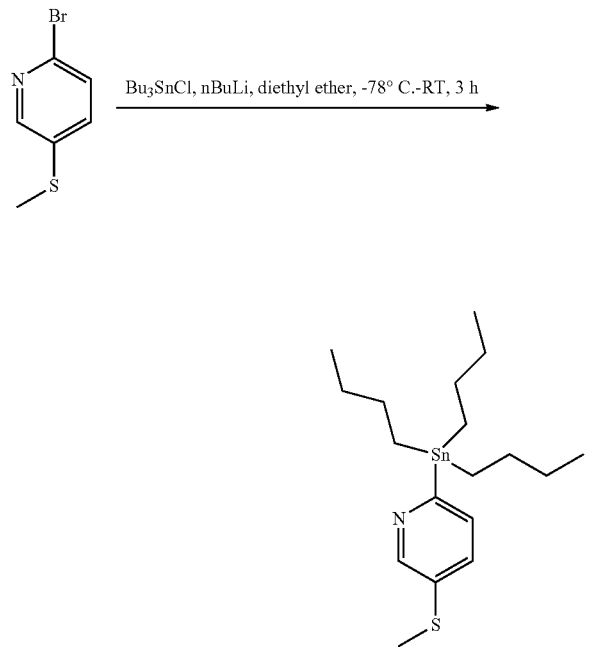

To a stirred solution of 2-bromo-5-(methylthio)pyridine (0.23 g, 1.127 mmol) in diethyl ether (15 mL) at −78° C. was added n-Butyl lithium (2.5M in hexane) (0.67 mL, 1.691 mmol) under nitrogen and stirred for 1 h at same temperature. Tributylchlorostannane (0.55 g, 1.691 mmol) was then added drop wise to the reaction mixture, stirred for 1 h at −78° C. and for 2 h at RT. Progress of reaction was monitored by TLC. After reaction completion reaction mass was quenched with water and extracted with diethyl ether. The organic layer was washed with brine, dried over sodium sulphate and concentrated under reduced pressure to obtain 2-(tributylstannyl)-5-(methylthio)pyridine (0.26 g, 55.67%) as yellow oil.

MS: 415.2 [M$^+$+1]

Step 3: Synthesis of 2-(1-(1-(3-isopropyl-1,2,4-oxadiazol-5-yl)piperidin-4-yl)ethoxy)-5-(5-(methylthio)pyridin-2-yl)thiazolo[5,4-b]pyridine

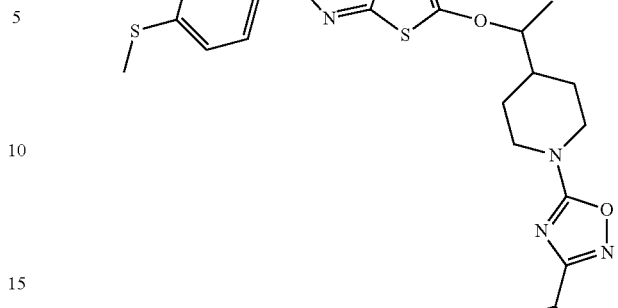

To a stirred solution of 2-(1-(1-(3-isopropyl-1,2,4-oxadiazol-5-yl)piperidin-4-yl)ethoxy)-5-bromothiazolo[5,4-b]pyridine (0.04 g, 0.0886 mmol) and 2-(tributylstannyl)-5-(methylthio)pyridine (0.047 g, 0.115 mmol) in toluene (5 mL) was added tetrakis (0.001 g, 0.00088 mmol) was added after degassing the mixture for 30 min. with nitrogen. The resulting mixture was then heated to 110° C. for 3 h. Progress of reaction was monitored by TLC. After reaction completion water (5 mL) was added to the reaction mixture and the product extracted with ethyl acetate. The organic layer was dried over sodium sulphate, concentrated under reduced pressure. Crude was purified by silica (100-200) column chromatography using DCM as eluent to give 2-(1-(1-(3-isopropyl-1,2,4-oxadiazol-5-yl)piperidin-4-yl)ethoxy)-5-(5-(methylthio)pyridin-2-yl)thiazolo[5,4-b]pyridine (0.015 g, 34%) as yellow solid.

MS: 497.5 [M$^+$+1]

Step 4: Synthesis of 2-(1-(1-(3-isopropyl-1,2,4-oxadiazol-5-yl)piperidin-4-yl)ethoxy)-5-(5-(methylsulfonyl)pyridin-2-yl)thiazolo[5,4-b]pyridine

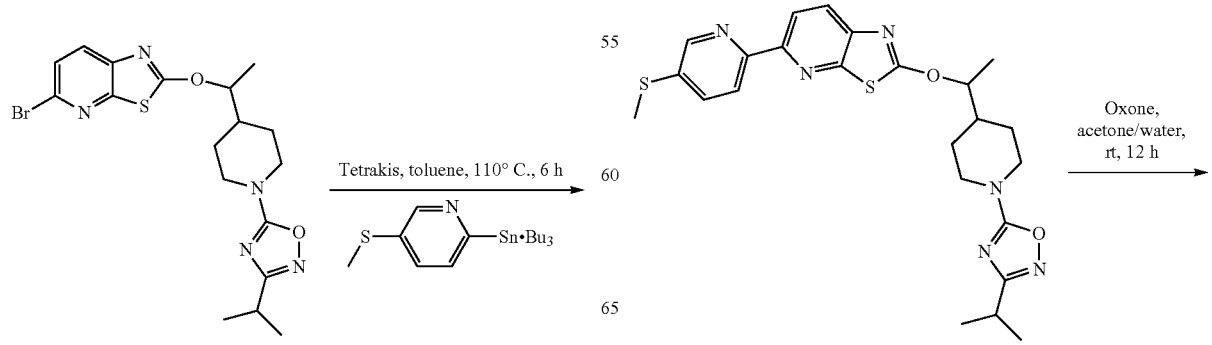

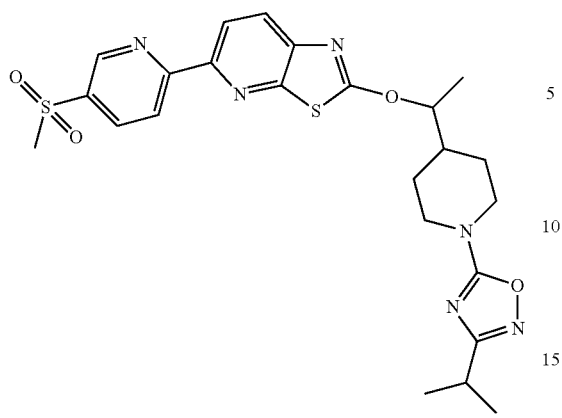

To a stirred solution of 2-(1-(1-(3-isopropyl-1,2,4-oxadiazol-5-yl)piperidin-4-yl)ethoxy)-5-(5-(methylthio)pyridin-2-yl)thiazolo[5,4-b]pyridine (0.015 g, 0.0302 mmol) in acetone (5 mL) and water (1 mL) was added oxone (0.027 g, 0.0907 mmol) and the mixture was stirred at 50° C. for 5 h then stirred overnight at RT. Progress of reaction was monitored by TLC. After reaction completion reaction mass was filtered, filtrate neutralised with 2M $Na_2CO_3$ solution and extracted with DCM. The organic layer was washed with brine, dried over sodium sulphate and concentrated under reduced pressure to give crude product. Crude was by neutral alumina column chromatography using 30% ethyl acetate in hexane as eluent to give 2-(1-(1-(3-isopropyl-1,2,4-oxadiazol-5-yl)piperidin-4-yl)ethoxy)-5-(5-(methylsulfonyl)pyridin-2-yl)thiazolo[5,4-b]pyridine (0.005 g, 31.3%) as white solid.

MS: 529.6 [$M^+$+1]

Example 34: 2-((S)-1-(1-(3-isopropyl-1,2,4-oxadiazol-5-yl)piperidin-4-yl)ethoxy)-5-(6-(cyclopropylsulfonyl)pyridin-3-yl)thiazolo[5,4-b]pyridine [1164]

Step 1: Synthesis of cyclopropanethiol

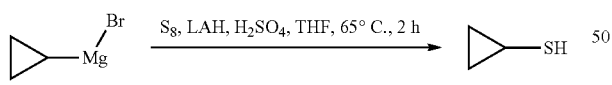

To a stirred solution of isopropyl magnesium bromide (0.5M in THF, 15 mL, 0.0075 mmol) was added sulfur powder (0.24 g, 0.0075 mmol) at 0° C. in small portions and heated to 50° C. for 3 h. LAH (0.227 g, 0.006 mmol) was then added at 0° C. and heated to 65° C. for 1 h, cooled to 0° C. and added 5% aq. sulfuric (3 mL) acid and ether (6 mL). Layers were separated and aq. extracted with ether. The organic layer was dried over sodium sulphate and concentrated to half volume to give crude product cyclopropanethiol (0.25 g, 50% assumed) as yellow liquid.

MS: 75.0 [$M^+$+1]

Step 2: Synthesis of 5-bromo-2-(cyclopropylthio)pyridine

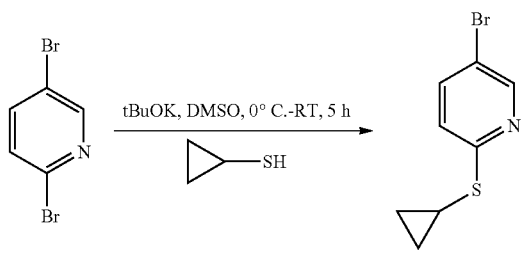

To a stirred solution of cyclopropanethiol (0.125 g, 1.688 mmol) in DMSO (3 mL) was added sodium potassium tertiary butoxide (0.283 g, 2.532 mmol) at 0° C. and stirred for 15 min at room temperature. After 15 min solution of 2,5-dibromopyridine (0.02 g, 0.844 mmol) in DMSO (2 mL) was added to the reaction mixture and stirred for 5 h. Progress of reaction was monitored by TLC. After completion reaction mass was quenched with ice cold water and extracted with ethyl acetate. The organic layer was washed with water, brine, dried over sodium sulphate and concentrated under reduced pressure to give crude product. Crude was purified by silica (60-120) column chromatography using 1% ethyl acetate in hexane as eluent to give 5-bromo-2-(cyclopropylthio)pyridine (0.082 g, 42.4%) as yellow oil.

MS: 231.1 [$M^+$+1]

Step 3: Synthesis of 2-(cyclopropylthio)-5-(4,4,5,5-tetramethyl-1,3,2-dioxaborolan-2-yl)pyridine

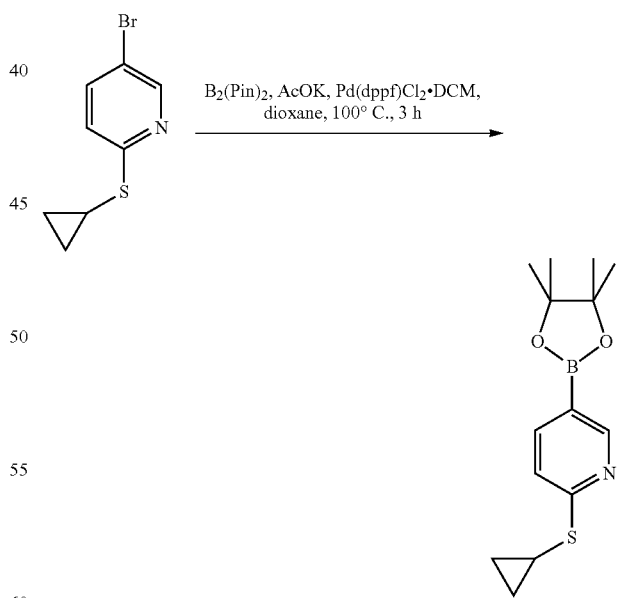

To a solution of 5-bromo-2-(cyclopropylthio)pyridine (0.082 g, 0.356 mmol) and bispinacolatodiborane (0.126 g, 0.499) in dioxane (5 mL) was added potassium carbonate (0.139 g, 1.426 mmol). Pd(dppf)Cl2.DCM (0.029 g, 0.0356 mmol) was added after degassing the mixture for 30 min. with nitrogen. The resulting mixture was then heated to 100°

C. for 3 h. Progress of reaction was monitored by TLC. After reaction completion water (5 mL) was added to the reaction mixture and the product extracted with ethyl acetate. The organic layer was dried over sodium sulphate, concentrated under reduced pressure. Crude was purified by washing with pentane to give 2-(cyclopropylthio)-5-(4,4,5,5-tetramethyl-1,3,2-dioxaborolan-2-yl)pyridine (0.04 g, 40.5%) as yellow solid.

MS: 278.1 [M⁺+1]

Step 4: Synthesis of 2-((S)-1-(1-(3-isopropyl-1,2,4-oxadiazol-5-yl)piperidin-4-yl)ethoxy)-5-(6-(cyclopropylthio)pyridin-3-yl)thiazolo[5,4-b]pyridine

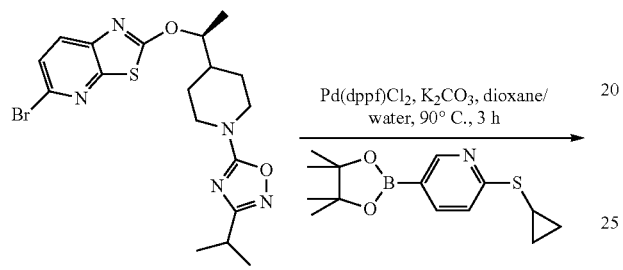

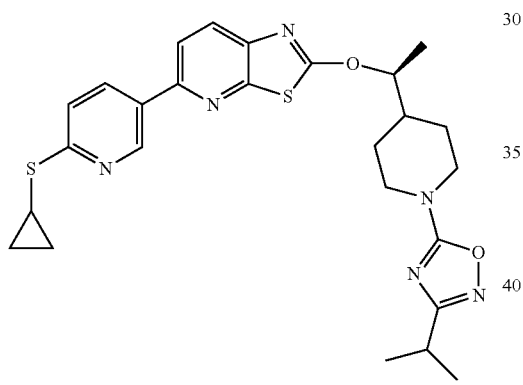

To a solution of compound 2-((S)-1-(1-(3-isopropyl-1,2,4-oxadiazol-5-yl)piperidin-4-yl)ethoxy)-5-bromothiazolo[5,4-b]pyridine (0.03 g, 0.066 mmol) and 2-(cyclopropylthio)-5-(4,4,5,5-tetramethyl-1,3,2-dioxaborolan-2-yl)pyridine (0.027 g, 0.099 mmol) in dioxane (5 mL) and water (1 mL) was added potassium carbonate (0.027 g, 0.199 mmol). Pd(dppf)Cl₂ (0.0024, 0.0033) was added after degassing the mixture for 30 min. with nitrogen. The resulting mixture was then heated to 90° C. for 3 h. Progress of reaction was monitored by TLC. After reaction completion reaction mass was quenched with water and extracted with ethyl acetate. The organic layer was washed with water, brine, dried over sodium sulphate, concentrated under reduced pressure. Crude was purified by silica (100-200) column chromatography using ethyl acetone/DCM (6%) as eluent to give 2-((S)-1-(1-(3-isopropyl-1,2,4-oxadiazol-5-yl)piperidin-4-yl)ethoxy)-5-(6-(cyclopropylthio)pyridin-3-yl)thiazolo[5,4-b]pyridine (0.018 g, 51.8%) as off white solid.

MS: 523.6 [M⁺+1]

Step 5: Synthesis of 2-((S)-1-(1-(3-isopropyl-1,2,4-oxadiazol-5-yl)piperidin-4-yl)ethoxy)-5-(6-(cyclopropylsulfonyl)pyridin-3-yl)thiazolo[5,4-b]pyridine

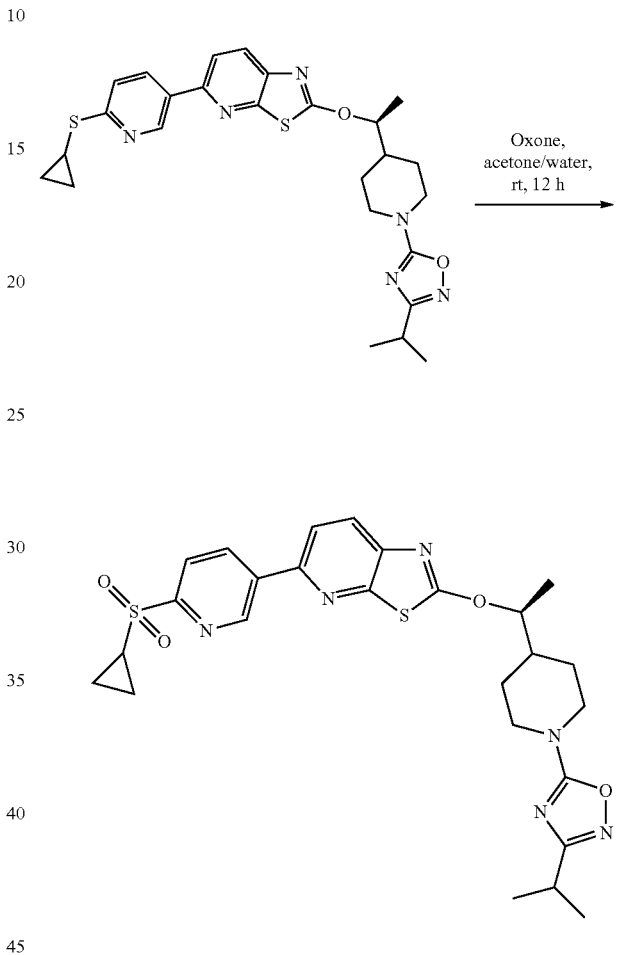

To a stirred solution of 2-((S)-1-(1-(3-isopropyl-1,2,4-oxadiazol-5-yl)piperidin-4-yl)ethoxy)-5-(6-(cyclopropylthio)pyridin-3-yl)thiazolo[5,4-b]pyridine (0.018 g, 0.0344 mmol) in acetone (5 mL) and water (1 mL) was added oxone (0.053 g, 0.172 mmol) and the mixture was stirred at 50° C. for 5 h. Progress of reaction was monitored by TLC. After reaction completion reaction mass was filtered, filtrate neutralised with 2M Na₂CO₃ solution and extracted with DCM. The organic layer was washed with brine, dried over sodium sulphate and concentrated under reduced pressure to give crude product. Crude was by neutral alumina column chromatography using 12% acetone in hexane as eluent to give 2-(1-(1-(3-isopropyl-1,2,4-oxadiazol-5-yl)piperidin-4-yl)ethoxy)-5-(5-(methylsulfonyl)pyridin-2-yl)thiazolo[5,4-b]pyridine (0.006 g, 31.4%) as white solid.

MS: 555.6 [M⁺+1]

Example 16: 2-((S)-1-(1-(5-(trifluoromethyl)pyrimi-din-2-yl)piperidin-4-yl)ethoxy)-5-(6-(methylsulfo-nyl)pyridin-3-yl)thiazolo[5,4-b]pyridine [1166]

Step 1: Synthesis of 4-(1-hydroxyethyl)piperidine-1-carboxamidine

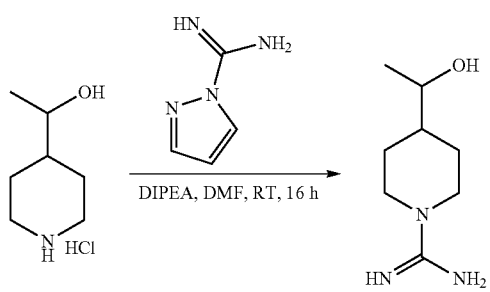

To a stirred solution of 1-(piperidin-4-yl)ethanol hydrochloride (2.6 g, 15.6 mmol) in DMF (14 mL) was added 1H-pyrazole-1-carboxamidine (2.3 g, 15.6 mmol) and DIPEA (6.44 mL, 34.9 mmol). The resulting mixture was allowed to stir at RT for 16 h. Completion of reaction was monitored by TLC. On completion, diethyl ether was added to reaction mixture and supernatant was decanted from oily precipitate. The precipitate was washed with diethyl ether, dried in Vacuo to give 4-(1-hydroxyethyl)piperidine-1-carboxamidine (Crude) (2.68 g, 100%) as white sticky solid.

MS: 172.1 [M$^+$+1]

Step 2: Synthesis of 4-(1-hydroxyethyl)piperidine-1-carboxamidine

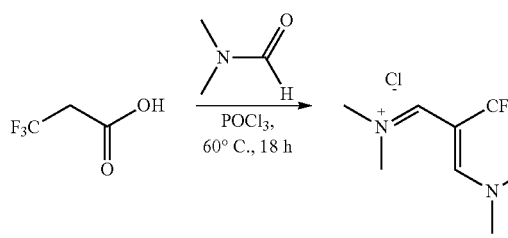

To a solution of 3,3,3-trifluoropropanoic acid (2.0 g, 15.6 mmol) and DMF (14.5 mL, 187 mmol) which was kept in H$_2$O both at 15-20° C., was added POCl$_3$ (7.175 g, 46.8 mmol) over a period of 30 min. The reaction was heated at 60° C. for 16 h. Reaction was directly loaded on SiO$_2$ column. First started with 50% EtOAc:Hexane, followed by 100% EtOAc, 50% Ethanol:EtOAc and finally eluted with ethanol to obtain the product. Ethanol was concentrated under reduced pressure to give (Z)—N-(3-(dimethylamino)-2-(trifluoromethyl)allylidene)-N-methylmethanaminium chloride salt (2.3 g, 63.7%) as yellow oil.

MS: 196.1 [M$^+$+1]

Step-3: Synthesis of 1-(1-(5-(trifluoromethyl)py-rimidin-2-yl)piperidin-4-yl)ethanol

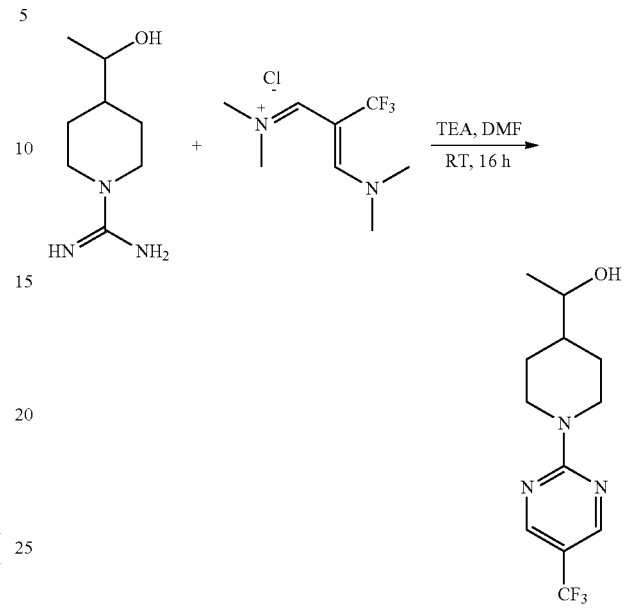

To a stirred solution of 4-(1-hydroxyethyl)piperidine-1-carboxamidine (0.3 g, 1.751 mmol) and TEA (0.35 g, 3.465 mmol) in DMF (10 mL) was added (Z)—N-(3-(dimethylamino)-2-(trifluoromethyl) allylidene)-N-methylmethanaminium chloride salt (0.606 g, 2.627 mmol). The resulting mixture was allowed to stir at RT for 16 h. Progress of reaction was monitored by TLC. On completion, cold D.M. water was added to reaction mixture and extracted with EtOAc. Organic layers were combined, washed with brine, saturated solution of NaHCO$_3$, dried over sodium sulphate and concentrated under reduced pressure to give crude product. Crude product was purified by column chromatography using (silica gel, 100-200 mesh, 0-14% EtOAc in Hexane as eluent) to give 1-(1-(5-(trifluoromethyl) pyrimidin-2-yl)piperidin-4-yl)ethanol (0.140 g, 7.25%) as yellow solid.

MS: 276.1 [M$^+$+1]

Step-4: Synthesis of (2S)—(R)-1-(1-(5-(trifluorom-ethyl)pyrimidin-2-yl)piperidin-4-yl)ethyl 2-methoxy-2-phenylacetate

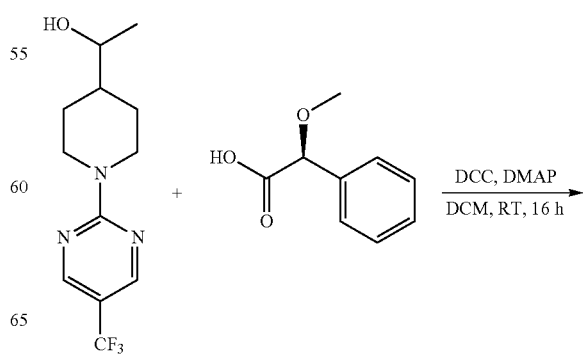

-continued

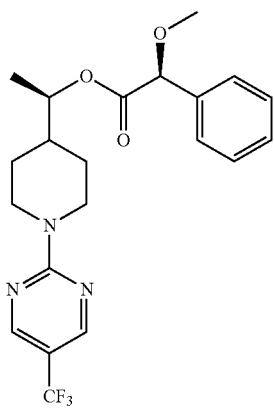

To a stirred solution of 1-(1-(5-(trifluoromethyl)pyrimidin-2-yl)piperidin-4-yl)ethanol (0.080 g, 0.290 mmol) and (S)-2-methoxy-2-phenylacetic acid (0.048 g, 0.319 mmol) in DCM (10 mL) was added DCC (0.089 g, 0.435 mmol), DMAP (0.014 g, 0.116 mmol) and stirred at room temperature for 16 h. Reaction was monitored by TLC. On completion, D.M. water was added to reaction mixture and extracted with DCM. Organic layers were combined, washed with brine solution, dried over sodium sulphate and concentrated under reduced pressure to give crude product. Crude product was purified by column chromatography using (silica gel, 100-200 mesh, 0-8% EtOAc in hexane as eluent) to give (0.120 g) mixture which was separated by Prep HPLC to give (2S)—(R)-1-(1-(5-(trifluoromethyl)pyrimidin-2-yl)piperidin-4-yl)ethyl 2-methoxy-2-phenylacetate (0.016 g, 26.59%) as colourless gum.

MS: 424.2 [M$^+$+1]

Step-5: Synthesis of (R)-1-(1-(5-(trifluoromethyl)pyrimidin-2-yl)piperidin-4-yl)ethanol

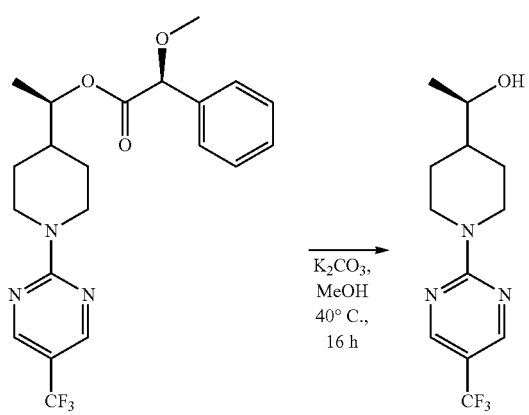 [SMILES: CO[C@H](C(=O)O[C@H](C)C1CCN(c2ncc(C(F)(F)F)cn2)CC1)c1ccccc1 ; C[C@@H](O)C1CCN(c2ncc(C(F)(F)F)cn2)CC1]

To a stirred solution of (2S)—(R)-1-(1-(5-(trifluoromethyl)pyrimidin-2-yl)piperidin-4-yl)ethyl 2-methoxy-2-phenylacetate (0.045 g, 0.106 mmol) in MeOH (10 mL) was added K$_2$CO$_3$ (0.029 g, 0.212 mmol) in water (5 mL) at room temperature and stirred at 40° C. for 16 h. Reaction was monitored by TLC. On completion, removed all volatiles, D.M. was added to reaction mixture and extracted with EtOAc. Organic layers were combined, washed with brine solution, dried over sodium sulphate and concentrated under reduced pressure to give (R)-1-(1-(5-(trifluoromethyl)pyrimidin-2-yl)piperidin-4-yl)ethanol (0.026 g, 88.8%) as white solid.

MS: 276.1 [M$^+$+1]

Step-6: Synthesis of 2-((S)-1-(1-(5-(trifluoromethyl)pyrimidin-2-yl)piperidin-4-yl)ethoxy)-5-bromothiazolo[5,4-b]pyridine

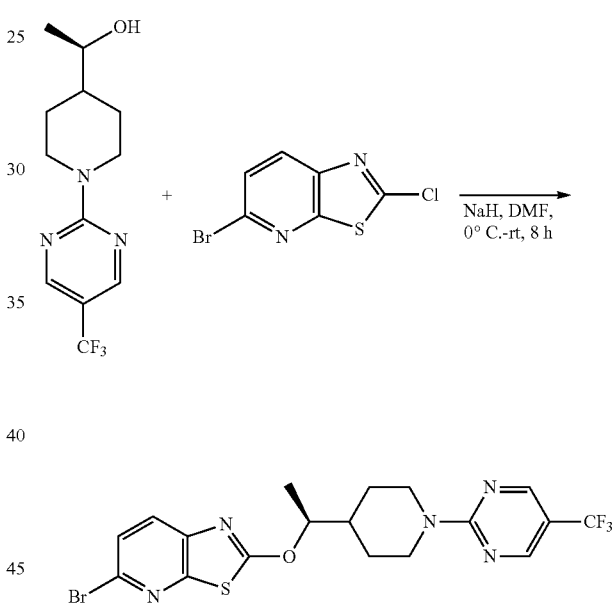

To a stirred solution of (R)-1-(1-(5-(trifluoromethyl)pyrimidin-2-yl)piperidin-4-yl)ethanol (0.026 g, 0.094 mmol) in DMF (8 mL) was added sodium hydride (0.011 g, 0.282 mmol) at RT and stirred for 30 min. After 30 min, 5-bromo-2-chlorothiazolo[5,4-b]pyridine (0.026 g, 0.104 mmol) in DMF (1 mL) was added to reaction mass and stir at room temperature for 6 h. Reaction was monitored by TLC. On completion reaction was quenched with ice cold water, extracted with ethyl acetate. The organic layer was washed with brine, dried over sodium sulphate, concentrated under reduced pressure to give crude product which was purified by (silica gel, 100-200 mesh, 0-10% EtOAc in hexane as eluent) to give 2-((S)-1-(1-(5-(trifluoromethyl)pyrimidin-2-yl)piperidin-4-yl)ethoxy)-5-bromothiazolo[5,4-b] pyridine (0.013 g, 28.1%) as yellow solid.

MS: 454.0 [M$^+$+1]

Step-7: 2-((S)-1-(1-(5-(trifluoromethyl)pyrimidin-2-yl)piperidin-4-yl)ethoxy)-5-(6-(methylthio) pyridin-3-yl)thiazolo[5,4-b]pyridine

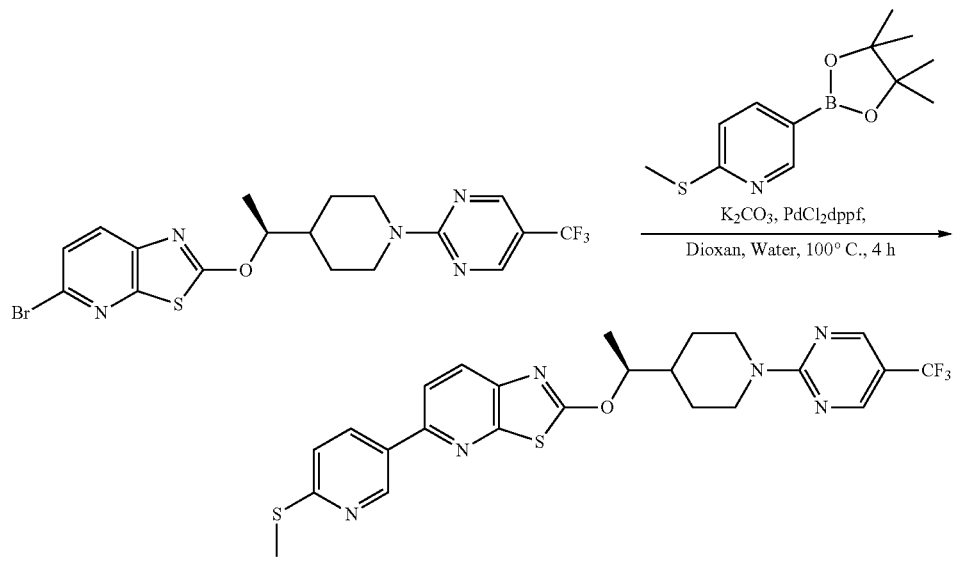

To a stirred solution of 2-((S)-1-(1-(5-(trifluoromethyl) pyrimidin-2-yl)piperidin-4-yl)ethoxy)-5-bromothiazolo[5,4-b]pyridine (0.020 g, 0.041 mmol) and 5-(4,4,5,5-tetramethyl-1,3,2-dioxaborolan-2-yl)-2-(methylthio)pyridine (0.013 g, 0.053 mmol) in dioxan (10 mL), $K_2CO_3$ (0.017 g, 0.122 mmol) in water (2.0 mL) was added at room temperature. Reaction was purged with nitrogen for 30 min. Then to it, $PdCl_2(dppf)$ (0.0015 g, 0.0020 mmol) was added and heated at 100° C. for 4 h. Reaction was monitored by TLC. On completion, D.M. water was added to reaction mixture and extracted with ethyl acetate. Organic layers were combined, dried over sodium sulphate and concentrated under reduced pressure to give crude product. Crude product was purified by column chromatography using (silica gel, 100-200 mesh, 0-15% Acetone in hexane as eluent) to give 2-((S)-1-(1-(5-(trifluoromethyl)pyrimidin-2-yl)piperidin-4-yl)ethoxy)-5-(6-(methylthio)pyridin-3-yl)thiazolo[5,4-b] pyridine (0.018 g, 82.53%) as white solid.

MS: 533.1 [M$^+$+1]

Step 8: Synthesis of 2-((S)-1-(1-(5-(trifluoromethyl) pyrimidin-2-yl)piperidin-4-yl)ethoxy)-5-(6-(methylsulfonyl) pyridin-3-yl)thiazolo[5,4-b]pyridine

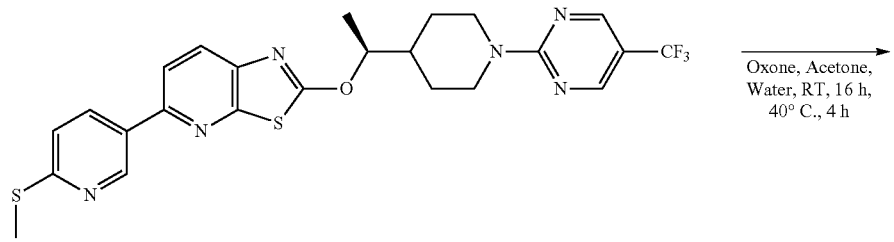

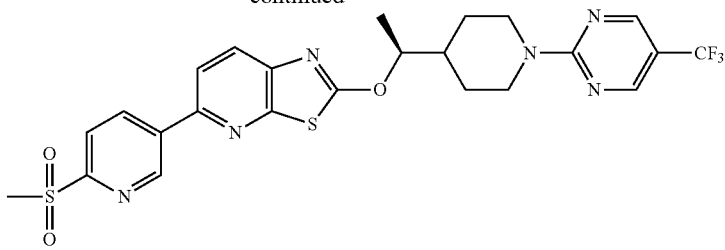

To a stirred solution of 2-((S)-1-(1-(5-(trifluoromethyl)pyrimidin-2-yl)piperidin-4-yl)ethoxy)-5-(6-(methylthio)pyridin-3-yl)thiazolo[5,4-b]pyridine (0.012 g, 0.022 mmol) in acetone (10.0 mL), Oxone (0.022 g, 0.067 mmol) in water (2 mL) was added drop wise at room temperature. Allowed the reaction to stir at RT for 16 h. Then heated at 40° C. for 4 h. Completion of reaction was monitored by TLC. Reaction mass was evaporated, diluted with water, extracted with EtOAc. Organic portions were combined, dried over $Na_2SO_4$, evaporated under reduced pressure to obtain crude product. Crude product was purified by column chromatography using (silica gel, 100-200 mesh, 0-50% EtOAc in hexane as eluent) to give 2-((S)-1-(1-(5-chloropyrimidin-2-yl)piperidin-4-yl)ethoxy)-5-(6-(methylthio) pyridin-3-yl)thiazolo[5,4-b]pyridine (0.006 g, 51.10%) as white solid.

MS: 565.1 [M$^+$+1]

Example 35: 2-((S)-1-(1-(3-isopropyl-1,2,4-oxadiazol-5-yl)piperidin-4-yl)ethoxy)-5-(2-fluoro-6-(methylsulfonyl)pyridin-3-yl)thiazolo[5,4-b]pyridine [1167]

Step-1: Synthesis of 2-fluoro-3-(4,4,5,5-tetramethyl-1,3,2-dioxaborolan-2-yl)-6-(methylthio)pyridine

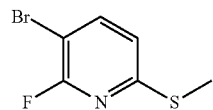

KOAc, PdCl$_2$dppf·DCM
Bispinacoleto diboron
1,4-Dioxan, 100° C., 4 h 3-bromo-2-fluoro-6-(methylthio)pyridine (0.050 g, 0.225 mmol), Potassium Acetate (0.066 g, 0.675 mmol) and Bis pinacoleto diboron (0.074 g, 0.292 mmol) were dissolved in 1,4-Dioxan (10.0 mL). Degassed the reaction using N$_2$ for 30 min. To it, PdCl$_2$dppf (0.009 g, 0.011 mmol) was added and heated at 100° C. for 4 h. Reaction was monitored by TLC. On completion, reaction mass was filtered through celite pad and washed with EtOAc (2×30 mL). Filtrate was evaporated to give crude product which was purified by column chromatography using (Silica gel 100-200 mesh, 0-10% EtOAc in hexane as eluent) to give 2-fluoro-3-(4,4,5,5-tetramethyl-1,3,2-dioxaborolan-2-yl)-6-(methylthio)pyridine (0.025 g, 40.9%) as colourless gum.

MS: 270.1 [M$^+$+1]

Step-2: 2-((S)-1-(1-(3-isopropyl-1,2,4-oxadiazol-5-yl)piperidin-4-yl) ethoxy)-5-(2-fluoro-6-(methylthio)pyridin-3-yl)thiazolo[5,4-b]pyridine

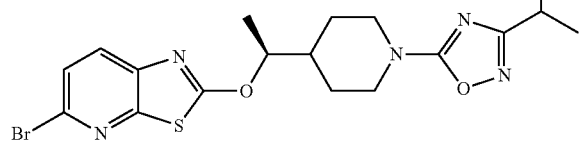
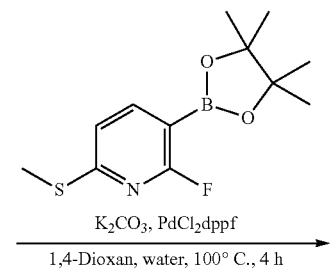

K$_2$CO$_3$, PdCl$_2$dppf
1,4-Dioxan, water, 100° C., 4 h

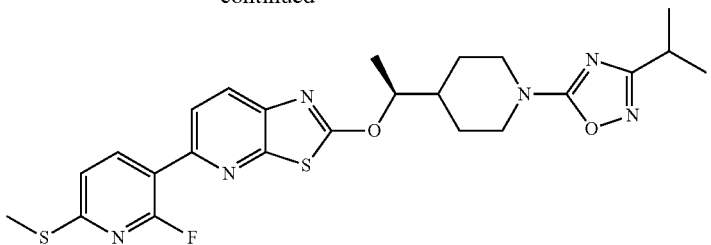

2-((S)-1-(1-(3-isopropyl-1,2,4-oxadiazol-5-yl)piperidin-4-yl)ethoxy)-5-bromothiazolo[5,4-b]pyridine (0.030 g, 0.0663 mmol), Potassium carbonate (0.027 g, 0.198 mmol) and 2-fluoro-3-(4,4,5,5-tetramethyl-1,3,2-dioxaborolan-2-yl)-6-(methylthio)pyridine (0.023 g, 0.0862 mmol) were dissolved in 1,4-Dioxan (10.0 mL). Degassed the reaction using $N_2$ for 30 min. To it, $PdCl_2dppf$ (0.002 g, 0.003 mmol) was added and heated at 100° C. for 4 h. Reaction was monitored by TLC. On completion, D.M. water (30 mL) was added to reaction mixture and extracted with EtOAc. Organic layers were combined, dried over sodium sulphate and concentrated under reduced pressure to give crude product. Crude product was purified by column chromatography using (silica gel, 100-200 mesh, 0-50% EtOAc in hexane as eluent) to give 2-((S)-1-(1-(3-isopropyl-1,2,4-oxadiazol-5-yl)piperidin-4-yl) ethoxy)-5-(2-fluoro-6-(methylthio)pyridin-3-yl)thiazolo[5,4-b]pyridine (0.029 g, 55.7%) as brown solid.

MS: 515.16 [M$^+$+1]

Step-3: 2-((S)-1-(1-(3-isopropyl-1,2,4-oxadiazol-5-yl)piperidin-4-yl)ethoxy)-5-(2-fluoro-6-(methylsulfonyl)pyridin-3-yl)thiazolo[5,4-b]pyridine

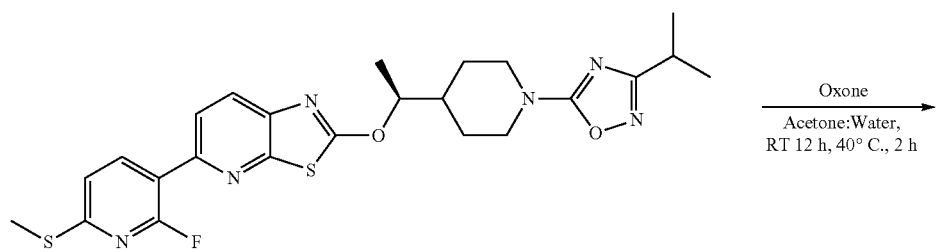

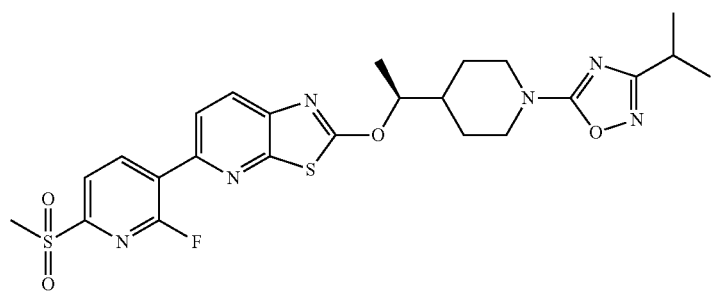

To a stirred solution of 2-((S)-1-(1-(3-isopropyl-1,2,4-oxadiazol-5-yl)piperidin-4-yl) ethoxy)-5-(2-fluoro-6-(methylthio)pyridin-3-yl)thiazolo[5,4-b]pyridine (0.019 g, 0.037 mmol) in acetone (16 mL) and water (4 mL) was added oxone (0.034 g, 0.110 mmol) and the mixture was stirred at RT for 12 h and then heated at 40° C. for 2 h. Progress of reaction was monitored by TLC. D.M. water was added to reaction mixture and extracted with EtOAc. Organic layers were combined, washed with brine, dried over sodium sulphate and concentrated under reduced pressure to give crude product. Crude product was purified by column chromatography using (silica gel, 100-200 mesh, 0-40% EtOAc in hexane as eluent) followed by (Neutral alumina, 0-28% EtOAc in Hexane as eluent) to give 2-((S)-1-(1-(3-isopropyl-1,2,4-oxadiazol-5-yl)piperidin-4-yl)ethoxy)-5-(2-fluoro-6-(methylsulfonyl)pyridin-3-yl)thiazolo[5,4-b] pyridine (0.005 g, 26.26%) as off white sticky solid.

MS: 547.15 [M$^+$+1]

Example 36: 2-((S)-1-(1-(3-isopropyl-1,2,4-oxadiazol-5-yl)piperidin-4-yl)ethoxy)-5-(2-methyl-6-(methylsulfonyl)pyridin-3-yl)thiazolo[5,4-b]pyridine [1168]

Step 1: Synthesis of 3-bromo-2-methyl-6-(methylthio)pyridine

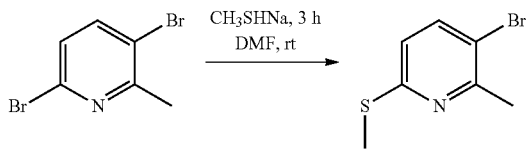

To a stirred solution of 5-bromo-2-chloropyrimidine (0.3 g, 1.19 mmol) in DMF (10 mL) was added methyl mercaptan (0.4 mL, 1.19 mmol) at room temperature and stirred for 6 h at room temperature. Completion of reaction was monitored by TLC. Reaction mixture was quenched by addition of water, extracted with EtOAc. Organic portions were combined, dried over Na$_2$SO$_4$, evaporated under reduced pressure to obtain crude which was purified by column chromatography using silica gel (100-200 mesh); eluent 1% ethyl acetate/hexane to obtain pure product 3-bromo-2-methyl-6-(methylthio)pyridine (0.200 g, 76%) as light yellow oil.

MS: 219.1 [M$^+$+1]

Step 2: Synthesis of 2-methyl-3-(4,4,5,5-tetramethyl-1,3,2-dioxaborolan-2-yl)-6-(methylthio)pyridine

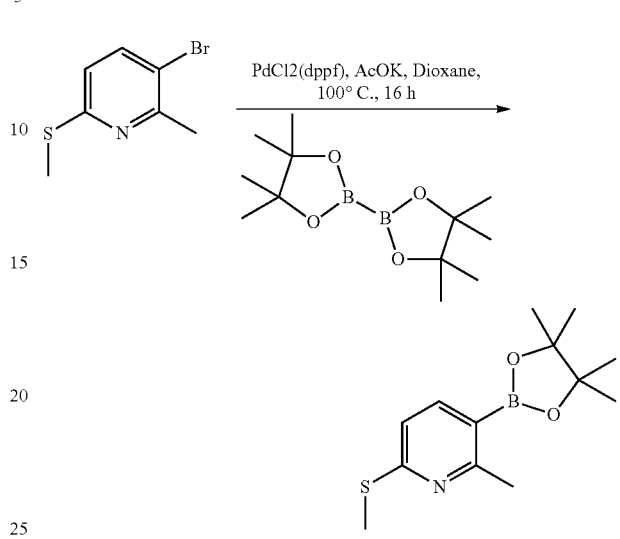

To a stirred solution of 3-bromo-2-methyl-6-(methylthio)pyridine (0.05 g, 0.229 mmol) and Bis(pinacolato)diboron (0.070 g, 0.275 mmol) in Dioxane (10 mL) was added AcOK (0.067 g, 0.688 mmol) and reaction mass was purged with nitrogen for 30 min. Then, PdCl2(dppf) (0.08 g, 0.011 mmol) was added to it and stirred at 100° C. for 16 h. Reaction was monitored by TLC. On completion reaction mass was concentrated under reduced pressure and extracted with ethyl acetate. The organic layer was washed with water, brine, dried over sodium sulphate, concentrated under reduced pressure obtained crude which was purified column chromatography; eluent 1% acetone/Hexane to afford 2-methyl-3-(4,4,5,5-tetramethyl-1,3,2-dioxaborolan-2-yl)-6-(methylthio)pyridine.

MS: 266.1 [M$^+$+1]

Step 3: Synthesis of 2-((S)-1-(1-(3-isopropyl-1,2,4-oxadiazol-5-yl)piperidin-4-yl)ethoxy)-5-(2-methyl-6-(methylthio)pyridin-3-yl)thiazolo[5,4-b]pyridine

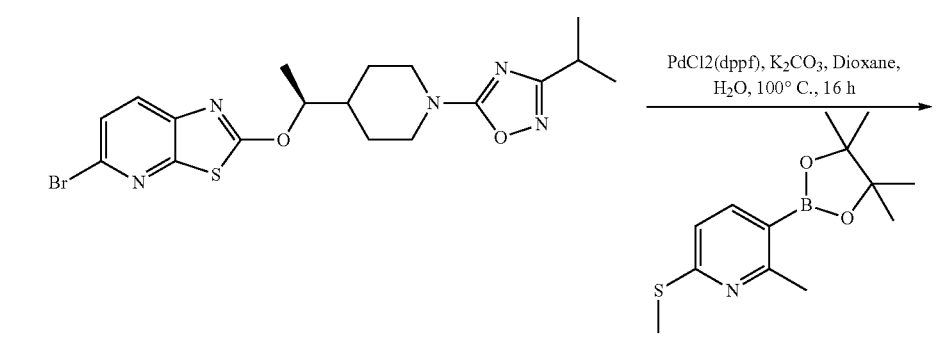

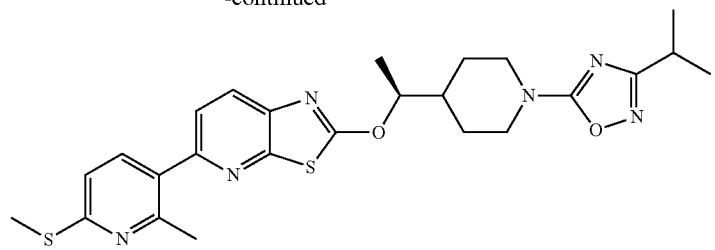

To a stirred solution of 2-((S)-1-(1-(3-isopropyl-1,2,4-oxadiazol-5-yl)piperidin-4-yl)ethoxy)-5-bromothiazolo[5,4-b]pyridine (0.03 g, 0.066 mmol) and 2-methyl-3-(4,4,5,5-tetramethyl-1,3,2-dioxaborolan-2-yl)-6-(methylthio)pyridine (0.020 g, 0.0731 mmol) in Dioxane (10 mL) was added $K_2CO_3$ (0.027 g, 0.199 mmol) in water (2 mL) and reaction mass was purged with nitrogen for 30 min. Then, $PdCl_2(dppf)$ (0.003 g, 0.0033 mmol) was added to it and stirred at 100° C. for 16 h. Reaction was monitored by TLC. On completion reaction was concentrated under reduced pressure obtained crude which was purified by column chromatography (100-200 Mesh); eluent 15% EtOAc/Hexane to afford 2-((S)-1-(1-(3-isopropyl-1,2,4-oxadiazol-5-yl)piperidin-4-yl)ethoxy)-5-(2-methyl-6-(methylthio)pyridin-3-yl)thiazolo[5,4-b]pyridine (0.010 g, 29%) as colourless sticky mass.

MS: 511.1 [M$^+$+1]

Step 4: Synthesis of 2-((S)-1-(1-(3-isopropyl-1,2,4-oxadiazol-5-yl)piperidin-4-yl)ethoxy)-5-(2-methyl-6-(methylsulfonyl)pyridin-3-yl)thiazolo[5,4-b]pyridine

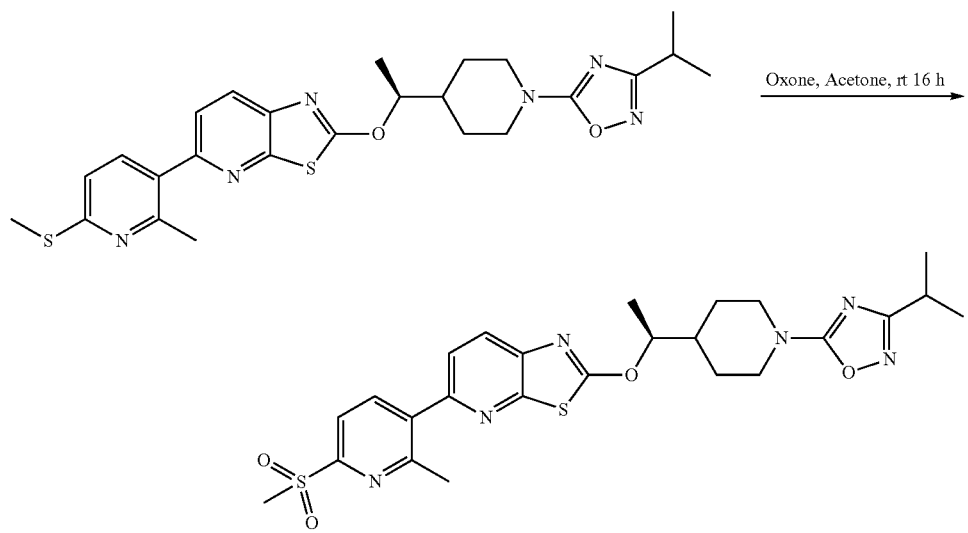

To a stirred solution of 2-((S)-1-(1-(3-isopropyl-1,2,4-oxadiazol-5-yl)piperidin-4-yl)ethoxy)-5-(2-methyl-6-(methylthio)pyridin-3-yl)thiazolo[5,4-b]pyridine (0.01 g, 0.019 mmol) in Acetone (5 mL) was added Oxone (0.012 g, 0.039 mmol) in water (2 mL) then, reaction mass was stirred at room temperature for 16 h. Reaction was monitored by TLC. On completion reaction was concentrated under reduced pressure and extracted with ethyl acetate. The organic layer was washed with water, brine, dried over sodium sulphate, concentrated under reduced pressure obtained crude which was purified column chromatography (100-200 Mesh); eluent 25% acetone/hexane to afford 2-((S)-1-(1-(3-isopropyl-1,2,4-oxadiazol-5-yl)piperidin-4-yl)ethoxy)-5-(2-methyl-6-(methylsulfonyl)pyridin-3-yl)thiazolo[5,4-b]pyridine (0.003 g, 30%) as colourless sticky mass.

MS: 542.1 [M$^+$+1]

Example 37: In Vitro Cyclic AMP Assay cAMP measurements were done using Cisbio dynamic 2 HTRF kit according to the manufacturer's protocol. Briefly, CHO-hGPR119 cells were plated at a cell density of 5000 cells/well/5 μl into a white small volume 384 well plate. The final concentrations of IBMX and DMSO used were 1 mM and 0.5% respectively. Cells were treated with various concentrations of the test compound for 60 min at room temperature. Cells were lysed by buffer containing Anti-cAMP antibody and d2-cAMP reagents and incubated for 1 hour at room temperature. HTRF was measured at 337 nm excitation and emission wavelengths of 665 nm and 620 nm on a microplate reader (Flurostar, BMG Labtech). Graphpad prism software was utilized for EC50 determinations.

Results: The results of the compounds were represented in terms of % induction at 1 μM and EC50 and the same is represented at Table 1 herein below.

TABLE 1

| Compound | Induction | EC50 |
|---|---|---|
| 1001 | NA | |
| 1002 | NA | |
| 1003 | 29 | |
| 1004 | 45 | |
| 1005 | 6 | |
| 1006 | 31 | |
| 1007 | 39 | |
| 1008 | 3 | |
| 1009 | 5 | |
| 1010 | 8 | |
| 1011 | 19 | |
| 1012 | 5 | |
| 1013 | 11 | |
| 1014 | 5 | |
| 1015 | 2 | |
| 1016 | 0 | |
| 1017 | NA | |
| 1018 | NA | |
| 1019 | 0 | |
| 1020 | 68 | B |
| 1021 | 13 | |
| 1022 | 35 | |
| 1023 | NA | |
| 1024 | 53 | |
| 1025 | 12 | |
| 1026 | 5 | |
| 1027 | 3 | |
| 1028 | 2 | |
| 1029 | 47 | |
| 1030 | NA | |
| 1031 | 76 | A |
| 1032 | 13 | |
| 1033 | NA | |
| 1034 | 0.3 | |
| 1035 | 2 | |
| 1036 | 47 | |
| 1037 | 18 | |
| 1038 | 11 | |
| 1039 | 20 | |
| 1040 | 48 | |
| 1041 | NA | |
| 1042 | NA | |
| 1043 | 4 | |
| 1044 | 3 | |
| 1045 | 31 | |
| 1046 | 1 | |
| 1047 | 17 | |
| 1048 | 57 | |
| 1049 | 14 | |
| 1050 | 16 | |
| 1051 | 24 | |
| 1052 | 13 | |
| 1053 | 73 | A |
| 1054 | 81 | A+ |
| 1055 | 76 | |
| 1056 | 51 | |
| 1057 | 28 | |
| 1058 | 48 | |
| 1059 | NA | |
| 1060 | 39 | |
| 1061 | 48 | |
| 1062 | 61 | |
| 1063 | 58 | |
| 1064 | NA | |
| 1065 | 60 | |
| 1066 | 30 | |
| 1067 | 36 | |
| 1068 | 13 | |
| 1069 | 80 | |
| 1070 | 83 | A |
| 1071 | 32 | |
| 1072 | 17 | |
| 1073 | 29 | |
| 1074 | 39 | |
| 1075 | 7 | |
| 1076 | 35 | |
| 1077 | 12 | |
| 1078 | 24 | |
| 1079 | 50 | |
| 1080 | 40 | |
| 1081 | 82 | |
| 1082 | 82 | A++ |
| 1083 | 14 | |
| 1084 | 12 | |
| 1085 | ND | |
| 1086 | 2 | |
| 1087 | 74 | |
| 1088 | 60 | |
| 1089 | 81 | A+ |
| 1090 | 54 | |
| 1091 | ND | |
| 1092 | 9 | |
| 1093 | 82 | A++ |
| 1094 | 24 | |
| 1095 | 84 | |
| 1096 | 66 | A |
| 1097 | 34 | |
| 1098 | 48 | |
| 1099 | 81 | A++ |
| 1100 | 65 | |
| 1101 | 74 | A+ |
| 1102 | 72 | |
| 1103 | 63 | |
| 1104 | 84 | A+ |
| 1105 | 13 | |
| 1106 | 75 | A++ |
| 1107 | 12 | |
| 1108 | 65 | |
| 1109 | 0 | |
| 1110 | 78 | |
| 1111 | 24 | |
| 1112 | 55 | |
| 1113 | 57 | |
| 1114 | 75 | A |
| 1115 | 12 | |
| 1116 | 61 | |
| 1117 | 2 | |
| 1118 | 47 | |
| 1119 | 75 | A++ |
| 1120 | 40 | |
| 1121 | 30 | |
| 1122 | 30 | |
| 1123 | 50 | |
| 1124 | 30 | |
| 1125 | 38 | |
| 1126 | 42 | |
| 1127 | 50 | |
| 1128 | 10 | |
| 1129 | 5 | |
| 1130 | 5 | |
| 1131 | 40 | |
| 1132 | 38 | |
| 1133 | 55 | |
| 1134 | 40 | |
| 1135 | 86 | A++ |
| 1136 | 82 | B |
| 1137 | 73 | |
| 1138 | NA | |
| 1139 | 65 | |
| 1140 | 4 | |
| 1141 | 3 | |
| 1142 | 72 | |
| 1143 | NA | |
| 1144 | 69 | |
| 1145 | 65 | |
| 1146 | 61 | |
| 1147 | NA | |
| 1148 | 70 | |
| 1149 | 64 | |
| 1150 | 67 | |
| 1151 | 66 | |
| 1152 | 77 | A |
| 1153 | 85 | B |
| 1154 | 65 | A+ |
| 1156 | 54 | |
| 1157 | 81 | |

TABLE 1-continued

| Compound | Induction | EC50 |
|---|---|---|
| 1158 | 80 | |
| 1159 | 70 | |
| 1160 | 76 | A+ |
| 1161 | 69 | |
| 1162 | 62 | |
| 1163 | 63 | |
| 1164 | 72 | |
| 1165 | 70 | |
| 1166 | 70 | |
| 1167 | 20 | |
| 1168 | 22 | |
| 1169 | 43 | |

NA: Not Active;
A++: <25 nM;
A+: >25 to <50 nM;
A: >50 to <100 nM;
B: >100 nM to 500 Nm;
NT: Not Tested Example 38: Anti-Diabetic Effect of Compounds of the Invention in an In-Vitro Model of Pancreatic Beta Cells (HIT-T15)

Cell Culture:

HIT-T15 cells were grown in Ham's F12K medium with 2 mM 1-glutamine containing 2.5% horse serum and 10% fetal bovine serum. Cells were grown in minimal glucose concentration for insulin secretion studies. Studies were performed with cell passage numbers between 65 to 72.

cAMP Assay:

HIT-T15 cells were plated at a cell density of 5000 cells/well/5 µl into a white small volume 384 well plate. The final concentrations of IBMX and DMSO used were 1 mM and 0.5% respectively. Cells were treated with various concentrations of the test compound for 60 min at room temperature. Cells were lysed by buffer containing Anti-cAMP antibody and d2-cAMP reagents and incubated for 1 hour at room temperature. HTRF was measured at 337 nm excitation and emission wavelengths of 665 nm and 620 nm on a microplate reader (Flurostar, BMG Labtech). GraphPad prism 6 software was utilized for EC50 determinations.

Representative compounds of the invention were found to increase cAMP at an EC50 of less than 10 µM. Compounds showing an EC50 of less than 1 µM in the cAMP assay may be preferred.

Insulin Secretion Assay:

HIT-T15 cells were utilised for assessment of potentiation of glucose stimulated insulin secretion (GSIS) by test compounds. Cells were seeded at a cell density of 50,000 cells per well in 96 well plate. After 48 hours, cells were washed with Krebs-Ringer Bicarbonate buffer (KRB) and incubated with buffer containing 0.2 mM glucose for 30 minutes. After incubating cells twice in KRB buffer containing 0.2 mM glucose, cells were exposed to 11 mM glucose and test compounds at 10 µM and 1 µM for 1 hour. Supernatants were collected for measurement of insulin secreted from the cells. Insulin was measured using Cisbio insulin test kit following manufacturer's instructions, with a standard curve of known insulin concentrations. For each well, insulin levels are corrected by subtraction of the basal secretion level from the preincubation in the absence of glucose. Data is analysed using GraphPad prism 6 software. Representative compounds of the invention were studied for their insulin potentiation capacity and showed increase in insulin secretion at an EC50 of less than 10 µM, however the compounds showing increase in insulin secretion at an EC50 of less than 1 µM may be preferred.

Example 39: Oral Glucose Tolerance Test

Male C57BL/6 mice (8-10 weeks) were grouped based on basal glucose levels and animals were fasted for 16 hours. Glucose level of each animal was estimated in blood collected from tail vein before animals were dosed orally with 0.5% Tween 80 and 0.5% NaCMC (vehicle control) and compounds at 3 and 10 mpk (n=5). After 30 minutes of compound dosing, blood glucose was again estimated and 2 g/kg/10 ml (20%) of Glucose solution was administered orally to all the animals. Blood glucose was estimated at 15, 30, 60, 90 and 120 minutes time points after glucose administration. Accu-Check active blood glucose meter was utilised for estimation of blood from tail vein.

Results:

Glucose reduction observed in animals treated with compounds of present invention is represented in terms of % AUC reduction. A greater glucose reduction in oral glucose tolerance test indicates the compound's efficacy in this rodent species. The compounds 1082, 1089, 1099, 1101, 1104, 1106, 1119, 1120, and 1135 showed significant dose dependent glucose reduction at both 3 mpk and 10 mpk respectively.

Example 40: Oral Glucose Tolerance Test in Sprague-Dawley Rats

Male SD rats (8-10 weeks) were grouped based on basal glucose levels and animals were fasted for 16 hours. Glucose level of each animal was estimated in blood collected from tail vein before animals were dosed orally with 0.5% Tween 80 and 0.5% NaCMC (vehicle control) and compounds at 3 and 10 mpk (n=5). After 30 minutes of compound dosing, blood glucose was again estimated and 2 g/kg/10 ml (20%) of Glucose solution was administered orally to all the animals. Blood glucose was estimated at 15, 30, 60, 90 and 120 minutes time points after glucose administration. Accu-Check active blood glucose meter was utilised for estimation of blood from tail vein.

Results:

Glucose reduction observed in animals treated with GPR119 agonists is represented in terms of % AUC reduction. A greater glucose reduction in oral glucose tolerance test indicates the compound's efficacy in this rodent species. The compounds 1082, 1099, 1101, 1106, 1119, and 1135 showed significant dose dependent glucose reduction at both 3 mpk and 10 mpk respectively.

Example 41: Glucagon-Like Peptide-1 (GLP-1) Secretion

To study the effect of GPR119 agonists on secretion of GLP-1 in C57BL/6 mice, animals were grouped based on basal glucose levels and fasted for 16 hours. Animals were dosed orally with vehicle or test compound at 10 mpk (n=20). After 30 minutes of compound dosing, ten animals were sacrificed from each group and blood was collected by cardiac puncture method. To the remaining 10 animals in each group, glucose, 3 g/kg, was administered. After ten minutes of glucose administration, animals were sacrificed by $CO_2$ asphyxiation method and blood was collected by cardiac puncture method. To avoid degradation of active GLP-1 in blood, DPP-IV inhibitor was added to the blood collection tubes. Plasma active GLP-1 levels were measured by using Merck Millipore ELISA kit. Statistical comparisons of the data were performed by one-way analysis of variance (ANOVA), followed by Bonferroni's test.

Results:

Compounds of the present invention showed significant increase in active GLP-1 secretion. Compounds which showed active GLP-1 secretion greater than ~1 fold with respect to vehicle may be preferred.

We claim:

1. A compound of formula (II):

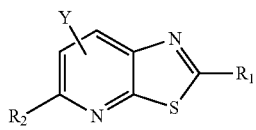

wherein,

Y is selected from H, OH, halogen, $C_{1-6}$ alkyl, $C_{1-6}$alkoxy, amino, —NH(Alkyl), —N(Alkyl)$_2$, —NH-aralkyl, —CONH$_2$, —OCH(CH$_3$)$_2$;

R$_1$ is selected from:

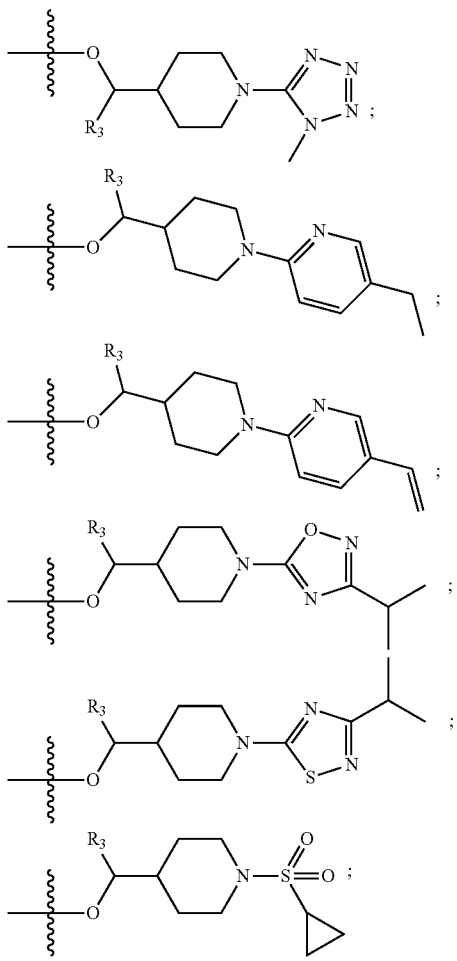

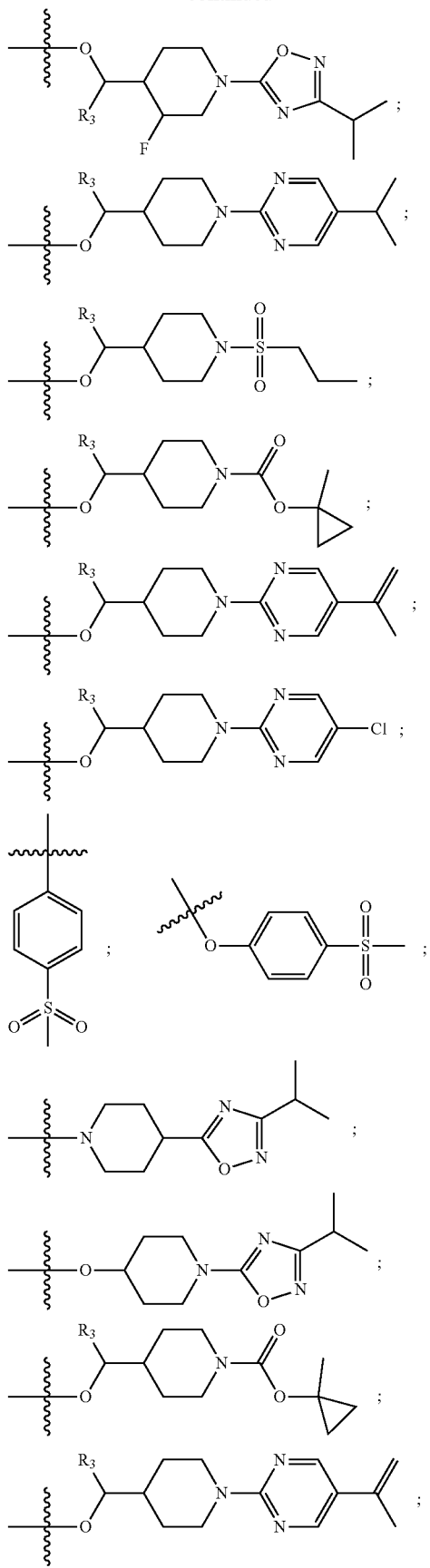

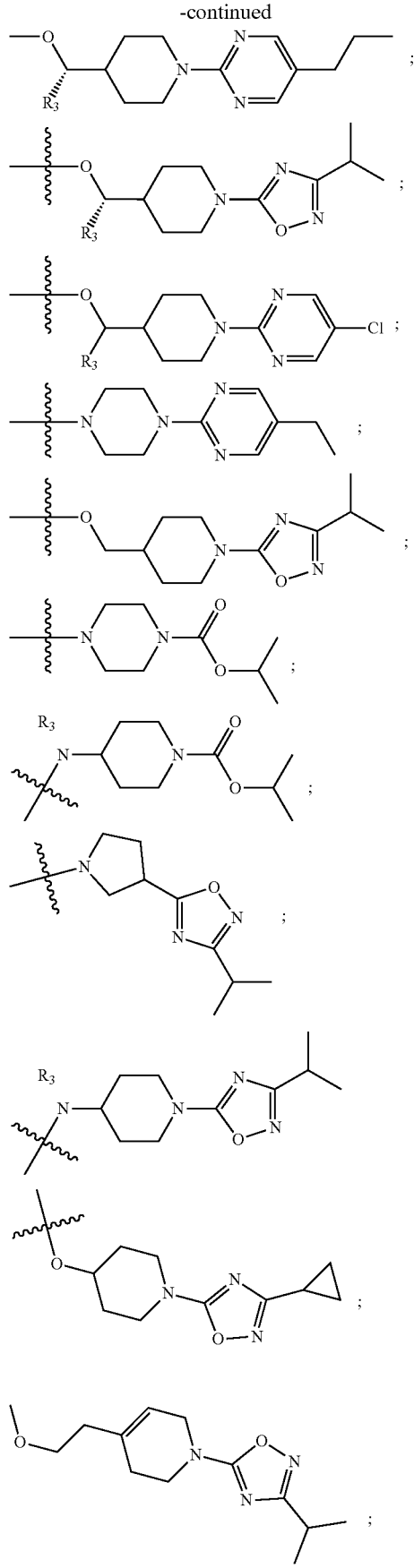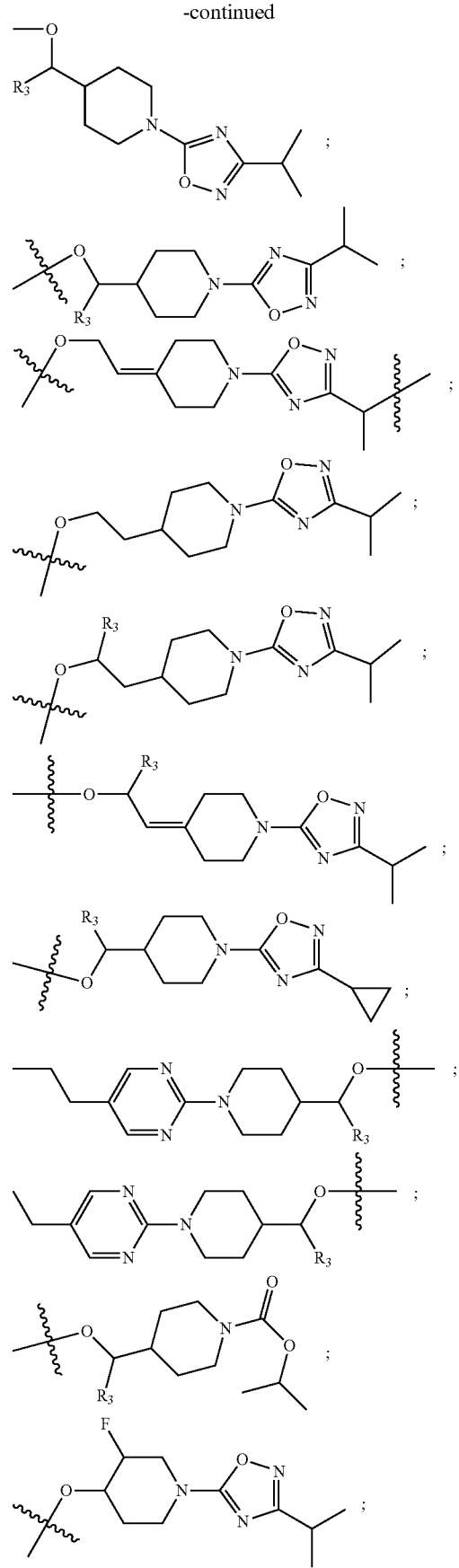

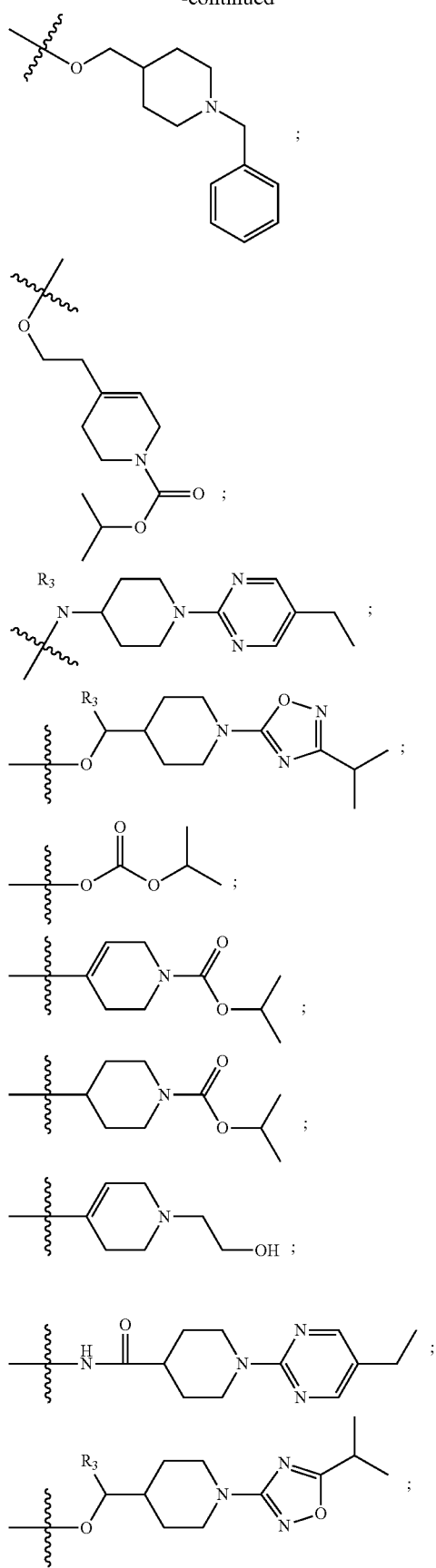
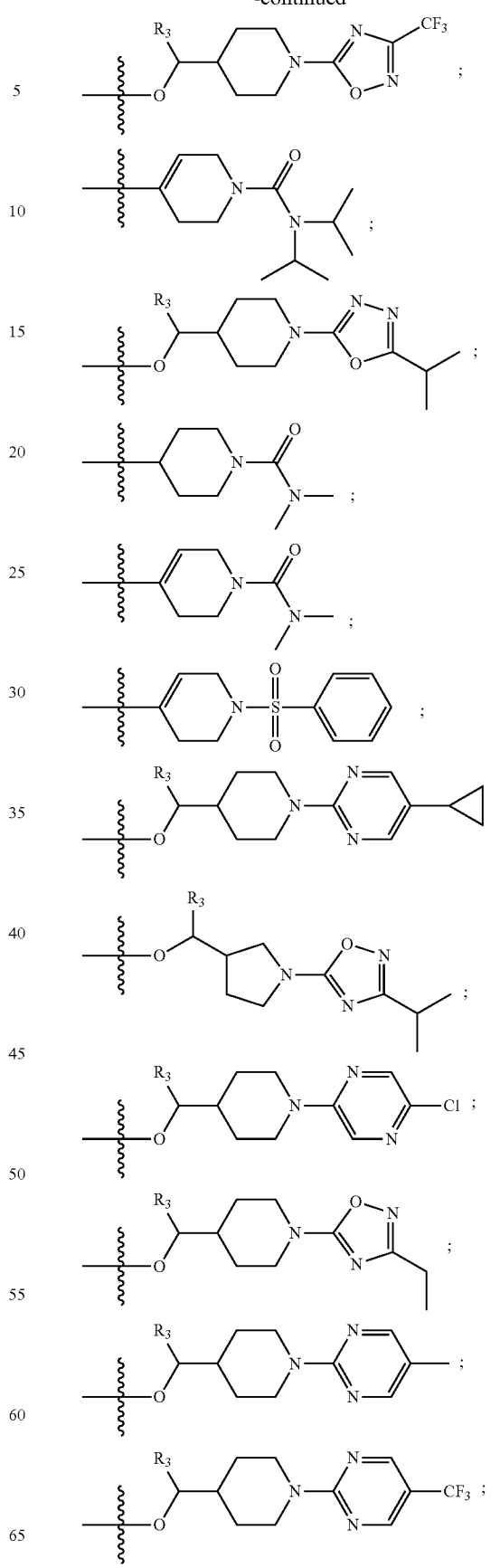

-continued
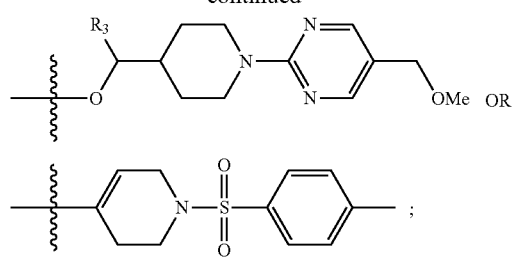
R₂ is selected from
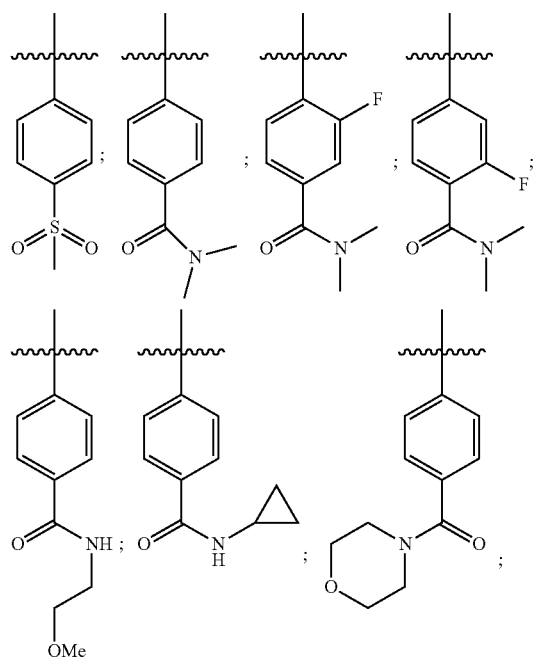
-continued
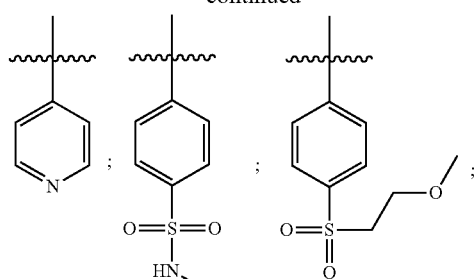
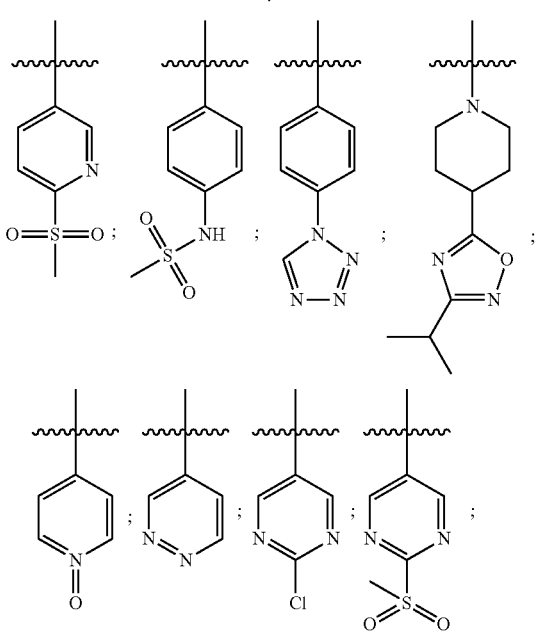
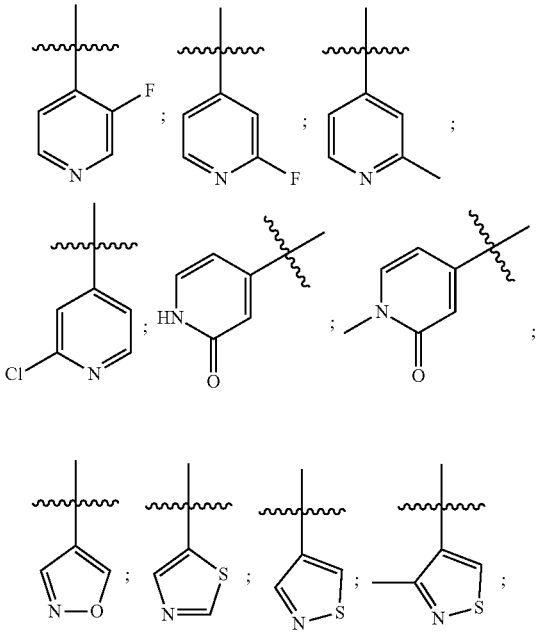

-continued

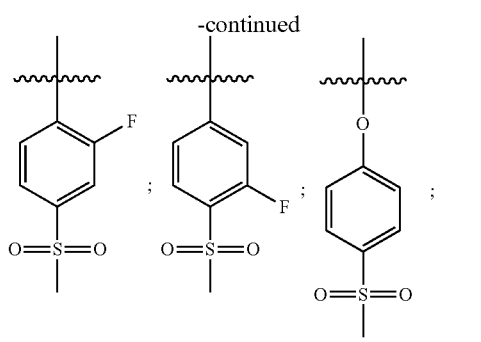
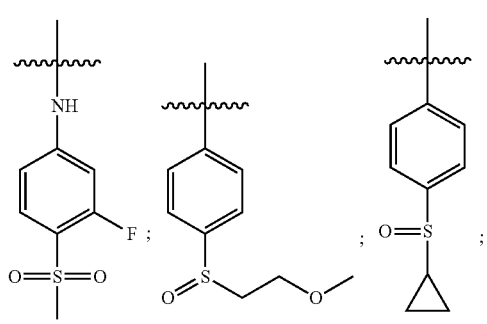
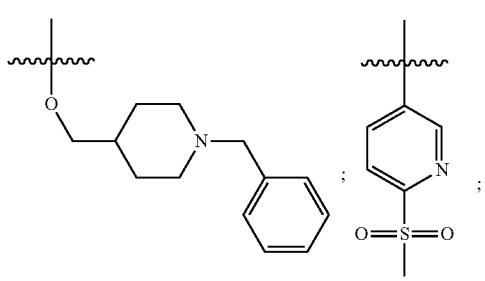
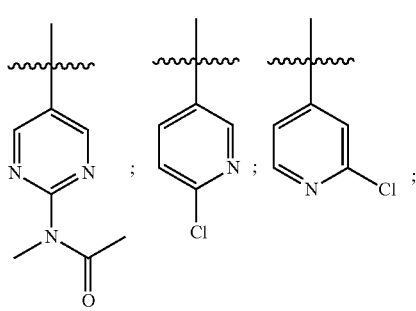
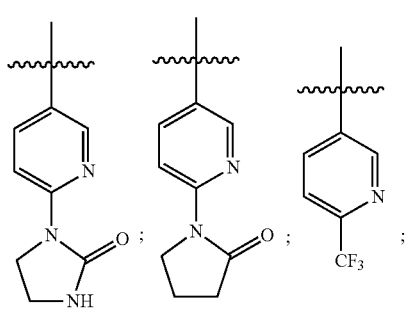

-continued

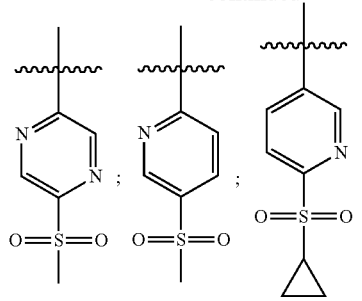
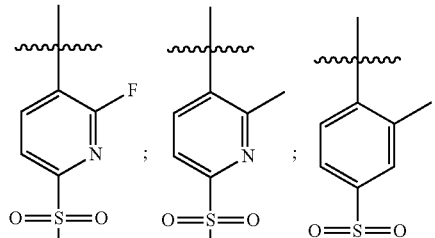
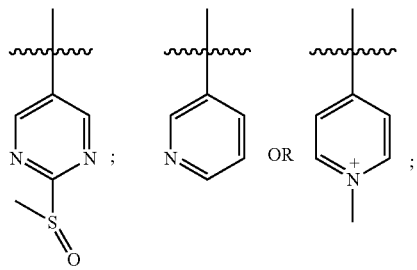

$R_3$ is selected from H, OH, halogen, $C_{1-6}$ alkyl, $C_{1-6}$alkoxy, amino, —NH(Alkyl), —N(Alkyl)$_2$, —NH-aralkyl, —CF$_3$, —CH$_2$OCH$_3$, OR

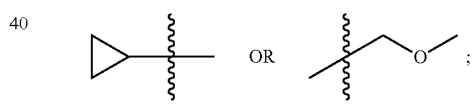

and pharmaceutically acceptable salts, hydrates and stereoisomers thereof.

2. The compound of claim 1, having active GLP-1 secretion greater than ~1 fold with respect to vehicle.

3. The compound of claim 1, having significant dose dependent glucose reduction at both 3 mpk and 10 mpk in oral glucose tolerance test in rat model.

4. The compound of claim 1, having significant dose dependent glucose reduction at both 3 mpk and 10 mpk in oral glucose tolerance test in mice model.

5. The compound of claim 1, showing increase in insulin secretion at an EC50 of less than 1 μM in an in-vitro model of pancreatic beta cells.

6. The compound of claim 1, wherein R1 is

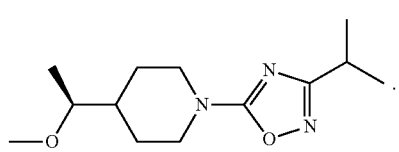 [SMILES: CO[C@@H](C)C1CCN(c2nc(C(C)C)no2)CC1]

7. The compound of claim 1, wherein R1 is

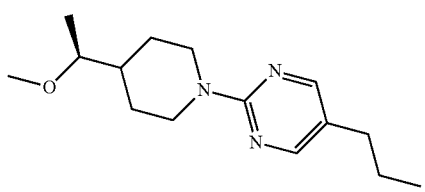

8. The compound of claim 1, wherein R1 is

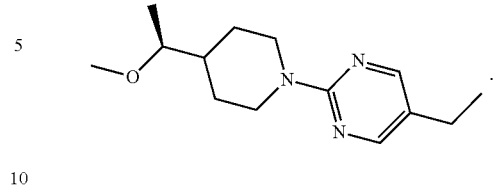

9. The compound of claim 1, wherein Y is hydrogen.

10. A compound of claim 1 having the structure:

| | | |
|---|---|---|
| 1001 | 3-isopropyl-5-(1-(5-(4-(methyl-sulfonyl)phenoxy)thiazolo[5,4-b]pyridin-2-yl)piperidin-4-yl)-1,2,4-oxadiazole | 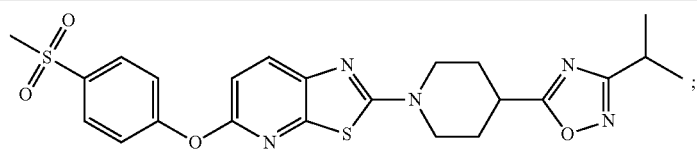; |
| 1002 | 3-isopropyl-5-(4-(((5-(4-(methylsulfonyl)phenoxy)thiazolo[5,4-b]pyridin-2-yl)oxy)methyl)piperidin-1-yl)-1,2,4-oxadiazole | 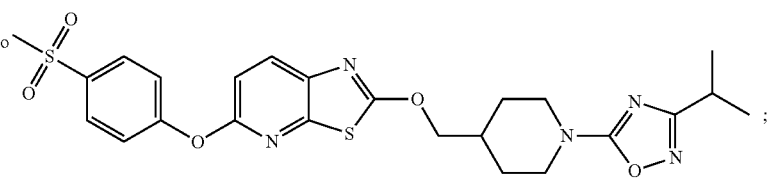; |
| 1003 | 3-isopropyl-5-(1-(2-(4-(methylsulfonyl)phenyl)thiazolo[5,4-b]pyridin-5-yl)piperidin-4-yl)-1,2,4-oxadiazole | 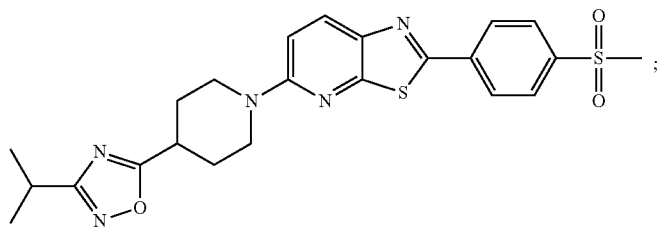; |
| 1004 | 3-isopropyl-5-(1-(5-(4-(methylsulfonyl)phenyl)thiazolo[5,4-b]pyridin-2-yl)piperidin-4-yl)-1,2,4-oxadiazole | 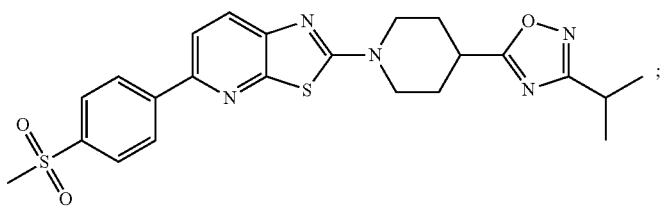; |
| 1005 | 3-isopropyl-5-(4-((5-(4-(methylsulfonyl)phenoxy)thiazolo[5,4-b]pyridin-2-yl)oxy)piperidin-1-yl)-1,2,4-oxadiazole | 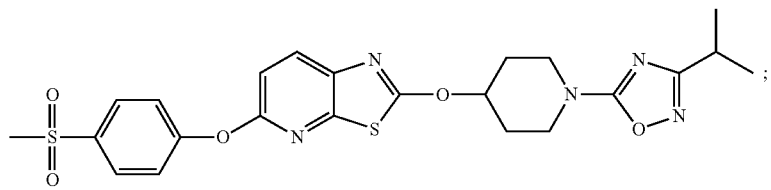; |
| 1006 | 3-isopropyl-5-(4-(((5-(4-(methylsulfonyl)phenyl)thiazolo[5,4-b]pyridin-2-yl)oxy)methyl)piperidin-1-yl)-1,2,4-oxadiazole | 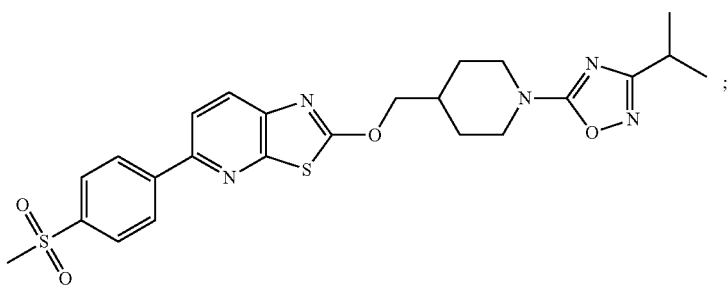; |

-continued

| | | |
|---|---|---|
| 1007 | 3-isopropyl-5-(4-((5-(4-(methylsulfonyl)phenyl)thiazolo[5,4-b]pyridin-2-yl)oxy)piperidin-1-yl)-1,2,4-oxadiazole | 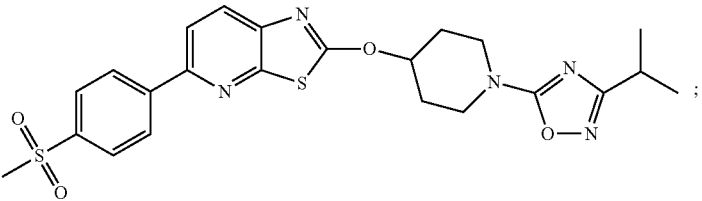 |
| 1008 | 2-(4-(5-ethylpyrimidin-2-yl)piperazin-1-yl)-5-(4-(methylsulfonyl)phenyl)thiazolo[5,4-b]pyridine | 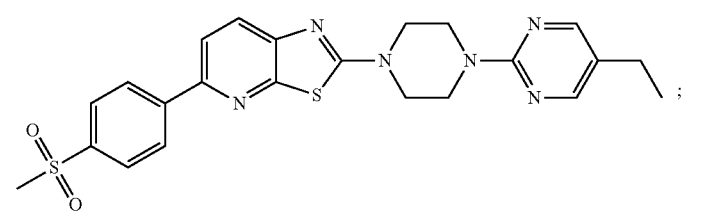 |
| 1009 | 5-((1-benzylpiperidin-4-yl)methoxy)-2-(4-(methylsulfonyl)phenyl)thiazolo[5,4-b]pyridine | 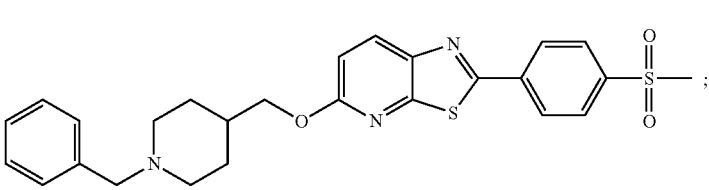 |
| 1010 | 2-(4-(5-ethylpyrimidin-2-yl)piperazin-1-yl)-5-(4-(methylsulfonyl)phenoxy)thiazolo[5,4-b]pyridine | 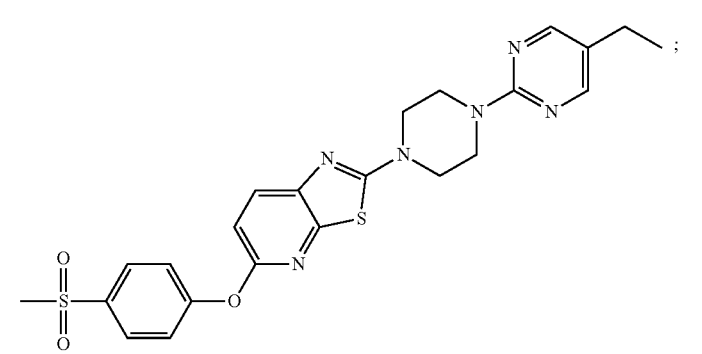 |
| 1011 | isopropyl 4-(5-(4-(methylsulfonyl)phenyl)thiazolo[5,4-b]pyridin-2-yl)-5,6-dihydropyridine-1(2H)-carboxylate | 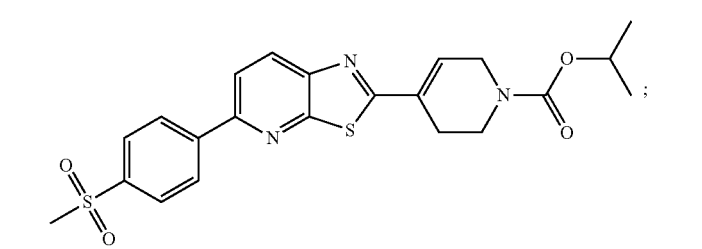 |
| 1012 | isopropyl 4-(5-(4-(methylsulfonyl)phenyl)thiazolo[5,4-b]pyridin-2-yl)piperazine-1-carboxylate | 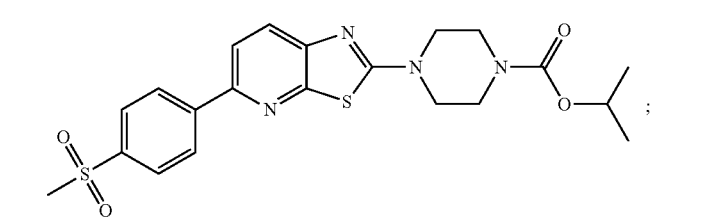 |
| 1013 | isopropyl 4-(5-(4-(methylsulfonyl)phenyl)thiazolo[5,4-b]pyridin-2-yl)piperidine-1-carboxylate | 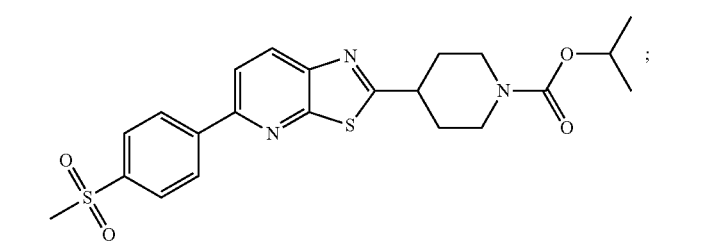 |

| | | |
|---|---|---|
| 1014 | 1-(5-ethylpyrimidin-2-yl)-N-(5-(4-(methylsulfonyl)phenyl)thiazolo[5,4-b]pyridin-2-yl)piperidine-4-carboxamide | 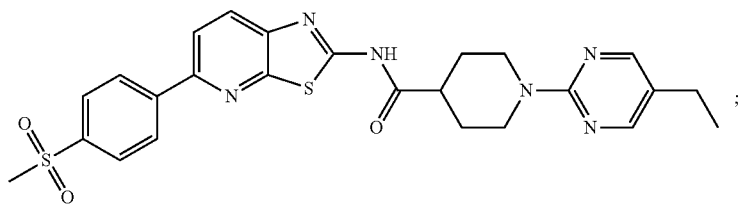 |
| 1015 | 2-(4-(5-(4-(methylsulfonyl)phenyl)thiazolo[5,4-b]pyridin-2-yl)-5,6-dihydropyridin-1(2H)-yl)ethanol | 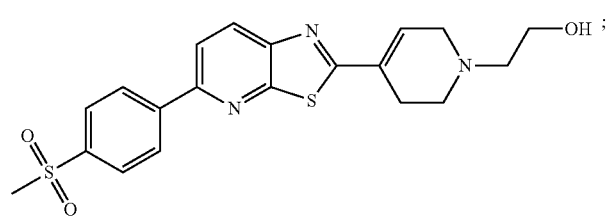 |
| 1016 | isopropyl 4-(methyl(5-(4-(methylsulfonyl)phenyl)thiazolo[5,4-b]pyridin-2-yl)amino)piperidine-1-carboxylate | 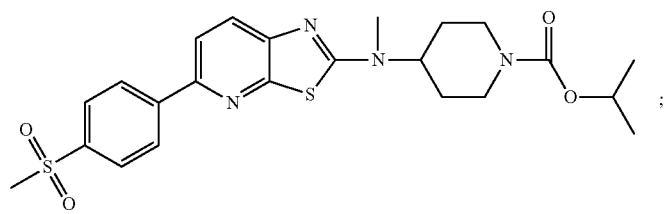 |
| 1017 | N-(1-(5-ethylpyrimidin-2-yl)piperidin-4-yl)-N-methyl-5-(4-(methylsulfonyl)phenyl)thiazolo[5,4-b]pyridin-2-amine | 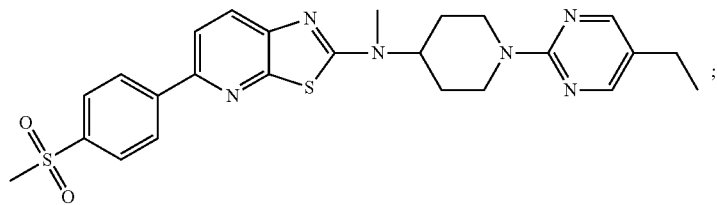 |
| 1018 | isopropyl 4-((5-(4-(dimethylcarbamoyl)phenyl)thiazolo[5,4-b]pyridin-2-yl)(methyl)amino)piperidine-1-carboxylate | 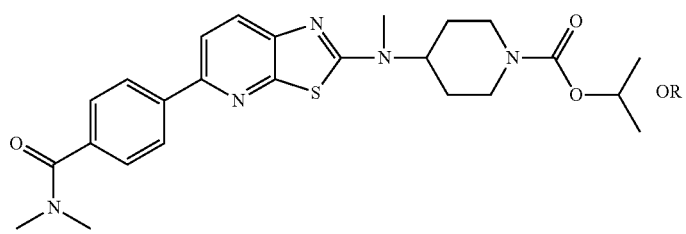 OR |
| 1019 | isopropyl (5-(4-(methylsulfonyl)phenyl)thiazolo[5,4-b]pyridin-2-yl)carbonate | 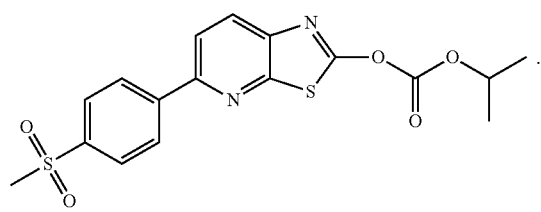 |

11. The compound of claim 1 having the structure:

| 1020 | 3-isopropyl-5-(4-(1-((5-(4-(methylsulfonyl)phenyl)thiazolo[5,4-b]pyridin-2-yl)oxy)ethyl)piperidin-1-yl)-1,2,4-oxadiazole | 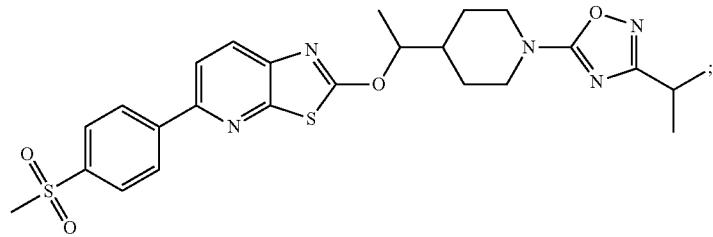 ; |
| 1021 | 3-isopropyl-5-(1-(5-(4-(methylsulfonyl)phenyl)thiazolo[5,4-b]pyridin-2-yl)pyrrolidin-3-yl)-1,2,4-oxadiazole | 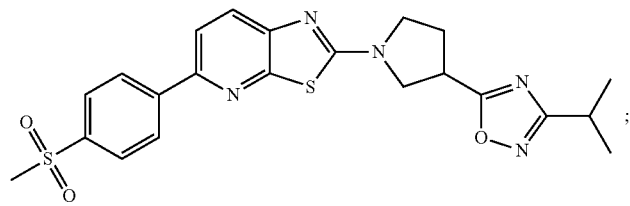 ; |
| 1022 | 4-(2-(4-(3-isopropyl-1,2,4-oxadiazol-5-yl)piperidin-1-yl)thiazolo[5,4-b]pyridin-5-yl)-N,N-dimethylbenzamide | 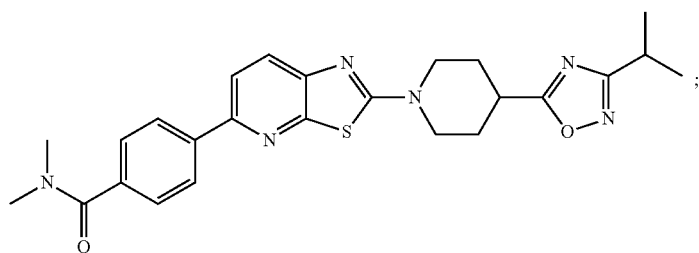 ; |
| 1023 | N-(1-(3-isopropyl-1,2,4-oxadiazol-5-yl)piperidin-4-yl)-N-methyl-5-(4-(methylsulfonyl)phenyl)thiazolo[5,4-b]pyridin-2-amine | 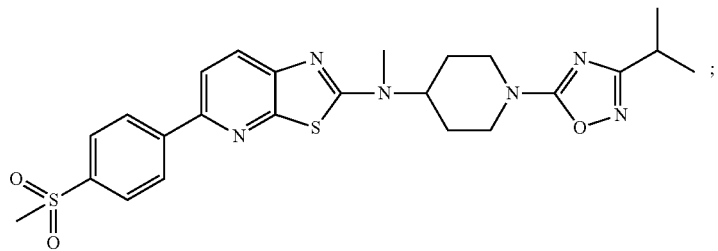 ; |
| 1024 | 4-(2-(4-(3-isopropyl-1,2,4-oxadiazol-5-yl)piperidin-1-yl)thiazolo[5,4-b]pyridin-5-yl)-N-(2-methoxyethyl)benzamide | 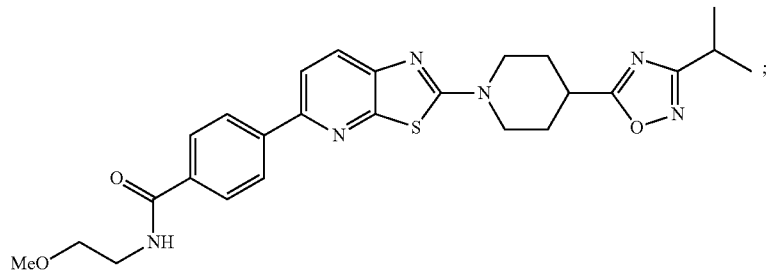 ; |
| 1025 | N-(3-fluoro-4-(methylsulfonyl)phenyl)-2-(4-(3-isopropyl-1,2,4-oxadiazol-5-yl)piperidin-1-yl)thiazolo[5,4-b]pyridin-5-amine | 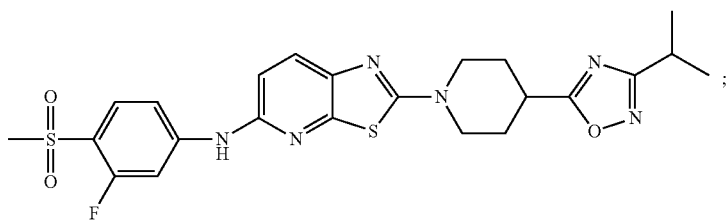 ; |

| | | |
|---|---|---|
| 1026 | 5-(4-(methylsulfonyl)phenyl)-2-(1-tosyl-1,2,3,6-tetrahydropyridin-4-yl)thiazolo[5,4-b]pyridine | 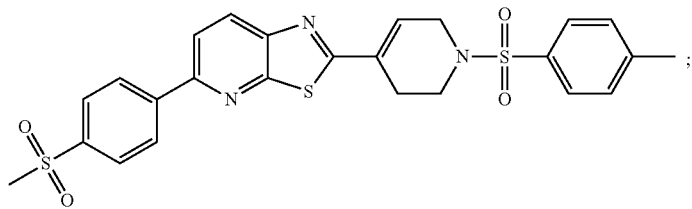 |
| 1027 | N,N-dimethyl-4-(5-(4-(methylsulfonyl)phenyl)thiazolo[5,4-b]pyridin-2-yl)-5,6-dihydropyridine-1(2H)-carboxamide | 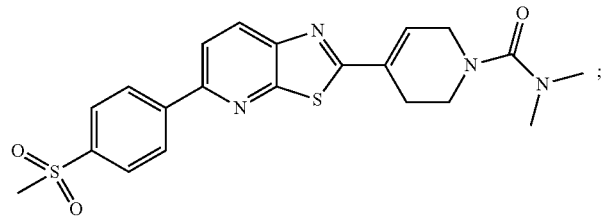 |
| 1028 | N,N-dimethyl-4-(5-(4-(methylsulfonyl)phenyl)thiazolo[5,4-b]pyridin-2-yl)piperidine-1-carboxamide | 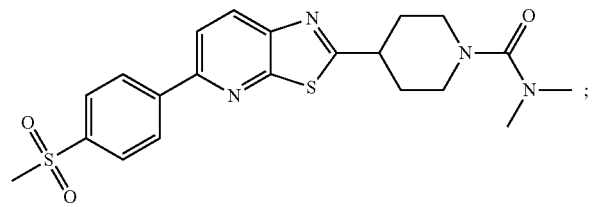 |
| 1029 | (4-(2-(4-(3-isopropyl-1,2,4-oxadiazol-5-yl)piperidin-1-yl)thiazolo[5,4-b]pyridin-5-yl)phenyl)(morpholino)methanone | 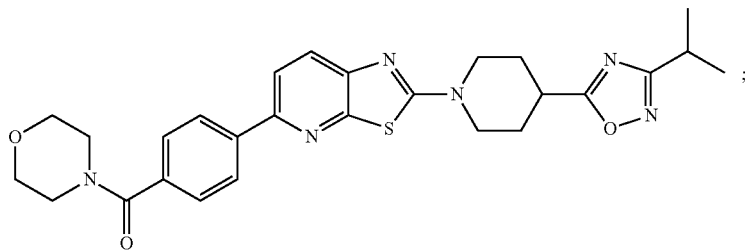 |
| 1030 | N,N-diisopropyl-4-(5-(4-(methylsulfonyl)phenyl)thiazolo[5,4-b]pyridin-2-yl)-5,6-dihydropyridine-1(2H)-carboxamide | 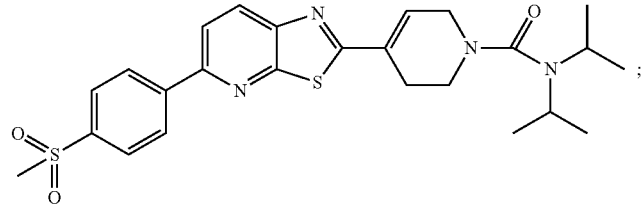 |
| 1031 | (S)-3-isopropyl-5-(4-(1-((5-(4-(methylsulfonyl)phenyl)thiazolo[5,4-b]pyridin-2-yl)oxy)ethyl)piperidin-1-yl)-1,2,4-oxadiazole | 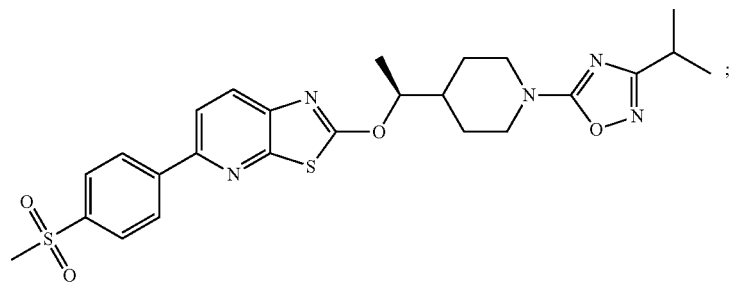 |

| | | |
|---|---|---|
| 1032 | (R)-3-isopropyl-5-(4-(1-((5-(4-(methylsulfonyl)phenyl)thiazolo[5,4-b]pyridin-2-yl)oxy)ethyl)piperidin-1-yl)-1,2,4-oxadiazole | 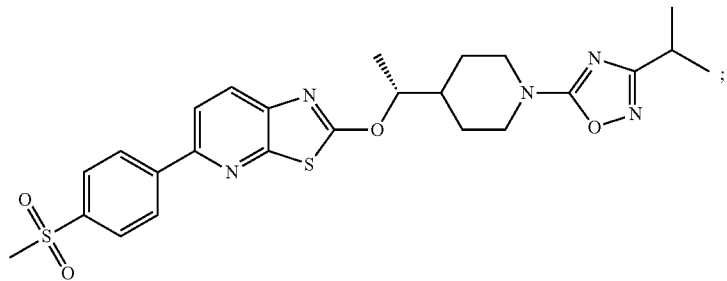 [SMILES: CC(C)c1noc(N2CCC([C@@H](C)Oc3nc4ccc(-c5ccc(S(C)(=O)=O)cc5)nc4s3)CC2)n1] |
| 1033 | 3-cyclopropyl-5-(4-((5-(4-(methylsulfonyl)phenyl)thiazolo[5,4-b]pyridin-2-yl)oxy)piperidin-1-yl)-1,2,4-oxadiazole | 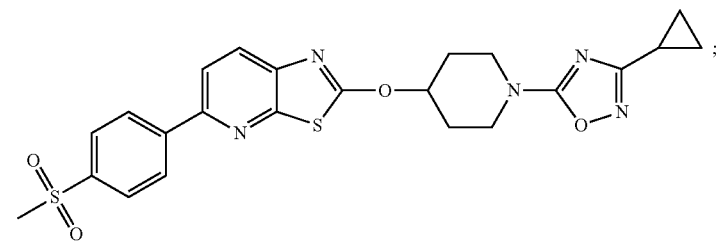 [SMILES: CS(=O)(=O)c1ccc(-c2ccc3nc(OC4CCN(c5nc(C6CC6)no5)CC4)sc3n2)cc1] |
| 1034 | isopropyl 4-(2-((5-(4-(methylsulfonyl)phenyl)thiazolo[5,4-b]pyridin-2-yl)oxy)ethyl)-5,6-dihydropyridine-1(2H)-carboxylate | 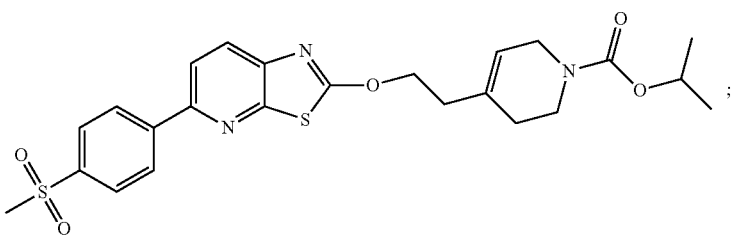 [SMILES: CC(C)OC(=O)N1CC=C(CCOc2nc3ccc(-c4ccc(S(C)(=O)=O)cc4)nc3s2)CC1] |
| 1035 | 3-isopropyl-5-(4-(2-((5-(4-(methylsulfonyl)phenyl)thiazolo[5,4-b]pyridin-2-yl)oxy)ethyl)-5,6-dihydropyridin-1(2H)-yl)-1,2,4-oxadiazole | 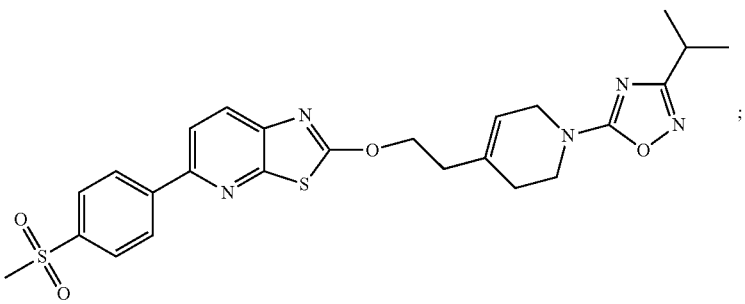 [SMILES: CC(C)c1noc(N2CC=C(CCOc3nc4ccc(-c5ccc(S(C)(=O)=O)cc5)nc4s3)CC2)n1] |
| 1036 | 3-isopropyl-5-(4-(2-methoxy-1-((5-(4-(methylsulfonyl)phenyl)thiazolo[5,4-b]pyridin-2-yl)oxy)ethyl)piperidin-1-yl)-1,2,4-oxadiazole | 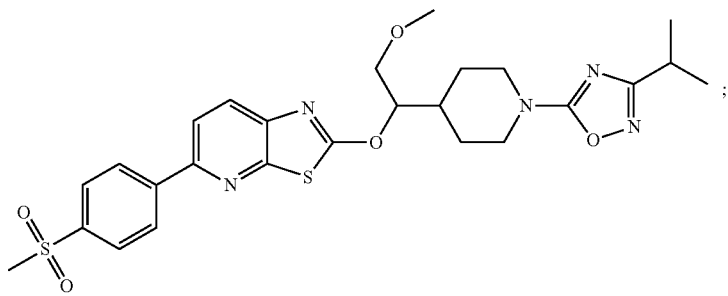 [SMILES: COCC(Oc1nc2ccc(-c3ccc(S(C)(=O)=O)cc3)nc2s1)C1CCN(c2nc(C(C)C)no2)CC1] |

-continued

| | | |
|---|---|---|
| 1037 | 3-isopropyl-5-(4-(1-((7-methyl-5-(4-(methylsulfonyl)phenyl)thiazolo[5,4-b]pyridin-2-yl)oxy)ethyl)piperidin-1-yl)-1,2,4-oxadiazole | 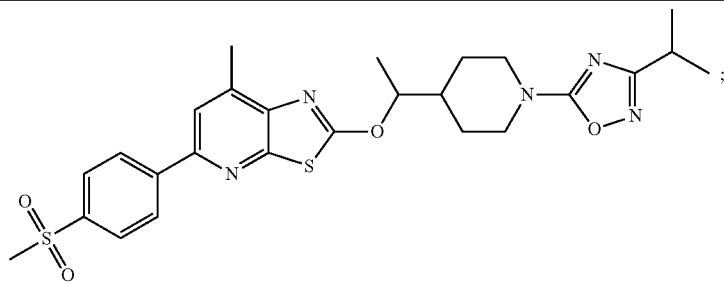 |
| 1038 | 3-isopropyl-5-(4-(((7-methyl-5-(4-(methylsulfonyl)phenyl)thiazolo[5,4-b]pyridin-2-yl)oxy)methyl)piperidin-1-yl)-1,2,4-oxadiazole | 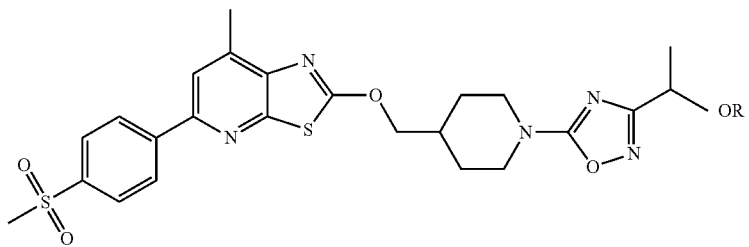 [SMILES: Cc1cc(-c2ccc(S(C)(=O)=O)cc2)nc2sc(OCC3CCN(c4nc(C(C)C)no4)CC3)nc12] |
| 1039 | 3-isopropyl-5-(4-(1-((6-methyl-5-(4-(methylsulfonyl)phenyl)thiazolo[5,4-b]pyridin-2-yl)oxy)ethyl)piperidin-1-yl)-1,2,4-oxadiazole | 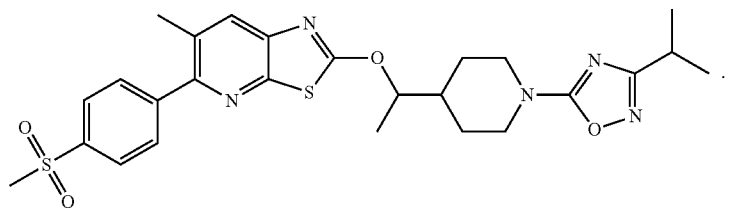 [SMILES: Cc1cc2nc(OC(C)C3CCN(c4nc(C(C)C)no4)CC3)sc2nc1-c1ccc(S(C)(=O)=O)cc1] |

12. The compound of claim 1 having the structure:

| | | |
|---|---|---|
| 1040 | 5-(4-(cyclopropyl((5-(4-(methylsulfonyl)phenyl)thiazolo[5,4-b]pyridin-2-yl)oxy)methyl)piperidin-1-yl)-3-isopropyl-1,2,4-oxadiazole | 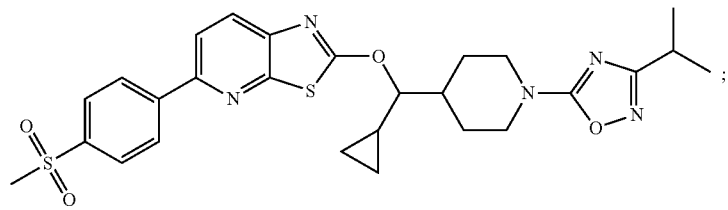 [SMILES: CC(C)c1noc(N2CCC(C(Oc3nc4ccc(-c5ccc(S(C)(=O)=O)cc5)nc4s3)C3CC3)CC2)n1] |
| 1041 | 3-isopropyl-5-(4-(2-((5-(4-(methylsulfonyl)phenyl)thiazolo[5,4-b]pyridin-2-yl)oxy)ethylidene)piperidin-1-yl)-1,2,4-oxadiazole | 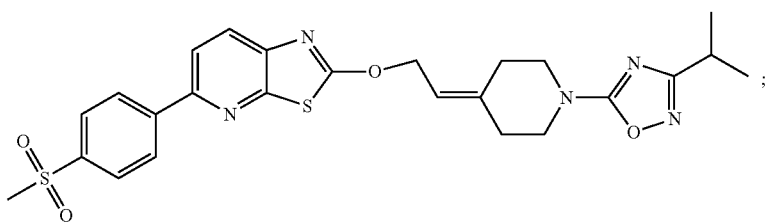 [SMILES: CC(C)c1noc(N2CCC(=CCOc3nc4ccc(-c5ccc(S(C)(=O)=O)cc5)nc4s3)CC2)n1] |
| 1042 | 3-isopropyl-5-(4-(2-((5-(4-(methylsulfonyl)phenyl)thiazolo[5,4-b]pyridin-2-yl)oxy)ethyl)piperidin-1-yl)-1,2,4-oxadiazole | 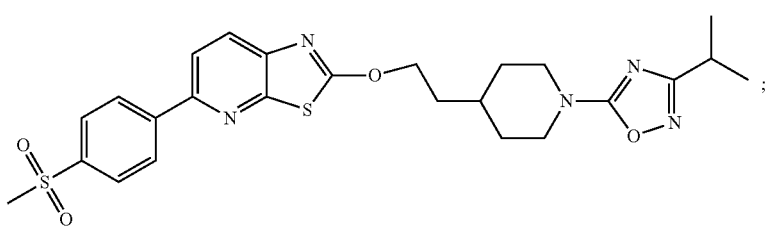 [SMILES: CC(C)c1noc(N2CCC(CCOc3nc4ccc(-c5ccc(S(C)(=O)=O)cc5)nc4s3)CC2)n1] |

| | | |
|---|---|---|
| 1043 | 3-isopropyl-5-(4-(2-((5-(4-(methylsulfonyl)phenyl)thiazolo[5,4-b]pyridin-2-yl)oxy)propyl)piperidin-1-yl)-1,2,4-oxadiazole | |
| 1044 | 3-isopropyl-5-(4-(2-((5-(4-(methylsulfonyl)phenyl)thiazolo[5,4-b]pyridin-2-yl)oxy)propylidene)piperidin-1-yl)-1,2,4-oxadiazole | |
| 1045 | (S)-4-(2-(1-(1-(3-isopropyl-1,2,4-oxadiazol-5-yl)piperidin-4-yl)ethoxy)thiazolo[5,4-b]pyridin-5-yl)-N,N-dimethylbenzamide | |
| 1046 | 3-fluoro-4-(2-(1-(1-(3-isopropyl-1,2,4-oxadiazol-5-yl)piperidin-4-yl)ethoxy)thiazolo[5,4-b]pyridin-5-yl)-N,N-dimethylbenzamide | |
| 1047 | 2-fluoro-4-(2-(1-(1-(3-isopropyl-1,2,4-oxadiazol-5-yl)piperidin-4-yl)ethoxy)thiazolo[5,4-b]pyridin-5-yl)-N,N-dimethylbenzamide | |
| 1048 | 3-cyclopropyl-5-(4-(1-((5-(4-(methylsulfonyl)phenyl)thiazolo[5,4-b]pyridin-2-yl)oxy)ethyl)piperidin-1-yl)-1,2,4-oxadiazole | |
| 1049 | N-cyclopropyl-4-(2-(1-(1-(3-isopropyl-1,2,4-oxadiazol-5-yl)piperidin-4-yl)ethoxy)thiazolo[5,4-b]pyridin-5-yl)benzamide | |
| 1050 | 4-(2-(1-(1-(3-isopropyl-1,2,4-oxadiazol-5-yl)piperidin-4-yl)ethoxy)thiazolo[5,4-b]pyridin-5-yl)-N-(2-methoxyethyl)benzamide | |

| | | |
|---|---|---|
| 1051 | (4-(2-(1-(1-(3-isopropyl-1,2,4-oxadiazol-5-yl)piperidin-4-yl)ethoxy)thiazolo[5,4-b]pyridin-5-yl)phenyl)(morpholino)methanone | 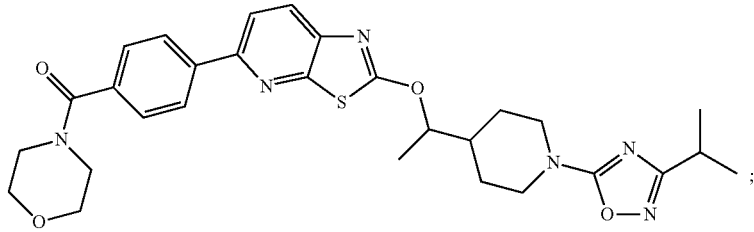 [SMILES: CC(C)c1noc(N2CCC(C(C)Oc3nc4ccc(-c5ccc(C(=O)N6CCOCC6)cc5)nc4s3)CC2)n1] |
| 1052 | N-cyclopropyl-4-(2-(1-(1-(3-isopropyl-1,2,4-oxadiazol-5-yl)piperidin-4-yl)ethoxy)thiazolo[5,4-b]pyridin-5-yl)-N-methyl benzamide | 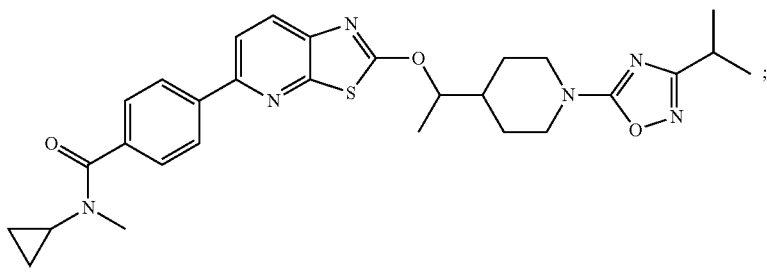 [SMILES: CC(C)c1noc(N2CCC(C(C)Oc3nc4ccc(-c5ccc(C(=O)N(C)C6CC6)cc5)nc4s3)CC2)n1] |
| 1053 | 5-(4-(methylsulfonyl)phenyl)-2-(1-(1-(5-propylpyrimidin-2-yl)piperidine-4-yl)ethoxy)thiazolo[5,4-b]pyridine | 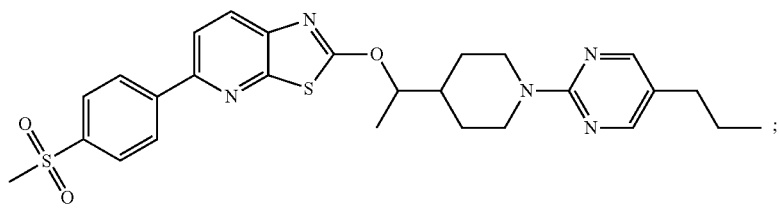 [SMILES: CCCc1cnc(N2CCC(C(C)Oc3nc4ccc(-c5ccc(S(C)(=O)=O)cc5)nc4s3)CC2)nc1] |
| 1054 | 3-isopropyl-5-(4-(1-((5-(pyridin-3-yl)thiazolo[5,4-b]pyridin-2-yl)oxy)ethyl)piperidin-1-yl)-1,2,4-oxadiazole | 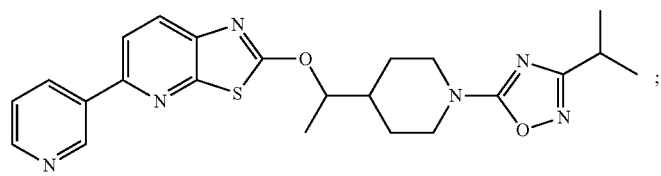 [SMILES: CC(C)c1noc(N2CCC(C(C)Oc3nc4ccc(-c5cccnc5)nc4s3)CC2)n1] |
| 1055 | 2-(1-(1-(5-ethylpyrimidin-2-yl)piperidin-4-yl)ethoxy)-5-(4-(methylsulfonyl)phenyl)thiazolo[5,4-b]pyridine | 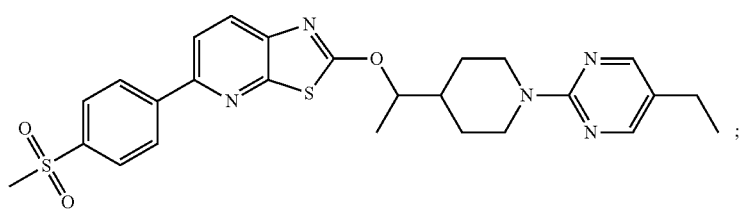 [SMILES: CCc1cnc(N2CCC(C(C)Oc3nc4ccc(-c5ccc(S(C)(=O)=O)cc5)nc4s3)CC2)nc1] |
| 1056 | isopropyl 4-(1-((5-(4-(methylsulfonyl)phenyl)thiazolo[5,4-b]pyridin-2-yl)oxy)ethyl)piperidine-1-carboxylate | 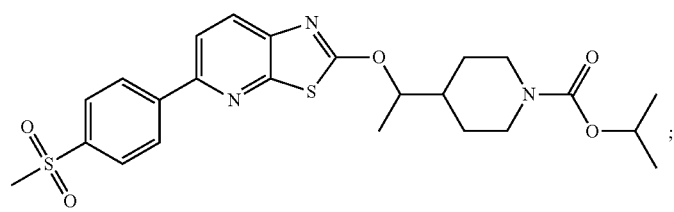 [SMILES: CC(C)OC(=O)N1CCC(C(C)Oc2nc3ccc(-c4ccc(S(C)(=O)=O)cc4)nc3s2)CC1] |
| 1057 | 3-isopropyl-5-(4-(1-((5-(4-((methylsulfonyl)methyl)phenyl)thiazolo[5,4-b]pyridin-2-yl)oxy)ethyl)piperidin-1-yl)-1,2,4-oxadiazole | 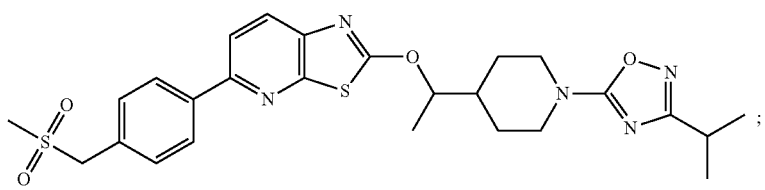 [SMILES: CC(C)c1noc(N2CCC(C(C)Oc3nc4ccc(-c5ccc(CS(C)(=O)=O)cc5)nc4s3)CC2)n1] |

-continued

| | | |
|---|---|---|
| 1058 | 5-isopropyl-3-(4-(1-((5-(4-(methylsulfonyl)phenyl)thiazolo[5,4-b]pyridin-2-yl)oxy)ethyl)piperidin-1-yl)-1,2,4-oxadiazole | 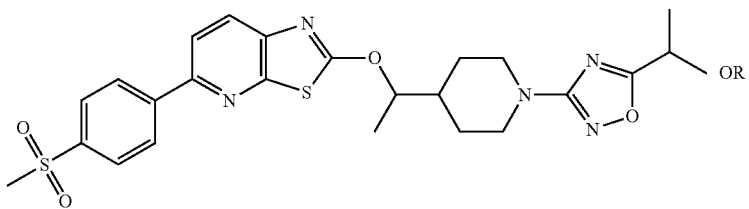 OR |
| 1059 | 3-isopropyl-5-(4-(1-((5-(4-(methylsulfonyl)phenyl)thiazolo[5,4-b]pyridin-2-yl)oxy)ethyl)phenyl)-1,2,4-oxadiazole | 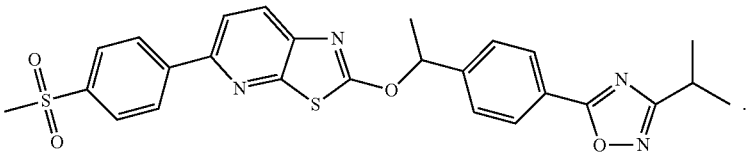 . |

13. The compound of claim 1 having the structure:

| | | |
|---|---|---|
| 1060 | 5-(3-fluoro-4-((5-(4-(methylsulfonyl)phenyl)thiazolo[5,4-b]pyridin-2-yl)oxy)piperidin-1-yl)-3-isopropyl-1,2,4-oxadiazole | 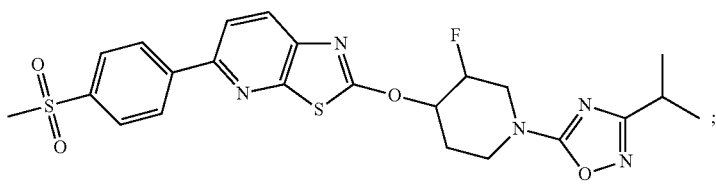 ; |
| 1061 | 4-(2-(1-(1-(3-isopropyl-1,2,4-oxadiazol-5-yl)piperidin-4-yl) ethoxy)thiazolo[5,4-b]pyridin-5-yl)-N-methylbenzenesulfonamide | 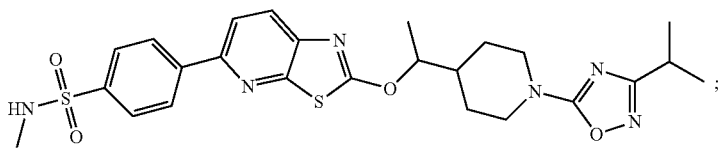 ; |
| 1062 | 5-(4-(1-((5-(4-(ethylsulfonyl)phenyl)thiazolo[5,4-b]pyridin-2-yl)oxy)ethyl)piperidin-1-yl)-3-isopropyl-1,2,4-oxadiazole | 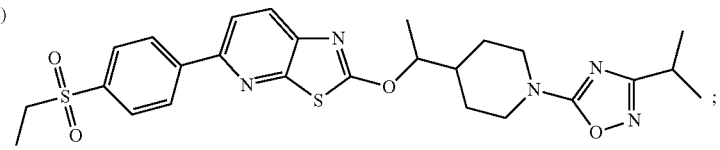 ; |
| 1063 | 5-(4-(1-((5-(4-(cyclopropylsulfonyl)phenyl)thiazolo[5,4-b]pyridin-2-yl)oxy)ethyl)piperidin-1-yl)-3-isopropyl-1,2,4-oxadiazole | 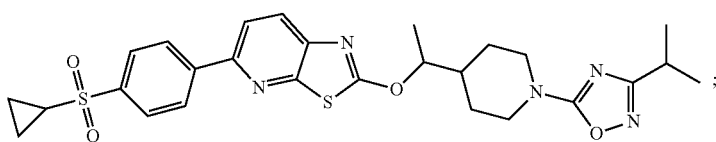 ; |
| 1064 | 5-(4-(1-((5-(4-(cyclopropylsulfinyl)phenyl)thiazolo[5,4-b]pyridin-2-yl)oxy)ethyl)piperidin-1-yl)-3-isopropyl-1,2,4-oxadiazole | 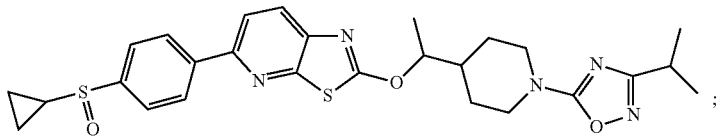 ; |
| 1065 | 4-(2-(1-(1-(3-isopropyl-1,2,4-oxadiazol-5-yl)piperidin-4-yl) ethoxy)thiazolo[5,4-b]pyridin-5-yl)benzonitrile | 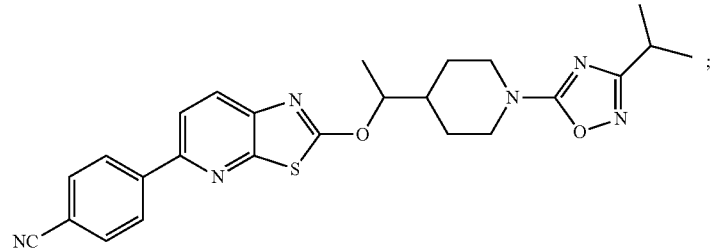 ; |

| | | |
|---|---|---|
| 1066 | 4-(2-(1-(1-(3-isopropyl-1,2,4-oxadiazol-5-yl)piperidin-4-yl)ethoxy)thiazolo[5,4-b]pyridin-5-yl)-N-(2-methoxyethyl)benzenesulfonamide | 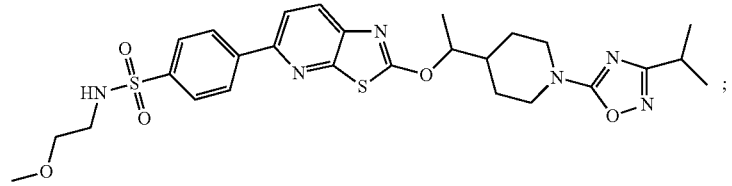 |
| 1067 | 3-isopropyl-5-(4-(1-((5-(4-((2-methoxyethyl)sulfonyl)phenyl)thiazolo[5,4-b]pyridin-2-yl)oxy) ethyl)piperidin-1-yl)-1,2,4-oxadiazole | 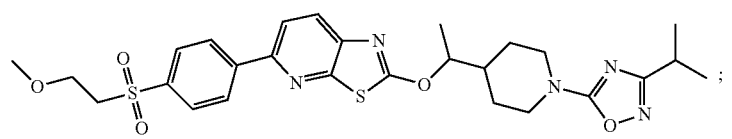 |
| 1068 | 3-isopropyl-5-(4-(1-((5-(4-((2-methoxyethyl)sulfinyl)phenyl)thiazolo[5,4-b]pyridin-2-yl)oxy) ethyl) piperidin-1-yl)-1,2,4-oxadiazole | 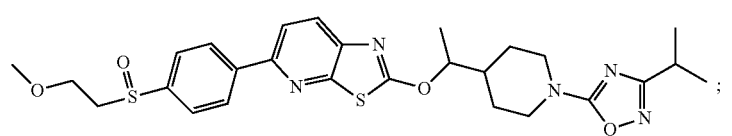 |
| 1069 | 3-isopropyl-5-(4-(1-((5-(6-(methylsulfonyl)pyridin-3-yl)thiazolo[5,4-b]pyridin-2-yl)oxy)ethyl)piperidin-1-yl)-1,2,4-oxadiazole | 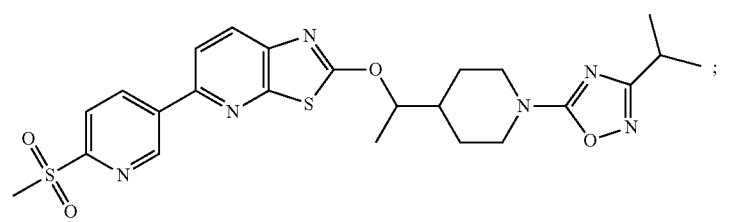 |
| 1070 | (R)-3-isopropyl-5-(4-(1-((5-(pyridin-4-yl)thiazolo[5,4-b]pyridin-2-yl)oxy)ethyl)piperidin-1-yl)-1,2,4-oxadiazole | 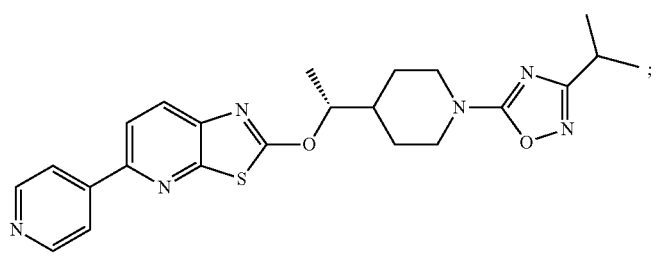 |
| 1071 | (R)-4-(2-(1-(1-(3-isopropyl-1,2,4-oxadiazol-5-yl)piperidin-4-yl)ethoxy)thiazolo[5,4-b]pyridin-5-yl)-1-methylpyridin-1-ium | 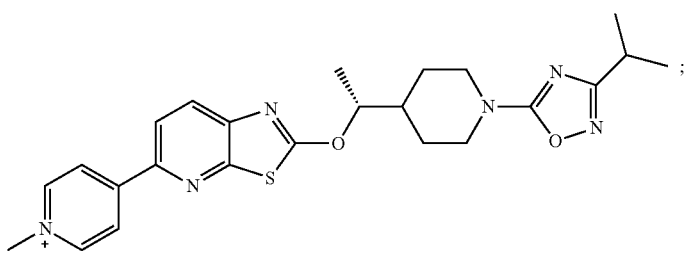 |
| 1072 | 4-(2-(4-(3-isopropyl-1,2,4-oxadiazol-5-yl)piperidin-1-yl) thiazolo[5,4-b]pyridin-5-yl)-N-methylbenzenesulfonamide | 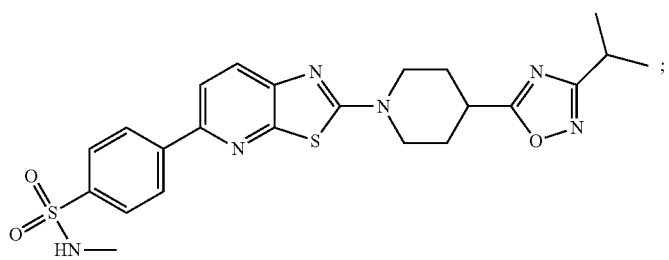 |

| | | |
|---|---|---|
| 1073 | 4-(2-(4-(3-isopropyl-1,2,4-oxadiazol-5-yl)piperidin-1-yl)thiazolo[5,4-b]pyridin-5-yl)-N-(2-methoxyethyl)benzenesulfonamide | 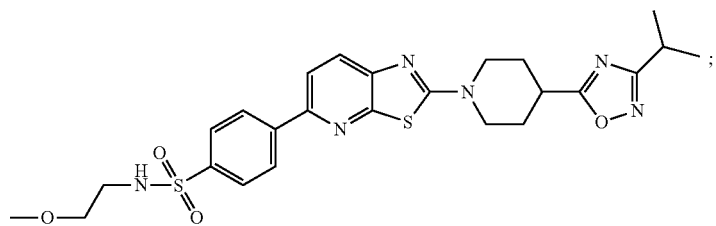 |
| 1074 | N-(4-(2-(1-(3-isopropyl-1,2,4-oxadiazol-5-yl)piperidin-4-yl)ethoxy)thiazolo[5,4-b]pyridin-5-yl)phenyl)methanesulfonamide | 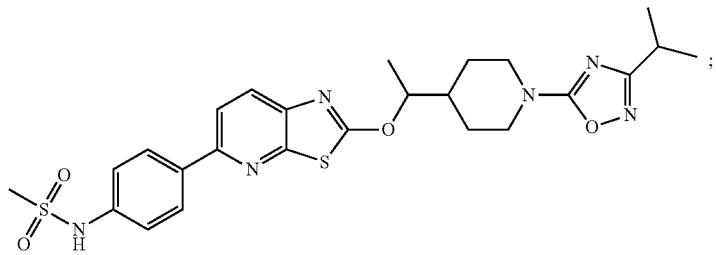 |
| 1075 | 2-(1-(1-(1-methyl-1H-tetrazol-5-yl)piperidin-4-yl)ethoxy)-5-(4-(methylsulfonyl)phenyl)thiazolo[5,4-b]pyridine | 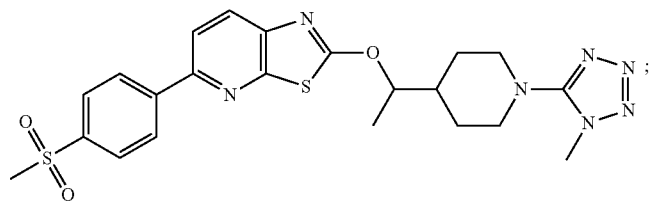 |
| 1076 | (S)-5-(4-(1-((5-(3-fluoropyridin-4-yl)thiazolo[5,4-b]pyridin-2-yl)oxy)ethyl)piperidin-1-yl)-3-isopropyl-1,2,4-oxadiazole | 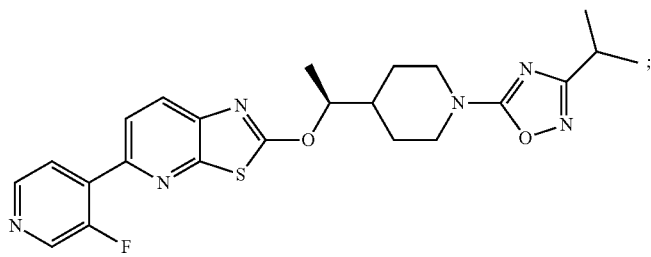 |
| 1077 | 3-isopropyl-5-(1-(5-(pyridin-4-yl)thiazolo[5,4-b]pyridin-2-yl)piperidin-4-yl)-1,2,4-oxadiazole | 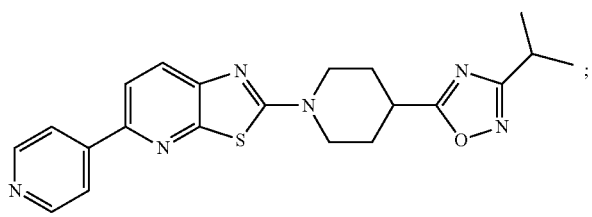 |
| 1078 | 3-isopropyl-5-(1-(5-(4-((2-methoxyethyl)sulfonyl)phenyl)thiazolo[5,4-b]pyridin-2-yl)piperidin-4-yl)-1,2,4-oxadiazole | 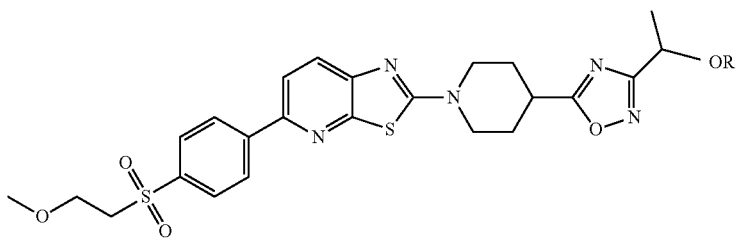 |

| | | |
|---|---|---|
| 1079 | 5-(4-(1-((5-(4-(1H-tetrazol-1-yl)phenyl)thiazolo[5,4-b]pyridin-2-yl)oxy)ethyl)piperidin-1-yl)-3-isopropyl-1,2,4-oxadiazole | 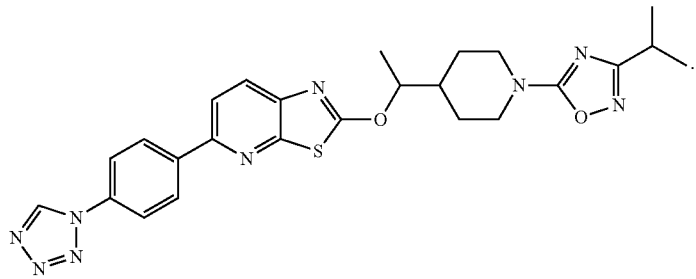 |

14. The compound of claim 1 having the structure:

| | | |
|---|---|---|
| 1080 | 3-isopropyl-5-(1-(5-(6-(methylsulfonyl)pyridin-3-yl)thiazolo[5,4-b]pyridin-2-yl)piperidin-4-yl)-1,2,4-oxadiazole | 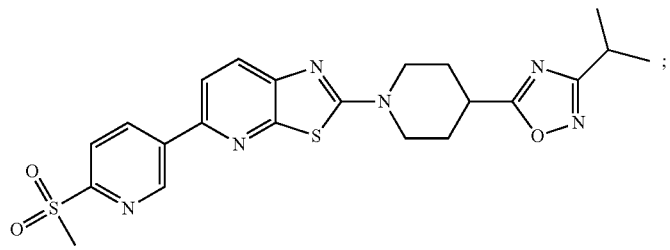 [SMILES: CC(C)c1noc(C2CCN(c3nc4ccc(-c5ccc(S(C)(=O)=O)nc5)nc4s3)CC2)n1]; |
| 1081 | 5-(4-(1-((5-(2-fluoropyridin-4-yl)thiazolo[5,4-b]pyridin-2-yl)oxy)ethyl)piperidin-1-yl)-3-isopropyl-1,2,4-oxadiazole | 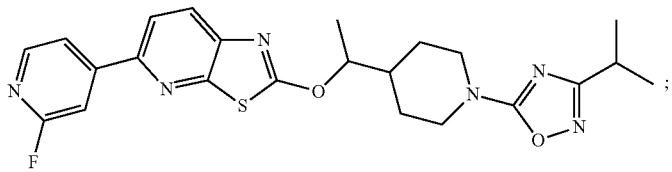 [SMILES: CC(C)c1noc(N2CCC(C(C)Oc3nc4ccc(-c5ccnc(F)c5)nc4s3)CC2)n1]; |
| 1082 | (S)-3-isopropyl-5-(4-(1-((5-(6-(methylsulfonyl)pyridin-3-yl)thiazolo[5,4-b]pyridin-2-yl)oxy)ethyl)piperidin-1-yl)-1,2,4-oxadiazole | 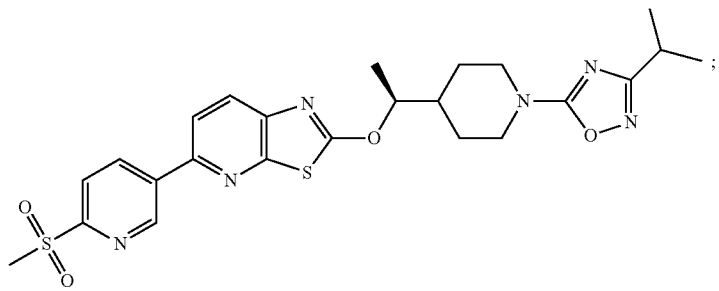 [SMILES: CC(C)c1noc(N2CCC([C@H](C)Oc3nc4ccc(-c5ccc(S(C)(=O)=O)nc5)nc4s3)CC2)n1]; |
| 1083 | 3-isopropyl-5-(4-(((5-(pyridin-4-yl)thiazolo[5,4-b]pyridin-2-yl)oxy)methyl)piperidin-1-yl)-1,2,4-oxadiazole | 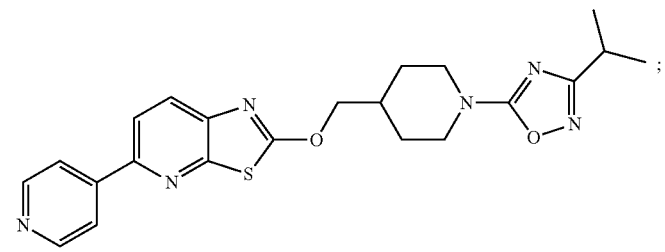 [SMILES: CC(C)c1noc(N2CCC(COc3nc4ccc(-c5ccncc5)nc4s3)CC2)n1]; |
| 1084 | 5-(4-(((5-(3-fluoropyridin-4-yl)thiazolo[5,4-b]pyridin-2-yl)oxy)methyl)piperidin-1-yl)-3-isopropyl-1,2,4-oxadiazole | 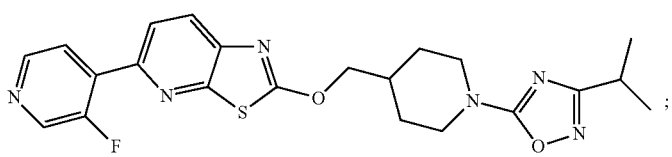 [SMILES: CC(C)c1noc(N2CCC(COc3nc4ccc(-c5ccncc5F)nc4s3)CC2)n1]; |

| | | |
|---|---|---|
| 1085 | 5-(4-(((5-(4-(1H-tetrazol-1-yl)phenyl)thiazolo[5,4-b]pyridin-2-yl)oxy)methyl)piperidin-1-yl)-3-isopropyl-1,2,4-oxadiazole | 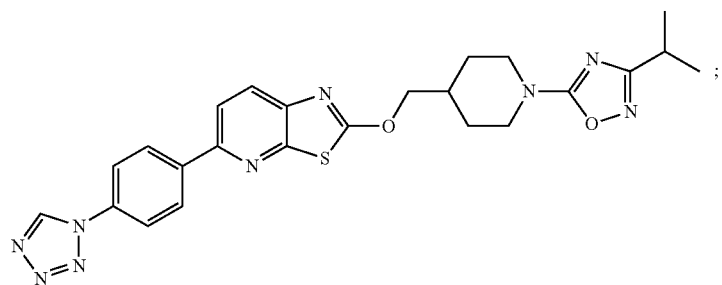 [SMILES: CC(C)c1noc(N2CCC(COc3nc4ccc(-c5ccc(-n6cnnn6)cc5)nc4s3)CC2)n1] |
| 1086 | 5-(4-(((5-(2-fluoropyridin-4-yl)thiazolo[5,4-b]pyridin-2-yl)oxy)methyl)piperidin-1-yl)-3-isopropyl-1,2,4-oxadiazole | 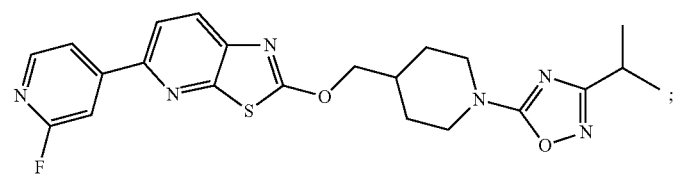 [SMILES: CC(C)c1noc(N2CCC(COc3nc4ccc(-c5ccnc(F)c5)nc4s3)CC2)n1] |
| 1087 | 2-(1-(1-(5-ethylpyridin-2-yl)piperidine-4-yl)ethoxy)-5-(4-(methylsulfonyl)phenyl)thiazolo[5,4-b]pyridine | 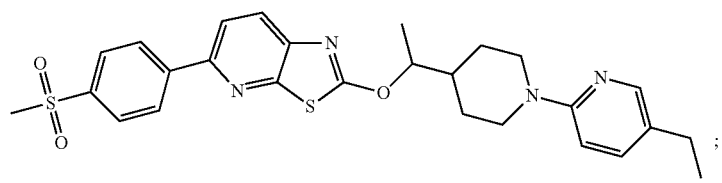 [SMILES: CCc1ccc(N2CCC(C(C)Oc3nc4ccc(-c5ccc(S(C)(=O)=O)cc5)nc4s3)CC2)nc1] |
| 1088 | 5-(4-(methylsulfonyl)phenyl)-2-(1-(1-(5-vinylpyridin-2-yl)piperidin-4-yl)ethoxy)thiazolo[5,4-b]pyridine | 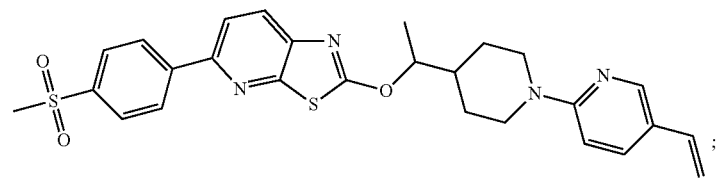 [SMILES: C=Cc1ccc(N2CCC(C(C)Oc3nc4ccc(-c5ccc(S(C)(=O)=O)cc5)nc4s3)CC2)nc1] |
| 1089 | (S)-5-(4-(methylsulfonyl)phenyl)-2-(1-(1-(5-propylpyrimidin-2-yl)piperidin-4-yl)ethoxy)thiazolo [5,4-b]pyridine | 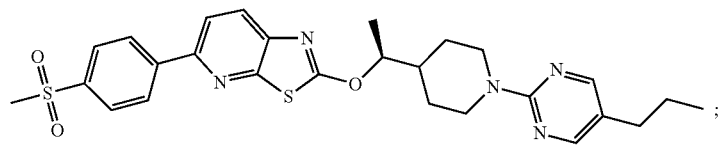 [SMILES: CCCc1cnc(N2CCC([C@H](C)Oc3nc4ccc(-c5ccc(S(C)(=O)=O)cc5)nc4s3)CC2)nc1] |
| 1090 | (R)-5-(4-(methylsulfonyl)phenyl)-2-(1-(1-(5-propylpyrimidin-2-yl)piperidin-4-yl)ethoxy)thiazolo[5,4-b]pyridine | 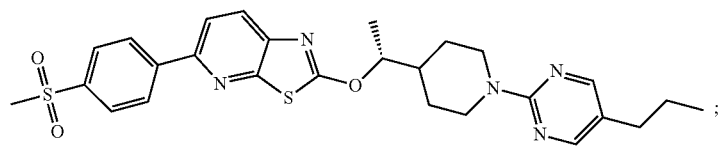 [SMILES: CCCc1cnc(N2CCC([C@@H](C)Oc3nc4ccc(-c5ccc(S(C)(=O)=O)cc5)nc4s3)CC2)nc1] |
| 1091 | 3-isopropyl-5-(4-(((5-(6-(methylsulfonyl)pyridin-3-yl)thiazolo[5,4-b]pyridin-2-yl)oxy)methyl)piperidin-1-yl)-1,2,4-oxadiazole | 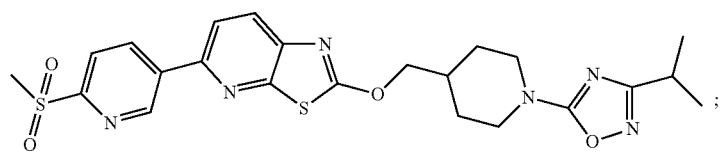 [SMILES: CC(C)c1noc(N2CCC(COc3nc4ccc(-c5ccc(S(C)(=O)=O)nc5)nc4s3)CC2)n1] |
| 1092 | (S)-3-isopropyl-5-(4-(1-((5-(pyridin-4-yl)thiazolo[5,4-b]pyridin-2-yl)oxy)ethyl)piperidin-1-yl)-1,2,4-oxadiazole | 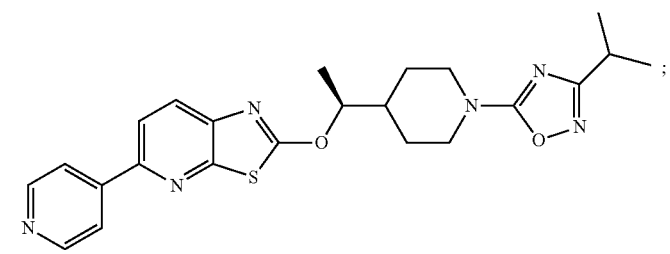 [SMILES: CC(C)c1noc(N2CCC([C@H](C)Oc3nc4ccc(-c5ccncc5)nc4s3)CC2)n1] |

| | | |
|---|---|---|
| 1093 | (S)-5-(4-(1-((5-(2-fluoropyridin-4-yl)thiazolo[5,4-b]pyridin-2-yl)oxy)ethyl)piperidin-1-yl)-3-isopropyl-1,2,4-oxadiazole | 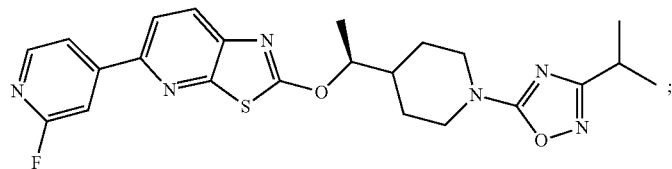 [SMILES: CC(C)c1noc(N2CCC([C@H](C)Oc3nc4ccc(-c5ccnc(F)c5)nc4s3)CC2)n1] |
| 1094 | 3-isopropyl-5-(4-(2,2,2-trifluoro-1-((5-(4-(methylsulfonyl)phenyl)thiazolo[5,4-b]pyridin-2-yl)oxy)ethyl)piperidin-1-yl)-1,2,4-oxadiazole | 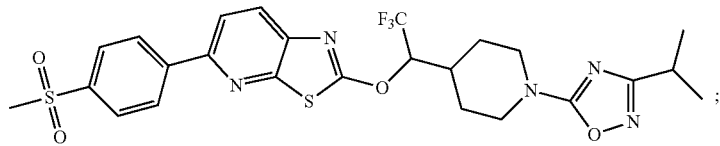 [SMILES: CC(C)c1noc(N2CCC(C(Oc3nc4ccc(-c5ccc(S(C)(=O)=O)cc5)nc4s3)C(F)(F)F)CC2)n1] |
| 1095 | (S)-5-(4-(1-((5-(4-(cyclopropylsulfonyl)phenyl)thiazolo[5,4-b] pyridin-2-yl)oxy)ethyl)piperidin-1-yl)-3-isopropyl-1,2,4-oxadiazole | 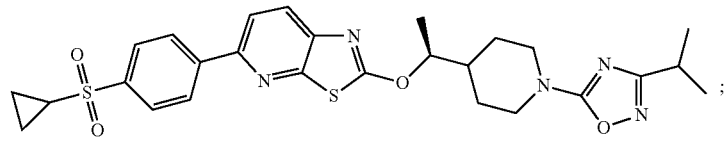 [SMILES: CC(C)c1noc(N2CCC([C@H](C)Oc3nc4ccc(-c5ccc(S(=O)(=O)C6CC6)cc5)nc4s3)CC2)n1] |
| 1096 | (S)-5-(4-(1-((5-(3-fluoropyridin-4-yl)thiazolo[5,4-b]pyridin-2-yl)oxy)ethyl)piperidin-1-yl)-3-isopropyl-1,2,4-oxadiazole | 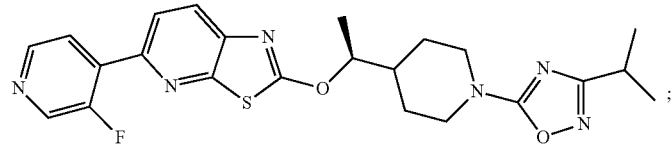 [SMILES: CC(C)c1noc(N2CCC([C@H](C)Oc3nc4ccc(-c5ccncc5F)nc4s3)CC2)n1] |
| 1097 | 2-isopropyl-5-(4-(1-((5-(4-(methylsulfonyl)phenyl)thiazolo[5,4-b]pyridin-2-yl)oxy)ethyl)piperidin-1-yl)-1,3,4-oxadiazole | 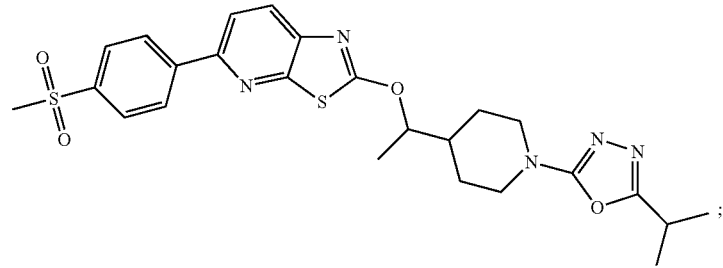 [SMILES: CC(C)c1nnc(N2CCC(C(C)Oc3nc4ccc(-c5ccc(S(C)(=O)=O)cc5)nc4s3)CC2)o1] |
| 1098 | 4-(2-(1-(1-(3-isopropyl-1,2,4-oxadiazol-5-yl)piperidin-4-yl) ethoxy)thiazolo[5,4-b]pyridin-5-yl)pyridine 1-oxide | 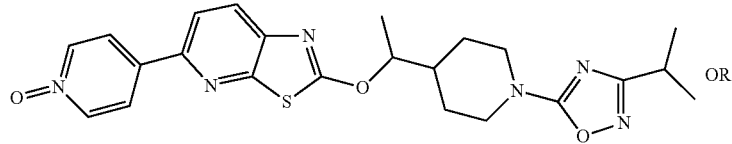 [SMILES: CC(C)c1noc(N2CCC(C(C)Oc3nc4ccc(-c5cc[n+]([O-])cc5)nc4s3)CC2)n1] OR |
| 1099 | (S)-5-(6-(methylsulfonyl)pyridin-3-yl)-2-(1-(1-(5-propyl-pyrimidin-2-yl)piperidin-4-yl)ethoxy)thiazolo [5,4-b] pyridine | 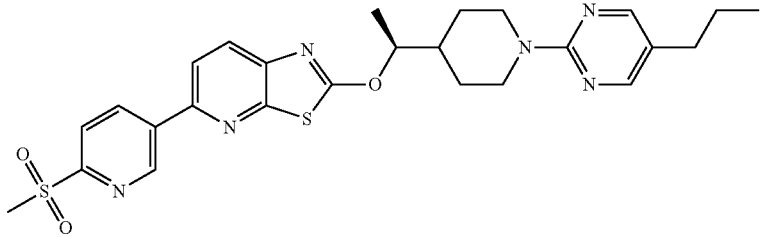 [SMILES: CCCc1cnc(N2CCC([C@H](C)Oc3nc4ccc(-c5ccc(S(C)(=O)=O)nc5)nc4s3)CC2)nc1] |

15. The compound of claim 1 having the structure

| | | |
|---|---|---|
| 1100 | 5-(4-(1-((5-(3-fluoro-4-(methylsulfonyl)phenyl)thiazolo[5,4-b]pyridin-2-yl)oxy)ethyl)piperidin-1-yl)-3-isopropyl-1,2,4-oxadiazole | 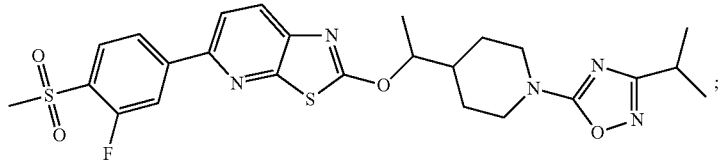 [SMILES: CC(C)c1noc(N2CCC(C(C)Oc3nc4ccc(-c5ccc(S(C)(=O)=O)c(F)c5)nc4s3)CC2)n1] |

| | | |
|---|---|---|
| 1101 | (S)-5-(2-fluoropyridin-4-yl)-2-(1-(1-(5-propyl-pyrimidin-2-yl)piperidin-4-yl)ethoxy)thiazolo [5,4-b]pyridine | 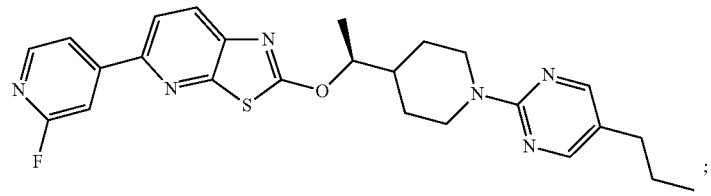 [SMILES: CCCc1cnc(N2CCC([C@H](C)Oc3nc4ccc(-c5ccnc(F)c5)nc4s3)CC2)nc1] |
| 1102 | 3-isopropyl-5-(4-(2,2,2-trifluoro-1-((5-(6-(methylsulfonyl)pyridin-3-yl)thiazolo[5,4-b]pyridin-2-yl)oxy) ethyl)piperidin-1-yl)-1,2,4-oxadiazole | 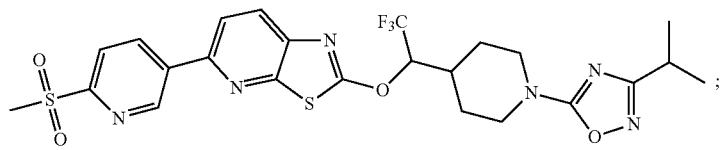 [SMILES: CC(C)c1noc(N2CCC(C(Oc3nc4ccc(-c5ccc(S(C)(=O)=O)nc5)nc4s3)C(F)(F)F)CC2)n1] |
| 1103 | 3-isopropyl-5-(4-(2,2,2-trifluoro-1-((5-(2-fluoropyridin-4-yl)thiazolo[5,4-b]pyridin-2-yl)oxy) ethyl) piperidin-1-yl)-1,2,4-oxadiazole | 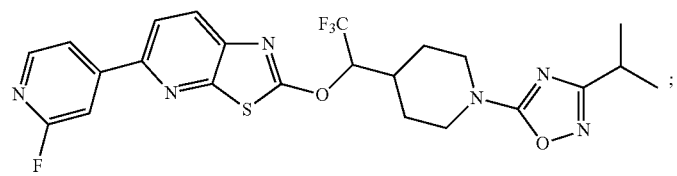 [SMILES: CC(C)c1noc(N2CCC(C(Oc3nc4ccc(-c5ccnc(F)c5)nc4s3)C(F)(F)F)CC2)n1] |
| 1104 | (S)-2-(1-(1-(5-ethyl-pyrimidin-2-yl)piperidin-4-yl)ethoxy)-5-(2-fluoropyridin-4-yl)thiazolo[5,4-b]pyridine | 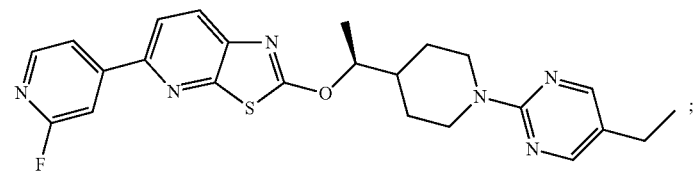 [SMILES: CCc1cnc(N2CCC([C@H](C)Oc3nc4ccc(-c5ccnc(F)c5)nc4s3)CC2)nc1] |
| 1105 | 3-isopropyl-5-(4-(1-((5-(4-(methylsulfonyl)phenyl)thiazolo[5,4-b]pyridin-2-yl)oxy)ethyl)cyclohexyl)-1,2,4-oxadiazole | 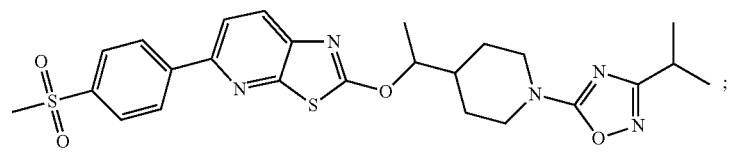 [SMILES: CC(C)c1noc(N2CCC(C(C)Oc3nc4ccc(-c5ccc(S(C)(=O)=O)cc5)nc4s3)CC2)n1] |
| 1106 | (S)-2-(1-(1-(5-ethyl-pyrimidin-2-yl)piperidin-4-yl)ethoxy)-5-(6-(methylsulfonyl)pyridin-3-yl) thiazolo [5,4-b]pyridine | 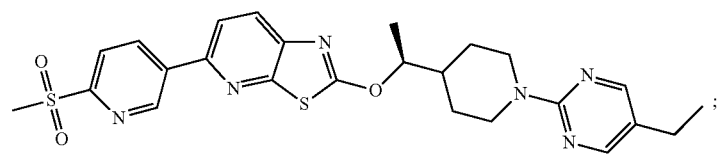 [SMILES: CCc1cnc(N2CCC([C@H](C)Oc3nc4ccc(-c5ccc(S(C)(=O)=O)nc5)nc4s3)CC2)nc1] |
| 1107 | 2-(1-(1-(3-isopropyl-1,2,4-thiadiazol-5-yl)piperidin-4-yl)ethoxy)-5-(4-(methylsulfonyl)phenyl)thiazolo[5,4-b]pyridine | 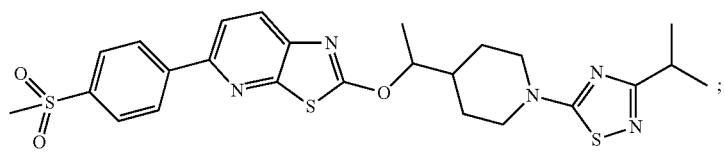 [SMILES: CC(C)c1nsc(N2CCC(C(C)Oc3nc4ccc(-c5ccc(S(C)(=O)=O)cc5)nc4s3)CC2)n1] |
| 1108 | 3-isopropyl-5-(4-(1-((6-(4-(methylsulfonyl)phenyl)thiazolo[4,5-b] pyrazin-2-yl)oxy)ethyl)piperidin-1-yl)-1,2,4-oxadiazole | 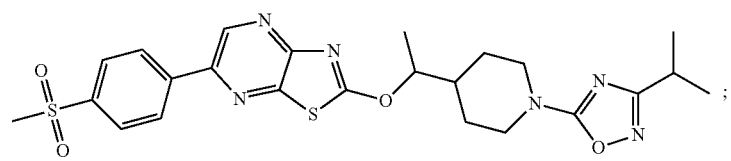 [SMILES: CC(C)c1noc(N2CCC(C(C)Oc3nc4ncc(-c5ccc(S(C)(=O)=O)cc5)nc4s3)CC2)n1] |
| 1109 | 2-(1-(1-(cyclopropyl-sulfonyl)piperidin-4-yl)ethoxy)-5-(4-(methylsulfonyl)phenyl)thiazolo[5,4-b]pyridine | 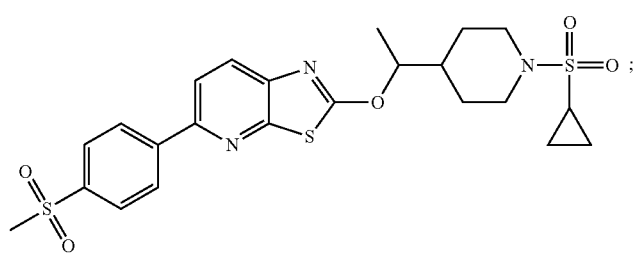 [SMILES: CC(Oc1nc2ccc(-c3ccc(S(C)(=O)=O)cc3)nc2s1)C1CCN(S(=O)(=O)C2CC2)CC1] |

| | | |
|---|---|---|
| 1110 | 6-(4-(methylsulfonyl)phenyl)-2-(1-(1-(5-propylpyrimidin-2-yl)piperidin-4-yl)ethoxy)thiazolo[4,5-b]pyrazine | 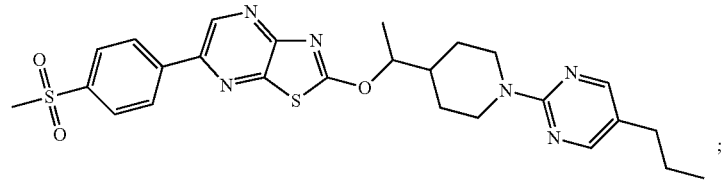 [SMILES: CCCc1cnc(N2CCC(C(C)Oc3nc4ncc(-c5ccc(S(C)(=O)=O)cc5)nc4s3)CC2)nc1] |
| 1111 | 5-(4-(1-((5-(2-fluoro-4-(methylsulfonyl)phenyl)thiazolo[5,4-b]pyridin-2-yl)oxy)ethyl)piperidin-1-yl)-3-isopropyl-1,2,4-oxadiazole | 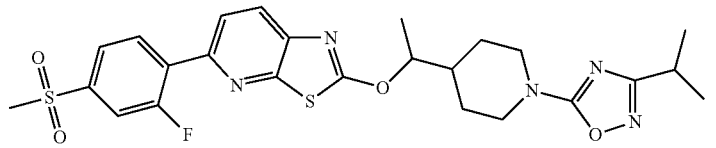 |
| 1112 | 5-(3-fluoro-4-(1-((5-(4-(methylsulfonyl)phenyl)thiazolo[5,4-b]pyridin-2-yl)oxy)ethyl)piperidin-1-yl)-3-isopropyl-1,2,4-oxadiazole | 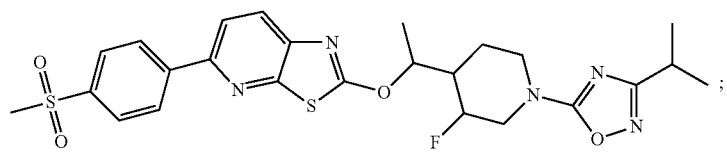 [SMILES: CC(C)c1noc(N2CCC(C(C)Oc3nc4ccc(-c5ccc(S(C)(=O)=O)cc5)nc4s3)C(F)C2)n1] |
| 1113 | 2-(1-(1-(5-isopropyl-pyrimidin-2-yl)piperidin-4-yl)ethoxy)-5-(4-(methylsulfonyl)phenyl)thiazolo[5,4-b]pyridine | 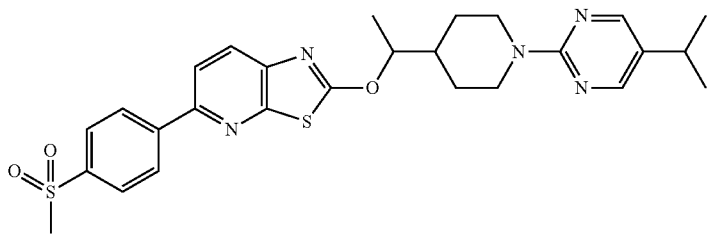 |
| 1114 | (S)-3-isopropyl-5-(4-(1-((6-(6-(methylsulfonyl)pyridin-3-yl)thiazolo[4,5-b]pyrazin-2-yl)oxy)ethyl)piperidin-1-yl)-1,2,4-oxadiazole | 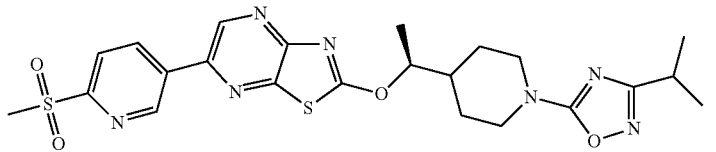 |
| 1115 | 5-(4-(methylsulfonyl)phenyl)-2-(1-(1-(propylsulfonyl)piperidin-4-yl)ethoxy)thiazolo[5,4-b]pyridine | 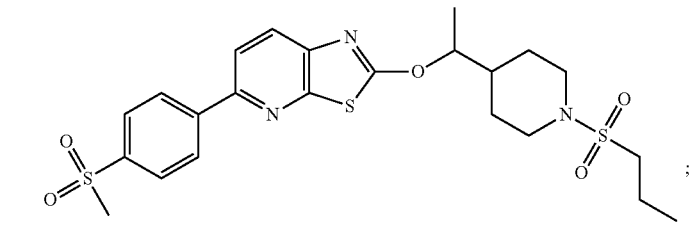 [SMILES: CCCS(=O)(=O)N1CCC(C(C)Oc2nc3ccc(-c4ccc(S(C)(=O)=O)cc4)nc3s2)CC1] |
| 1116 | 5-(4-(1-((5-(2-chloropyrimidin-5-yl)thiazolo[5,4-b]pyridin-2-yl)oxy)ethyl)piperidin-1-yl)-3-isopropyl-1,2,4-oxadiazole | 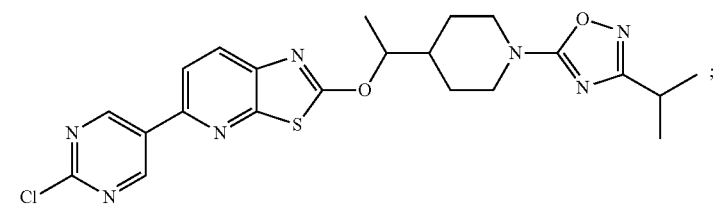 [SMILES: CC(C)c1noc(N2CCC(C(C)Oc3nc4ccc(-c5cnc(Cl)nc5)nc4s3)CC2)n1] |
| 1117 | 1-methylcyclopropyl 4-(1-((5-(4-(methyl-sulfonyl)phenyl)thiazolo[5,4-b]pyridin-2-yl)oxy)ethyl)piperidine-1-carboxylate | 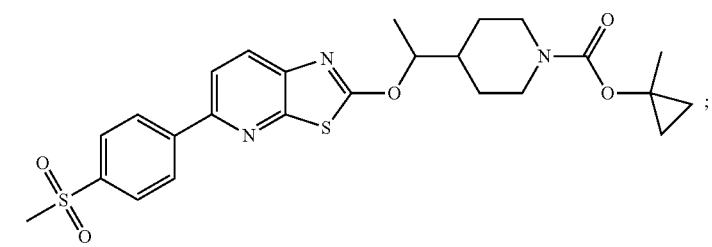 [SMILES: CC(Oc1nc2ccc(-c3ccc(S(C)(=O)=O)cc3)nc2s1)C1CCN(C(=O)OC2(C)CC2)CC1] |

| | | |
|---|---|---|
| 1118 | 5-(4-(methylsulfonyl)phenyl)-2-(1-(1-(5-(prop-1-en-2-yl)pyrimidin-2-yl)piperidin-4-yl)ethoxy)thiazolo [5,4-b] pyridine | 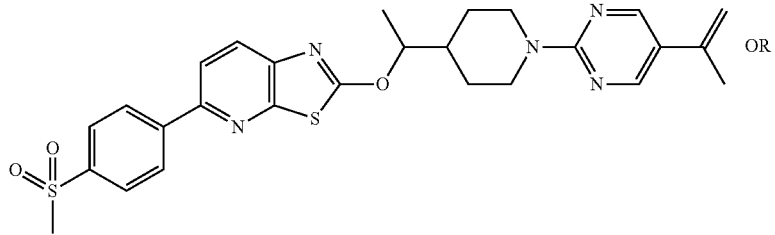 OR |
| 1119 | (S)-5-(4-(1-((5-(2-chloropyrimidin-5-yl)thiazolo[5,4-b]pyridin-2-yl)oxy)ethyl) piperidin-1-yl)-3-isopropyl-1,2,4-oxadiazole | 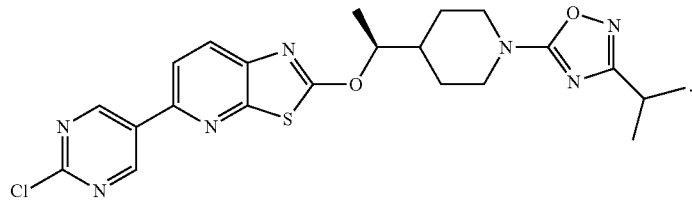 . |

16. The compound of claim 1 having the structure:

| | | |
|---|---|---|
| 1120 | 2-(1-(1-(5-chloro-pyrimidin-2-yl)piperidin-4-yl)ethoxy)-5-(4-(methylsulfonyl)phenyl)thiazolo[5,4-b] pyridine | 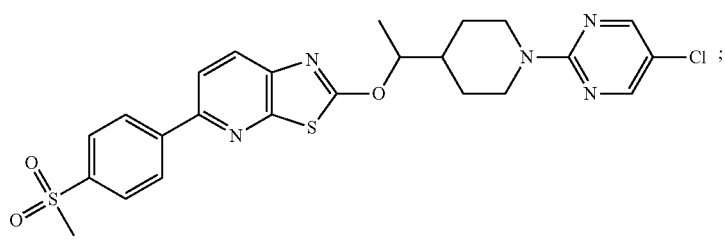 ; |
| 1121 | 3-isopropyl-5-(4-(1-((5-(thiazol-5-yl)thiazolo [5,4-b]pyridin-2-yl)oxy)ethyl)piperidin-1-yl)-1,2,4-oxadiazole | 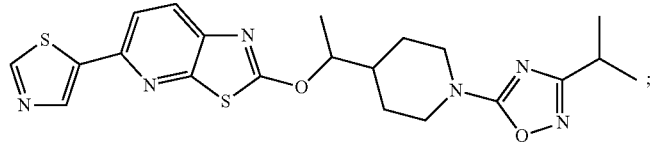 ; |
| 1122 | 3-isopropyl-5-(4-(1-((5-(isoxazol-4-yl)thiazolo [5,4-b]pyridin-2-yl)oxy)ethyl)piperidin-1-yl)-1,2,4-oxadiazole | 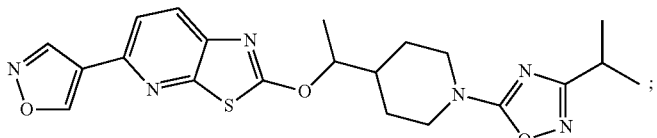 ; |
| 1123 | 3-isopropyl-5-(4-(1-((5-(2-methylpyridin-4-yl)thiazolo[5,4-b]pyridin-2-yl)oxy)ethyl)piperidin-1-yl)-1,2,4-oxadiazole | 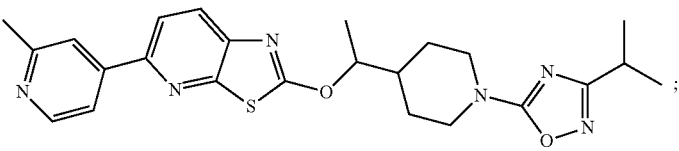 ; |
| 1124 | 3-isopropyl-5-(4-(1-((5-(isothiazol-4-yl)thiazolo [5,4-b]pyridin-2-yl)oxy)ethyl)piperidin-1-yl)-1,2,4-oxadiazole | 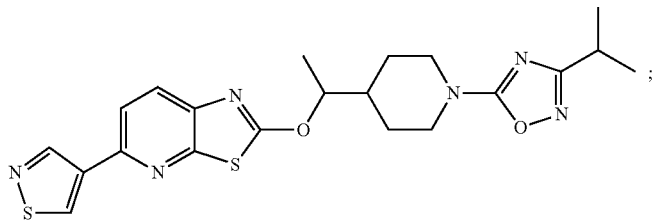 ; |

| | | |
|---|---|---|
| 1125 | 3-isopropyl-5-(4-(1-((5-(3-methylisothiazol-4-yl)thiazolo[5,4-b]pyridin-2-yl)oxy)ethyl) piperidin-1-yl)-1,2,4-oxadiazole | 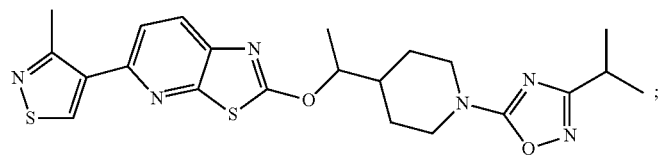 |
| 1126 | 4-(2-(1-(1-(3-isopropyl-1,2,4-oxadiazol-5-yl) piperidin-4-yl)ethoxy) thiazolo[5,4-b]pyridin-5-yl)pyridin-2(1H)-one | 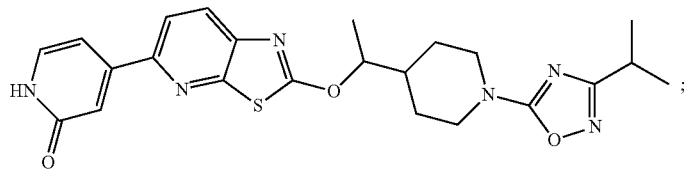 |
| 1127 | 4-(2-(1-(1-(3-isopropyl-1,2,4-oxadiazol-5-yl) piperidin-4-yl)ethoxy) thiazolo[5,4-b]pyridin-5-yl)-1-methylpyridin-2(1H)-one | 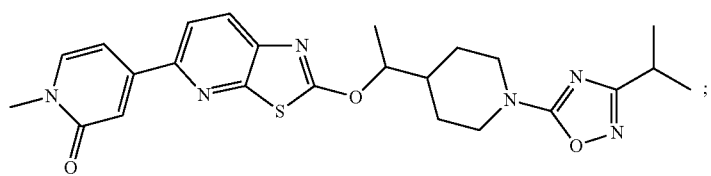 |
| 1128 | 5-((3R,4S)-3-fluoro-4-(((5-(4-(methylsulfonyl)phenyl)thiazolo[5,4-b]pyridin-2-yl)oxy)methyl)piperidin-1-yl)-3-isopropyl-1,2,4-oxadiazole | 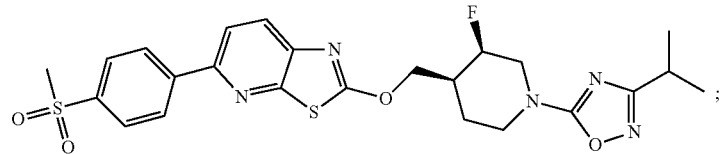 |
| 1129 | 5-((3S,4S)-3-fluoro-4-(((5-(4-(methylsulfonyl)phenyl)thiazolo[5,4-b]pyridin-2-yl)oxy)methyl)piperidin-1-yl)-3-isopropyl-1,2,4-oxadiazole | 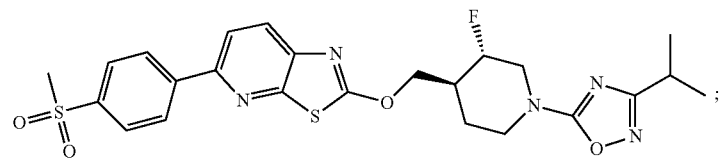 |
| 1130 | 3-isopropyl-5-(4-(1-(5-(4-(methylsulfonyl)phenyl)thiazolo[5,4-b]pyridin-2-yl)ethoxy)piperidin-1-yl)-1,2,4-oxadiazole | 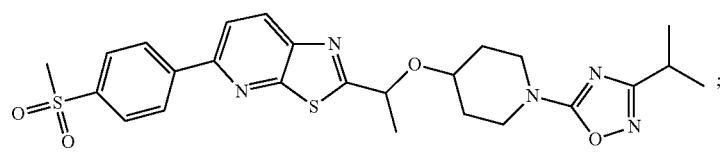 |
| 1131 | 5-(4-(1-((5-(4-(methylsulfonyl)phenyl)thiazolo[5,4-b]pyridin-2-yl)oxy)ethyl)piperidin-1-yl)-3-(trifluoromethyl)-1,2,4-oxadiazole | 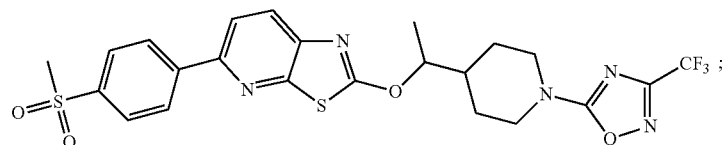 |
| 1132 | 5-(4-(1-((5-(2-chloropyridin-4-yl)thiazolo[5,4-b]pyridin-2-yl)oxy)ethyl)piperidin-1-yl)-3-isopropyl-1,2,4-oxadiazole | 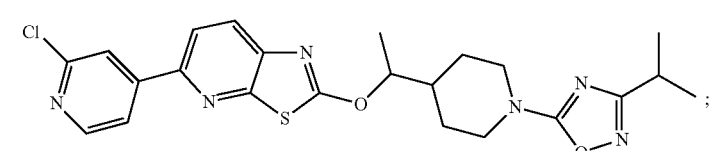 |
| 1133 | 3-isopropyl-5-(4-(1-((5-(2-(methylsulfonyl)pyrimidin-5-yl)thiazolo[5,4-b]pyridin-2-yl)oxy)ethyl)piperidin-1-yl)-1,2,4-oxadiazole | 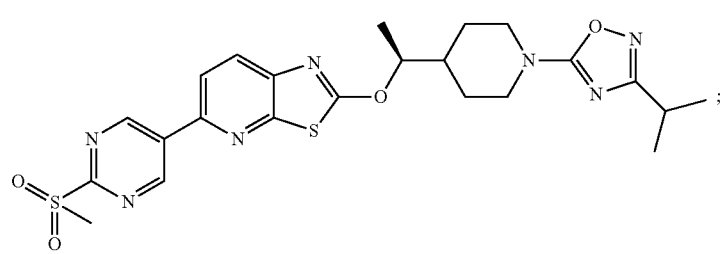 |

| | | |
|---|---|---|
| 1134 | 3-isopropyl-5-(4-(1-((5-(pyridazin-4-yl)thiazolo[5,4-b]pyridin-2-yl)oxy)ethyl)piperidin-1-yl)-1,2,4-oxadiazole | 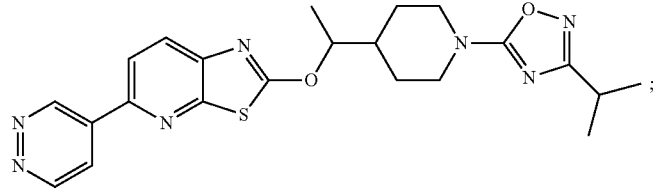 |
| 1135 | 2-((S)-1-(1-(5-ethyl-pyrimidin-2-yl)piperidin-4-yl)ethoxy)-5-(2-chloropyrimidin-5-yl)thiazolo[5,4-b]pyridine | 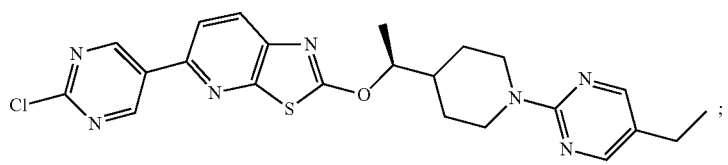 |
| 1136 | 2-((S)-1-(1-(5-chloro-pyrimidin-2-yl)piperidin-4-yl)ethoxy)-5-(6-(methylsulfonyl)pyridin-3-yl)thiazolo[5,4-b]pyridine | 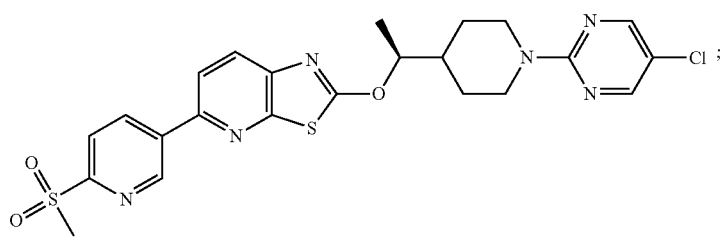 |
| 1137 | 2-(1-(1-(5-cyclopropyl-pyrimidin-2-yl)piperidin-4-yl)ethoxy)-5-(6-(methylsulfonyl)pyridin-3-yl)thiazolo[5,4-b]pyridine | 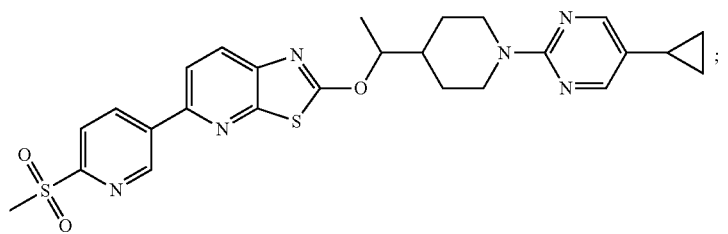 |
| 1138 | 2-((S)-1-(1-(3-isopropyl-1,2,4-oxadiazol-5-yl)piperidin-4-yl)ethoxy)-5-(2-(methylsulfinyl)pyrimidin-5-yl)thiazolo[5,4-b]pyridine | 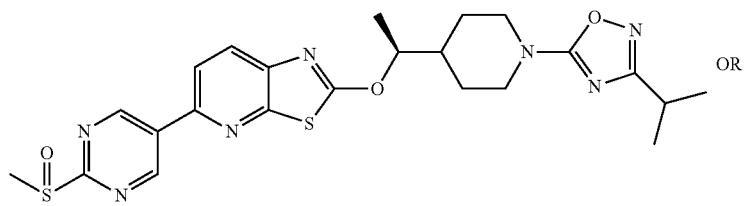 OR |
| 1139 | N-(5-(2-(1-(1-(3-isopropyl-1,2,4-oxadiazol-5-yl)piperidin-4-yl)ethoxy)thiazolo[5,4-b]pyridin-5-yl)pyrimidin-2-yl)-N-methylacetamide | 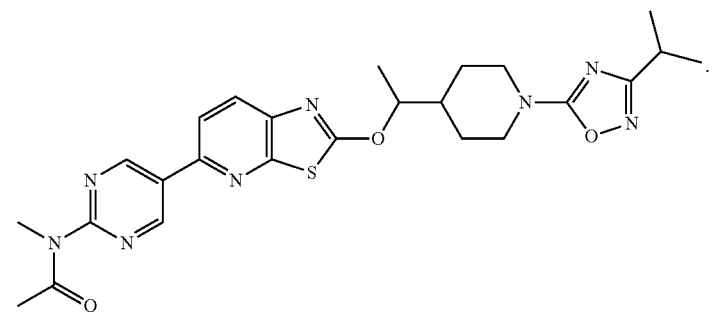 |

17. The compound of claim 1 having the structure:

| 1140 | 2-((R)-1-(1-(3-isopropyl-1,2,4-oxadiazol-5-yl)pyrrolidin-3-yl)ethoxy)-5-(6-(methylsulfonyl)pyridin-3-yl)thiazolo[5,4-b]pyridine | 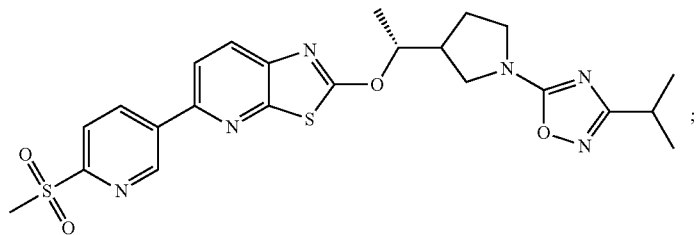 ; |
| --- | --- | --- |
| 1141 | 2-((S)-1-(1-(3-isopropyl-1,2,4-oxadiazol-5-yl)pyrrolidin-3-yl)ethoxy)-5-(6-(methylsulfonyl)pyridin-3-yl)thiazolo[5,4-b]pyridine | 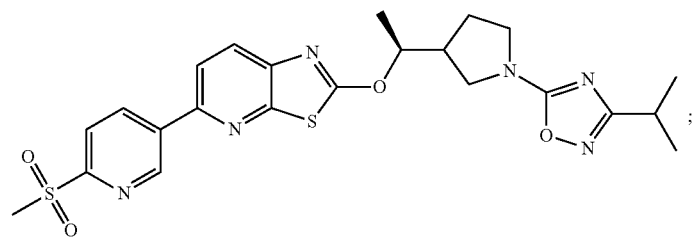 [SMILES: CC(C)c1noc(N2CCC([C@H](C)Oc3nc4ccc(-c5ccc(S(C)(=O)=O)nc5)nc4s3)C2)n1] ; |
| 1142 | 2-(1-(1-(3-isopropyl-1,2,4-oxadiazol-5-yl)piperidin-4-yl)ethoxy)-5-(6-chloropyridin-3-yl)thiazolo[5,4-b]pyridine | 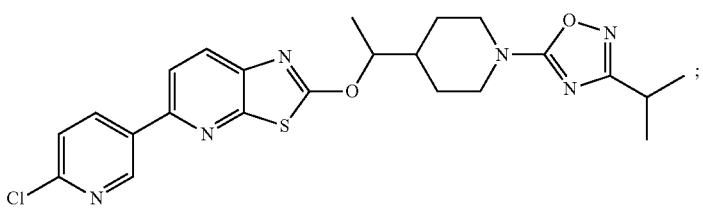 [SMILES: CC(C)c1noc(N2CCC(C(C)Oc3nc4ccc(-c5ccc(Cl)nc5)nc4s3)CC2)n1] ; |
| 1143 | 2-((S)-1-(1-(3-isopropyl-1,2,4-oxadiazol-5-yl)piperidin-4-yl)ethoxy)-5-(2-chloropyridin-4-yl)thiazolo[5,4-b]pyridine | 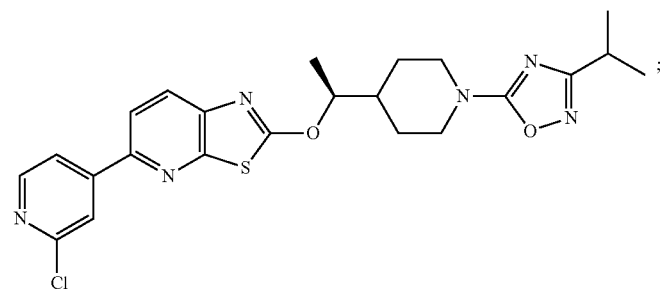 [SMILES: CC(C)c1noc(N2CCC([C@H](C)Oc3nc4ccc(-c5ccnc(Cl)c5)nc4s3)CC2)n1] ; |
| 1144 | 1-(5-(2-(1-(1-(3-isopropyl-1,2,4-oxadiazol-5-yl)piperidin-4-yl)ethoxy)thiazolo[5,4-b]pyridin-5-yl)pyridin-2-yl)imidazolidin-2-one | 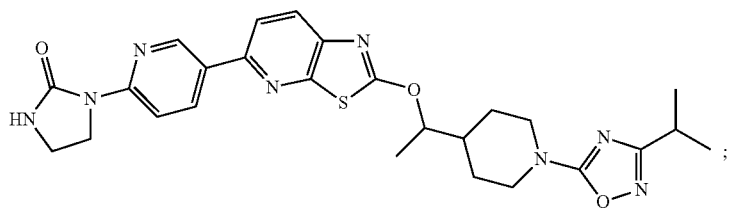 [SMILES: CC(C)c1noc(N2CCC(C(C)Oc3nc4ccc(-c5ccc(N6CCNC6=O)nc5)nc4s3)CC2)n1] ; |
| 1145 | 2-((S)-1-(1-(3-(trifluoromethyl)-1,2,4-oxadiazol-5-yl)piperidin-4-yl)ethoxy)-5-(6-(methylsulfonyl)pyridin-3-yl)thiazolo[5,4-b]pyridine | 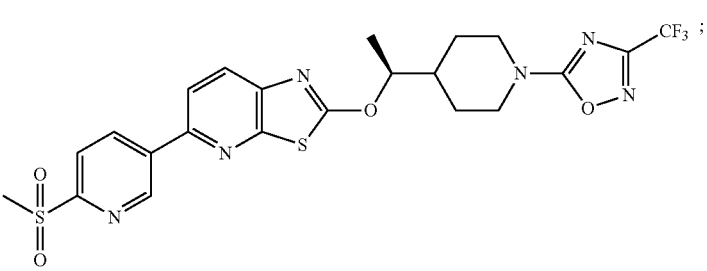 [SMILES: C[C@H](Oc1nc2ccc(-c3ccc(S(C)(=O)=O)nc3)nc2s1)C1CCN(c2nc(C(F)(F)F)no2)CC1] ; |

-continued

| | | |
|---|---|---|
| 1146 | 1-(5-(2-(1-(1-(3-isopropyl-1,2,4-oxadiazol-5-yl)piperidin-4-yl)ethoxy)thiazolo[5,4-b]pyridin-5-yl)pyridin-2-yl)pyrrolidin-2-one | 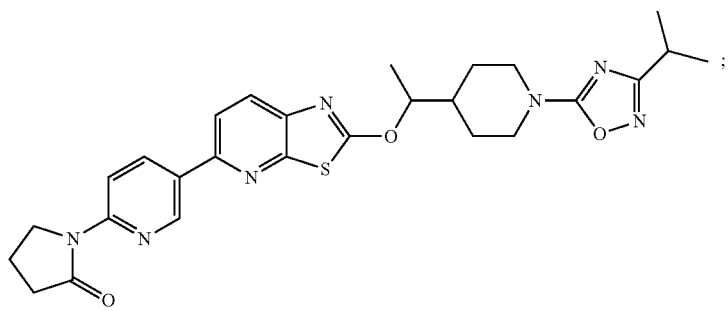 [SMILES: CC(C)c1noc(N2CCC(C(C)Oc3nc4ccc(-c5ccc(N6CCCC6=O)nc5)nc4s3)CC2)n1] |
| 1147 | 2-(1-(1-(3-isopropyl-1,2,4-oxadiazol-5-yl)piperidin-4-yl)ethoxy)-5-(6-(trifluoromethyl)pyridin-3-yl)thiazolo[5,4-b]pyridine | 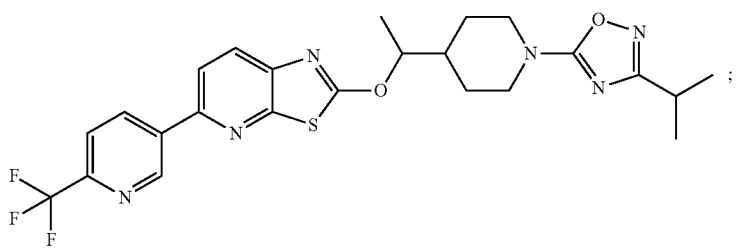 [SMILES: CC(C)c1noc(N2CCC(C(C)Oc3nc4ccc(-c5ccc(C(F)(F)F)nc5)nc4s3)CC2)n1] |
| 1148 | 2-(1-(1-(5-chloropyrazin-2-yl)piperidin-4-yl)ethoxy)-5-(4-(methylsulfonyl)phenyl)thiazolo[5,4-b]pyridine | 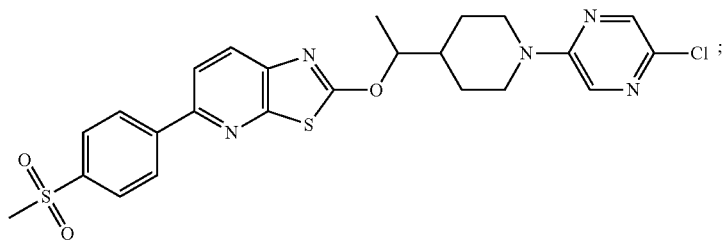 [SMILES: CC(Oc1nc2ccc(-c3ccc(S(C)(=O)=O)cc3)nc2s1)C1CCN(c2cnc(Cl)cn2)CC1] |
| 1149 | 2-(1-(1-(5-ethylpyrimidin-2-yl)piperidin-4-yl)ethoxy)-5-(pyridin-4-yl)thiazolo[5,4-b]pyridine | 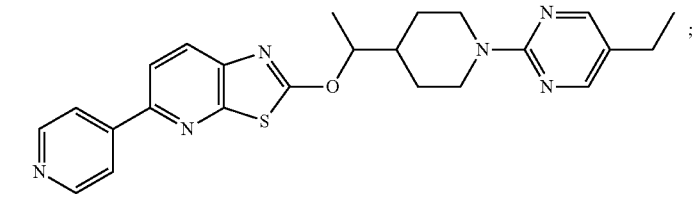 [SMILES: CCc1cnc(N2CCC(C(C)Oc3nc4ccc(-c5ccncc5)nc4s3)CC2)nc1] |
| 1150 | 2-(1-(1-(5-propylpyrimidin-2-yl)piperidin-4-yl)ethoxy)-5-(pyridin-4-yl)thiazolo[5,4-b]pyridine | 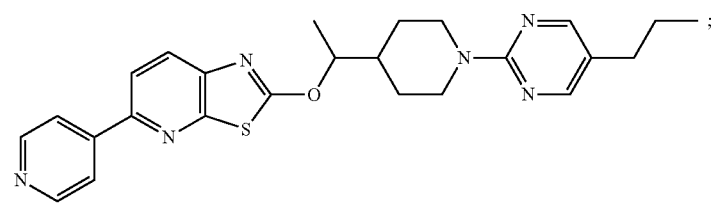 [SMILES: CCCc1cnc(N2CCC(C(C)Oc3nc4ccc(-c5ccncc5)nc4s3)CC2)nc1] |
| 1151 | 2-(1-(1-(5-chloropyrazin-2-yl)piperidin-4-yl)ethoxy)-5-(6-(methylsulfonyl)pyridin-3-yl)thiazolo[5,4-b]pyridine | 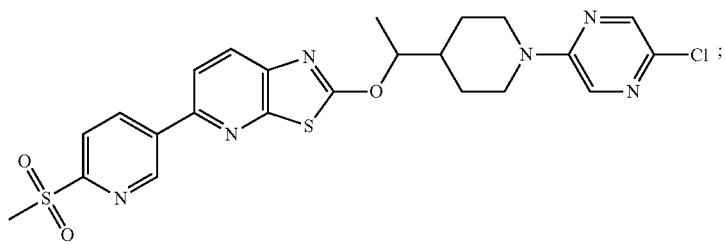 [SMILES: CC(Oc1nc2ccc(-c3ccc(S(C)(=O)=O)nc3)nc2s1)C1CCN(c2cnc(Cl)cn2)CC1] |

| | | |
|---|---|---|
| 1152 | 2-((S)-1-(1-(3-isopropyl-1,2,4-oxadiazol-5-yl)piperidin-4-yl)ethoxy)-5-(6-(trifluoromethyl)pyridin-3-yl)thiazolo[5,4-b]pyridine | 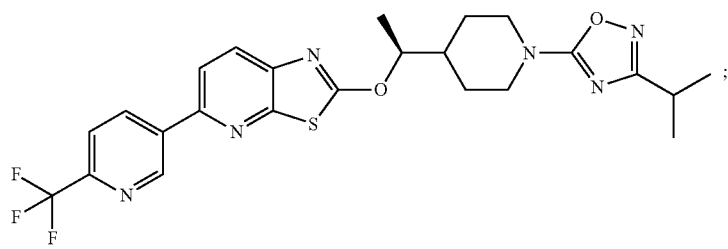 [SMILES: CC(C)c1noc(N2CCC([C@H](C)Oc3nc4ccc(-c5ccc(C(F)(F)F)nc5)nc4s3)CC2)n1] |
| 1153 | 2-((S)-1-(1-(5-propylpyrimidin-2-yl)piperidin-4-yl)ethoxy)-5-(pyridin-4-yl)thiazolo[5,4-b]pyridine | 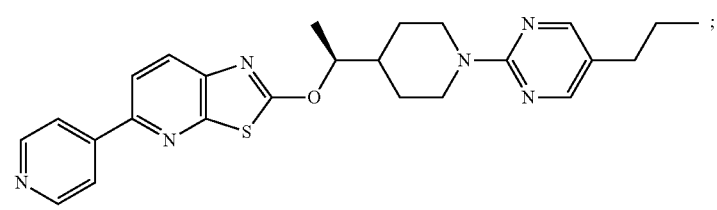 [SMILES: CCCc1cnc(N2CCC([C@H](C)Oc3nc4ccc(-c5ccncc5)nc4s3)CC2)nc1] |
| 1154 | 2-((S)-1-(1-(5-ethylpyrimidin-2-yl)piperidin-4-yl)ethoxy)-5-(6-(trifluoromethyl)pyridin-3-yl)thiazolo[5,4-b]pyridine | 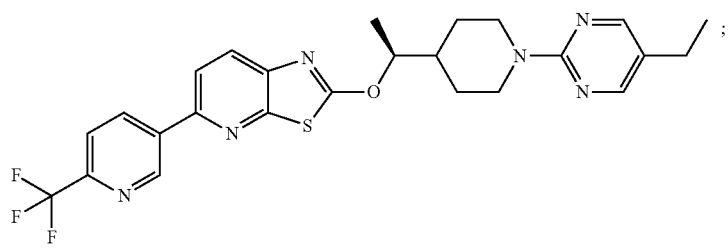 [SMILES: CCc1cnc(N2CCC([C@H](C)Oc3nc4ccc(-c5ccc(C(F)(F)F)nc5)nc4s3)CC2)nc1] |
| 1155 | 2-((S)-1-(1-(3-isopropyl-1,2,4-oxadiazol-5-yl)piperidin-4-yl)ethoxy)-5-(3-fluoro-4-(methylsulfonyl)phenyl)thiazolo[5,4-b]pyridine | 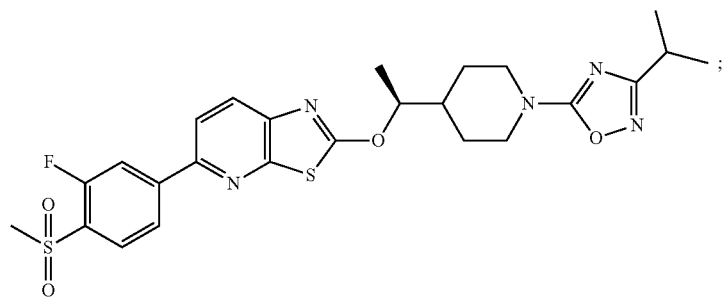 [SMILES: CC(C)c1noc(N2CCC([C@H](C)Oc3nc4ccc(-c5ccc(S(C)(=O)=O)c(F)c5)nc4s3)CC2)n1] |
| 1156 | 2-(1-(1-(3-ethyl-1,2,4-oxadiazol-5-yl)piperidin-4-yl)ethoxy)-5-(6-(methylsulfonyl)pyridin-3-yl)thiazolo[5,4-b]pyridine | 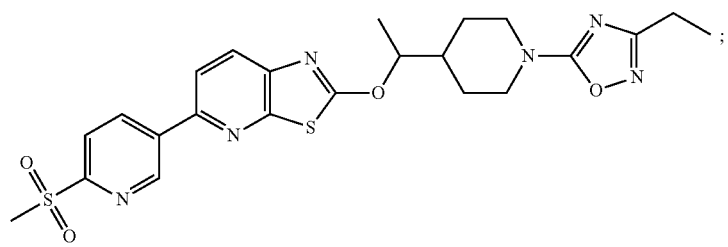 [SMILES: CCc1noc(N2CCC(C(C)Oc3nc4ccc(-c5ccc(S(C)(=O)=O)nc5)nc4s3)CC2)n1] |
| 1157 | 2-(1-(1-(5-methylpyrimidin-2-yl)piperidin-4-yl)ethoxy)-5-(6-(methylsulfonyl)pyridin-3-yl)thiazolo[5,4-b]pyridine | 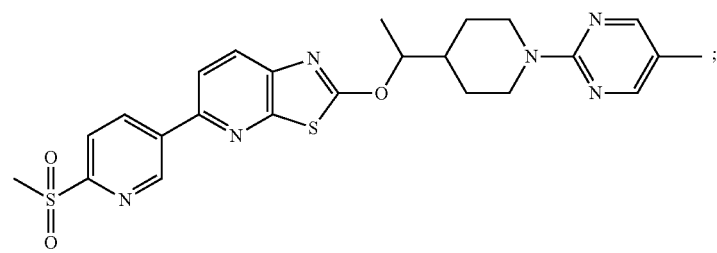 |

| | | |
|---|---|---|
| 1158 | 2-(1-(1-(3-isopropyl-1,2,4-oxadiazol-5-yl)piperidin-4-yl)ethoxy)-5-(5-(methylsulfonyl)pyrazin-2-yl)thiazolo[5,4-b]pyridine | 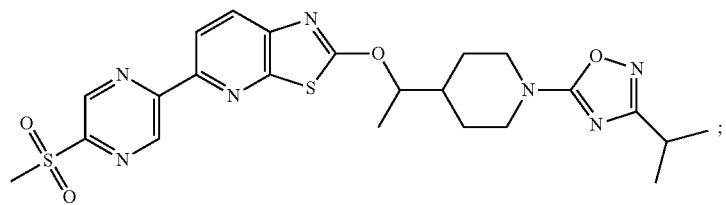 [SMILES: CC(C)c1noc(N2CCC(C(C)Oc3nc4ccc(-c5cnc(S(C)(=O)=O)cn5)nc4s3)CC2)n1] |
| 1159 | 2-(1-(1-(5-(trifluoromethyl)pyrimidin-2-yl)piperidin-4-yl)ethoxy)-5-(6-(methylsulfonyl)pyridin-3-yl)thiazolo[5,4-b]pyridine | 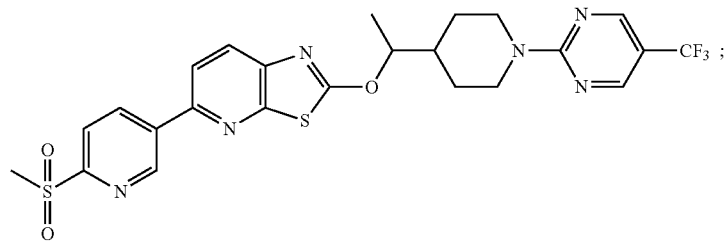 [SMILES: CC(Oc1nc2ccc(-c3ccc(S(C)(=O)=O)nc3)nc2s1)C1CCN(c2ncc(C(F)(F)F)cn2)CC1] |
| 1160 | 2-((S)-1-(1-(3-ethyl-1,2,4-oxadiazol-5-yl)piperidin-4-yl)ethoxy)-5-(6-(methylsulfonyl)pyridin-3-yl)thiazolo[5,4-b]pyridine | 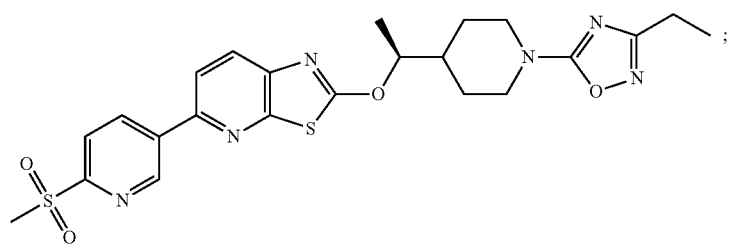 [SMILES: CCc1noc(N2CCC([C@H](C)Oc3nc4ccc(-c5ccc(S(C)(=O)=O)nc5)nc4s3)CC2)n1] |
| 1161 | 2-(1-(1-(3-isopropyl-1,2,4-oxadiazol-5-yl)piperidin-4-yl)ethoxy)-5-(5-(methylsulfonyl)pyridin-2-yl)thiazolo[5,4-b]pyridine | 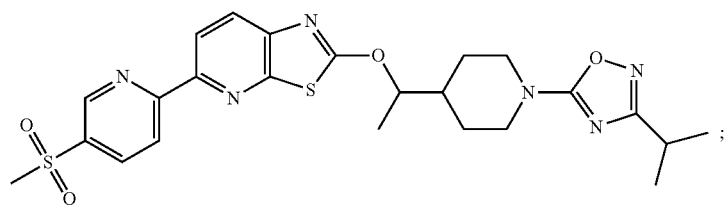 [SMILES: CC(C)c1noc(N2CCC(C(C)Oc3nc4ccc(-c5ccc(S(C)(=O)=O)cn5)nc4s3)CC2)n1] |
| 1162 | 2-(1-(1-(3-isopropyl-1,2,4-oxadiazol-5-yl)piperidin-4-yl)ethoxy)-5-(6-(methylsulfonyl)pyridin-3-yl)thiazolo[5,4-d]pyrimidine | 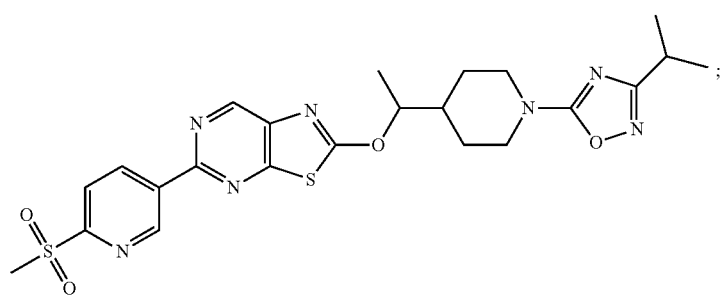 [SMILES: CC(C)c1noc(N2CCC(C(C)Oc3nc4cnc(-c5ccc(S(C)(=O)=O)nc5)nc4s3)CC2)n1] |
| 1163 | 2-(1-(1-(5-(methoxymethyl)pyrimidin-2-yl)piperidin-4-yl)ethoxy)-5-(6-(methylsulfonyl)pyridin-3-yl)thiazolo[5,4-b]pyridine | 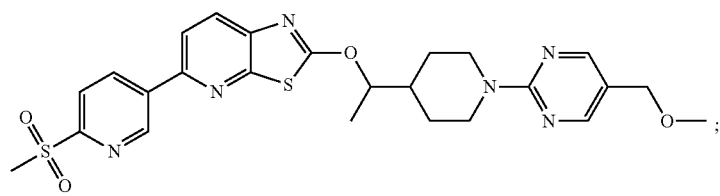 |
| 1164 | 2-((R)-1-(1-(3-isopropyl-1,2,4-oxadiazol-5-yl)piperidin-4-yl)ethoxy)-5-(6-(cyclopropylsulfonyl)pyridin-3-yl)thiazolo[5,4-b]pyridine | 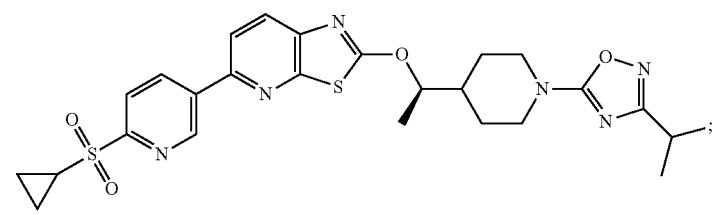 |

| | | |
|---|---|---|
| 1165 | 2-((R)-1-(1-(5-(methoxymethyl)pyrimidin-2-yl)piperidin-4-yl)ethoxy)-5-(6-(methylsulfonyl)pyridin-3-yl)thiazolo[5,4-b]pyridine | 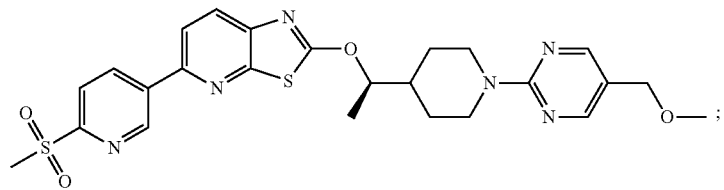 |
| 1166 | 2-((S)-(1-(1-(5-(trifluoromethyl)pyrimidin-2-yl)piperidin-4-yl)ethoxy)-5-(6-(methylsulfonyl)pyridin-3-yl)thiazolo[5,4-b]pyridine | 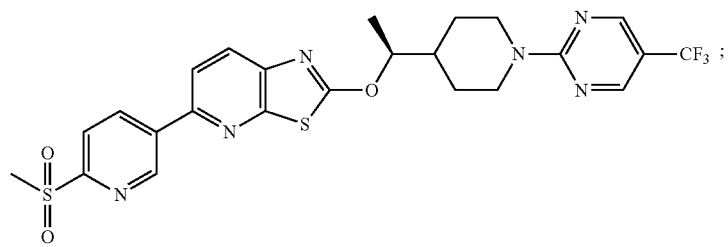 [SMILES: C[C@H](Oc1nc2ccc(-c3ccc(S(C)(=O)=O)nc3)nc2s1)C1CCN(c2ncc(C(F)(F)F)cn2)CC1] |
| 1167 | 2-((S)-1-(1-(3-isopropyl-1,2,4-oxadiazol-5-yl)piperidin-4-yl)ethoxy)-5-(2-fluoro-6-(methylsulfonyl)pyridin-3-yl)thiazolo[5,4-b]pyridine | 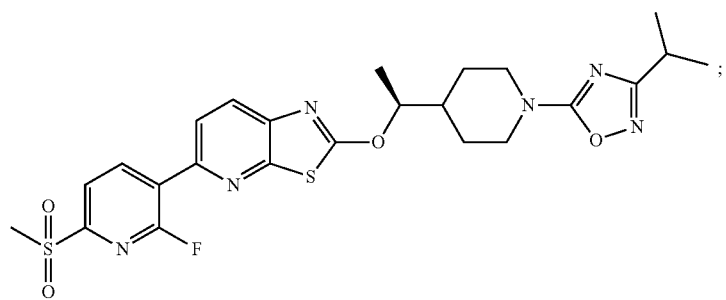 [SMILES: CC(C)c1noc(N2CCC([C@H](C)Oc3nc4ccc(-c5ccc(S(C)(=O)=O)nc5F)nc4s3)CC2)n1] |
| 1168 | 2-((R)-1-(1-(3-isopropyl-1,2,4-oxadiazol-5-yl)piperidin-4-yl)ethoxy)-5-(2-methyl-6-(methylsulfonyl)pyridin-3-yl)thiazolo[5,4-b]pyridine | 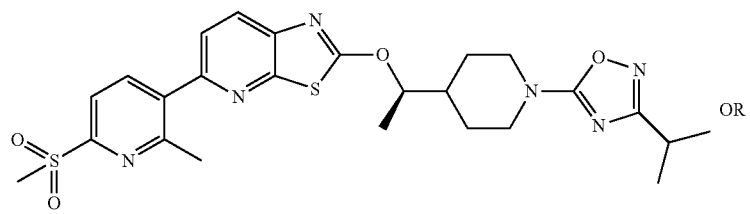 [SMILES: Cc1nc(S(C)(=O)=O)ccc1-c1ccc2nc(O[C@H](C)C3CCN(c4nc(C(C)C)no4)CC3)sc2n1] |
| 1169 | 2-((R)-1-(1-(3-isopropyl-1,2,4-oxadiazol-5-yl)piperidin-4-yl)ethoxy)-5-(2-methyl-4-(methylsulfonyl)phenyl)thiazolo[5,4-b]pyridine | 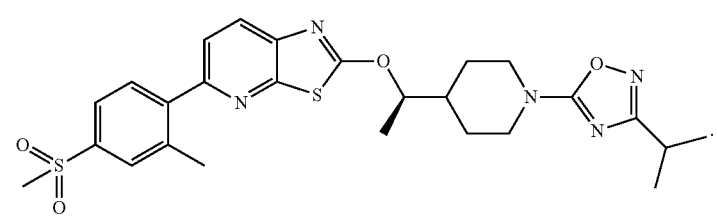 [SMILES: Cc1cc(S(C)(=O)=O)ccc1-c1ccc2nc(O[C@H](C)C3CCN(c4nc(C(C)C)no4)CC3)sc2n1] |

18. The compound of claim 1, which is
3-isopropyl-5-(1-(5-(4-(methylsulfonyl)phenoxy)thiazolo[5,4-b]pyridin-2-yl)piperidin-4-yl)-1,2,4-oxadiazole;
3-isopropyl-5-(4-(((5-(4-(methylsulfonyl)phenoxy)thiazolo[5,4-b]pyridin-2-yl)oxy)methyl)piperidin-1-yl)-1,2,4-oxadiazole;
3-isopropyl-5-(1-(2-(4-(methylsulfonyl)phenyl)thiazolo[5,4-b]pyridin-5-yl)piperidin-4-yl)-1,2,4-oxadiazole;
3-isopropyl-5-(1-(5-(4-(methylsulfonyl)phenyl)thiazolo[5,4-b]pyridin-2-yl)piperidin-4-yl)-1,2,4-oxadiazole;
3-isopropyl-5-(4-((5-(4-(methylsulfonyl)phenoxy)thiazolo[5,4-b]pyridin-2-yl)oxy)piperidin-1-yl)-1,2,4-oxadiazole;
3-isopropyl-5-(4-(((5-(4-(methylsulfonyl)phenyl)thiazolo[5,4-b]pyridin-2-yl)oxy)methyl)piperidin-1-yl)-1,2,4-oxadiazole;
3-isopropyl-5-(4-((5-(4-(methylsulfonyl)phenyl)thiazolo[5,4-b]pyridin-2-yl)oxy)piperidin-1-yl)-1,2,4-oxadiazole;
2-(4-(5-ethylpyrimidin-2-yl)piperazin-1-yl)-5-(4-(methylsulfonyl)phenyl)thiazolo[5,4-b]pyridine;
5-((1-benzylpiperidin-4-yl)methoxy)-2-(4-(methylsulfonyl)phenyl)thiazolo[5,4-b]pyridine;
2-(4-(5-ethylpyrimidin-2-yl)piperazin-1-yl)-5-(4-(methylsulfonyl)phenoxy)thiazolo[5,4-b]pyridine;
isopropyl 4-(5-(4-(methyl sulfonyl)phenyl)thiazolo[5,4-b]pyridin-2-yl)-5,6-dihydropyridine-1 (2H)-carboxylate;
isopropyl 4-(5-(4-(methylsulfonyl)phenyl)thiazolo[5,4-b]pyridin-2-yl) piperazine-1-carboxylate;
isopropyl-4-(5-(4-(methylsulfonyl)phenyl)thiazolo[5,4-b]pyridin-2-yl) piperidine-1-carboxylate;

1-(5-ethylpyrimidin-2-yl)-N-(5-(4-(methylsulfonyl)phenyl)thiazolo[5,4-b]pyridin-2-yl)piperidine-4-carboxamide;

2-(4-(5-(4-(methylsulfonyl)phenyl)thiazolo[5,4-b]pyridin-2-yl)-5,6-dihydropyridin-1(2H)-yl)ethanol;

isopropyl-4-(methyl(5-(4-(methylsulfonyl)phenyl)thiazolo[5,4-b]pyridin-2-yl)amino)piperidine-1-carboxylate;

N-(1-(5-ethylpyrimidin-2-yl)piperidin-4-yl)-N-methyl-5-(4-(methylsulfonyl)phenyl) thiazolo[5,4-b]pyridin-2-amine;

isopropyl 4-((5-(4-(dimethyl carbamoyl)phenyl)thiazolo[5,4-b]pyridin-2-yl)(methyl)amino)piperidine-1-carboxylate;

isopropyl (5-(4-(methyl sulfonyl)phenyl)thiazolo[5,4-b]pyridin-2-yl) carbonate;

3-isopropyl-5-(4-(1-((5-(4-(methylsulfonyl)phenyl)thiazolo[5,4-b]pyridin-2-yl)oxy)ethyl)piperidin-1-yl)-1,2,4-oxadiazole;

3-isopropyl-5-(1-(5-(4-(methylsulfonyl)phenyl)thiazolo[5,4-b]pyridin-2-yl)pyrrolidin-3-yl)-1,2,4-oxadiazole;

4-(2-(4-(3-isopropyl-1,2,4-oxadiazol-5-yl)piperidin-1-yl)thiazolo[5,4-b]pyridin-5-yl)-N,N-dimethylbenzamide;

N-(1-(3-isopropyl-1,2,4-oxadiazol-5-yl)piperidin-4-yl)-N-methyl-5-(4-(methylsulfonyl)phenyl)thiazolo[5,4-b]pyridin-2-amine;

4-(2-(4-(3-isopropyl-1,2,4-oxadiazol-5-yl)piperidin-1-yl)thiazolo[5,4-b]pyridin-5-yl)-N-(2-methoxyethyl)benzamide; OR N-(3-fluoro-4-(methylsulfonyl)phenyl)-2-(4-(3-isopropyl-1,2,4-oxadiazol-5-yl)piperidin-1-yl)thiazolo[5,4-b]pyridin-5-amine.

19. The compound of claim 1, which is 5-(4-(methylsulfonyl)phenyl)-2-(1-tosyl-1,2,3,6-tetrahydropyridin-4-yl)thiazolo[5,4-b]pyridine;

N,N-dimethyl-4-(5-(4-(methylsulfonyl)phenyl)thiazolo[5,4-b]pyridin-2-yl)-5,6-dihydropyridine-1 (2H)-carboxamide;

N,N-dimethyl-4-(5-(4-(methylsulfonyl)phenyl)thiazolo[5,4-b]pyridin-2-yl)piperidine-1-carboxamide;

(4-(2-(4-(3-isopropyl-1,2,4-oxadiazol-5-yl)piperidin-1-yl)thiazolo[5,4-b]pyridin-5-yl)phenyl)(morpholino)methanone;

N,N-diisopropyl-4-(5-(4-(methylsulfonyl)phenyl)thiazolo[5,4-b]pyridin-2-yl)-5,6-dihydropyridine-1 (2H)-carboxamide;

(S)-3-isopropyl-5-(4-(1-((5-(4-(methylsulfonyl)phenyl)thiazolo[5,4-b]pyridin-2-yl)oxy)ethyl)piperidin-1-yl)-1,2,4-oxadiazole;

(R)-3-isopropyl-5-(4-(1-((5-(4-(methylsulfonyl)phenyl)thiazolo[5,4-b]pyridin-2-yl)oxy)ethyl)piperidin-1-yl)-1,2,4-oxadiazole;

3-cyclopropyl-5-(4-((5-(4-(methylsulfonyl)phenyl)thiazolo[5,4-b]pyridin-2-yl)oxy)piperidin-1-yl)-1,2,4-oxadiazole;

isopropyl 4-(2-((5-(4-(methyl sulfonyl)phenyl)thiazolo[5,4-b]pyridin-2-yl)oxy)ethyl)-5,6-dihydropyridine-1 (2H)-carboxylate;

3-isopropyl-5-(4-(2-((5-(4-(methyl sulfonyl)phenyl)thiazolo[5,4-b]pyridin-2-yl)oxy)ethyl)-5,6-dihydropyridin-1 (2H)-yl)-1,2,4-oxadiazole;

3-isopropyl-5-(4-(2-methoxy-1-((5-(4-(methylsulfonyl)phenyl)thiazolo[5,4-b]pyridin-2-yl)oxy)ethyl)piperidin-1-yl)-1,2,4-oxadiazole 3-isopropyl-5-(4-(1-((7-methyl-5-(4-(methylsulfonyl)phenyl)thiazolo[5,4-b]pyridin-2-yl)oxy)ethyl)piperidin-1-yl)-1,2,4-oxadiazole;

3-isopropyl-5-(4-(((7-methyl-5-(4-(methylsulfonyl)phenyl)thiazolo[5,4-b]pyridin-2-yl)oxy)methyl)piperidin-1-yl)-1,2,4-oxadiazole;

3-isopropyl-5-(4-(1-((6-methyl-5-(4-(methylsulfonyl)phenyl)thiazolo[5,4-b]pyridin-2-yl)oxy)ethyl)piperidin-1-yl)-1,2,4-oxadiazole;

5-(4-(cyclopropyl((5-(4-(methylsulfonyl)phenyl)thiazolo[5,4-b]pyridin-2-yl)oxy)methyl)piperidin-1-yl)-3-isopropyl-1,2,4-oxadiazole;

3-isopropyl-5-(4-(2-((5-(4-(methylsulfonyl)phenyl)thiazolo[5,4-b]pyridin-2-yl)oxy)ethylidene) piperidin-1-yl)-1,2,4-oxadiazole; OR 3-isopropyl-5-(4-(2-((5-(4-(methylsulfonyl)phenyl)thiazolo[5,4-b]pyridin-2-yl)oxy)ethyl)piperidin-1-yl)-1,2,4-oxadiazole.

20. The compound of claim 1, which is 3-isopropyl-5-(4-(2-((5-(4-(methylsulfonyl)phenyl)thiazolo[5,4-b]pyridin-2-yl)oxy)propyl) piperidin-1-yl)-1,2,4-oxadiazole;

3-isopropyl-5-(4-(2-((5-(4-(methylsulfonyl)phenyl)thiazolo[5,4-b]pyridin-2-yl)oxy)propylidene) piperidin-1-yl)-1,2,4-oxadiazole;

(S)-4-(2-(1-(1-(3-isopropyl-1,2,4-oxadiazol-5-yl)piperidin-4-yl)ethoxy)thiazolo[5,4-b]pyridin-5-yl)-N,N-dimethylbenzamide;

3-fluoro-4-(2-(1-(1-(3-isopropyl-1,2,4-oxadiazol-5-yl)piperidin-4-yl)ethoxy)thiazolo[5,4-b]pyridin-5-yl)-N,N-dimethylbenzamide;

2-fluoro-4-(2-(1-(1-(3-isopropyl-1,2,4-oxadiazol-5-yl)piperidin-4-yl)ethoxy)thiazolo[5,4-b]pyridin-5-yl)-N,N-dimethylbenzamide;

3-cyclopropyl-5-(4-(1-((5-(4-(methylsulfonyl)phenyl)thiazolo[5,4-b]pyridin-2-yl)oxy)ethyl)piperidin-1-yl)-1,2,4-oxadiazole;

N-cyclopropyl-4-(2-(1-(1-(3-isopropyl-1,2,4-oxadiazol-5-yl)piperidin-4-yl)ethoxy)thiazolo [5,4-b]pyridin-5-yl)benzamide;

4-(2-(1-(1-(3-isopropyl-1,2,4-oxadiazol-5-yl)piperidin-4-yl)ethoxy)thiazolo[5,4-b]pyridin-5-yl)-N-(2-methoxyethyl)benzamide;

(4-(2-(1-(1-(3-isopropyl-1,2,4-oxadiazol-5-yl)piperidin-4-yl) ethoxy)thiazolo[5,4-b]pyridin-5-yl)phenyl)(morpholino)methanone;

N-cyclopropyl-4-(2-(1-(1-(3-isopropyl-1,2,4-oxadiazol-5-yl)piperidin-4-yl)ethoxy)thiazolo [5,4-b]pyridin-5-yl)-N-methylbenzamide;

5-(4-(methylsulfonyl)phenyl)-2-(1-(1-(5-propylpyrimidin-2-yl) piperidine-4-yl)ethoxy)thiazolo [5,4-b]pyridine;

3-isopropyl-5-(4-(1-((5-(pyridin-3-yl)thiazolo[5,4-b]pyridin-2-yl)oxy) ethyl)piperidin-1-yl)-1,2,4-oxadiazole;

2-(1-(1-(5-ethylpyrimidin-2-yl)piperidin-4-yl)ethoxy)-5-(4-(methylsulfonyl)phenyl)thiazolo[5,4-b]pyridine;

isopropyl-4-(1-((5-(4-(methylsulfonyl)phenyl)thiazolo[5,4-b]pyridin-2-yl)oxy)ethyl)piperidine-1-carboxylate;

3-isopropyl-5-(4-(1-((5-(4-((methylsulfonyl)methyl)phenyl)thiazolo[5,4-b]pyridin-2-yl)oxy)ethyl)piperidin-1-yl)-1,2,4-oxadiazole;

5-isopropyl-3-(4-(1-((5-(4-(methylsulfonyl)phenyl)thiazolo[5,4-b]pyridin-2-yl)oxy)ethyl)piperidin-1-yl)-1,2,4-oxadiazole;

3-isopropyl-5-(4-(1-((5-(4-(methylsulfonyl)phenyl)thiazolo[5,4-b]pyridin-2-yl)oxy)ethyl)phenyl)-1,2,4-oxadiazole;

5-(3-fluoro-4-((5-(4-(methylsulfonyl)phenyl)thiazolo[5,4-b]pyridin-2-yl)oxy)piperidin-1-yl)-3-isopropyl-1,2,4-oxadiazole;
4-(2-(1-(1-(3-isopropyl-1,2,4-oxadiazol-5-yl)piperidin-4-yl)ethoxy)thiazolo[5,4-b]pyridin-5-yl)-N-methylbenzenesulfonamide;
5-(4-(1-((5-(4-(ethylsulfonyl)phenyl)thiazolo[5,4-b]pyridin-2-yl)oxy)ethyl)piperidin-1-yl)-3-isopropyl-1,2,4-oxadiazole;
5-(4-(1-((5-(4-(cyclopropylsulfonyl)phenyl)thiazolo[5,4-b]pyridin-2-yl)oxy)ethyl)piperidin-1-yl)-3-isopropyl-1,2,4-oxadiazole;
5-(4-(1-((5-(4-(cyclopropylsulfinyl)phenyl)thiazolo[5,4-b]pyridin-2-yl)oxy)ethyl)piperidin-1-yl)-3-isopropyl-1,2,4-oxadiazole;
4-(2-(1-(1-(3-isopropyl-1,2,4-oxadiazol-5-yl)piperidin-4-yl)ethoxy)thiazolo[5,4-b]pyridin-5-yl)benzonitrile;
4-(2-(1-(1-(3-isopropyl-1,2,4-oxadiazol-5-yl)piperidin-4-yl)ethoxy)thiazolo[5,4-b]pyridin-5-yl)-N-(2-methoxyethyl)benzene sulfonamide;
3-isopropyl-5-(4-(1-((5-(4-((2-methoxyethyl)sulfonyl)phenyl)thiazolo[5,4-b]pyridin-2-yl)oxy)ethyl) piperidin-1-yl)-1,2,4-oxadiazole;
3-isopropyl-5-(4-(1-((5-(4-((2-methoxyethyl)sulfinyl)phenyl)thiazolo[5,4-b]pyridin-2-yl)oxy)ethyl) piperidin-1-yl)-1,2,4-oxadiazole;
3-isopropyl-5-(4-(1-((5-(6-(methylsulfonyl)pyridin-3-yl)thiazolo[5,4-b]pyridin-2-yl)oxy)ethyl)piperidin-1-yl)-1,2,4-oxadiazole;
(R)-3-isopropyl-5-(4-(1-((5-(pyridin-4-yl)thiazolo[5,4-b]pyridin-2-yl)oxy)ethyl)piperidin-1-yl)-1,2,4-oxadiazole;
(R)-4-(2-(1-(1-(3-isopropyl-1,2,4-oxadiazol-5-yl)piperidin-4-yl)ethoxy)thiazolo[5,4-b]pyridin-5-yl)-1-methylpyridin-1-ium;
4-(2-(4-(3-isopropyl-1,2,4-oxadiazol-5-yl)piperidin-1-yl)thiazolo[5,4-b]pyridin-5-yl)-N-methylbenzenesulfonamide;
4-(2-(4-(3-isopropyl-1,2,4-oxadiazol-5-yl)piperidin-1-yl)thiazolo[5,4-b]pyridin-5-yl)-N-(2-methoxyethyl) benzenesulfonamide;
N-(4-(2-(1-(1-(3-isopropyl-1,2,4-oxadiazol-5-yl)piperidin-4-yl)ethoxy)thiazolo[5,4-b]pyridin-5-yl)phenyl) methanesulfonamide;
2-(1-(1-methyl-1H-tetrazol-5-yl)piperidin-4-yl) ethoxy)-5-(4-(methylsulfonyl)phenyl)thiazolo[5,4-b]pyridine;
(S)-5-(4-(1-((5-(3-fluoropyridin-4-yl)thiazolo[5,4-b]pyridin-2-yl)oxy)ethyl)piperidin-1-yl)-3-isopropyl-1,2,4-oxadiazole;
3-isopropyl-5-(1-(5-(pyridin-4-yl)thiazolo[5,4-b]pyridin-2-yl)piperidin-4-yl)-1,2,4-oxadiazole;
3-isopropyl-5-(1-(5-(4-((2-methoxyethyl)sulfonyl)phenyl)thiazolo[5,4-b]pyridin-2-yl)piperidin-4-yl)-1,2,4-oxadiazole;
5-(4-(1-((5-(4-(1H-tetrazol-1-yl)phenyl)thiazolo[5,4-b]pyridin-2-yl)oxy)ethyl)piperidin-1-yl)-3-isopropyl-1,2,4-oxadiazole;
3-isopropyl-5-(1-(5-(6-(methylsulfonyl)pyridin-3-yl)thiazolo[5,4-b]pyridin-2-yl)piperidin-4-yl)-1,2,4-oxadiazole; OR
5-(4-(1-((5-(2-fluoropyridin-4-yl)thiazolo[5,4-b]pyridin-2-yl)oxy)ethyl)piperidin-1-yl)-3-isopropyl-1,2,4-oxadiazole.

21. The compound of claim 1, which is
(S)-3-isopropyl-5-(4-(1-((5-(6-(methylsulfonyl)pyridin-3-yl)thiazolo[5,4-b]pyridin-2-yl)oxy)ethyl)piperidin-1-yl)-1,2,4-oxadiazole;
3-isopropyl-5-(4-(((5-(pyridin-4-yl)thiazolo[5,4-b]pyridin-2-yl)oxy)methyl)piperidin-1-yl)-1,2,4-oxadiazole;
5-(4-(((5-(3-fluoropyridin-4-yl)thiazolo[5,4-b]pyridin-2-yl)oxy)methyl)piperidin-1-yl)-3-isopropyl-1,2,4-oxadiazole;
5-(4-(((5-(4-(1H-tetrazol-1-yl)phenyl)thiazolo[5,4-b]pyridin-2-yl)oxy)methyl)piperidin-1-yl)-3-isopropyl-1,2,4-oxadiazole;
5-(4-(((5-(2-fluoropyridin-4-yl)thiazolo[5,4-b]pyridin-2-yl)oxy)methyl)piperidin-1-yl)-3-isopropyl-1,2,4-oxadiazole;
2-(1-(1-(5-ethylpyridin-2-yl)piperidine-4-yl)ethoxy)-5-(4-(methylsulfonyl)phenyl)thiazolo[5,4-b]pyridine;
5-(4-(methylsulfonyl)phenyl)-2-(1-(1-(5-vinylpyridin-2-yl)piperidin-4-yl)ethoxy)thiazolo[5,4-b]pyridine;
(S)-5-(4-(methylsulfonyl)phenyl)-2-(1-(1-(5-propylpyrimidin-2-yl)piperidin-4-yl)ethoxy)thiazolo [5,4-b] pyridine;
(R)-5-(4-(methylsulfonyl)phenyl)-2-(1-(1-(5-propylpyrimidin-2-yl)piperidin-4-yl)ethoxy)thiazolo [5,4-b] pyridine;
3-isopropyl-5-(4-(((5-(6-(methylsulfonyl)pyridin-3-yl)thiazolo[5,4-b]pyridin-2-yl)oxy)methyl)piperidin-1-yl)-1,2,4-oxadiazole;
(S)-3-isopropyl-5-(4-(1-((5-(pyridin-4-yl)thiazolo[5,4-b]pyridin-2-yl)oxy)ethyl)piperidin-1-yl)-1,2,4-oxadiazole;
(S)-5-(4-(1-((5-(2-fluoropyridin-4-yl)thiazolo[5,4-b]pyridin-2-yl)oxy)ethyl)piperidin-1-yl)-3-isopropyl-1,2,4-oxadiazole;
3-isopropyl-5-(4-(2,2,2-trifluoro-1-((5-(4-(methylsulfonyl)phenyl) thiazolo[5,4-b]pyridin-2-yl)oxy)ethyl)piperidin-1-yl)-1,2,4-oxadiazole;
(S)-5-(4-(1-((5-(4-(cyclopropylsulfonyl)phenyl)thiazolo [5,4-b]pyridin-2-yl)oxy)ethyl)piperidin-1-yl)-3-isopropyl-1,2,4-oxadiazole;
(S)-5-(4-(1-((5-(3-fluoropyridin-4-yl)thiazolo[5,4-b]pyridin-2-yl)oxy)ethyl)piperidin-1-yl)-3-isopropyl-1,2,4-oxadiazole;
2-isopropyl-5-(4-(1-((5-(4-(methylsulfonyl)phenyl)thiazolo[5,4-b]pyridin-2-yl)oxy)ethyl)piperidin-1-yl)-1,3,4-oxadiazole;
4-(2-(1-(1-(3-isopropyl-1,2,4-oxadiazol-5-yl)piperidin-4-yl) ethoxy)thiazolo[5,4-b]pyridin-5-yl)pyridine 1-oxide;
(S)-5-(6-(methylsulfonyl)pyridin-3-yl)-2-(1-(1-(5-propylpyrimidin-2-yl)piperidin-4-yl)ethoxy)thiazolo [5,4-b] pyridine;
5-(4-(1-((5-(3-fluoro-4-(methylsulfonyl)phenyl)thiazolo [5,4-b]pyridin-2-yl)oxy)ethyl)piperidin-1-yl)-3-isopropyl-1,2,4-oxadiazole;
(S)-5-(2-fluoropyridin-4-yl)-2-(1-(1-(5-propylpyrimidin-2-yl)piperidin-4-yl)ethoxy)thiazolo[5,4-b]pyridine;
3-isopropyl-5-(4-(2,2,2-trifluoro-1-((5-(6-(methylsulfonyl)pyridin-3-yl)thiazolo[5,4-b]pyridin-2-yl)oxy) ethyl)piperidin-1-yl)-1,2,4-oxadiazole;
3-isopropyl-5-(4-(2,2,2-trifluoro-1-((5-(2-fluoropyridin-4-yl)thiazolo[5,4-b]pyridin-2-yl)oxy)ethyl) piperidin-1-yl)-1,2,4-oxadiazole;
(S)-2-(1-(1-(5-ethylpyrimidin-2-yl)piperidin-4-yl) ethoxy)-5-(2-fluoropyridin-4-yl)thiazolo[5,4-b]pyridine;

3-isopropyl-5-(4-(1-((5-(4-(methylsulfonyl)phenyl)thi-azolo[5,4-b]pyridin-2-yl)oxy)ethyl) cyclohexyl)-1,2,4-oxadiazole;

(S)-2-(1-(1-(5-ethylpyrimidin-2-yl)piperidin-4-yl) ethoxy)-5-(6-(methylsulfonyl)pyridin-3-yl) thiazolo[5,4-b]pyridine;

2-(1-(1-(3-isopropyl-1,2,4-thiadiazol-5-yl)piperidin-4-yl) ethoxy)-5-(4-(methyl sulfonyl)phenyl)thiazolo[5,4-b]pyridine;

3-isopropyl-5-(4-(1-((6-(4-(methyl sulfonyl)phenyl)thi-azolo[4,5-b] pyrazin-2-yl)oxy)ethyl)piperidin-1-yl)-1,2,4-oxadiazole;

2-(1-(1-(cyclopropylsulfonyl)piperidin-4-yl)ethoxy)-5-(4-(methyl sulfonyl)phenyl)thiazolo[5,4-b] pyridine;

6-(4-(methylsulfonyl)phenyl)-2-(1-(1-(5-propylpyrimi-din-2-yl)piperidin-4-yl)ethoxy)thiazolo[4,5-b]pyrazine;

5-(4-(1-((5-(2-fluoro-4-(methylsulfonyl)phenyl)thiazolo [5,4-b]pyridin-2-yl)oxy)ethyl)piperidin-1-yl)-3-isopro-pyl-1,2,4-oxadiazole; OR 5-(3-fluoro-4-(1-((5-(4-(methylsulfonyl)phenyl)thiazolo [5,4-b]pyridin-2-yl)oxy)ethyl)piperidin-1-yl)-3-isopro-pyl-1,2,4-oxadiazole.

22. The compound of claim 1, which is
2-(1-(1-(5-isopropylpyrimidin-2-yl)piperidin-4-yl) ethoxy)-5-(4-(methylsulfonyl)phenyl)thiazolo[5,4-b]pyridine;

(S)-3-isopropyl-5-(4-(1-((6-(6-(methylsulfonyl)pyridin-3-yl)thiazolo[4,5-b]pyrazin-2-yl)oxy) ethyl)piperidin-1-yl)-1,2,4-oxadiazole;

5-(4-(methylsulfonyl)phenyl)-2-(1-(1-(propylsulfonyl)pi-peridin-4-yl)ethoxy)thiazolo[5,4-b]pyridine;

5-(4-(1-((5-(2-chloropyrimidin-5-yl)thiazolo[5,4-b]pyri-din-2-yl) oxy)ethyl)piperidin-1-yl)-3-isopropyl-1,2,4-oxadiazole;

1-methylcyclopropyl4-(1-((5-(4-(methylsulfonyl)phenyl) thiazolo[5,4-b]pyridin-2-yl)oxy)ethyl) piperidine-1-carboxylate;

5-(4-(methylsulfonyl)phenyl)-2-(1-(1-(5-(prop-1-en-2-yl) pyrimidin-2-yl)piperidin-4-yl)ethoxy)thiazolo [5,4-b]pyridine;

(S)-5-(4-(1-((5-(2-chloropyrimidin-5-yl)thiazolo[5,4-b] pyridin-2-yl)oxy)ethyl)piperidin-1-yl)-3-isopropyl-1,2,4-oxadiazole;

2-(1-(1-(5-chloropyrimidin-2-yl)piperidin-4-yl)ethoxy)-5-(4-(methylsulfonyl)phenyl)thiazolo[5,4-b]pyridine;

3-isopropyl-5-(4-(1-((5-(thiazol-5-yl)thiazolo[5,4-b]pyri-din-2-yl)oxy)ethyl)piperidin-1-yl)-1,2,4-oxadiazole;

3-isopropyl-5-(4-(1-((5-(isoxazol-4-yl)thiazolo[5,4-b] pyridin-2-yl)oxy)ethyl)piperidin-1-yl)-1,2,4-oxadiaz-ole;

3-isopropyl-5-(4-(1-((5-(2-methylpyridin-4-yl)thiazolo [5,4-b]pyridin-2-yl)oxy)ethyl)piperidin-1-yl)-1,2,4-ox-adiazole;

3-isopropyl-5-(4-(1-((5-(isothiazol-4-yl)thiazolo[5,4-b] pyridin-2-yl)oxy)ethyl)piperidin-1-yl)-1,2,4-oxadiaz-ole;

3-isopropyl-5-(4-(1-((5-(3-methylisothiazol-4-yl)thiazolo [5,4-b]pyridin-2-yl)oxy)ethyl)piperidin-1-yl)-1,2,4-ox-adiazole;

4-(2-(1-(1-(3-isopropyl-1,2,4-oxadiazol-5-yl)piperidin-4-yl)ethoxy)thiazolo[5,4-b]pyridin-5-yl)pyridin-2(1H)-one;

4-(2-(1-(1-(3-isopropyl-1,2,4-oxadiazol-5-yl)piperidin-4-yl)ethoxy)thiazolo[5,4-b]pyridin-5-yl)-1-methylpyri-din-2(1H)-one;

5-((3R,4S)-3-fluoro-4-(((5-(4-(methylsulfonyl)phenyl) thiazolo[5,4-b]pyridin-2-yl)oxy)methyl)piperidin-1-yl)-3-isopropyl-1,2,4-oxadiazole;

5-((3S,4S)-3-fluoro-4-(((5-(4-(methylsulfonyl)phenyl) thiazolo[5,4-b]pyridin-2-yl)oxy)methyl) piperidin-1-yl)-3-isopropyl-1,2,4-oxadiazole;

3-isopropyl-5-(4-(1-(5-(4-(methyl sulfonyl)phenyl)thi-azolo[5,4-b]pyridin-2-yl)ethoxy)piperidin-1-yl)-1,2,4-oxadiazole;

5-(4-(1-((5-(4-(methylsulfonyl)phenyl)thiazolo[5,4-b] pyridin-2-yl)oxy)ethyl)piperidin-1-yl)-3-(trifluorom-ethyl)-1,2,4-oxadiazole;

5-(4-(1-((5-(2-chloropyridin-4-yl)thiazolo[5,4-b]pyridin-2-yl)oxy)ethyl)piperidin-1-yl)-3-isopropyl-1,2,4-ox-adiazole;

3-isopropyl-5-(4-(1-((5-(2-(methylsulfonyl)pyrimidin-5-yl)thiazolo[5,4-b]pyridin-2-yl)oxy)ethyl)piperidin-1-yl)-1,2,4-oxadiazole;

3-isopropyl-5-(4-(1-((5-(pyridazin-4-yl)thiazolo[5,4-b] pyridin-2-yl)oxy)ethyl)piperidin-1-yl)-1,2,4-oxadiaz-ole;

3-isopropyl-5-(4-(1-((5-(pyridazin-4-yl)thiazolo[5,4-b] pyridin-2-yl)oxy)ethyl)piperidin-1-yl)-1,2,4-oxadiaz-ole;

2-((S)-1-(1-(5-ethylpyrimidin-2-yl)piperidin-4-yl) ethoxy)-5-(2-chloropyrimidin-5-yl)thiazolo[5,4-b] pyridine;

2-((S)-1-(1-(5-chloropyrimidin-2-yl)piperidin-4-yl) ethoxy)-5-(6-(methylsulfonyl)pyridin-3-yl)thiazolo[5,4-b]pyridine;

2-(1-(1-(5-cyclopropylpyrimidin-2-yl)piperidin-4-yl) ethoxy)-5-(6-(methylsulfonyl)pyridin-3-yl)thiazolo[5,4-b]pyridine;

2-((S)-1-(1-(3-isopropyl-1,2,4-oxadiazol-5-yl)piperidin-4-yl)ethoxy)-5-(2-(methylsulfinyl)pyrimidin-5-yl)thi-azolo[5,4-b]pyridine;

N-(5-(2-(1-(1-(3-isopropyl-1,2,4-oxadiazol-5-yl)piperi-din-4-yl)ethoxy)thiazolo[5,4-b]pyridin-5-yl)pyrimi-din-2-yl)-N-methylacetamide;

2-((R)-1-(1-(3-isopropyl-1,2,4-oxadiazol-5-yl)pyrrolidin-3-yl)ethoxy)-5-(6-(methylsulfonyl)pyridin-3-yl)thi-azolo[5,4-b]pyridine;

2-((S)-1-(1-(3-isopropyl-1,2,4-oxadiazol-5-yl)pyrrolidin-3-yl)ethoxy)-5-(6-(methylsulfonyl)pyridin-3-yl)thi-azolo[5,4-b]pyridine; OR 2-(1-(1-(3-isopropyl-1,2,4-oxadiazol-5-yl)piperidin-4-yl) ethoxy)-5-(6-chloropyridin-3-yl)thiazolo[5,4-b]pyri-dine.

23. The compound of claim 1, which is
2-((S)-1-(1-(3-isopropyl-1,2,4-oxadiazol-5-yl)piperidin-4-yl)ethoxy)-5-(2-chloropyridin-4-yl)thiazolo[5,4-b] pyridine;

1-(5-(2-(1-(1-(3-isopropyl-1,2,4-oxadiazol-5-yl)piperi-din-4-yl)ethoxy)thiazolo[5,4-b]pyridin-5-yl)pyridin-2-yl)imidazolidin-2-one;

2-((S)-1-(1-(3-(trifluoromethyl)-1,2,4-oxadiazol-5-yl)pi-peridin-4-yl)ethoxy)-5-(6-(methylsulfonyl)pyridin-3-yl)thiazolo[5,4-b]pyridine;

1-(5-(2-(1-(1-(3-isopropyl-1,2,4-oxadiazol-5-yl)piperi-din-4-yl)ethoxy)thiazolo[5,4-b]pyridin-5-yl)pyridin-2-yl)pyrrolidin-2-one;

2-(1-(1-(3-isopropyl-1,2,4-oxadiazol-5-yl)piperidin-4-yl) ethoxy)-5-(6-(trifluoromethyl)pyridin-3-yl)thiazolo[5,4-b]pyridine;

2-(1-(1-(5-chloropyrazin-2-yl)piperidin-4-yl)ethoxy)-5-(4-(methylsulfonyl)phenyl)thiazolo[5,4-b]pyridine;

2-(1-(1-(5-ethylpyrimidin-2-yl)piperidin-4-yl)ethoxy)-5-(pyridin-4-yl)thiazolo[5,4-b]pyridine;

2-(1-(1-(5-propylpyrimidin-2-yl)piperidin-4-yl)ethoxy)-5-(pyridin-4-yl)thiazolo[5,4-b]pyridine;

2-(1-(1-(5-chloropyrazin-2-yl)piperidin-4-yl)ethoxy)-5-(6-(methylsulfonyl)pyridin-3-yl)thiazolo[5,4-b]pyridine;

2-((S)-1-(1-(3-isopropyl-1,2,4-oxadiazol-5-yl)piperidin-4-yl)ethoxy)-5-(6-(trifluoromethyl)pyridin-3-yl)thiazolo[5,4-b]pyridine;

2-(S)-1-(1-(5-propylpyrimidin-2-yl)piperidin-4-yl)ethoxy)-5-(pyridin-4-yl)thiazolo[5,4-b]pyridine;

2-((S)-1-(1-(5-ethylpyrimidin-2-yl)piperidin-4-yl)ethoxy)-5-(6-(trifluoromethyl)pyridin-3-yl)thiazolo[5,4-b]pyridine;

2-((S)-1-(1-(3-isopropyl-1,2,4-oxadiazol-5-yl)piperidin-4-yl)ethoxy)-5-(3-fluoro-4-(methylsulfonyl)phenyl)thiazolo[5,4-b]pyridine;

2-(1-(1-(3-ethyl-1,2,4-oxadiazol-5-yl)piperidin-4-yl)ethoxy)-5-(6-(methylsulfonyl)pyridin-3-yl)thiazolo[5,4-b]pyridine;

2-(1-(1-(5-methylpyrimidin-2-yl)piperidin-4-yl)ethoxy)-5-(6-(methylsulfonyl)pyridin-3-yl)thiazolo[5,4-b]pyridine;

2-(1-(1-(3-isopropyl-1,2,4-oxadiazol-5-yl)piperidin-4-yl)ethoxy)-5-(5-(methylsulfonyl)pyrazin-2-yl)thiazolo[5,4-b]pyridine;

2-(1-(1-(5-(trifluoromethyl)pyrimidin-2-yl)piperidin-4-yl)ethoxy)-5-(6-(methylsulfonyl)pyridin-3-yl)thiazolo[5,4-b]pyridine;

2-((S)-1-(1-(3-ethyl-1,2,4-oxadiazol-5-yl)piperidin-4-yl)ethoxy)-5-(6-(methylsulfonyl)pyridin-3-yl)thiazolo[5,4-b]pyridine;

2-(1-(1-(3-isopropyl-1,2,4-oxadiazol-5-yl)piperidin-4-yl)ethoxy)-5-(5-(methylsulfonyl)pyridin-2-yl)thiazolo[5,4-b]pyridine;

2-(1-(1-(3-isopropyl-1,2,4-oxadiazol-5-yl)piperidin-4-yl)ethoxy)-5-(6-(methylsulfonyl)pyridin-3-yl)thiazolo[5,4-d]pyrimidine;

2-(1-(1-(5-(methoxymethyl)pyrimidin-2-yl)piperidin-4-yl)ethoxy)-5-(6-(methylsulfonyl)pyridin-3-yl)thiazolo[5,4-b]pyridine;

2-((R)-1-(1-(3-isopropyl-1,2,4-oxadiazol-5-yl)piperidin-4-yl)ethoxy)-5-(6-(cyclopropylsulfonyl)pyridin-3-yl)thiazolo[5,4-b]pyridine;

2-((R)-1-(1-(5-(methoxymethyl)pyrimidin-2-yl)piperidin-4-yl)ethoxy)-5-(6-(methylsulfonyl)pyridin-3-yl)thiazolo[5,4-b]pyridine;

2-((S)-1-(1-(5-(trifluoromethyl)pyrimidin-2-yl)piperidin-4-yl)ethoxy)-5-(6-(methylsulfonyl)pyridin-3-yl)thiazolo[5,4-b]pyridine;

2-((S)-1-(1-(3-isopropyl-1,2,4-oxadiazol-5-yl)piperidin-4-yl)ethoxy)-5-(2-fluoro-6-(methylsulfonyl)pyridin-3-yl)thiazolo[5,4-b]pyridine;

2-((R)-1-(1-(3-isopropyl-1,2,4-oxadiazol-5-yl)piperidin-4-yl)ethoxy)-5-(2-methyl-6-(methylsulfonyl)pyridin-3-yl)thiazolo[5,4-b]pyridine; OR 2-((R)-1-(1-(3-isopropyl-1,2,4-oxadiazol-5-yl)piperidin-4-yl)ethoxy)-5-(2-methyl-4-(methylsulfonyl)phenyl)thiazolo[5,4-b]pyridine.

24. A method of treating diseases and conditions mediated through GPR119 comprising administering the compound of claim 1 to a patient in need thereof.

25. The method of claim 24, wherein said disease is metabolic disorder.

26. The method of claim 2, wherein said disease is diabetes.

27. The method of claim 2, wherein said disease is Type II diabetes.

* * * * *